United States Patent
Yang et al.

(10) Patent No.: US 9,309,522 B2
(45) Date of Patent: Apr. 12, 2016

(54) PHAGE DISPLAYING SYSTEM EXPRESSING SINGLE CHAIN ANTIBODY

(71) Applicant: Academia Sinica, Taipei (TW)

(72) Inventors: An-Suei Yang, Taipei (TW); Yu-Ching Lee, Taipei (TW); Ing-Chien Chen, Taipei (TW); Chung-Ming Yu, Taipei (TW); Hung-Ju Hsu, Taipei (TW); Yi-Jen Huang, Taipei (TW); Hung-Ju Chang, Taipei (TW); Keng-Chang Tsai, Taipei (TW); Hung-Pin Peng, Taipei (TW)

(73) Assignee: Academia Sinica, Taipei (TW)

( * ) Notice: Subject to any disclaimer, the term of this patent is extended or adjusted under 35 U.S.C. 154(b) by 367 days.

(21) Appl. No.: 13/897,850

(22) Filed: May 20, 2013

(65) Prior Publication Data

US 2013/0323787 A1   Dec. 5, 2013

Related U.S. Application Data

(62) Division of application No. 12/854,632, filed on Aug. 11, 2010, now abandoned.

(60) Provisional application No. 61/232,819, filed on Aug. 11, 2009.

(51) Int. Cl.
| | |
|---|---|
| *C40B 40/08* | (2006.01) |
| *C12N 15/73* | (2006.01) |
| *C07K 16/00* | (2006.01) |
| *C07K 16/10* | (2006.01) |
| *C07K 16/22* | (2006.01) |
| *C12N 15/10* | (2006.01) |
| *C40B 50/06* | (2006.01) |

(52) U.S. Cl.
CPC ............... *C12N 15/73* (2013.01); *C07K 16/005* (2013.01); *C07K 16/1018* (2013.01); *C07K 16/22* (2013.01); *C12N 15/1037* (2013.01); *C12N 15/1051* (2013.01); *C40B 40/08* (2013.01); *C40B 50/06* (2013.01); *C07K 2317/622* (2013.01); *C07K 2317/624* (2013.01); *C12N 2795/00022* (2013.01)

(58) Field of Classification Search
None
See application file for complete search history.

(56) References Cited

U.S. PATENT DOCUMENTS 5,837,242 A   11/1998 Holliger et al.

OTHER PUBLICATIONS

Prust et al. (Feb. 2005) Nature Biotechnology vol. 23 pp. 195 to 200.*
Jestin et al.; (Feb. 2001) Research in Microbiology; 152:187-191.
Rajagopal et al., "A form of anti-Tac(Fv) which is both single-chain and disulfide stabilized: comparison with its single-chain and disulfide-stabilized homologs", *Protein Engineering* vol. 10 No. 12 pp. 1453-1459, 1997.

(Continued)

*Primary Examiner* — Christian Boesen
(74) *Attorney, Agent, or Firm* — Cesari and McKenna, LLP

(57) ABSTRACT

Disclosed are nucleic acid libraries for identifying a signal peptide that facilitates production of disulfide-stabilized single chain antibody, and for facilitating production of a disulfide-stabilized single chain antibody. Also disclosed are host cell libraries and phage libraries including the nucleic acid libraries. Further disclosed are methods for identifying a signal peptide that facilitates production of disulfide-stabilized single chain antibody, and methods for producing a disulfide-stabilized single chain antibody and non-fusion form thereof.

16 Claims, 7 Drawing Sheets

(56) References Cited

OTHER PUBLICATIONS

Wörn et al., "Different Equilibrium Stability Behavior of ScFv Fragments: Identification, Classification, and Improvement by Protein Engineering", *Biochemistry* 1999, 38, 8739-8750.

Steiner et al., "Signal sequences directing cotranslational translocation expand the range of proteins amenable to phage display", *Nature Biotechnology* vol. 24 No. 7 pp. 823-831, 2006.

Young et al., "Thermal stabilization of a single-chain Fv antibody fragment by introduction of a disulphide bond", *FEBS Letters* 377 (1995) 135-139.

* cited by examiner

```
               Open reading frame starting site
               ↓                                                       |<------
               ....|....|....|....|....|....|....|....|....|....|....|....|
                   5       15      25      35      45      55
SEQ ID NO:602 ATGACCATGATTACGCCAAGCTTTGGAGCCTTTTTTTTGGAGATTTTCAACGTGAAAAAA
SEQ ID NO:603 -M--T--M--I--T--P--S--F--G--A--F--F--L--E--I--F--N--V--K--K-
SEQ ID NO:604 L2 library                    CTTTTTTTTGGAGATTTTCAACGTGAAAAAA
SEQ ID NO:605 L3 library                                   CAACGTGAAAAAA
SEQ ID NO:606 L4 library                                              AAAA pelB peptidase
              - M13 p III signal sequence ------>|<----- cutting site --->|
               ....|....|....|....|....|....|....|....|....|....|....|....|
                   65      75      85      95      105     115
              TTATTATTCGCAATTCCTTTAGTTGTTCCTTTCTATGCGGCCCAGCCGGCCATGGCCCAT
              -L--L--F--A--I--P--L--V--V--P--F--Y--A--A--Q--P--A--M--A--H-
              TTATTANNKNNKNNKNNKNNKNNKNNKNNKNNKGCGGCCCAGCCGGCCATGGCCCAT
              TTATTATTCGCAATTCCTTTANNKNNKNNKNNKNNKNNKNNKNNKNNKATGGCCCAT
              TTATTATTCGCAATTCCTTTAGTTGTTCCTTTCTATNNKNNKNNKNNKNNKNNKNNK <---His tag -->|<----- scFv/sc-dsFv ----->>>
               ....|....|....|....|....|....|....|
                   125     135     145     155
              CATCACCACCATCATGGCCACGGGTCCGGCGATATTCAAATG
              -H--H--H--H--H--G--H--G--S--G--D--I--Q--M-
              CATCAC
              CATCACCACCATCATGGCCAC
              NNKNNKCACCATCATGGCCACGGGTCCG
```

FIG. 1

```
                 ....|....|  ....|....|  ....|....|  ....|....|  ....|....|  ....|....|  ....|....|  ....|....|  ....|....|  ....|....|
                     5           15          25          35          45          55          65          75          85          95
SEQ ID NO:607 TTAGTGTTC  CTTTCTATGC  GGCCCAGCCG  GCCATGGCCC  ATCATCACCA  CCATCATGGC  CACGGGTCCG  GCGATATTCA  AATGACCCAG  AGCCCGAGCA
SEQ ID NO:608 -L--V--V--  P--F--Y--A  --A--Q--P-  -A--M--A--  H--H--H--H  --H--H--G-  -H--G--S--  G--D--I--Q  --M--T--Q-  -S--P--S--
                         |---SfiI--  --|                                              VL Kappa1 1......  .....5....  ..........

....|....|  ....|....|  ....|....|  ....|....|  ....|....|  ....|....|  ....|....|  ....|....|  ....|....|  ....|....|
                    105         115         125         135         145         155         165         175         185         195
              GCCTGAGCGC  GAGCGTGGGA  GATCGCGTGA  CCATTACCTG  CCGTGCGAGC  CAGGATGTTA  GCACGGCGGT  CGCATGGTAT  CAGCAGAAAC  CAGGCAAAGC
              S--L--S--A  --S--V--G-  -D--R--V--  T--I--T--C  --R--A--S-  -Q--D--V--  S--T--A--V  --A--W--Y-  -Q--Q--K--  P--G--K--A
              10........  .....15...  ..........  20........  .....25...  ..........  30........  .....35...  ..........  40........

....|....|  ....|....|  ....|....|  ....|....|  ....|....|  ....|....|  ....|....|  ....|....|  ....|....|  ....|....|
                    205         215         225         235         245         255         265         275         285         295
              GCCGAAACTT  CTGATATACT  CTGCGTCCTT  CCTGTATAGC  GGGGTGCCGT  CGCGTTTTTC  GGGCAGTGGC  AGCGGCACGG  ACTTTACCCT  GACGATATCT
              --P--K--L-  -L--I--Y--  S--A--S--F  --L--Y--S-  -G--V--P--  S--R--F--S  --G--S--G-  -S--G--T--  D--F--T--L  --T--I--S-
              .....45...  ..........  50........  .....55...  ..........  60........  .....65...  ..........  70........  .....75...

....|....|  ....|....|  ....|....|  ....|....|  ....|....|  ....|....|  ....|....|  ....|....|  ....|....|  ....|....|
                    305         315         325         335         345         355         365         375         385         395
              TCCTTACAAC  CGGAGGATTT  TGCCGACCTAC  TACTGTCAAC  AGCATTATAC  CACACCGCCG  ACCTTCGGTT  GTGGCACCAA  AGTGGAAATC  AAACGCGGAG
              -S--L--Q--  P--E--D--F  --A--T--Y-  -Y--C--Q--  Q--H--Y--T  --T--P--P-  -T--F--G--  C--G--T--K  --V--E--I-  -K--R--G--
              ..........  80........  .....85...  ..........  90........  .....95...  ..........  100.......  .....105..  ...108

....|....|  ....|....|  ....|....|  ....|....|  ....|....|  ....|....|  ....|....|  ....|....|  ....|....|  ....|....|
                    405         415         425         435         445         455         465         475         485         495
              GGGGAGGTAG  CATCGAGGGC  CGTAGCGGAG  GTGGCGGGAG  CGAAGTGCAG  CTGGTGGAAT  CGGGAGGCGG  TCTGGTGCAA  CCTGGCGGCA  GCCTTCGTCT
              G--G--G--S  --I--E--G-  -R--S--G--  G--G--G--S  --E--V--Q-  -L--V--E--  S--G--G--G  --L--V--Q-  -P--G--G--  S--L--R--L
                         |<--fxa-->|                          VH3 1.......  .....5....  .........10..........  ....15....  ........20
                         cutting site ....|....|  ....|....|  ....|....|  ....|....|  ....|....|  ....|....|  ....|....|  ....|....|  ....|....|  ....|....|
                    505         515         525         535         545         555         565         575         585         595
              GAGCTGTGCG  GCGAGCGGGT  TCACCATTAG  CGATTACTGG  ATTCATTGGG  TGCGTCAAGC  TCCCGGCAAG  TGTCTGGAGT  GGGTCGCGGG  CATTACGCCC
              --S--C--A-  -A--S--G--  F--T--I--S  --D--Y--W-  -I--H--W--  V--R--Q--A  --P--G--K-  -C--L--E--  W--V--A--G  --I--T--P-
              ..........  ....25....  ........30  ..........  ....35....  ........40  ..........  ....45....  ........50  ..........

....|....|  ....|....|  ....|....|  ....|....|  ....|....|  ....|....|  ....|....|  ....|....|  ....|....|  ....|....|
                    605         615         625         635         645         655         665         675         685         695
              GCTGGCGGTT  ACACATATTA  TGCCGACAGC  GTGAAAGGTC  GCTTTACGAT  TAGTGCGGAC  ACCAGCAAAA  ATACCGCGTA  CCTGCAGATG  AATAGCCTGC
              -A--G--G--  Y--T--Y--Y  --A--D--S-  -V--K--G--  R--F--T--I  --S--A--D-  -T--S--K--  N--T--A--Y  --L--Q--M-  -N--S--L--
              ....55....  .........60  ..........  ....65....  .........70  ..........  ....75....  .........80  ..........  ....85....

....|....|  ....|....|  ....|....|  ....|....|  ....|....|  ....|....|  ....|....|  ....|....|  ....|....|  ....|....|
                    705         715         725         735         745         755         765         775         785         795
              GTGCGGAAGA  CACAGCGGTG  TATTATTGCG  CGCGTTTCGT  GTTTTTTCTG  CCGTATGCGA  TGGATTATTG  GGGGCAGGGC  ACCCTTGTTA  CCGTGAGCTC
              R--A--E--D  --T--A--V-  -Y--Y--C--  A--R--F--V  --F--F--L-  -P--Y--A--  M--D--Y--W  --G--Q--G-  -T--L--V--  T--V--S--S
              .........90  ..........  ....95....  .........100  ..........  ....105,....  .........110  ..........  ....115....  ........120

....|....|  ....|....|  ....|....|  ....|....|  ....|....|  ....|....|  ....|....|  ....|....|  ....|....|  ....|....|
                    805         815         825         835         845         855         865         875         885         895
              GGGCGTCAGCG  GCCGCAGGTG  CGCCGGTGCC  GTATCCGGAT  CCGCTGGAAC  CGCGTGCCGC  ATAGACTGTT  GAAAGTTGTT  TAGCAAAACC  TCATACAGAA
              --A--S--A-  -A--A--G--  A--P--V--P  --Y--P--D-  -P--L--E--  P--R--A--A  --*--T--V-  -E--S--C--  L--A--K--P  --H--T--E-
              ....122|--NotI-|  |<-------------  E-tag ----------------->|  Amber|<-------------  M13 gIII ------------>>>
                                                                     stop codon
```

FIG. 3

SEQUENCE LISTING

```
<160> NUMBER OF SEQ ID NOS: 609

<210> SEQ ID NO 1
<211> LENGTH: 30
<212> TYPE: PRT
<213> ORGANISM: artificial
<220> FEATURE:
<223> OTHER INFORMATION: Synthetic polypeptide
<220> FEATURE:
<221> NAME/KEY: misc_feature
<222> LOCATION: (6)..(15)
<223> OTHER INFORMATION: Xaa can be any naturally occurring amino acid

<400> SEQUENCE: 1

Val Lys Lys Leu Leu Xaa Xaa Xaa Xaa Xaa Xaa Xaa Xaa Xaa Ala
1               5                   10                  15

Ala Gln Pro Ala Met Ala His His His His His His Gly His
            20                  25                  30

<210> SEQ ID NO 2
<211> LENGTH: 30
<212> TYPE: PRT
<213> ORGANISM: artificial
<220> FEATURE:
<223> OTHER INFORMATION: Synthetic polypeptide
<220> FEATURE:
<221> NAME/KEY: misc_feature
<222> LOCATION: (11)..(20)
<223> OTHER INFORMATION: Xaa can be any naturally occurring amino acid
```

```
<400> SEQUENCE: 2

Val Lys Lys Leu Leu Phe Ala Ile Pro Leu Xaa Xaa Xaa Xaa Xaa
1               5                   10                  15

Xaa Xaa Xaa Xaa Met Ala His His His His His His Gly His
                20                  25                  30

<210> SEQ ID NO 3
<211> LENGTH: 30
<212> TYPE: PRT
<213> ORGANISM: artificial
<220> FEATURE:
<223> OTHER INFORMATION: Synthetic polypeptide
<220> FEATURE:
<221> NAME/KEY: misc_feature
<222> LOCATION: (16)..(25)
<223> OTHER INFORMATION: Xaa can be any naturally occurring amino acid

<400> SEQUENCE: 3

Val Lys Lys Leu Leu Phe Ala Ile Pro Leu Val Val Pro Phe Tyr Xaa
1               5                   10                  15

Xaa Xaa Xaa Xaa Xaa Xaa Xaa Xaa Xaa His His His Gly His
                20                  25                  30

<210> SEQ ID NO 4
<211> LENGTH: 28
<212> TYPE: PRT
<213> ORGANISM: artificial
<220> FEATURE:
<223> OTHER INFORMATION: Synthetic polypeptide

<400> SEQUENCE: 4

Val Lys Lys Leu Leu Phe Ala Ile Pro Leu Val Val Pro Phe Tyr Ala
1               5                   10                  15

Ala Gln Pro Ala Met Ala His His His His His His
                20                  25

<210> SEQ ID NO 5
<211> LENGTH: 28
<212> TYPE: PRT
<213> ORGANISM: artificial
<220> FEATURE:
<223> OTHER INFORMATION: Synthetic polypeptide

<400> SEQUENCE: 5

Val Lys Lys Leu Leu Val Leu Ser His Leu Pro Phe Met Thr Asp Ala
1               5                   10                  15

Ala Gln Pro Ala Met Ala His His His His His His
                20                  25

<210> SEQ ID NO 6
<211> LENGTH: 28
<212> TYPE: PRT
<213> ORGANISM: artificial
<220> FEATURE:
<223> OTHER INFORMATION: Synthetic polypeptide

<400> SEQUENCE: 6

Val Lys Lys Leu Leu Ser His Trp Leu Leu Ser Ser Gln Leu Gln Ala
1               5                   10                  15

Ala Gln Pro Ala Met Ala His His His His His His
                20                  25

<210> SEQ ID NO 7
<211> LENGTH: 28
```

```
<212> TYPE: PRT
<213> ORGANISM: artificial
<220> FEATURE:
<223> OTHER INFORMATION: Synthetic polypeptide

<400> SEQUENCE: 7

Val Lys Lys Leu Leu Ala Met Ser Leu Ala Pro Ser Val Phe Pro Ala
1               5                   10                  15

Ala Gln Pro Ala Met Ala His His His His His His
            20                  25

<210> SEQ ID NO 8
<211> LENGTH: 28
<212> TYPE: PRT
<213> ORGANISM: artificial
<220> FEATURE:
<223> OTHER INFORMATION: Synthetic polypeptide

<400> SEQUENCE: 8

Val Lys Lys Leu Leu Trp Ser Leu Phe Phe Gln Gln Leu Asn Pro Ala
1               5                   10                  15

Ala Gln Pro Ala Met Ala His His His His His His
            20                  25

<210> SEQ ID NO 9
<211> LENGTH: 28
<212> TYPE: PRT
<213> ORGANISM: artificial
<220> FEATURE:
<223> OTHER INFORMATION: Synthetic polypeptide

<400> SEQUENCE: 9

Val Lys Lys Leu Leu Leu Leu Ser Leu Leu Gln Arg Pro Leu Pro Ala
1               5                   10                  15

Ala Gln Pro Ala Met Ala His His His His His His
            20                  25

<210> SEQ ID NO 10
<211> LENGTH: 28
<212> TYPE: PRT
<213> ORGANISM: artificial
<220> FEATURE:
<223> OTHER INFORMATION: Synthetic polypeptide

<400> SEQUENCE: 10

Val Lys Lys Leu Leu Leu Ser Ser Trp Leu Met Thr Arg Phe Pro Ala
1               5                   10                  15

Ala Gln Pro Ala Met Ala His His His His His His
            20                  25

<210> SEQ ID NO 11
<211> LENGTH: 28
<212> TYPE: PRT
<213> ORGANISM: artificial
<220> FEATURE:
<223> OTHER INFORMATION: Synthetic polypeptide

<400> SEQUENCE: 11

Val Lys Lys Leu Leu Val Leu Ser His Phe Pro Ala Phe Val Pro Ala
1               5                   10                  15

Ala Gln Pro Ala Met Ala His His His His His His
            20                  25

<210> SEQ ID NO 12
```

-continued

```
<211> LENGTH: 28
<212> TYPE: PRT
<213> ORGANISM: artificial
<220> FEATURE:
<223> OTHER INFORMATION: Synthetic polypeptide

<400> SEQUENCE: 12

Val Lys Lys Leu Leu Pro Leu Leu Ser Leu Pro Leu Pro Pro Asn Ala
1               5                   10                  15

Ala Gln Pro Ala Met Ala His His His His His His
            20                  25

<210> SEQ ID NO 13
<211> LENGTH: 28
<212> TYPE: PRT
<213> ORGANISM: artificial
<220> FEATURE:
<223> OTHER INFORMATION: Synthetic polypeptide

<400> SEQUENCE: 13

Val Lys Lys Leu Leu Val Leu Thr Pro Met His Phe Ser Ser Pro Ala
1               5                   10                  15

Ala Gln Pro Ala Met Ala His His His His His His
            20                  25

<210> SEQ ID NO 14
<211> LENGTH: 28
<212> TYPE: PRT
<213> ORGANISM: artificial
<220> FEATURE:
<223> OTHER INFORMATION: Synthetic polypeptide

<400> SEQUENCE: 14

Val Lys Lys Leu Leu Ile Leu Ala Leu Pro Gln Ser Tyr Pro Leu Ala
1               5                   10                  15

Ala Gln Pro Ala Met Ala His His His His His His
            20                  25

<210> SEQ ID NO 15
<211> LENGTH: 28
<212> TYPE: PRT
<213> ORGANISM: artificial
<220> FEATURE:
<223> OTHER INFORMATION: Synthetic polypeptide

<400> SEQUENCE: 15

Val Lys Lys Leu Leu Gln Ala Leu Tyr Phe Ser Leu Pro Ser Ser Ala
1               5                   10                  15

Ala Gln Pro Ala Met Ala His His His His His His
            20                  25

<210> SEQ ID NO 16
<211> LENGTH: 28
<212> TYPE: PRT
<213> ORGANISM: artificial
<220> FEATURE:
<223> OTHER INFORMATION: Synthetic polypeptide

<400> SEQUENCE: 16

Val Lys Lys Leu Leu Val Ser Ala Met Thr Ser Ala Ser Phe Pro Ala
1               5                   10                  15

Ala Gln Pro Ala Met Ala His His His His His His
            20                  25
```

```
<210> SEQ ID NO 17
<211> LENGTH: 28
<212> TYPE: PRT
<213> ORGANISM: artificial
<220> FEATURE:
<223> OTHER INFORMATION: Synthetic polypeptide

<400> SEQUENCE: 17

Val Lys Lys Leu Leu Pro Ala Ser Trp Leu Phe Gly Gln Pro Ala
1               5                   10                  15

Ala Gln Pro Ala Met Ala His His His His His His
            20                  25

<210> SEQ ID NO 18
<211> LENGTH: 28
<212> TYPE: PRT
<213> ORGANISM: artificial
<220> FEATURE:
<223> OTHER INFORMATION: Synthetic polypeptide

<400> SEQUENCE: 18

Val Lys Lys Leu Leu Trp Ser Leu Phe Phe Gln Gln Leu Asn Pro Ala
1               5                   10                  15

Ala Gln Pro Ala Met Ala His His His His His His
            20                  25

<210> SEQ ID NO 19
<211> LENGTH: 28
<212> TYPE: PRT
<213> ORGANISM: artificial
<220> FEATURE:
<223> OTHER INFORMATION: Synthetic polypeptide

<400> SEQUENCE: 19

Val Lys Lys Leu Leu Phe Val Met Ala Leu Arg Ser Ser Ala Pro Ala
1               5                   10                  15

Ala Gln Pro Ala Met Ala His His His His His His
            20                  25

<210> SEQ ID NO 20
<211> LENGTH: 28
<212> TYPE: PRT
<213> ORGANISM: artificial
<220> FEATURE:
<223> OTHER INFORMATION: Synthetic polypeptide

<400> SEQUENCE: 20

Val Lys Lys Leu Leu Phe Leu Trp Pro Phe Tyr Asn Gly His Ile Ala
1               5                   10                  15

Ala Gln Pro Ala Met Ala His His His His His His
            20                  25

<210> SEQ ID NO 21
<211> LENGTH: 28
<212> TYPE: PRT
<213> ORGANISM: artificial
<220> FEATURE:
<223> OTHER INFORMATION: Synthetic polypeptide

<400> SEQUENCE: 21

Val Lys Lys Leu Leu Gln Ser Phe Tyr Leu Ser Leu Gln Leu Asp Ala
1               5                   10                  15

Ala Gln Pro Ala Met Ala His His His His His His
            20                  25
```

```
<210> SEQ ID NO 22
<211> LENGTH: 28
<212> TYPE: PRT
<213> ORGANISM: artificial
<220> FEATURE:
<223> OTHER INFORMATION: Synthetic polypeptide

<400> SEQUENCE: 22

Val Lys Lys Leu Leu Ser Leu Thr Phe Pro Phe Thr Ile His Ser Ala
1               5                   10                  15

Ala Gln Pro Ala Met Ala His His His His His His
            20                  25

<210> SEQ ID NO 23
<211> LENGTH: 28
<212> TYPE: PRT
<213> ORGANISM: artificial
<220> FEATURE:
<223> OTHER INFORMATION: Synthetic polypeptide

<400> SEQUENCE: 23

Val Lys Lys Leu Leu Trp Pro Val Leu Ser Pro Ser Leu Phe Pro Ala
1               5                   10                  15

Ala Gln Pro Ala Met Ala His His His His His His
            20                  25

<210> SEQ ID NO 24
<211> LENGTH: 28
<212> TYPE: PRT
<213> ORGANISM: artificial
<220> FEATURE:
<223> OTHER INFORMATION: Synthetic polypeptide

<400> SEQUENCE: 24

Val Lys Lys Leu Leu Pro Trp Leu Phe Ser Thr Phe Pro Ser Ser Ala
1               5                   10                  15

Ala Gln Pro Ala Met Ala His His His His His His
            20                  25

<210> SEQ ID NO 25
<211> LENGTH: 28
<212> TYPE: PRT
<213> ORGANISM: artificial
<220> FEATURE:
<223> OTHER INFORMATION: Synthetic polypeptide

<400> SEQUENCE: 25

Val Lys Lys Leu Leu Ile Met Ser Ser Leu Pro Thr Leu Ser Pro Ala
1               5                   10                  15

Ala Gln Pro Ala Met Ala His His His His His His
            20                  25

<210> SEQ ID NO 26
<211> LENGTH: 28
<212> TYPE: PRT
<213> ORGANISM: artificial
<220> FEATURE:
<223> OTHER INFORMATION: Synthetic polypeptide

<400> SEQUENCE: 26

Val Lys Lys Leu Leu Ile Met Ser Arg Val Leu Ala Pro Asp Phe Ala
1               5                   10                  15

Ala Gln Pro Ala Met Ala His His His His His His
            20                  25
```

```
<210> SEQ ID NO 27
<211> LENGTH: 28
<212> TYPE: PRT
<213> ORGANISM: artificial
<220> FEATURE:
<223> OTHER INFORMATION: Synthetic polypeptide

<400> SEQUENCE: 27

Val Lys Lys Leu Leu Phe Asp Phe Trp Phe Ser Ser Phe Leu Gln Ala
 1               5                  10                  15

Ala Gln Pro Ala Met Ala His His His His His His
             20                  25

<210> SEQ ID NO 28
<211> LENGTH: 28
<212> TYPE: PRT
<213> ORGANISM: artificial
<220> FEATURE:
<223> OTHER INFORMATION: Synthetic polypeptide

<400> SEQUENCE: 28

Val Lys Lys Leu Leu Tyr Gly Gln Leu Met Leu Leu Ser Ser Asp Ala
 1               5                  10                  15

Ala Gln Pro Ala Met Ala His His His His His His
             20                  25

<210> SEQ ID NO 29
<211> LENGTH: 28
<212> TYPE: PRT
<213> ORGANISM: artificial
<220> FEATURE:
<223> OTHER INFORMATION: Synthetic polypeptide

<400> SEQUENCE: 29

Val Lys Lys Leu Leu Pro Trp Leu Phe Pro Phe His Ala Tyr Pro Ala
 1               5                  10                  15

Ala Gln Pro Ala Met Ala His His His His His His
             20                  25

<210> SEQ ID NO 30
<211> LENGTH: 28
<212> TYPE: PRT
<213> ORGANISM: artificial
<220> FEATURE:
<223> OTHER INFORMATION: Synthetic polypeptide

<400> SEQUENCE: 30

Val Lys Lys Leu Leu Leu Val Met Thr Leu Ser Arg Gln Pro Phe Ala
 1               5                  10                  15

Ala Gln Pro Ala Met Ala His His His His His His
             20                  25

<210> SEQ ID NO 31
<211> LENGTH: 28
<212> TYPE: PRT
<213> ORGANISM: artificial
<220> FEATURE:
<223> OTHER INFORMATION: Synthetic polypeptide

<400> SEQUENCE: 31

Val Lys Lys Leu Leu Ala Ser Ala Tyr Leu Tyr His Gly Leu Ser Ala
 1               5                  10                  15

Ala Gln Pro Ala Met Ala His His His His His His
```

```
                      20                  25

<210> SEQ ID NO 32
<211> LENGTH: 28
<212> TYPE: PRT
<213> ORGANISM: artificial
<220> FEATURE:
<223> OTHER INFORMATION: Synthetic polypeptide

<400> SEQUENCE: 32

Val Lys Lys Leu Leu Pro Phe Phe Ala Gly Val Leu Gln His Pro Ala
1               5                   10                  15

Ala Gln Pro Ala Met Ala His His His His His His
            20                  25

<210> SEQ ID NO 33
<211> LENGTH: 28
<212> TYPE: PRT
<213> ORGANISM: artificial
<220> FEATURE:
<223> OTHER INFORMATION: Synthetic polypeptide

<400> SEQUENCE: 33

Val Lys Lys Leu Leu Ala Leu Ser Ser Pro Phe Phe His Ile Pro Ala
1               5                   10                  15

Ala Gln Pro Ala Met Ala His His His His His His
            20                  25

<210> SEQ ID NO 34
<211> LENGTH: 28
<212> TYPE: PRT
<213> ORGANISM: artificial
<220> FEATURE:
<223> OTHER INFORMATION: Synthetic polypeptide

<400> SEQUENCE: 34

Val Lys Lys Leu Leu Pro Thr Arg Gln Pro Met Met Tyr Pro Pro Ala
1               5                   10                  15

Ala Gln Pro Ala Met Ala His His His His His His
            20                  25

<210> SEQ ID NO 35
<211> LENGTH: 28
<212> TYPE: PRT
<213> ORGANISM: artificial
<220> FEATURE:
<223> OTHER INFORMATION: Synthetic polypeptide

<400> SEQUENCE: 35

Val Lys Lys Leu Leu Gln Leu Leu Met Pro Phe Leu Asn Ser Pro Ala
1               5                   10                  15

Ala Gln Pro Ala Met Ala His His His His His His
            20                  25

<210> SEQ ID NO 36
<211> LENGTH: 28
<212> TYPE: PRT
<213> ORGANISM: artificial
<220> FEATURE:
<223> OTHER INFORMATION: Synthetic polypeptide

<400> SEQUENCE: 36

Val Lys Lys Leu Leu Cys Ser Leu Gly Tyr Ala Cys Ile Pro Pro Ala
1               5                   10                  15
```

Ala Gln Pro Ala Met Ala His His His His His His
        20                  25

<210> SEQ ID NO 37
<211> LENGTH: 28
<212> TYPE: PRT
<213> ORGANISM: artificial
<220> FEATURE:
<223> OTHER INFORMATION: Synthetic polypeptide

<400> SEQUENCE: 37

Val Lys Lys Leu Leu Met Pro Trp Leu Phe Asn Ser Pro Pro Ala
1               5                   10                  15

Ala Gln Pro Ala Met Ala His His His His His His
        20                  25

<210> SEQ ID NO 38
<211> LENGTH: 28
<212> TYPE: PRT
<213> ORGANISM: artificial
<220> FEATURE:
<223> OTHER INFORMATION: Synthetic polypeptide

<400> SEQUENCE: 38

Val Lys Lys Leu Leu Leu Asp Gln Leu Ala Tyr Ala Ala Leu Ser Ala
1               5                   10                  15

Ala Gln Pro Ala Met Ala His His His His His His
        20                  25

<210> SEQ ID NO 39
<211> LENGTH: 28
<212> TYPE: PRT
<213> ORGANISM: artificial
<220> FEATURE:
<223> OTHER INFORMATION: Synthetic polypeptide

<400> SEQUENCE: 39

Val Lys Lys Leu Leu Gln Ser Thr Val Phe Phe Ser Trp Leu Ser Ala
1               5                   10                  15

Ala Gln Pro Ala Met Ala His His His His His His
        20                  25

<210> SEQ ID NO 40
<211> LENGTH: 28
<212> TYPE: PRT
<213> ORGANISM: artificial
<220> FEATURE:
<223> OTHER INFORMATION: Synthetic polypeptide

<400> SEQUENCE: 40

Val Lys Lys Leu Leu Leu Pro Trp Ala Leu Ser His Gln Val Leu Ala
1               5                   10                  15

Ala Gln Pro Ala Met Ala His His His His His His
        20                  25

<210> SEQ ID NO 41
<211> LENGTH: 28
<212> TYPE: PRT
<213> ORGANISM: artificial
<220> FEATURE:
<223> OTHER INFORMATION: Synthetic polypeptide

<400> SEQUENCE: 41

Val Lys Lys Leu Leu Ala Leu Thr Tyr Pro Ala Phe Leu Tyr Asp Ala
1               5                   10                  15

```
Ala Gln Pro Ala Met Ala His His His His His
            20                  25

<210> SEQ ID NO 42
<211> LENGTH: 28
<212> TYPE: PRT
<213> ORGANISM: artificial
<220> FEATURE:
<223> OTHER INFORMATION: Synthetic polypeptide

<400> SEQUENCE: 42

Val Lys Lys Leu Leu Ala Met Ala Pro Pro Met Met Ser Met Asn Ala
1               5                   10                  15

Ala Gln Pro Ala Met Ala His His His His His
            20                  25

<210> SEQ ID NO 43
<211> LENGTH: 28
<212> TYPE: PRT
<213> ORGANISM: artificial
<220> FEATURE:
<223> OTHER INFORMATION: Synthetic polypeptide

<400> SEQUENCE: 43

Val Lys Lys Leu Leu Trp Trp Ser Ser Leu Phe Ala Pro Ser Pro Ala
1               5                   10                  15

Ala Gln Pro Ala Met Ala His His His His His
            20                  25

<210> SEQ ID NO 44
<211> LENGTH: 28
<212> TYPE: PRT
<213> ORGANISM: artificial
<220> FEATURE:
<223> OTHER INFORMATION: Synthetic polypeptide

<400> SEQUENCE: 44

Val Lys Lys Leu Leu Gly Ser Phe Ile Leu Ala Arg Ser Met Asp Ala
1               5                   10                  15

Ala Gln Pro Ala Met Ala His His His His His
            20                  25

<210> SEQ ID NO 45
<211> LENGTH: 28
<212> TYPE: PRT
<213> ORGANISM: artificial
<220> FEATURE:
<223> OTHER INFORMATION: Synthetic polypeptide

<400> SEQUENCE: 45

Val Lys Lys Leu Leu Met Val Leu Thr Ser Trp His Pro Tyr Pro Ala
1               5                   10                  15

Ala Gln Pro Ala Met Ala His His His His His
            20                  25

<210> SEQ ID NO 46
<211> LENGTH: 28
<212> TYPE: PRT
<213> ORGANISM: artificial
<220> FEATURE:
<223> OTHER INFORMATION: Synthetic polypeptide

<400> SEQUENCE: 46

Val Lys Lys Leu Leu Phe Ser Leu Arg Phe Phe Phe Pro Ser Ser Ala
```

```
                1               5                   10                  15
Ala Gln Pro Ala Met Ala His His His His His His
            20                  25

<210> SEQ ID NO 47
<211> LENGTH: 28
<212> TYPE: PRT
<213> ORGANISM: artificial
<220> FEATURE:
<223> OTHER INFORMATION: Synthetic polypeptide

<400> SEQUENCE: 47

Val Lys Lys Leu Leu Trp Leu Trp Ser Thr Pro Leu Phe Pro His Ala
1               5                   10                  15
Ala Gln Pro Ala Met Ala His His His His His His
            20                  25

<210> SEQ ID NO 48
<211> LENGTH: 28
<212> TYPE: PRT
<213> ORGANISM: artificial
<220> FEATURE:
<223> OTHER INFORMATION: Synthetic polypeptide

<400> SEQUENCE: 48

Val Lys Lys Leu Leu Pro Leu Leu Phe Ser Leu Asp Gly Asp Pro Ala
1               5                   10                  15
Ala Gln Pro Ala Met Ala His His His His His His
            20                  25

<210> SEQ ID NO 49
<211> LENGTH: 28
<212> TYPE: PRT
<213> ORGANISM: artificial
<220> FEATURE:
<223> OTHER INFORMATION: Synthetic polypeptide

<400> SEQUENCE: 49

Val Lys Lys Leu Leu Ser Val Ser Leu Ser Ser Tyr Ser Phe Tyr Ala
1               5                   10                  15
Ala Gln Pro Ala Met Ala His His His His His His
            20                  25

<210> SEQ ID NO 50
<211> LENGTH: 28
<212> TYPE: PRT
<213> ORGANISM: artificial
<220> FEATURE:
<223> OTHER INFORMATION: Synthetic polypeptide

<400> SEQUENCE: 50

Val Lys Lys Leu Leu Leu Asn Gly Thr Phe Ser Ala Gln Leu Phe Ala
1               5                   10                  15
Ala Gln Pro Ala Met Ala His His His His His His
            20                  25

<210> SEQ ID NO 51
<211> LENGTH: 28
<212> TYPE: PRT
<213> ORGANISM: artificial
<220> FEATURE:
<223> OTHER INFORMATION: Synthetic polypeptide

<400> SEQUENCE: 51
```

Val Lys Lys Leu Leu Trp His Val Leu Pro Tyr Leu Pro Asn Ser Ala
1               5                   10                  15

Ala Gln Pro Ala Met Ala His His His His His His
            20                  25

<210> SEQ ID NO 52
<211> LENGTH: 28
<212> TYPE: PRT
<213> ORGANISM: artificial
<220> FEATURE:
<223> OTHER INFORMATION: Synthetic polypeptide

<400> SEQUENCE: 52

Val Lys Lys Leu Leu Ser Ile Val Pro Leu Phe Ser Pro Gln Ser Ala
1               5                   10                  15

Ala Gln Pro Ala Met Ala His His His His His His
            20                  25

<210> SEQ ID NO 53
<211> LENGTH: 28
<212> TYPE: PRT
<213> ORGANISM: artificial
<220> FEATURE:
<223> OTHER INFORMATION: Synthetic polypeptide

<400> SEQUENCE: 53

Val Lys Lys Leu Leu Val Met Thr Ser Pro Met Leu Ala Pro Gly Ala
1               5                   10                  15

Ala Gln Pro Ala Met Ala His His His His His His
            20                  25

<210> SEQ ID NO 54
<211> LENGTH: 28
<212> TYPE: PRT
<213> ORGANISM: artificial
<220> FEATURE:
<223> OTHER INFORMATION: Synthetic polypeptide

<400> SEQUENCE: 54

Val Lys Lys Leu Leu Val Leu Ser Leu Pro Ser Ile Ala Pro His Ala
1               5                   10                  15

Ala Gln Pro Ala Met Ala His His His His His His
            20                  25

<210> SEQ ID NO 55
<211> LENGTH: 28
<212> TYPE: PRT
<213> ORGANISM: artificial
<220> FEATURE:
<223> OTHER INFORMATION: Synthetic polypeptide

<400> SEQUENCE: 55

Val Lys Lys Leu Leu Gln Ser Leu Leu Leu Leu Arg Ala Leu Leu Ala
1               5                   10                  15

Ala Gln Pro Ala Met Ala His His His His His His
            20                  25

<210> SEQ ID NO 56
<211> LENGTH: 28
<212> TYPE: PRT
<213> ORGANISM: artificial
<220> FEATURE:
<223> OTHER INFORMATION: Synthetic polypeptide

<400> SEQUENCE: 56

Val Lys Lys Leu Leu Phe Ser Leu Pro Val Phe Phe Asp Leu Pro Ala
1               5                   10                  15

Ala Gln Pro Ala Met Ala His His His His His His
            20                  25

<210> SEQ ID NO 57
<211> LENGTH: 28
<212> TYPE: PRT
<213> ORGANISM: artificial
<220> FEATURE:
<223> OTHER INFORMATION: Synthetic polypeptide

<400> SEQUENCE: 57

Val Lys Lys Leu Leu Leu Phe Ser Met Ala Arg Pro Leu Pro Ala
1               5                   10                  15

Ala Gln Pro Ala Met Ala His His His His His His
            20                  25

<210> SEQ ID NO 58
<211> LENGTH: 28
<212> TYPE: PRT
<213> ORGANISM: artificial
<220> FEATURE:
<223> OTHER INFORMATION: Synthetic polypeptide

<400> SEQUENCE: 58

Val Lys Lys Leu Leu Thr Gln Ala Val Phe Pro Phe Thr Phe Asn Ala
1               5                   10                  15

Ala Gln Pro Ala Met Ala His His His His His His
            20                  25

<210> SEQ ID NO 59
<211> LENGTH: 28
<212> TYPE: PRT
<213> ORGANISM: artificial
<220> FEATURE:
<223> OTHER INFORMATION: Synthetic polypeptide

<400> SEQUENCE: 59

Val Lys Lys Leu Leu Leu Ala Ser Trp Leu Phe Arg Ala Asp Met Ala
1               5                   10                  15

Ala Gln Pro Ala Met Ala His His His His His His
            20                  25

<210> SEQ ID NO 60
<211> LENGTH: 28
<212> TYPE: PRT
<213> ORGANISM: artificial
<220> FEATURE:
<223> OTHER INFORMATION: Synthetic polypeptide

<400> SEQUENCE: 60

Val Lys Lys Leu Leu Pro Phe Leu Phe Pro Phe Pro Ser Pro Ser Ala
1               5                   10                  15

Ala Gln Pro Ala Met Ala His His His His His His
            20                  25

<210> SEQ ID NO 61
<211> LENGTH: 28
<212> TYPE: PRT
<213> ORGANISM: artificial
<220> FEATURE:
<223> OTHER INFORMATION: Synthetic polypeptide

```
<400> SEQUENCE: 61

Val Lys Lys Leu Leu Ala Leu Ser Ala Trp Ser Leu Ser Gln Thr Ala
1               5                   10                  15

Ala Gln Pro Ala Met Ala His His His His His His
            20                  25

<210> SEQ ID NO 62
<211> LENGTH: 28
<212> TYPE: PRT
<213> ORGANISM: artificial
<220> FEATURE:
<223> OTHER INFORMATION: Synthetic polypeptide

<400> SEQUENCE: 62

Val Lys Lys Leu Leu Ala Leu Leu Pro Leu Phe Pro Thr Gln His Ala
1               5                   10                  15

Ala Gln Pro Ala Met Ala His His His His His His
            20                  25

<210> SEQ ID NO 63
<211> LENGTH: 28
<212> TYPE: PRT
<213> ORGANISM: artificial
<220> FEATURE:
<223> OTHER INFORMATION: Synthetic polypeptide

<400> SEQUENCE: 63

Val Lys Lys Leu Leu Ala Ala Leu Ala Ser Phe Pro Ala Pro Ala
1               5                   10                  15

Ala Gln Pro Ala Met Ala His His His His His His
            20                  25

<210> SEQ ID NO 64
<211> LENGTH: 28
<212> TYPE: PRT
<213> ORGANISM: artificial
<220> FEATURE:
<223> OTHER INFORMATION: Synthetic polypeptide

<400> SEQUENCE: 64

Val Lys Lys Leu Leu Leu Leu Met Pro Phe Leu Asn Gln Ser Pro Ala
1               5                   10                  15

Ala Gln Pro Ala Met Ala His His His His His His
            20                  25

<210> SEQ ID NO 65
<211> LENGTH: 28
<212> TYPE: PRT
<213> ORGANISM: artificial
<220> FEATURE:
<223> OTHER INFORMATION: Synthetic polypeptide

<400> SEQUENCE: 65

Val Lys Lys Leu Leu Phe Thr Ser Gly Leu Lys Leu Val Pro Pro Ala
1               5                   10                  15

Ala Gln Pro Ala Met Ala His His His His His His
            20                  25

<210> SEQ ID NO 66
<211> LENGTH: 28
<212> TYPE: PRT
<213> ORGANISM: artificial
<220> FEATURE:
<223> OTHER INFORMATION: Synthetic polypeptide
```

-continued

```
<400> SEQUENCE: 66

Val Lys Lys Leu Leu Leu Gln Pro Leu Ser Ile Tyr Leu Asn Ala
1               5                   10                  15

Ala Gln Pro Ala Met Ala His His His His His His
            20                  25

<210> SEQ ID NO 67
<211> LENGTH: 28
<212> TYPE: PRT
<213> ORGANISM: artificial
<220> FEATURE:
<223> OTHER INFORMATION: Synthetic polypeptide

<400> SEQUENCE: 67

Val Lys Lys Leu Leu Leu Ser Ser Leu Trp Ser Ala Tyr Met Asp Ala
1               5                   10                  15

Ala Gln Pro Ala Met Ala His His His His His His
            20                  25

<210> SEQ ID NO 68
<211> LENGTH: 28
<212> TYPE: PRT
<213> ORGANISM: artificial
<220> FEATURE:
<223> OTHER INFORMATION: Synthetic polypeptide

<400> SEQUENCE: 68

Val Lys Lys Leu Leu Leu Leu Gly Gln Ser Leu Met His Phe Gln Ala
1               5                   10                  15

Ala Gln Pro Ala Met Ala His His His His His His
            20                  25

<210> SEQ ID NO 69
<211> LENGTH: 28
<212> TYPE: PRT
<213> ORGANISM: artificial
<220> FEATURE:
<223> OTHER INFORMATION: Synthetic polypeptide

<400> SEQUENCE: 69

Val Lys Lys Leu Leu Pro Gln Leu Ala Met Ser Leu Pro Ser Ile Ala
1               5                   10                  15

Ala Gln Pro Ala Met Ala His His His His His His
            20                  25

<210> SEQ ID NO 70
<211> LENGTH: 28
<212> TYPE: PRT
<213> ORGANISM: artificial
<220> FEATURE:
<223> OTHER INFORMATION: Synthetic polypeptide

<400> SEQUENCE: 70

Val Lys Lys Leu Leu Tyr Glu Thr Met Leu Ser Ser Tyr Leu Tyr Ala
1               5                   10                  15

Ala Gln Pro Ala Met Ala His His His His His His
            20                  25

<210> SEQ ID NO 71
<211> LENGTH: 28
<212> TYPE: PRT
<213> ORGANISM: artificial
<220> FEATURE:
```

<223> OTHER INFORMATION: Synthetic polypeptide

<400> SEQUENCE: 71

Val Lys Lys Leu Leu Ser Leu Tyr Tyr Phe Pro Leu Val Pro Tyr Ala
1               5                   10                  15

Ala Gln Pro Ala Met Ala His His His His His His
            20                  25

<210> SEQ ID NO 72
<211> LENGTH: 28
<212> TYPE: PRT
<213> ORGANISM: artificial
<220> FEATURE:
<223> OTHER INFORMATION: Synthetic polypeptide

<400> SEQUENCE: 72

Val Lys Lys Leu Leu Gln Arg Thr Val Ala Ala Tyr Phe Trp Ala
1               5                   10                  15

Ala Gln Pro Ala Met Ala His His His His His His
            20                  25

<210> SEQ ID NO 73
<211> LENGTH: 28
<212> TYPE: PRT
<213> ORGANISM: artificial
<220> FEATURE:
<223> OTHER INFORMATION: Synthetic polypeptide

<400> SEQUENCE: 73

Val Lys Lys Leu Leu Phe Leu Thr Trp Leu Arg Tyr Gly Phe Pro Ala
1               5                   10                  15

Ala Gln Pro Ala Met Ala His His His His His His
            20                  25

<210> SEQ ID NO 74
<211> LENGTH: 28
<212> TYPE: PRT
<213> ORGANISM: artificial
<220> FEATURE:
<223> OTHER INFORMATION: Synthetic polypeptide

<400> SEQUENCE: 74

Val Lys Lys Leu Leu Leu Leu Leu Thr Leu Met Gln Pro Thr Ser Ala
1               5                   10                  15

Ala Gln Pro Ala Met Ala His His His His His His
            20                  25

<210> SEQ ID NO 75
<211> LENGTH: 28
<212> TYPE: PRT
<213> ORGANISM: artificial
<220> FEATURE:
<223> OTHER INFORMATION: Synthetic polypeptide

<400> SEQUENCE: 75

Val Lys Lys Leu Leu Phe Asp Phe Phe Thr His Val His Leu Phe Ala
1               5                   10                  15

Ala Gln Pro Ala Met Ala His His His His His His
            20                  25

<210> SEQ ID NO 76
<211> LENGTH: 28
<212> TYPE: PRT
<213> ORGANISM: artificial

<220> FEATURE:
<223> OTHER INFORMATION: Synthetic polypeptide

<400> SEQUENCE: 76

Val Lys Lys Leu Leu Ala Leu Tyr Pro His Phe Val Ser Phe Thr Ala
1               5                   10                  15

Ala Gln Pro Ala Met Ala His His His His His His
            20                  25

<210> SEQ ID NO 77
<211> LENGTH: 28
<212> TYPE: PRT
<213> ORGANISM: artificial
<220> FEATURE:
<223> OTHER INFORMATION: Synthetic polypeptide

<400> SEQUENCE: 77

Val Lys Lys Leu Leu Leu Pro Tyr Ala Ile Gln Leu Phe Ser Pro Ala
1               5                   10                  15

Ala Gln Pro Ala Met Ala His His His His His His
            20                  25

<210> SEQ ID NO 78
<211> LENGTH: 28
<212> TYPE: PRT
<213> ORGANISM: artificial
<220> FEATURE:
<223> OTHER INFORMATION: Synthetic polypeptide

<400> SEQUENCE: 78

Val Lys Lys Leu Leu Trp Phe Pro Leu His Ser Ser Leu Leu Pro Ala
1               5                   10                  15

Ala Gln Pro Ala Met Ala His His His His His His
            20                  25

<210> SEQ ID NO 79
<211> LENGTH: 28
<212> TYPE: PRT
<213> ORGANISM: artificial
<220> FEATURE:
<223> OTHER INFORMATION: Synthetic polypeptide

<400> SEQUENCE: 79

Val Lys Lys Leu Leu Pro Ala Leu Leu Leu Ala Thr Ala Ala Phe Ala
1               5                   10                  15

Ala Gln Pro Ala Met Ala His His His His His His
            20                  25

<210> SEQ ID NO 80
<211> LENGTH: 28
<212> TYPE: PRT
<213> ORGANISM: artificial
<220> FEATURE:
<223> OTHER INFORMATION: Synthetic polypeptide

<400> SEQUENCE: 80

Val Lys Lys Leu Leu Leu Ala Ser Val Ala Trp Asn Leu Asp Ser Ala
1               5                   10                  15

Ala Gln Pro Ala Met Ala His His His His His His
            20                  25

<210> SEQ ID NO 81
<211> LENGTH: 28
<212> TYPE: PRT

```
<213> ORGANISM: artificial
<220> FEATURE:
<223> OTHER INFORMATION: Synthetic polypeptide

<400> SEQUENCE: 81

Val Lys Lys Leu Leu Val Gly Ser Leu Leu Phe Trp Pro Gln Gln Ala
1               5                   10                  15

Ala Gln Pro Ala Met Ala His His His His His His
            20                  25

<210> SEQ ID NO 82
<211> LENGTH: 28
<212> TYPE: PRT
<213> ORGANISM: artificial
<220> FEATURE:
<223> OTHER INFORMATION: Synthetic polypeptide

<400> SEQUENCE: 82

Val Lys Lys Leu Leu Ser Pro Leu Leu Phe Leu Gln Asn Tyr Thr Ala
1               5                   10                  15

Ala Gln Pro Ala Met Ala His His His His His His
            20                  25

<210> SEQ ID NO 83
<211> LENGTH: 28
<212> TYPE: PRT
<213> ORGANISM: artificial
<220> FEATURE:
<223> OTHER INFORMATION: Synthetic polypeptide

<400> SEQUENCE: 83

Val Lys Lys Leu Leu Ser Tyr Trp Leu Asp Phe Ile Gln Val Leu Ala
1               5                   10                  15

Ala Gln Pro Ala Met Ala His His His His His His
            20                  25

<210> SEQ ID NO 84
<211> LENGTH: 28
<212> TYPE: PRT
<213> ORGANISM: artificial
<220> FEATURE:
<223> OTHER INFORMATION: Synthetic polypeptide

<400> SEQUENCE: 84

Val Lys Lys Leu Leu Val Pro Ser Phe Leu Leu Ser Pro Ser Pro Ala
1               5                   10                  15

Ala Gln Pro Ala Met Ala His His His His His His
            20                  25

<210> SEQ ID NO 85
<211> LENGTH: 28
<212> TYPE: PRT
<213> ORGANISM: artificial
<220> FEATURE:
<223> OTHER INFORMATION: Synthetic polypeptide

<400> SEQUENCE: 85

Val Lys Lys Leu Leu Ser Leu Tyr Trp Leu Thr Ser Gln Pro Leu Ala
1               5                   10                  15

Ala Gln Pro Ala Met Ala His His His His His His
            20                  25

<210> SEQ ID NO 86
<211> LENGTH: 28
```

```
<212> TYPE: PRT
<213> ORGANISM: artificial
<220> FEATURE:
<223> OTHER INFORMATION: Synthetic polypeptide

<400> SEQUENCE: 86

Val Lys Lys Leu Leu Phe Ala Leu Ser Ser Val His Ser Pro Ala
1               5                  10                  15

Ala Gln Pro Ala Met Ala His His His His His His
            20                  25

<210> SEQ ID NO 87
<211> LENGTH: 28
<212> TYPE: PRT
<213> ORGANISM: artificial
<220> FEATURE:
<223> OTHER INFORMATION: Synthetic polypeptide

<400> SEQUENCE: 87

Val Lys Lys Leu Leu Ser Tyr Tyr Ser Leu Leu Tyr Ser Tyr Pro Ala
1               5                  10                  15

Ala Gln Pro Ala Met Ala His His His His His His
            20                  25

<210> SEQ ID NO 88
<211> LENGTH: 28
<212> TYPE: PRT
<213> ORGANISM: artificial
<220> FEATURE:
<223> OTHER INFORMATION: Synthetic polypeptide

<400> SEQUENCE: 88

Val Lys Lys Leu Leu Leu Val Ser Gly Leu Gln Pro Trp Tyr Phe Ala
1               5                  10                  15

Ala Gln Pro Ala Met Ala His His His His His His
            20                  25

<210> SEQ ID NO 89
<211> LENGTH: 28
<212> TYPE: PRT
<213> ORGANISM: artificial
<220> FEATURE:
<223> OTHER INFORMATION: Synthetic polypeptide

<400> SEQUENCE: 89

Val Lys Lys Leu Leu Val Leu Ala Thr Pro Leu His Leu Ser Pro Ala
1               5                  10                  15

Ala Gln Pro Ala Met Ala His His His His His His
            20                  25

<210> SEQ ID NO 90
<211> LENGTH: 28
<212> TYPE: PRT
<213> ORGANISM: artificial
<220> FEATURE:
<223> OTHER INFORMATION: Synthetic polypeptide

<400> SEQUENCE: 90

Val Lys Lys Leu Leu Ser Leu Ala Phe Pro Leu Phe Thr Pro Pro Ala
1               5                  10                  15

Ala Gln Pro Ala Met Ala His His His His His His
            20                  25

<210> SEQ ID NO 91
```

```
<211> LENGTH: 28
<212> TYPE: PRT
<213> ORGANISM: artificial
<220> FEATURE:
<223> OTHER INFORMATION: Synthetic polypeptide

<400> SEQUENCE: 91

Val Lys Lys Leu Leu Ser Leu Val Pro Ile Phe Pro Phe Ser Thr Ala
1               5                   10                  15

Ala Gln Pro Ala Met Ala His His His His His His
            20                  25

<210> SEQ ID NO 92
<211> LENGTH: 28
<212> TYPE: PRT
<213> ORGANISM: artificial
<220> FEATURE:
<223> OTHER INFORMATION: Synthetic polypeptide

<400> SEQUENCE: 92

Val Lys Lys Leu Leu Gln Pro Val Leu Phe Ser Phe Phe Ile Arg Ala
1               5                   10                  15

Ala Gln Pro Ala Met Ala His His His His His His
            20                  25

<210> SEQ ID NO 93
<211> LENGTH: 28
<212> TYPE: PRT
<213> ORGANISM: artificial
<220> FEATURE:
<223> OTHER INFORMATION: Synthetic polypeptide

<400> SEQUENCE: 93

Val Lys Lys Leu Leu Met Ser Gln Phe Leu Asn Leu Leu Ser Pro Ala
1               5                   10                  15

Ala Gln Pro Ala Met Ala His His His His His His
            20                  25

<210> SEQ ID NO 94
<211> LENGTH: 28
<212> TYPE: PRT
<213> ORGANISM: artificial
<220> FEATURE:
<223> OTHER INFORMATION: Synthetic polypeptide

<400> SEQUENCE: 94

Val Lys Lys Leu Leu Trp Ala Val Gln Pro Leu Phe Pro Leu Asn Ala
1               5                   10                  15

Ala Gln Pro Ala Met Ala His His His His His His
            20                  25

<210> SEQ ID NO 95
<211> LENGTH: 28
<212> TYPE: PRT
<213> ORGANISM: artificial
<220> FEATURE:
<223> OTHER INFORMATION: Synthetic polypeptide

<400> SEQUENCE: 95

Val Lys Lys Leu Leu Met Phe Ser Leu Val Pro Ser Pro Pro Ile Ala
1               5                   10                  15

Ala Gln Pro Ala Met Ala His His His His His His
            20                  25
```

-continued

```
<210> SEQ ID NO 96
<211> LENGTH: 28
<212> TYPE: PRT
<213> ORGANISM: artificial
<220> FEATURE:
<223> OTHER INFORMATION: Synthetic polypeptide

<400> SEQUENCE: 96
```

Val Lys Lys Leu Leu Pro Phe Phe Leu Gln Pro Phe Gln Phe Pro Ala
1               5                   10                  15

Ala Gln Pro Ala Met Ala His His His His His His
            20                  25

```
<210> SEQ ID NO 97
<211> LENGTH: 28
<212> TYPE: PRT
<213> ORGANISM: artificial
<220> FEATURE:
<223> OTHER INFORMATION: Synthetic polypeptide

<400> SEQUENCE: 97
```

Val Lys Lys Leu Leu Pro Asp Leu Leu Ala Ser Val Leu Pro Val Ala
1               5                   10                  15

Ala Gln Pro Ala Met Ala His His His His His His
            20                  25

```
<210> SEQ ID NO 98
<211> LENGTH: 28
<212> TYPE: PRT
<213> ORGANISM: artificial
<220> FEATURE:
<223> OTHER INFORMATION: Synthetic polypeptide

<400> SEQUENCE: 98
```

Val Lys Lys Leu Leu Phe Trp Gln Phe Leu Trp Pro Ser Leu Pro Ala
1               5                   10                  15

Ala Gln Pro Ala Met Ala His His His His His His
            20                  25

```
<210> SEQ ID NO 99
<211> LENGTH: 28
<212> TYPE: PRT
<213> ORGANISM: artificial
<220> FEATURE:
<223> OTHER INFORMATION: Synthetic polypeptide

<400> SEQUENCE: 99
```

Val Lys Lys Leu Leu Leu Leu Gly Gln Phe Phe Pro Asn Pro Met Ala
1               5                   10                  15

Ala Gln Pro Ala Met Ala His His His His His His
            20                  25

```
<210> SEQ ID NO 100
<211> LENGTH: 28
<212> TYPE: PRT
<213> ORGANISM: artificial
<220> FEATURE:
<223> OTHER INFORMATION: Synthetic polypeptide

<400> SEQUENCE: 100
```

Val Lys Lys Leu Leu Thr Leu Ser Ala Leu Ser Gln Trp His Pro Ala
1               5                   10                  15

Ala Gln Pro Ala Met Ala His His His His His His
            20                  25

<210> SEQ ID NO 101
<211> LENGTH: 28
<212> TYPE: PRT
<213> ORGANISM: artificial
<220> FEATURE:
<223> OTHER INFORMATION: Synthetic polypeptide

<400> SEQUENCE: 101

Val Lys Lys Leu Leu Ser Leu Val Tyr Phe Phe Pro Phe Tyr Pro Ala
1               5                   10                  15

Ala Gln Pro Ala Met Ala His His His His His His
            20                  25

<210> SEQ ID NO 102
<211> LENGTH: 28
<212> TYPE: PRT
<213> ORGANISM: artificial
<220> FEATURE:
<223> OTHER INFORMATION: Synthetic polypeptide

<400> SEQUENCE: 102

Val Lys Lys Leu Leu Phe Ala Phe Ala Pro Ala Pro Phe Tyr His Ala
1               5                   10                  15

Ala Gln Pro Ala Met Ala His His His His His His
            20                  25

<210> SEQ ID NO 103
<211> LENGTH: 28
<212> TYPE: PRT
<213> ORGANISM: artificial
<220> FEATURE:
<223> OTHER INFORMATION: Synthetic polypeptide

<400> SEQUENCE: 103

Val Lys Lys Leu Leu Phe Leu Pro Phe Ala Leu Val Pro Arg Gln Ala
1               5                   10                  15

Ala Gln Pro Ala Met Ala His His His His His His
            20                  25

<210> SEQ ID NO 104
<211> LENGTH: 28
<212> TYPE: PRT
<213> ORGANISM: artificial
<220> FEATURE:
<223> OTHER INFORMATION: Synthetic polypeptide

<400> SEQUENCE: 104

Val Lys Lys Leu Leu Ala Leu Trp Met Gln Leu Tyr Pro Gln Asp Ala
1               5                   10                  15

Ala Gln Pro Ala Met Ala His His His His His His
            20                  25

<210> SEQ ID NO 105
<211> LENGTH: 28
<212> TYPE: PRT
<213> ORGANISM: artificial
<220> FEATURE:
<223> OTHER INFORMATION: Synthetic polypeptide

<400> SEQUENCE: 105

Val Lys Lys Leu Leu Ala Ser Ile Leu Phe Ser His Ala Ala Pro Ala
1               5                   10                  15

Ala Gln Pro Ala Met Ala His His His His His His
            20                  25

```
<210> SEQ ID NO 106
<211> LENGTH: 28
<212> TYPE: PRT
<213> ORGANISM: artificial
<220> FEATURE:
<223> OTHER INFORMATION: Synthetic polypeptide

<400> SEQUENCE: 106

Val Lys Lys Leu Leu Pro Leu Pro Trp Ser Leu His Leu Tyr Ala
1               5                   10                  15

Ala Gln Pro Ala Met Ala His His His His His His
            20                  25

<210> SEQ ID NO 107
<211> LENGTH: 28
<212> TYPE: PRT
<213> ORGANISM: artificial
<220> FEATURE:
<223> OTHER INFORMATION: Synthetic polypeptide

<400> SEQUENCE: 107

Val Lys Lys Leu Leu Leu Pro His Phe Met Ser Phe Trp Phe Glu Ala
1               5                   10                  15

Ala Gln Pro Ala Met Ala His His His His His His
            20                  25

<210> SEQ ID NO 108
<211> LENGTH: 28
<212> TYPE: PRT
<213> ORGANISM: artificial
<220> FEATURE:
<223> OTHER INFORMATION: Synthetic polypeptide

<400> SEQUENCE: 108

Val Lys Lys Leu Leu Leu Phe Gln Pro Phe Trp Pro Ile Pro Tyr Ala
1               5                   10                  15

Ala Gln Pro Ala Met Ala His His His His His His
            20                  25

<210> SEQ ID NO 109
<211> LENGTH: 28
<212> TYPE: PRT
<213> ORGANISM: artificial
<220> FEATURE:
<223> OTHER INFORMATION: Synthetic polypeptide

<400> SEQUENCE: 109

Val Lys Lys Leu Leu Leu Leu Phe Ser Leu Gly Arg Leu Pro Pro Ala
1               5                   10                  15

Ala Gln Pro Ala Met Ala His His His His His His
            20                  25

<210> SEQ ID NO 110
<211> LENGTH: 28
<212> TYPE: PRT
<213> ORGANISM: artificial
<220> FEATURE:
<223> OTHER INFORMATION: Synthetic polypeptide

<400> SEQUENCE: 110

Val Lys Lys Leu Leu Pro Leu Trp Val Leu Leu Lys Asp Pro Leu Ala
1               5                   10                  15

Ala Gln Pro Ala Met Ala His His His His His His
```

```
<210> SEQ ID NO 111
<211> LENGTH: 28
<212> TYPE: PRT
<213> ORGANISM: artificial
<220> FEATURE:
<223> OTHER INFORMATION: Synthetic polypeptide

<400> SEQUENCE: 111

Val Lys Lys Leu Leu Met Ser Phe Ala Thr Leu Phe Pro His Asn Ala
1               5                   10                  15

Ala Gln Pro Ala Met Ala His His His His His His
            20                  25

<210> SEQ ID NO 112
<211> LENGTH: 28
<212> TYPE: PRT
<213> ORGANISM: artificial
<220> FEATURE:
<223> OTHER INFORMATION: Synthetic polypeptide

<400> SEQUENCE: 112

Val Lys Lys Leu Leu Gln His Ser Leu Val Thr Ser Trp Leu Cys Ala
1               5                   10                  15

Ala Gln Pro Ala Met Ala His His His His His His
            20                  25

<210> SEQ ID NO 113
<211> LENGTH: 28
<212> TYPE: PRT
<213> ORGANISM: artificial
<220> FEATURE:
<223> OTHER INFORMATION: Synthetic polypeptide

<400> SEQUENCE: 113

Val Lys Lys Leu Leu Leu Leu Phe Gln Gly Ala Phe Val Gly Gln Ala
1               5                   10                  15

Ala Gln Pro Ala Met Ala His His His His His His
            20                  25

<210> SEQ ID NO 114
<211> LENGTH: 28
<212> TYPE: PRT
<213> ORGANISM: artificial
<220> FEATURE:
<223> OTHER INFORMATION: Synthetic polypeptide

<400> SEQUENCE: 114

Val Lys Lys Leu Leu Trp Met Phe His Ser Leu Pro Phe Ser Pro Ala
1               5                   10                  15

Ala Gln Pro Ala Met Ala His His His His His His
            20                  25

<210> SEQ ID NO 115
<211> LENGTH: 28
<212> TYPE: PRT
<213> ORGANISM: artificial
<220> FEATURE:
<223> OTHER INFORMATION: Synthetic polypeptide

<400> SEQUENCE: 115

Val Lys Lys Leu Leu Leu Thr Gln Leu Leu Thr Arg Leu His Ala
1               5                   10                  15
```

Ala Gln Pro Ala Met Ala His His His His His His
            20                  25

<210> SEQ ID NO 116
<211> LENGTH: 28
<212> TYPE: PRT
<213> ORGANISM: artificial
<220> FEATURE:
<223> OTHER INFORMATION: Synthetic polypeptide

<400> SEQUENCE: 116

Val Lys Lys Leu Leu Ala Leu Thr Leu Val Pro Ser Ser Tyr Pro Ala
1               5                   10                  15

Ala Gln Pro Ala Met Ala His His His His His His
            20                  25

<210> SEQ ID NO 117
<211> LENGTH: 28
<212> TYPE: PRT
<213> ORGANISM: artificial
<220> FEATURE:
<223> OTHER INFORMATION: Synthetic polypeptide

<400> SEQUENCE: 117

Val Lys Lys Leu Leu Leu Pro Trp Tyr Met Leu Leu Ser Asp Ser Ala
1               5                   10                  15

Ala Gln Pro Ala Met Ala His His His His His His
            20                  25

<210> SEQ ID NO 118
<211> LENGTH: 28
<212> TYPE: PRT
<213> ORGANISM: artificial
<220> FEATURE:
<223> OTHER INFORMATION: Synthetic polypeptide

<400> SEQUENCE: 118

Val Lys Lys Leu Leu Val Val Thr Gln Phe Trp Pro Ser Leu Pro Ala
1               5                   10                  15

Ala Gln Pro Ala Met Ala His His His His His His
            20                  25

<210> SEQ ID NO 119
<211> LENGTH: 28
<212> TYPE: PRT
<213> ORGANISM: artificial
<220> FEATURE:
<223> OTHER INFORMATION: Synthetic polypeptide

<400> SEQUENCE: 119

Val Lys Lys Leu Leu Leu Ser Thr Leu Phe Leu Trp His Val Arg Ala
1               5                   10                  15

Ala Gln Pro Ala Met Ala His His His His His His
            20                  25

<210> SEQ ID NO 120
<211> LENGTH: 28
<212> TYPE: PRT
<213> ORGANISM: artificial
<220> FEATURE:
<223> OTHER INFORMATION: Synthetic polypeptide

<400> SEQUENCE: 120

Val Lys Lys Leu Leu Arg Ser Leu Phe Phe Gln Gln Leu Tyr Pro Ala
1               5                   10                  15

Ala Gln Pro Ala Met Ala His His His His His
         20                  25

<210> SEQ ID NO 121
<211> LENGTH: 28
<212> TYPE: PRT
<213> ORGANISM: artificial
<220> FEATURE:
<223> OTHER INFORMATION: Synthetic polypeptide

<400> SEQUENCE: 121

Val Lys Lys Leu Leu Thr Leu Thr Thr Leu His Gln Thr Phe Pro Ala
1               5                   10                  15

Ala Gln Pro Ala Met Ala His His His His His
         20                  25

<210> SEQ ID NO 122
<211> LENGTH: 28
<212> TYPE: PRT
<213> ORGANISM: artificial
<220> FEATURE:
<223> OTHER INFORMATION: Synthetic polypeptide

<400> SEQUENCE: 122

Val Lys Lys Leu Leu Ser Ala Leu Leu Ala Pro Trp Tyr Trp Asp Ala
1               5                   10                  15

Ala Gln Pro Ala Met Ala His His His His His
         20                  25

<210> SEQ ID NO 123
<211> LENGTH: 28
<212> TYPE: PRT
<213> ORGANISM: artificial
<220> FEATURE:
<223> OTHER INFORMATION: Synthetic polypeptide

<400> SEQUENCE: 123

Val Lys Lys Leu Leu Ala Ile Gln Gln Arg Met Gln Ile Tyr Thr Ala
1               5                   10                  15

Ala Gln Pro Ala Met Ala His His His His His
         20                  25

<210> SEQ ID NO 124
<211> LENGTH: 28
<212> TYPE: PRT
<213> ORGANISM: artificial
<220> FEATURE:
<223> OTHER INFORMATION: Synthetic polypeptide

<400> SEQUENCE: 124

Val Lys Lys Leu Leu Leu Leu Phe Pro Trp Phe Gln Pro Pro Tyr Ala
1               5                   10                  15

Ala Gln Pro Ala Met Ala His His His His His
         20                  25

<210> SEQ ID NO 125
<211> LENGTH: 28
<212> TYPE: PRT
<213> ORGANISM: artificial
<220> FEATURE:
<223> OTHER INFORMATION: Synthetic polypeptide

<400> SEQUENCE: 125

Val Lys Lys Leu Leu Tyr Phe Thr Ser Leu Leu Gly Gln Phe Pro Ala

```
                 1               5                  10                  15
Ala Gln Pro Ala Met Ala His His His His His His
             20                  25

<210> SEQ ID NO 126
<211> LENGTH: 28
<212> TYPE: PRT
<213> ORGANISM: artificial
<220> FEATURE:
<223> OTHER INFORMATION: Synthetic polypeptide

<400> SEQUENCE: 126

Val Lys Lys Leu Leu Pro Val Leu Ile Phe Leu Ser Glu Ile Arg Ala
1               5                  10                  15

Ala Gln Pro Ala Met Ala His His His His His His
             20                  25

<210> SEQ ID NO 127
<211> LENGTH: 28
<212> TYPE: PRT
<213> ORGANISM: artificial
<220> FEATURE:
<223> OTHER INFORMATION: Synthetic polypeptide

<400> SEQUENCE: 127

Val Lys Lys Leu Leu Val Ala Thr Ser Leu Arg Trp Ala Val Thr Ala
1               5                  10                  15

Ala Gln Pro Ala Met Ala His His His His His His
             20                  25

<210> SEQ ID NO 128
<211> LENGTH: 28
<212> TYPE: PRT
<213> ORGANISM: artificial
<220> FEATURE:
<223> OTHER INFORMATION: Synthetic polypeptide

<400> SEQUENCE: 128

Val Lys Lys Leu Leu Ala Gln Leu Phe His Leu Phe Ala Thr His Ala
1               5                  10                  15

Ala Gln Pro Ala Met Ala His His His His His His
             20                  25

<210> SEQ ID NO 129
<211> LENGTH: 28
<212> TYPE: PRT
<213> ORGANISM: artificial
<220> FEATURE:
<223> OTHER INFORMATION: Synthetic polypeptide

<400> SEQUENCE: 129

Val Lys Lys Leu Leu Leu Gln Phe Ser Ala Leu Phe Asn Ser Phe Ala
1               5                  10                  15

Ala Gln Pro Ala Met Ala His His His His His His
             20                  25

<210> SEQ ID NO 130
<211> LENGTH: 28
<212> TYPE: PRT
<213> ORGANISM: artificial
<220> FEATURE:
<223> OTHER INFORMATION: Synthetic polypeptide

<400> SEQUENCE: 130
```

```
Val Lys Lys Leu Leu Phe His Leu Met Ser Met Leu Pro Pro Pro Ala
1               5                   10                  15

Ala Gln Pro Ala Met Ala His His His His His His
            20                  25
```

<210> SEQ ID NO 131
<211> LENGTH: 28
<212> TYPE: PRT
<213> ORGANISM: artificial
<220> FEATURE:
<223> OTHER INFORMATION: Synthetic polypeptide

<400> SEQUENCE: 131

```
Val Lys Lys Leu Leu Pro Val Cys Ser Gln Ser Met Phe Pro Ile Ala
1               5                   10                  15

Ala Gln Pro Ala Met Ala His His His His His His
            20                  25
```

<210> SEQ ID NO 132
<211> LENGTH: 28
<212> TYPE: PRT
<213> ORGANISM: artificial
<220> FEATURE:
<223> OTHER INFORMATION: Synthetic polypeptide

<400> SEQUENCE: 132

```
Val Lys Lys Leu Leu Leu Leu Ser Ser Tyr Gln Ser Pro Ala
1               5                   10                  15

Ala Gln Pro Ala Met Ala His His His His His His
            20                  25
```

<210> SEQ ID NO 133
<211> LENGTH: 28
<212> TYPE: PRT
<213> ORGANISM: artificial
<220> FEATURE:
<223> OTHER INFORMATION: Synthetic polypeptide

<400> SEQUENCE: 133

```
Val Lys Lys Leu Leu Leu Asp Ser Leu Phe Phe His Ala Pro Leu Ala
1               5                   10                  15

Ala Gln Pro Ala Met Ala His His His His His His
            20                  25
```

<210> SEQ ID NO 134
<211> LENGTH: 28
<212> TYPE: PRT
<213> ORGANISM: artificial
<220> FEATURE:
<223> OTHER INFORMATION: Synthetic polypeptide

<400> SEQUENCE: 134

```
Val Lys Lys Leu Leu Gln Ala Trp Val Phe Ser Ala His Gln Leu Ala
1               5                   10                  15

Ala Gln Pro Ala Met Ala His His His His His His
            20                  25
```

<210> SEQ ID NO 135
<211> LENGTH: 28
<212> TYPE: PRT
<213> ORGANISM: artificial
<220> FEATURE:
<223> OTHER INFORMATION: Synthetic polypeptide

<400> SEQUENCE: 135

Val Lys Lys Leu Leu Phe Gln Ala Leu Gly Ala Leu Thr Ser Pro Ala
1               5                   10                  15

Ala Gln Pro Ala Met Ala His His His His His His
            20                  25

<210> SEQ ID NO 136
<211> LENGTH: 28
<212> TYPE: PRT
<213> ORGANISM: artificial
<220> FEATURE:
<223> OTHER INFORMATION: Synthetic polypeptide

<400> SEQUENCE: 136

Val Lys Lys Leu Leu Cys Phe Phe Phe Phe Leu Gln Phe His Pro Ala
1               5                   10                  15

Ala Gln Pro Ala Met Ala His His His His His His
            20                  25

<210> SEQ ID NO 137
<211> LENGTH: 28
<212> TYPE: PRT
<213> ORGANISM: artificial
<220> FEATURE:
<223> OTHER INFORMATION: Synthetic polypeptide

<400> SEQUENCE: 137

Val Lys Lys Leu Leu Cys Phe Ser His Leu Ala Leu Pro Ser Pro Ala
1               5                   10                  15

Ala Gln Pro Ala Met Ala His His His His His His
            20                  25

<210> SEQ ID NO 138
<211> LENGTH: 28
<212> TYPE: PRT
<213> ORGANISM: artificial
<220> FEATURE:
<223> OTHER INFORMATION: Synthetic polypeptide

<400> SEQUENCE: 138

Val Lys Lys Leu Leu Phe Gly Ser Trp Ile Pro Phe Thr Gln Met Ala
1               5                   10                  15

Ala Gln Pro Ala Met Ala His His His His His His
            20                  25

<210> SEQ ID NO 139
<211> LENGTH: 28
<212> TYPE: PRT
<213> ORGANISM: artificial
<220> FEATURE:
<223> OTHER INFORMATION: Synthetic polypeptide

<400> SEQUENCE: 139

Val Lys Lys Leu Leu Gly Leu Gly Tyr Phe Asn Trp Thr Leu Leu Ala
1               5                   10                  15

Ala Gln Pro Ala Met Ala His His His His His His
            20                  25

<210> SEQ ID NO 140
<211> LENGTH: 28
<212> TYPE: PRT
<213> ORGANISM: artificial
<220> FEATURE:
<223> OTHER INFORMATION: Synthetic polypeptide

```
<400> SEQUENCE: 140

Val Lys Lys Leu Leu His Leu Phe Pro Leu Phe Gln Phe His His Ala
1               5                   10                  15

Ala Gln Pro Ala Met Ala His His His His His His
            20                  25

<210> SEQ ID NO 141
<211> LENGTH: 28
<212> TYPE: PRT
<213> ORGANISM: artificial
<220> FEATURE:
<223> OTHER INFORMATION: Synthetic polypeptide

<400> SEQUENCE: 141

Val Lys Lys Leu Leu Ser Glu His Val Ser Ser Ile Cys Val Leu Ala
1               5                   10                  15

Ala Gln Pro Ala Met Ala His His His His His His
            20                  25

<210> SEQ ID NO 142
<211> LENGTH: 28
<212> TYPE: PRT
<213> ORGANISM: artificial
<220> FEATURE:
<223> OTHER INFORMATION: Synthetic polypeptide

<400> SEQUENCE: 142

Val Lys Lys Leu Leu Phe Ser Cys Leu Leu Asp Pro Thr Cys Pro Ala
1               5                   10                  15

Ala Gln Pro Ala Met Ala His His His His His His
            20                  25

<210> SEQ ID NO 143
<211> LENGTH: 28
<212> TYPE: PRT
<213> ORGANISM: artificial
<220> FEATURE:
<223> OTHER INFORMATION: Synthetic polypeptide

<400> SEQUENCE: 143

Val Lys Lys Leu Leu Leu Tyr Leu Leu His Pro Ser Phe Leu Pro Ala
1               5                   10                  15

Ala Gln Pro Ala Met Ala His His His His His His
            20                  25

<210> SEQ ID NO 144
<211> LENGTH: 28
<212> TYPE: PRT
<213> ORGANISM: artificial
<220> FEATURE:
<223> OTHER INFORMATION: Synthetic polypeptide

<400> SEQUENCE: 144

Val Lys Lys Leu Leu Trp Cys Ala Pro Leu Leu Tyr Ser Leu Arg Ala
1               5                   10                  15

Ala Gln Pro Ala Met Ala His His His His His His
            20                  25

<210> SEQ ID NO 145
<211> LENGTH: 28
<212> TYPE: PRT
<213> ORGANISM: artificial
<220> FEATURE:
<223> OTHER INFORMATION: Synthetic polypeptide
```

<400> SEQUENCE: 145

Val Lys Lys Leu Leu Phe Ala Met Phe Pro Tyr Thr Phe Gln Thr Ala
1               5                   10                  15

Ala Gln Pro Ala Met Ala His His His His His His
            20                  25

<210> SEQ ID NO 146
<211> LENGTH: 28
<212> TYPE: PRT
<213> ORGANISM: artificial
<220> FEATURE:
<223> OTHER INFORMATION: Synthetic polypeptide

<400> SEQUENCE: 146

Val Lys Lys Leu Leu Leu Pro Ser Leu Phe Tyr Val Glu Ser Leu Ala
1               5                   10                  15

Ala Gln Pro Ala Met Ala His His His His His His
            20                  25

<210> SEQ ID NO 147
<211> LENGTH: 28
<212> TYPE: PRT
<213> ORGANISM: artificial
<220> FEATURE:
<223> OTHER INFORMATION: Synthetic polypeptide

<400> SEQUENCE: 147

Val Lys Lys Leu Leu Ser Leu Trp Leu Ser Ser Leu Ser Val Leu Ala
1               5                   10                  15

Ala Gln Pro Ala Met Ala His His His His His His
            20                  25

<210> SEQ ID NO 148
<211> LENGTH: 28
<212> TYPE: PRT
<213> ORGANISM: artificial
<220> FEATURE:
<223> OTHER INFORMATION: Synthetic polypeptide

<400> SEQUENCE: 148

Val Lys Lys Leu Leu Pro His Leu Trp Phe Leu Trp Ser Leu Lys Ala
1               5                   10                  15

Ala Gln Pro Ala Met Ala His His His His His His
            20                  25

<210> SEQ ID NO 149
<211> LENGTH: 28
<212> TYPE: PRT
<213> ORGANISM: artificial
<220> FEATURE:
<223> OTHER INFORMATION: Synthetic polypeptide

<400> SEQUENCE: 149

Val Lys Lys Leu Leu Ala Ser Asp Pro Val Trp Tyr Phe Leu Trp Ala
1               5                   10                  15

Ala Gln Pro Ala Met Ala His His His His His His
            20                  25

<210> SEQ ID NO 150
<211> LENGTH: 28
<212> TYPE: PRT
<213> ORGANISM: artificial
<220> FEATURE:

<223> OTHER INFORMATION: Synthetic polypeptide

<400> SEQUENCE: 150

Val Lys Lys Leu Leu Gly Leu Pro Leu Met Gly Leu Gln Ser Leu Ala
1               5                   10                  15

Ala Gln Pro Ala Met Ala His His His His His His
            20                  25

<210> SEQ ID NO 151
<211> LENGTH: 28
<212> TYPE: PRT
<213> ORGANISM: artificial
<220> FEATURE:
<223> OTHER INFORMATION: Synthetic polypeptide

<400> SEQUENCE: 151

Val Lys Lys Leu Leu Pro Gln Leu Leu Leu Arg Ala Leu Ser Ala
1               5                   10                  15

Ala Gln Pro Ala Met Ala His His His His His His
            20                  25

<210> SEQ ID NO 152
<211> LENGTH: 28
<212> TYPE: PRT
<213> ORGANISM: artificial
<220> FEATURE:
<223> OTHER INFORMATION: Synthetic polypeptide

<400> SEQUENCE: 152

Val Lys Lys Leu Leu Ala Pro Ser Ala Phe Ser Leu His Leu Phe Ala
1               5                   10                  15

Ala Gln Pro Ala Met Ala His His His His His His
            20                  25

<210> SEQ ID NO 153
<211> LENGTH: 28
<212> TYPE: PRT
<213> ORGANISM: artificial
<220> FEATURE:
<223> OTHER INFORMATION: Synthetic polypeptide

<400> SEQUENCE: 153

Val Lys Lys Leu Leu Phe Gln Leu Ser Ser Leu Phe Val Pro Tyr Ala
1               5                   10                  15

Ala Gln Pro Ala Met Ala His His His His His His
            20                  25

<210> SEQ ID NO 154
<211> LENGTH: 28
<212> TYPE: PRT
<213> ORGANISM: artificial
<220> FEATURE:
<223> OTHER INFORMATION: Synthetic polypeptide

<400> SEQUENCE: 154

Val Lys Lys Leu Leu Val Pro Ser Phe Leu Ser Thr Met Ile Glu Ala
1               5                   10                  15

Ala Gln Pro Ala Met Ala His His His His His His
            20                  25

<210> SEQ ID NO 155
<211> LENGTH: 28
<212> TYPE: PRT
<213> ORGANISM: artificial

```
<220> FEATURE:
<223> OTHER INFORMATION: Synthetic polypeptide

<400> SEQUENCE: 155

Val Lys Lys Leu Leu Ala Ser Pro Phe Phe Ala Ser Tyr Leu Trp Ala
1               5                   10                  15

Ala Gln Pro Ala Met Ala His His His His His His
            20                  25

<210> SEQ ID NO 156
<211> LENGTH: 28
<212> TYPE: PRT
<213> ORGANISM: artificial
<220> FEATURE:
<223> OTHER INFORMATION: Synthetic polypeptide

<400> SEQUENCE: 156

Val Lys Lys Leu Leu Leu Gln Tyr Leu Leu Ser Pro Ile Gly Tyr Ala
1               5                   10                  15

Ala Gln Pro Ala Met Ala His His His His His His
            20                  25

<210> SEQ ID NO 157
<211> LENGTH: 28
<212> TYPE: PRT
<213> ORGANISM: artificial
<220> FEATURE:
<223> OTHER INFORMATION: Synthetic polypeptide

<400> SEQUENCE: 157

Val Lys Lys Leu Leu Val Leu Ser Val Pro Ile Ser Ala His His Ala
1               5                   10                  15

Ala Gln Pro Ala Met Ala His His His His His His
            20                  25

<210> SEQ ID NO 158
<211> LENGTH: 28
<212> TYPE: PRT
<213> ORGANISM: artificial
<220> FEATURE:
<223> OTHER INFORMATION: Synthetic polypeptide

<400> SEQUENCE: 158

Val Lys Lys Leu Leu Met Met Gln Ala Leu Ser Ser Leu Pro Glu Ala
1               5                   10                  15

Ala Gln Pro Ala Met Ala His His His His His His
            20                  25

<210> SEQ ID NO 159
<211> LENGTH: 28
<212> TYPE: PRT
<213> ORGANISM: artificial
<220> FEATURE:
<223> OTHER INFORMATION: Synthetic polypeptide

<400> SEQUENCE: 159

Val Lys Lys Leu Leu Met Pro Ala Val Leu Ala Thr Arg Leu Thr Ala
1               5                   10                  15

Ala Gln Pro Ala Met Ala His His His His His His
            20                  25

<210> SEQ ID NO 160
<211> LENGTH: 28
<212> TYPE: PRT
```

```
<213> ORGANISM: artificial
<220> FEATURE:
<223> OTHER INFORMATION: Synthetic polypeptide

<400> SEQUENCE: 160

Val Lys Lys Leu Leu Pro Phe Thr Ala Trp Ile Ile Asp Gly Trp Ala
1               5                   10                  15

Ala Gln Pro Ala Met Ala His His His His His His
            20                  25

<210> SEQ ID NO 161
<211> LENGTH: 28
<212> TYPE: PRT
<213> ORGANISM: artificial
<220> FEATURE:
<223> OTHER INFORMATION: Synthetic polypeptide

<400> SEQUENCE: 161

Val Lys Lys Leu Leu Thr Gln Leu Leu Pro Leu Trp Gln Pro Leu Ala
1               5                   10                  15

Ala Gln Pro Ala Met Ala His His His His His His
            20                  25

<210> SEQ ID NO 162
<211> LENGTH: 28
<212> TYPE: PRT
<213> ORGANISM: artificial
<220> FEATURE:
<223> OTHER INFORMATION: Synthetic polypeptide

<400> SEQUENCE: 162

Val Lys Lys Leu Leu Leu Val Pro Ser Leu Leu Pro Leu Thr Gln Ala
1               5                   10                  15

Ala Gln Pro Ala Met Ala His His His His His His
            20                  25

<210> SEQ ID NO 163
<211> LENGTH: 28
<212> TYPE: PRT
<213> ORGANISM: artificial
<220> FEATURE:
<223> OTHER INFORMATION: Synthetic polypeptide

<400> SEQUENCE: 163

Val Lys Lys Leu Leu Pro Ile Gln Ser Cys Met Val Ile Pro Ser Ala
1               5                   10                  15

Ala Gln Pro Ala Met Ala His His His His His His
            20                  25

<210> SEQ ID NO 164
<211> LENGTH: 28
<212> TYPE: PRT
<213> ORGANISM: artificial
<220> FEATURE:
<223> OTHER INFORMATION: Synthetic polypeptide

<400> SEQUENCE: 164

Val Lys Lys Leu Leu Trp Ser Leu His Leu Ala Thr Arg Leu Leu Ala
1               5                   10                  15

Ala Gln Pro Ala Met Ala His His His His His His
            20                  25

<210> SEQ ID NO 165
<211> LENGTH: 28
```

```
<212> TYPE: PRT
<213> ORGANISM: artificial
<220> FEATURE:
<223> OTHER INFORMATION: Synthetic polypeptide

<400> SEQUENCE: 165

Val Lys Lys Leu Leu Gln Gln Val Leu Leu Cys Ser Thr Leu Arg Ala
1               5                   10                  15

Ala Gln Pro Ala Met Ala His His His His His His
            20                  25

<210> SEQ ID NO 166
<211> LENGTH: 28
<212> TYPE: PRT
<213> ORGANISM: artificial
<220> FEATURE:
<223> OTHER INFORMATION: Synthetic polypeptide

<400> SEQUENCE: 166

Val Lys Lys Leu Leu Leu Leu Arg Tyr Phe Leu Asp Pro Met Tyr Ala
1               5                   10                  15

Ala Gln Pro Ala Met Ala His His His His His His
            20                  25

<210> SEQ ID NO 167
<211> LENGTH: 28
<212> TYPE: PRT
<213> ORGANISM: artificial
<220> FEATURE:
<223> OTHER INFORMATION: Synthetic polypeptide

<400> SEQUENCE: 167

Val Lys Lys Leu Leu Ile Pro Gln Phe Leu Arg Ser His His Arg Ala
1               5                   10                  15

Ala Gln Pro Ala Met Ala His His His His His His
            20                  25

<210> SEQ ID NO 168
<211> LENGTH: 28
<212> TYPE: PRT
<213> ORGANISM: artificial
<220> FEATURE:
<223> OTHER INFORMATION: Synthetic polypeptide

<400> SEQUENCE: 168

Val Lys Lys Leu Leu Gly Val Leu His Leu Ala Leu Ser Leu Arg Ala
1               5                   10                  15

Ala Gln Pro Ala Met Ala His His His His His His
            20                  25

<210> SEQ ID NO 169
<211> LENGTH: 28
<212> TYPE: PRT
<213> ORGANISM: artificial
<220> FEATURE:
<223> OTHER INFORMATION: Synthetic polypeptide

<400> SEQUENCE: 169

Val Lys Lys Leu Leu Leu Val Thr Ser Gln Phe Ser Leu Val Pro Ala
1               5                   10                  15

Ala Gln Pro Ala Met Ala His His His His His His
            20                  25

<210> SEQ ID NO 170
```

```
<211> LENGTH: 28
<212> TYPE: PRT
<213> ORGANISM: artificial
<220> FEATURE:
<223> OTHER INFORMATION: Synthetic polypeptide

<400> SEQUENCE: 170

Val Lys Lys Leu Leu Pro Leu Ala Leu Ser Trp Phe Gln Leu Arg Ala
1               5                   10                  15

Ala Gln Pro Ala Met Ala His His His His His His
            20                  25

<210> SEQ ID NO 171
<211> LENGTH: 28
<212> TYPE: PRT
<213> ORGANISM: artificial
<220> FEATURE:
<223> OTHER INFORMATION: Synthetic polypeptide

<400> SEQUENCE: 171

Val Lys Lys Leu Leu Gln His Gln Trp Tyr Pro Thr Val Leu Met Ala
1               5                   10                  15

Ala Gln Pro Ala Met Ala His His His His His His
            20                  25

<210> SEQ ID NO 172
<211> LENGTH: 28
<212> TYPE: PRT
<213> ORGANISM: artificial
<220> FEATURE:
<223> OTHER INFORMATION: Synthetic polypeptide

<400> SEQUENCE: 172

Val Lys Lys Leu Leu Leu Met Tyr Trp Leu Ser Lys Pro Leu Ser Ala
1               5                   10                  15

Ala Gln Pro Ala Met Ala His His His His His His
            20                  25

<210> SEQ ID NO 173
<211> LENGTH: 28
<212> TYPE: PRT
<213> ORGANISM: artificial
<220> FEATURE:
<223> OTHER INFORMATION: Synthetic polypeptide

<400> SEQUENCE: 173

Val Lys Lys Leu Leu Thr Gln Leu Thr Leu Ser Ser Ser Pro Ile Ala
1               5                   10                  15

Ala Gln Pro Ala Met Ala His His His His His His
            20                  25

<210> SEQ ID NO 174
<211> LENGTH: 28
<212> TYPE: PRT
<213> ORGANISM: artificial
<220> FEATURE:
<223> OTHER INFORMATION: Synthetic polypeptide

<400> SEQUENCE: 174

Val Lys Lys Leu Leu Gln Leu Thr Ala Leu Leu Ser Arg Leu Ile Ala
1               5                   10                  15

Ala Gln Pro Ala Met Ala His His His His His His
            20                  25
```

```
<210> SEQ ID NO 175
<211> LENGTH: 28
<212> TYPE: PRT
<213> ORGANISM: artificial
<220> FEATURE:
<223> OTHER INFORMATION: Synthetic polypeptide

<400> SEQUENCE: 175

Val Lys Lys Leu Leu Met Thr Phe Gly Thr Thr Pro Gln Ser Ala
1               5                   10                  15

Ala Gln Pro Ala Met Ala His His His His His His
            20                  25

<210> SEQ ID NO 176
<211> LENGTH: 28
<212> TYPE: PRT
<213> ORGANISM: artificial
<220> FEATURE:
<223> OTHER INFORMATION: Synthetic polypeptide

<400> SEQUENCE: 176

Val Lys Lys Leu Leu Ser Ala Phe Ser Phe Ser Leu Ser Ser Thr Ala
1               5                   10                  15

Ala Gln Pro Ala Met Ala His His His His His His
            20                  25

<210> SEQ ID NO 177
<211> LENGTH: 28
<212> TYPE: PRT
<213> ORGANISM: artificial
<220> FEATURE:
<223> OTHER INFORMATION: Synthetic polypeptide

<400> SEQUENCE: 177

Val Lys Lys Leu Leu Ala Pro Trp Leu Val Leu Pro His Phe Pro Ala
1               5                   10                  15

Ala Gln Pro Ala Met Ala His His His His His His
            20                  25

<210> SEQ ID NO 178
<211> LENGTH: 28
<212> TYPE: PRT
<213> ORGANISM: artificial
<220> FEATURE:
<223> OTHER INFORMATION: Synthetic polypeptide

<400> SEQUENCE: 178

Val Lys Lys Leu Leu His Val Leu Ser Phe Ala Pro Pro Met Pro Ala
1               5                   10                  15

Ala Gln Pro Ala Met Ala His His His His His His
            20                  25

<210> SEQ ID NO 179
<211> LENGTH: 28
<212> TYPE: PRT
<213> ORGANISM: artificial
<220> FEATURE:
<223> OTHER INFORMATION: Synthetic polypeptide

<400> SEQUENCE: 179

Val Lys Lys Leu Leu Asn Trp Leu Phe Phe Ala His Pro Phe Ser Ala
1               5                   10                  15

Ala Gln Pro Ala Met Ala His His His His His His
            20                  25
```

<210> SEQ ID NO 180
<211> LENGTH: 28
<212> TYPE: PRT
<213> ORGANISM: artificial
<220> FEATURE:
<223> OTHER INFORMATION: Synthetic polypeptide

<400> SEQUENCE: 180

Val Lys Lys Leu Leu Gln Leu Ala Val Leu Leu Gly Ser Leu Arg Ala
1               5                   10                  15

Ala Gln Pro Ala Met Ala His His His His His His
            20                  25

<210> SEQ ID NO 181
<211> LENGTH: 28
<212> TYPE: PRT
<213> ORGANISM: artificial
<220> FEATURE:
<223> OTHER INFORMATION: Synthetic polypeptide

<400> SEQUENCE: 181

Val Lys Lys Leu Leu Leu Phe Gly Leu Phe Tyr Phe Arg Ala Cys Ala
1               5                   10                  15

Ala Gln Pro Ala Met Ala His His His His His His
            20                  25

<210> SEQ ID NO 182
<211> LENGTH: 28
<212> TYPE: PRT
<213> ORGANISM: artificial
<220> FEATURE:
<223> OTHER INFORMATION: Synthetic polypeptide

<400> SEQUENCE: 182

Val Lys Lys Leu Leu Phe Gln Phe Phe Val Val Trp Arg Leu Leu Ala
1               5                   10                  15

Ala Gln Pro Ala Met Ala His His His His His His
            20                  25

<210> SEQ ID NO 183
<211> LENGTH: 28
<212> TYPE: PRT
<213> ORGANISM: artificial
<220> FEATURE:
<223> OTHER INFORMATION: Synthetic polypeptide

<400> SEQUENCE: 183

Val Lys Lys Leu Leu Pro Trp Ala Trp Pro Pro Pro Pro Phe Trp Ala
1               5                   10                  15

Ala Gln Pro Ala Met Ala His His His His His His
            20                  25

<210> SEQ ID NO 184
<211> LENGTH: 28
<212> TYPE: PRT
<213> ORGANISM: artificial
<220> FEATURE:
<223> OTHER INFORMATION: Synthetic polypeptide

<400> SEQUENCE: 184

Val Lys Lys Leu Leu Leu Gln Leu Val Ile Val Tyr Tyr Leu Arg Ala
1               5                   10                  15

Ala Gln Pro Ala Met Ala His His His His His His
            20                  25

```
<210> SEQ ID NO 185
<211> LENGTH: 28
<212> TYPE: PRT
<213> ORGANISM: artificial
<220> FEATURE:
<223> OTHER INFORMATION: Synthetic polypeptide

<400> SEQUENCE: 185

Val Lys Lys Leu Leu Arg Gln Ser Val Leu Ser Ala Leu His Ala
1               5                   10                  15

Ala Gln Pro Ala Met Ala His His His His His His
            20                  25

<210> SEQ ID NO 186
<211> LENGTH: 28
<212> TYPE: PRT
<213> ORGANISM: artificial
<220> FEATURE:
<223> OTHER INFORMATION: Synthetic polypeptide

<400> SEQUENCE: 186

Val Lys Lys Leu Leu Val Tyr Gly Tyr Phe Leu Thr Thr Phe Arg Ala
1               5                   10                  15

Ala Gln Pro Ala Met Ala His His His His His His
            20                  25

<210> SEQ ID NO 187
<211> LENGTH: 28
<212> TYPE: PRT
<213> ORGANISM: artificial
<220> FEATURE:
<223> OTHER INFORMATION: Synthetic polypeptide

<400> SEQUENCE: 187

Val Lys Lys Leu Leu Cys Phe Ser Pro Leu Phe Gly Phe His Thr Ala
1               5                   10                  15

Ala Gln Pro Ala Met Ala His His His His His His
            20                  25

<210> SEQ ID NO 188
<211> LENGTH: 28
<212> TYPE: PRT
<213> ORGANISM: artificial
<220> FEATURE:
<223> OTHER INFORMATION: Synthetic polypeptide

<400> SEQUENCE: 188

Val Lys Lys Leu Leu Pro Gly Tyr Ala Leu Trp Gln Thr Ile Pro Ala
1               5                   10                  15

Ala Gln Pro Ala Met Ala His His His His His His
            20                  25

<210> SEQ ID NO 189
<211> LENGTH: 28
<212> TYPE: PRT
<213> ORGANISM: artificial
<220> FEATURE:
<223> OTHER INFORMATION: Synthetic polypeptide

<400> SEQUENCE: 189

Val Lys Lys Leu Leu Gln Arg Ile Phe Ile Cys Phe Phe Leu Arg Ala
1               5                   10                  15

Ala Gln Pro Ala Met Ala His His His His His His
```

20                  25

<210> SEQ ID NO 190
<211> LENGTH: 28
<212> TYPE: PRT
<213> ORGANISM: artificial
<220> FEATURE:
<223> OTHER INFORMATION: Synthetic polypeptide

<400> SEQUENCE: 190

Val Lys Lys Leu Leu Pro His Val Phe Ser Cys Gln Leu Ser Ala Ala
1               5                   10                  15

Ala Gln Pro Ala Met Ala His His His His His His
            20                  25

<210> SEQ ID NO 191
<211> LENGTH: 28
<212> TYPE: PRT
<213> ORGANISM: artificial
<220> FEATURE:
<223> OTHER INFORMATION: Synthetic polypeptide

<400> SEQUENCE: 191

Val Lys Lys Leu Leu Ser Pro Leu Ser Leu Ser Val Lys Leu Leu Ala
1               5                   10                  15

Ala Gln Pro Ala Met Ala His His His His His His
            20                  25

<210> SEQ ID NO 192
<211> LENGTH: 28
<212> TYPE: PRT
<213> ORGANISM: artificial
<220> FEATURE:
<223> OTHER INFORMATION: Synthetic polypeptide

<400> SEQUENCE: 192

Val Lys Lys Leu Leu Ala Arg Ser Leu Phe Ser Gly Ser Met Leu Ala
1               5                   10                  15

Ala Gln Pro Ala Met Ala His His His His His His
            20                  25

<210> SEQ ID NO 193
<211> LENGTH: 28
<212> TYPE: PRT
<213> ORGANISM: artificial
<220> FEATURE:
<223> OTHER INFORMATION: Synthetic polypeptide

<400> SEQUENCE: 193

Val Lys Lys Leu Leu Leu Gln Phe Leu Ile Val Phe Pro Leu Arg Ala
1               5                   10                  15

Ala Gln Pro Ala Met Ala His His His His His His
            20                  25

<210> SEQ ID NO 194
<211> LENGTH: 28
<212> TYPE: PRT
<213> ORGANISM: artificial
<220> FEATURE:
<223> OTHER INFORMATION: Synthetic polypeptide

<400> SEQUENCE: 194

Val Lys Lys Leu Leu Leu Ala Val Leu Leu Gly Gln Ser Leu Arg Ala
1               5                   10                  15

Ala Gln Pro Ala Met Ala His His His His His His
            20                  25

<210> SEQ ID NO 195
<211> LENGTH: 28
<212> TYPE: PRT
<213> ORGANISM: artificial
<220> FEATURE:
<223> OTHER INFORMATION: Synthetic polypeptide

<400> SEQUENCE: 195

Val Lys Lys Leu Leu Leu Leu Ser His Leu Phe Leu Arg Leu His Ala
1               5                   10                  15

Ala Gln Pro Ala Met Ala His His His His His His
            20                  25

<210> SEQ ID NO 196
<211> LENGTH: 28
<212> TYPE: PRT
<213> ORGANISM: artificial
<220> FEATURE:
<223> OTHER INFORMATION: Synthetic polypeptide

<400> SEQUENCE: 196

Val Lys Lys Leu Leu Leu Ala Met Val Phe Phe Val Thr Leu Arg Ala
1               5                   10                  15

Ala Gln Pro Ala Met Ala His His His His His His
            20                  25

<210> SEQ ID NO 197
<211> LENGTH: 28
<212> TYPE: PRT
<213> ORGANISM: artificial
<220> FEATURE:
<223> OTHER INFORMATION: Synthetic polypeptide

<400> SEQUENCE: 197

Val Lys Lys Leu Leu Trp Leu Phe Ala Leu Pro Gln Glu Asn Val Ala
1               5                   10                  15

Ala Gln Pro Ala Met Ala His His His His His His
            20                  25

<210> SEQ ID NO 198
<211> LENGTH: 28
<212> TYPE: PRT
<213> ORGANISM: artificial
<220> FEATURE:
<223> OTHER INFORMATION: Synthetic polypeptide

<400> SEQUENCE: 198

Val Lys Lys Leu Leu His Pro Leu Val Leu Leu Ser Ser Ser Pro Ala
1               5                   10                  15

Ala Gln Pro Ala Met Ala His His His His His His
            20                  25

<210> SEQ ID NO 199
<211> LENGTH: 28
<212> TYPE: PRT
<213> ORGANISM: artificial
<220> FEATURE:
<223> OTHER INFORMATION: Synthetic polypeptide

<400> SEQUENCE: 199

Val Lys Lys Leu Leu Leu Gln Tyr Leu Phe Met Leu Ser Met Arg Ala
1               5                   10                  15

```
Ala Gln Pro Ala Met Ala His His His His His
            20                  25

<210> SEQ ID NO 200
<211> LENGTH: 28
<212> TYPE: PRT
<213> ORGANISM: artificial
<220> FEATURE:
<223> OTHER INFORMATION: Synthetic polypeptide

<400> SEQUENCE: 200

Val Lys Lys Leu Leu Pro Ala Leu Leu Ile Arg Tyr Ala Ser Val Ala
1               5                   10                  15

Ala Gln Pro Ala Met Ala His His His His His
            20                  25

<210> SEQ ID NO 201
<211> LENGTH: 28
<212> TYPE: PRT
<213> ORGANISM: artificial
<220> FEATURE:
<223> OTHER INFORMATION: Synthetic polypeptide

<400> SEQUENCE: 201

Val Lys Lys Leu Leu Gln Gln Phe Thr Ser Pro Phe Leu Leu Leu Ala
1               5                   10                  15

Ala Gln Pro Ala Met Ala His His His His His
            20                  25

<210> SEQ ID NO 202
<211> LENGTH: 28
<212> TYPE: PRT
<213> ORGANISM: artificial
<220> FEATURE:
<223> OTHER INFORMATION: Synthetic polypeptide

<400> SEQUENCE: 202

Val Lys Lys Leu Leu Ser Pro Cys Phe Phe Leu Leu Tyr Leu Arg Ala
1               5                   10                  15

Ala Gln Pro Ala Met Ala His His His His His
            20                  25

<210> SEQ ID NO 203
<211> LENGTH: 28
<212> TYPE: PRT
<213> ORGANISM: artificial
<220> FEATURE:
<223> OTHER INFORMATION: Synthetic polypeptide

<400> SEQUENCE: 203

Val Lys Lys Leu Leu Pro Gly Met Pro Leu Phe Phe Thr Asn Ser Ala
1               5                   10                  15

Ala Gln Pro Ala Met Ala His His His His His
            20                  25

<210> SEQ ID NO 204
<211> LENGTH: 28
<212> TYPE: PRT
<213> ORGANISM: artificial
<220> FEATURE:
<223> OTHER INFORMATION: Synthetic polypeptide

<400> SEQUENCE: 204

Val Lys Lys Leu Leu Pro Gln Val Phe Phe Leu Phe Arg Pro Phe Ala
```

```
                1               5                   10                  15
Ala Gln Pro Ala Met Ala His His His His His His
            20                  25

<210> SEQ ID NO 205
<211> LENGTH: 28
<212> TYPE: PRT
<213> ORGANISM: artificial
<220> FEATURE:
<223> OTHER INFORMATION: Synthetic polypeptide

<400> SEQUENCE: 205

Val Lys Lys Leu Leu Pro Phe Pro Ile Leu Leu Gln Ser Pro Phe Ala
1               5                   10                  15

Ala Gln Pro Ala Met Ala His His His His His His
            20                  25

<210> SEQ ID NO 206
<211> LENGTH: 28
<212> TYPE: PRT
<213> ORGANISM: artificial
<220> FEATURE:
<223> OTHER INFORMATION: Synthetic polypeptide

<400> SEQUENCE: 206

Val Lys Lys Leu Leu Phe Gln Ala Cys Cys Leu Phe Pro Leu Gln Ala
1               5                   10                  15

Ala Gln Pro Ala Met Ala His His His His His His
            20                  25

<210> SEQ ID NO 207
<211> LENGTH: 28
<212> TYPE: PRT
<213> ORGANISM: artificial
<220> FEATURE:
<223> OTHER INFORMATION: Synthetic polypeptide

<400> SEQUENCE: 207

Val Lys Lys Leu Leu Ala Val Val His Thr Met Pro Leu Phe Ser Ala
1               5                   10                  15

Ala Gln Pro Ala Met Ala His His His His His His
            20                  25

<210> SEQ ID NO 208
<211> LENGTH: 28
<212> TYPE: PRT
<213> ORGANISM: artificial
<220> FEATURE:
<223> OTHER INFORMATION: Synthetic polypeptide

<400> SEQUENCE: 208

Val Lys Lys Leu Leu Gln Phe Ser Trp Ala Phe Val Ser Ile Leu Ala
1               5                   10                  15

Ala Gln Pro Ala Met Ala His His His His His His
            20                  25

<210> SEQ ID NO 209
<211> LENGTH: 28
<212> TYPE: PRT
<213> ORGANISM: artificial
<220> FEATURE:
<223> OTHER INFORMATION: Synthetic polypeptide

<400> SEQUENCE: 209
```

```
Val Lys Lys Leu Leu Pro Val Cys Leu Phe Trp Ser Phe Phe Arg Ala
1               5                   10                  15

Ala Gln Pro Ala Met Ala His His His His His His
            20                  25
```

<210> SEQ ID NO 210
<211> LENGTH: 28
<212> TYPE: PRT
<213> ORGANISM: artificial
<220> FEATURE:
<223> OTHER INFORMATION: Synthetic polypeptide

<400> SEQUENCE: 210

```
Val Lys Lys Leu Leu Gln Leu Leu Trp Gln Gln Gln Val Pro Val Ala
1               5                   10                  15

Ala Gln Pro Ala Met Ala His His His His His His
            20                  25
```

<210> SEQ ID NO 211
<211> LENGTH: 28
<212> TYPE: PRT
<213> ORGANISM: artificial
<220> FEATURE:
<223> OTHER INFORMATION: Synthetic polypeptide

<400> SEQUENCE: 211

```
Val Lys Lys Leu Leu Pro Leu Gln Ala Leu Ser Trp Phe Leu Arg Ala
1               5                   10                  15

Ala Gln Pro Ala Met Ala His His His His His His
            20                  25
```

<210> SEQ ID NO 212
<211> LENGTH: 28
<212> TYPE: PRT
<213> ORGANISM: artificial
<220> FEATURE:
<223> OTHER INFORMATION: Synthetic polypeptide

<400> SEQUENCE: 212

```
Val Lys Lys Leu Leu Phe Tyr Leu Leu Cys Arg Leu Ser Leu Gln Ala
1               5                   10                  15

Ala Gln Pro Ala Met Ala His His His His His His
            20                  25
```

<210> SEQ ID NO 213
<211> LENGTH: 28
<212> TYPE: PRT
<213> ORGANISM: artificial
<220> FEATURE:
<223> OTHER INFORMATION: Synthetic polypeptide

<400> SEQUENCE: 213

```
Val Lys Lys Leu Leu Tyr Leu Gln Ile Leu Val Ile Cys Leu Arg Ala
1               5                   10                  15

Ala Gln Pro Ala Met Ala His His His His His His
            20                  25
```

<210> SEQ ID NO 214
<211> LENGTH: 28
<212> TYPE: PRT
<213> ORGANISM: artificial
<220> FEATURE:
<223> OTHER INFORMATION: Synthetic polypeptide

<400> SEQUENCE: 214

Val Lys Lys Leu Leu Gln Leu Phe Leu Ile Val Phe Pro Leu Arg Ala
1               5                   10                  15

Ala Gln Pro Ala Met Ala His His His His His His
            20                  25

<210> SEQ ID NO 215
<211> LENGTH: 28
<212> TYPE: PRT
<213> ORGANISM: artificial
<220> FEATURE:
<223> OTHER INFORMATION: Synthetic polypeptide

<400> SEQUENCE: 215

Val Lys Lys Leu Leu Pro Leu His Phe Ala Leu Phe Phe Arg Leu Ala
1               5                   10                  15

Ala Gln Pro Ala Met Ala His His His His His His
            20                  25

<210> SEQ ID NO 216
<211> LENGTH: 28
<212> TYPE: PRT
<213> ORGANISM: artificial
<220> FEATURE:
<223> OTHER INFORMATION: Synthetic polypeptide

<400> SEQUENCE: 216

Val Lys Lys Leu Leu Pro Phe Pro Met His Leu Val Leu Pro Phe Ala
1               5                   10                  15

Ala Gln Pro Ala Met Ala His His His His His His
            20                  25

<210> SEQ ID NO 217
<211> LENGTH: 28
<212> TYPE: PRT
<213> ORGANISM: artificial
<220> FEATURE:
<223> OTHER INFORMATION: Synthetic polypeptide

<400> SEQUENCE: 217

Val Lys Lys Leu Leu Pro Leu Leu Phe Ser Pro Pro Ser Leu His Ala
1               5                   10                  15

Ala Gln Pro Ala Met Ala His His His His His His
            20                  25

<210> SEQ ID NO 218
<211> LENGTH: 28
<212> TYPE: PRT
<213> ORGANISM: artificial
<220> FEATURE:
<223> OTHER INFORMATION: Synthetic polypeptide

<400> SEQUENCE: 218

Val Lys Lys Leu Leu Cys Gln Ser Ile Thr Phe Ser Ser Ile Trp Ala
1               5                   10                  15

Ala Gln Pro Ala Met Ala His His His His His His
            20                  25

<210> SEQ ID NO 219
<211> LENGTH: 28
<212> TYPE: PRT
<213> ORGANISM: artificial
<220> FEATURE:
<223> OTHER INFORMATION: Synthetic polypeptide

```
<400> SEQUENCE: 219

Val Lys Lys Leu Leu Trp Gln Arg Leu Phe Pro Phe Leu Leu Ile Ala
1               5                   10                  15

Ala Gln Pro Ala Met Ala His His His His His His
                20                  25

<210> SEQ ID NO 220
<211> LENGTH: 28
<212> TYPE: PRT
<213> ORGANISM: artificial
<220> FEATURE:
<223> OTHER INFORMATION: Synthetic polypeptide

<400> SEQUENCE: 220

Val Lys Lys Leu Leu Met Val Pro Phe Trp Pro Phe Ser Phe Thr Ala
1               5                   10                  15

Ala Gln Pro Ala Met Ala His His His His His His
                20                  25

<210> SEQ ID NO 221
<211> LENGTH: 28
<212> TYPE: PRT
<213> ORGANISM: artificial
<220> FEATURE:
<223> OTHER INFORMATION: Synthetic polypeptide

<400> SEQUENCE: 221

Val Lys Lys Leu Leu Gln Ala Phe Pro Leu Pro Pro Leu Leu Val Ala
1               5                   10                  15

Ala Gln Pro Ala Met Ala His His His His His His
                20                  25

<210> SEQ ID NO 222
<211> LENGTH: 28
<212> TYPE: PRT
<213> ORGANISM: artificial
<220> FEATURE:
<223> OTHER INFORMATION: Synthetic polypeptide

<400> SEQUENCE: 222

Val Lys Lys Leu Leu Pro Leu Tyr Leu Leu Phe Arg Ser Phe Val Ala
1               5                   10                  15

Ala Gln Pro Ala Met Ala His His His His His His
                20                  25

<210> SEQ ID NO 223
<211> LENGTH: 28
<212> TYPE: PRT
<213> ORGANISM: artificial
<220> FEATURE:
<223> OTHER INFORMATION: Synthetic polypeptide

<400> SEQUENCE: 223

Val Lys Lys Leu Leu His Arg Ser Met Tyr Leu Ser Trp Leu Tyr Ala
1               5                   10                  15

Ala Gln Pro Ala Met Ala His His His His His His
                20                  25

<210> SEQ ID NO 224
<211> LENGTH: 28
<212> TYPE: PRT
<213> ORGANISM: artificial
<220> FEATURE:
<223> OTHER INFORMATION: Synthetic polypeptide
```

<400> SEQUENCE: 224

Val Lys Lys Leu Leu Leu Leu Ser Thr Leu Val Arg Ala Pro Tyr Ala
1               5                   10                  15

Ala Gln Pro Ala Met Ala His His His His His His
            20                  25

<210> SEQ ID NO 225
<211> LENGTH: 28
<212> TYPE: PRT
<213> ORGANISM: artificial
<220> FEATURE:
<223> OTHER INFORMATION: Synthetic polypeptide

<400> SEQUENCE: 225

Val Lys Lys Leu Leu Pro Leu Ala Leu Ser Gln Trp Phe Leu Arg Ala
1               5                   10                  15

Ala Gln Pro Ala Met Ala His His His His His His
            20                  25

<210> SEQ ID NO 226
<211> LENGTH: 28
<212> TYPE: PRT
<213> ORGANISM: artificial
<220> FEATURE:
<223> OTHER INFORMATION: Synthetic polypeptide

<400> SEQUENCE: 226

Val Lys Lys Leu Leu Ala Gln Gly Met Ile Phe Phe Leu Arg Leu Ala
1               5                   10                  15

Ala Gln Pro Ala Met Ala His His His His His His
            20                  25

<210> SEQ ID NO 227
<211> LENGTH: 28
<212> TYPE: PRT
<213> ORGANISM: artificial
<220> FEATURE:
<223> OTHER INFORMATION: Synthetic polypeptide

<400> SEQUENCE: 227

Val Lys Lys Leu Leu Phe Cys Cys Arg Leu Ala Leu Gln Phe Phe Ala
1               5                   10                  15

Ala Gln Pro Ala Met Ala His His His His His His
            20                  25

<210> SEQ ID NO 228
<211> LENGTH: 28
<212> TYPE: PRT
<213> ORGANISM: artificial
<220> FEATURE:
<223> OTHER INFORMATION: Synthetic polypeptide

<400> SEQUENCE: 228

Val Lys Lys Leu Leu Tyr Leu Gln Phe Leu Ser Leu Met Leu Ser Ala
1               5                   10                  15

Ala Gln Pro Ala Met Ala His His His His His His
            20                  25

<210> SEQ ID NO 229
<211> LENGTH: 28
<212> TYPE: PRT
<213> ORGANISM: artificial
<220> FEATURE:

```
<223> OTHER INFORMATION: Synthetic polypeptide

<400> SEQUENCE: 229

Val Lys Lys Leu Leu Cys Gln Ala Thr Phe Pro Thr Leu Leu Cys Ala
1               5                   10                  15

Ala Gln Pro Ala Met Ala His His His His His His
            20                  25

<210> SEQ ID NO 230
<211> LENGTH: 28
<212> TYPE: PRT
<213> ORGANISM: artificial
<220> FEATURE:
<223> OTHER INFORMATION: Synthetic polypeptide

<400> SEQUENCE: 230

Val Lys Lys Leu Leu Ala Arg Ser Tyr Leu Tyr Phe Ser Leu Ser Ala
1               5                   10                  15

Ala Gln Pro Ala Met Ala His His His His His His
            20                  25

<210> SEQ ID NO 231
<211> LENGTH: 28
<212> TYPE: PRT
<213> ORGANISM: artificial
<220> FEATURE:
<223> OTHER INFORMATION: Synthetic polypeptide

<400> SEQUENCE: 231

Val Lys Lys Leu Leu Tyr Gln Ser Ser Phe Leu Pro Leu Phe Trp Ala
1               5                   10                  15

Ala Gln Pro Ala Met Ala His His His His His His
            20                  25

<210> SEQ ID NO 232
<211> LENGTH: 28
<212> TYPE: PRT
<213> ORGANISM: artificial
<220> FEATURE:
<223> OTHER INFORMATION: Synthetic polypeptide

<400> SEQUENCE: 232

Val Lys Lys Leu Leu Ser Ala Ser Phe Leu Ala Phe Arg Ile Thr Ala
1               5                   10                  15

Ala Gln Pro Ala Met Ala His His His His His His
            20                  25

<210> SEQ ID NO 233
<211> LENGTH: 28
<212> TYPE: PRT
<213> ORGANISM: artificial
<220> FEATURE:
<223> OTHER INFORMATION: Synthetic polypeptide

<400> SEQUENCE: 233

Val Lys Lys Leu Leu Ser Val Leu Phe Leu Ser His Tyr His Ser Ala
1               5                   10                  15

Ala Gln Pro Ala Met Ala His His His His His His
            20                  25

<210> SEQ ID NO 234
<211> LENGTH: 28
<212> TYPE: PRT
<213> ORGANISM: artificial
```

```
<220> FEATURE:
<223> OTHER INFORMATION: Synthetic polypeptide

<400> SEQUENCE: 234

Val Lys Lys Leu Leu Pro Leu Ala Leu Leu Tyr Val Arg Leu Ser Ala
1               5                   10                  15

Ala Gln Pro Ala Met Ala His His His His His His
            20                  25

<210> SEQ ID NO 235
<211> LENGTH: 28
<212> TYPE: PRT
<213> ORGANISM: artificial
<220> FEATURE:
<223> OTHER INFORMATION: Synthetic polypeptide

<400> SEQUENCE: 235

Val Lys Lys Leu Leu Pro Glu Phe Leu Leu Phe Arg Phe Phe Ala
1               5                   10                  15

Ala Gln Pro Ala Met Ala His His His His His His
            20                  25

<210> SEQ ID NO 236
<211> LENGTH: 28
<212> TYPE: PRT
<213> ORGANISM: artificial
<220> FEATURE:
<223> OTHER INFORMATION: Synthetic polypeptide

<400> SEQUENCE: 236

Val Lys Lys Leu Leu Phe Pro Ser Leu Tyr Ala Trp Gly Gly Leu Ala
1               5                   10                  15

Ala Gln Pro Ala Met Ala His His His His His His
            20                  25

<210> SEQ ID NO 237
<211> LENGTH: 28
<212> TYPE: PRT
<213> ORGANISM: artificial
<220> FEATURE:
<223> OTHER INFORMATION: Synthetic polypeptide

<400> SEQUENCE: 237

Val Lys Lys Leu Leu Leu Gln Ala Ala Ala Phe Phe Cys Trp Leu Ala
1               5                   10                  15

Ala Gln Pro Ala Met Ala His His His His His His
            20                  25

<210> SEQ ID NO 238
<211> LENGTH: 28
<212> TYPE: PRT
<213> ORGANISM: artificial
<220> FEATURE:
<223> OTHER INFORMATION: Synthetic polypeptide

<400> SEQUENCE: 238

Val Lys Lys Leu Leu Pro Phe Phe Leu Phe Cys Ser Ser Leu Arg Ala
1               5                   10                  15

Ala Gln Pro Ala Met Ala His His His His His His
            20                  25

<210> SEQ ID NO 239
<211> LENGTH: 28
<212> TYPE: PRT
```

```
<213> ORGANISM: artificial
<220> FEATURE:
<223> OTHER INFORMATION: Synthetic polypeptide

<400> SEQUENCE: 239

Val Lys Lys Leu Leu Glu Leu Thr Gln Leu Trp Leu Phe His Leu Ala
1               5                   10                  15

Ala Gln Pro Ala Met Ala His His His His His His
            20                  25

<210> SEQ ID NO 240
<211> LENGTH: 28
<212> TYPE: PRT
<213> ORGANISM: artificial
<220> FEATURE:
<223> OTHER INFORMATION: Synthetic polypeptide

<400> SEQUENCE: 240

Val Lys Lys Leu Leu Pro Gly Val Pro Leu Leu Leu Cys Phe Arg Ala
1               5                   10                  15

Ala Gln Pro Ala Met Ala His His His His His His
            20                  25

<210> SEQ ID NO 241
<211> LENGTH: 28
<212> TYPE: PRT
<213> ORGANISM: artificial
<220> FEATURE:
<223> OTHER INFORMATION: Synthetic polypeptide

<400> SEQUENCE: 241

Val Lys Lys Leu Leu Ser Gln Ala Tyr Leu Ser Tyr Phe Leu Tyr Ala
1               5                   10                  15

Ala Gln Pro Ala Met Ala His His His His His His
            20                  25

<210> SEQ ID NO 242
<211> LENGTH: 28
<212> TYPE: PRT
<213> ORGANISM: artificial
<220> FEATURE:
<223> OTHER INFORMATION: Synthetic polypeptide

<400> SEQUENCE: 242

Val Lys Lys Leu Leu Ile Ser Tyr Ala Phe Leu Val Arg Val Thr Ala
1               5                   10                  15

Ala Gln Pro Ala Met Ala His His His His His His
            20                  25

<210> SEQ ID NO 243
<211> LENGTH: 28
<212> TYPE: PRT
<213> ORGANISM: artificial
<220> FEATURE:
<223> OTHER INFORMATION: Synthetic polypeptide

<400> SEQUENCE: 243

Val Lys Lys Leu Leu Ala Pro Ala Leu Leu Arg Ser Ile Leu Ala Ala
1               5                   10                  15

Ala Gln Pro Ala Met Ala His His His His His His
            20                  25

<210> SEQ ID NO 244
<211> LENGTH: 28
```

```
<212> TYPE: PRT
<213> ORGANISM: artificial
<220> FEATURE:
<223> OTHER INFORMATION: Synthetic polypeptide

<400> SEQUENCE: 244

Val Lys Lys Leu Leu His Ser His Thr Leu Leu Met Ser Leu His Ala
1               5                   10                  15

Ala Gln Pro Ala Met Ala His His His His His His
            20                  25

<210> SEQ ID NO 245
<211> LENGTH: 28
<212> TYPE: PRT
<213> ORGANISM: artificial
<220> FEATURE:
<223> OTHER INFORMATION: Synthetic polypeptide

<400> SEQUENCE: 245

Val Lys Lys Leu Leu Ala Val Ser Ala Phe Val Ser Leu Val Arg Ala
1               5                   10                  15

Ala Gln Pro Ala Met Ala His His His His His His
            20                  25

<210> SEQ ID NO 246
<211> LENGTH: 28
<212> TYPE: PRT
<213> ORGANISM: artificial
<220> FEATURE:
<223> OTHER INFORMATION: Synthetic polypeptide

<400> SEQUENCE: 246

Val Lys Lys Leu Leu Thr Leu Ile Thr Phe Lys Phe Leu Pro His Ala
1               5                   10                  15

Ala Gln Pro Ala Met Ala His His His His His His
            20                  25

<210> SEQ ID NO 247
<211> LENGTH: 28
<212> TYPE: PRT
<213> ORGANISM: artificial
<220> FEATURE:
<223> OTHER INFORMATION: Synthetic polypeptide

<400> SEQUENCE: 247

Val Lys Lys Leu Leu Gln Gln Phe Ala Ile Pro Leu Val Glu Phe Ala
1               5                   10                  15

Ala Gln Pro Ala Met Ala His His His His His His
            20                  25

<210> SEQ ID NO 248
<211> LENGTH: 28
<212> TYPE: PRT
<213> ORGANISM: artificial
<220> FEATURE:
<223> OTHER INFORMATION: Synthetic polypeptide

<400> SEQUENCE: 248

Val Lys Lys Leu Leu Met Pro Cys Leu Leu Val Tyr Tyr Leu Glu Ala
1               5                   10                  15

Ala Gln Pro Ala Met Ala His His His His His His
            20                  25

<210> SEQ ID NO 249
```

```
<211> LENGTH: 28
<212> TYPE: PRT
<213> ORGANISM: artificial
<220> FEATURE:
<223> OTHER INFORMATION: Synthetic polypeptide

<400> SEQUENCE: 249

Val Lys Lys Leu Leu Arg Tyr Cys Leu Leu Gln Ile Val Arg Ala
1               5                   10                  15

Ala Gln Pro Ala Met Ala His His His His His His
            20                  25

<210> SEQ ID NO 250
<211> LENGTH: 28
<212> TYPE: PRT
<213> ORGANISM: artificial
<220> FEATURE:
<223> OTHER INFORMATION: Synthetic polypeptide

<400> SEQUENCE: 250

Val Lys Lys Leu Leu Ser Leu Ala Leu Leu Arg Val Ser Leu Gly Ala
1               5                   10                  15

Ala Gln Pro Ala Met Ala His His His His His His
            20                  25

<210> SEQ ID NO 251
<211> LENGTH: 28
<212> TYPE: PRT
<213> ORGANISM: artificial
<220> FEATURE:
<223> OTHER INFORMATION: Synthetic polypeptide

<400> SEQUENCE: 251

Val Lys Lys Leu Leu Ile Ile Gly Arg Ile Ala Leu Ile Leu Arg Ala
1               5                   10                  15

Ala Gln Pro Ala Met Ala His His His His His His
            20                  25

<210> SEQ ID NO 252
<211> LENGTH: 28
<212> TYPE: PRT
<213> ORGANISM: artificial
<220> FEATURE:
<223> OTHER INFORMATION: Synthetic polypeptide

<400> SEQUENCE: 252

Val Lys Lys Leu Leu Pro Gln Leu Ile Cys Ala Phe Ile Leu Arg Ala
1               5                   10                  15

Ala Gln Pro Ala Met Ala His His His His His His
            20                  25

<210> SEQ ID NO 253
<211> LENGTH: 28
<212> TYPE: PRT
<213> ORGANISM: artificial
<220> FEATURE:
<223> OTHER INFORMATION: Synthetic polypeptide

<400> SEQUENCE: 253

Val Lys Lys Leu Leu Met Val Pro Leu Phe Pro Leu Pro Leu Pro Ala
1               5                   10                  15

Ala Gln Pro Ala Met Ala His His His His His His
            20                  25
```

```
<210> SEQ ID NO 254
<211> LENGTH: 28
<212> TYPE: PRT
<213> ORGANISM: artificial
<220> FEATURE:
<223> OTHER INFORMATION: Synthetic polypeptide

<400> SEQUENCE: 254

Val Lys Lys Leu Leu His Gln Ala Ile Leu Tyr Tyr Tyr Leu Asn Ala
1               5                   10                  15

Ala Gln Pro Ala Met Ala His His His His His His
            20                  25

<210> SEQ ID NO 255
<211> LENGTH: 28
<212> TYPE: PRT
<213> ORGANISM: artificial
<220> FEATURE:
<223> OTHER INFORMATION: Synthetic polypeptide

<400> SEQUENCE: 255

Val Lys Lys Leu Leu Phe Ala Ile Pro Leu Leu Pro Ala Gln Ala Met
1               5                   10                  15

Pro Met Ser Arg Met Ala His His His His His His
            20                  25

<210> SEQ ID NO 256
<211> LENGTH: 28
<212> TYPE: PRT
<213> ORGANISM: artificial
<220> FEATURE:
<223> OTHER INFORMATION: Synthetic polypeptide

<400> SEQUENCE: 256

Val Lys Lys Leu Leu Phe Ala Ile Pro Leu Tyr Phe Val Leu Val Arg
1               5                   10                  15

Glu Ser Ser Ser Met Ala His His His His His His
            20                  25

<210> SEQ ID NO 257
<211> LENGTH: 28
<212> TYPE: PRT
<213> ORGANISM: artificial
<220> FEATURE:
<223> OTHER INFORMATION: Synthetic polypeptide

<400> SEQUENCE: 257

Val Lys Lys Leu Leu Phe Ala Ile Pro Leu Val Leu Val Val Ser Ser
1               5                   10                  15

Arg Thr Arg Ala Met Ala His His His His His His
            20                  25

<210> SEQ ID NO 258
<211> LENGTH: 28
<212> TYPE: PRT
<213> ORGANISM: artificial
<220> FEATURE:
<223> OTHER INFORMATION: Synthetic polypeptide

<400> SEQUENCE: 258

Val Lys Lys Leu Leu Phe Ala Ile Pro Leu Leu Leu Ser Arg Pro Arg
1               5                   10                  15

Ala Val Pro Asp Met Ala His His His His His His
            20                  25
```

<210> SEQ ID NO 259
<211> LENGTH: 28
<212> TYPE: PRT
<213> ORGANISM: artificial
<220> FEATURE:
<223> OTHER INFORMATION: Synthetic polypeptide

<400> SEQUENCE: 259

Val Lys Lys Leu Leu Phe Ala Ile Pro Leu Cys Val Ser Val Arg Ser
1               5                   10                  15

Pro Ala Phe Ala Met Ala His His His His His His
            20                  25

<210> SEQ ID NO 260
<211> LENGTH: 28
<212> TYPE: PRT
<213> ORGANISM: artificial
<220> FEATURE:
<223> OTHER INFORMATION: Synthetic polypeptide

<400> SEQUENCE: 260

Val Lys Lys Leu Leu Phe Ala Ile Pro Leu Met Thr Thr Leu Ala Ser
1               5                   10                  15

Arg Thr His Ala Met Ala His His His His His His
            20                  25

<210> SEQ ID NO 261
<211> LENGTH: 28
<212> TYPE: PRT
<213> ORGANISM: artificial
<220> FEATURE:
<223> OTHER INFORMATION: Synthetic polypeptide

<400> SEQUENCE: 261

Val Lys Lys Leu Leu Phe Ala Ile Pro Leu Tyr Leu Ser Met Thr Arg
1               5                   10                  15

Ser Gly Ala Ala Met Ala His His His His His His
            20                  25

<210> SEQ ID NO 262
<211> LENGTH: 28
<212> TYPE: PRT
<213> ORGANISM: artificial
<220> FEATURE:
<223> OTHER INFORMATION: Synthetic polypeptide

<400> SEQUENCE: 262

Val Lys Lys Leu Leu Phe Ala Ile Pro Leu Trp Leu Arg Ser Ser Val
1               5                   10                  15

Pro Val Asp Ser Met Ala His His His His His His
            20                  25

<210> SEQ ID NO 263
<211> LENGTH: 28
<212> TYPE: PRT
<213> ORGANISM: artificial
<220> FEATURE:
<223> OTHER INFORMATION: Synthetic polypeptide

<400> SEQUENCE: 263

Val Lys Lys Leu Leu Phe Ala Ile Pro Leu Leu Ser Ser Leu Thr Arg
1               5                   10                  15

Asp Ser Ser Ser Met Ala His His His His His His
            20                  25

```
<210> SEQ ID NO 264
<211> LENGTH: 28
<212> TYPE: PRT
<213> ORGANISM: artificial
<220> FEATURE:
<223> OTHER INFORMATION: Synthetic polypeptide

<400> SEQUENCE: 264

Val Lys Lys Leu Leu Phe Ala Ile Pro Leu Gly Leu Phe Thr Ile Arg
1               5                   10                  15

Asp Ser Phe Ala Met Ala His His His His His His
            20                  25

<210> SEQ ID NO 265
<211> LENGTH: 28
<212> TYPE: PRT
<213> ORGANISM: artificial
<220> FEATURE:
<223> OTHER INFORMATION: Synthetic polypeptide

<400> SEQUENCE: 265

Val Lys Lys Leu Leu Phe Ala Ile Pro Leu Trp Leu Gly Ile Thr Lys
1               5                   10                  15

Pro Val Trp Ser Met Ala His His His His His His
            20                  25

<210> SEQ ID NO 266
<211> LENGTH: 28
<212> TYPE: PRT
<213> ORGANISM: artificial
<220> FEATURE:
<223> OTHER INFORMATION: Synthetic polypeptide

<400> SEQUENCE: 266

Val Lys Lys Leu Leu Phe Ala Ile Pro Leu Tyr Thr Leu Thr Pro Arg
1               5                   10                  15

Pro Val Phe Ser Met Ala His His His His His His
            20                  25

<210> SEQ ID NO 267
<211> LENGTH: 28
<212> TYPE: PRT
<213> ORGANISM: artificial
<220> FEATURE:
<223> OTHER INFORMATION: Synthetic polypeptide

<400> SEQUENCE: 267

Val Lys Lys Leu Leu Phe Ala Ile Pro Leu Gln Leu Ala Leu Ser Arg
1               5                   10                  15

Pro Ser Phe Pro Met Ala His His His His His His
            20                  25

<210> SEQ ID NO 268
<211> LENGTH: 28
<212> TYPE: PRT
<213> ORGANISM: artificial
<220> FEATURE:
<223> OTHER INFORMATION: Synthetic polypeptide

<400> SEQUENCE: 268

Val Lys Lys Leu Leu Phe Ala Ile Pro Leu Ser Ser Phe Leu Val Ala
1               5                   10                  15

Asp Gln Ser Ser Met Ala His His His His His His
```

```
                20                  25

<210> SEQ ID NO 269
<211> LENGTH: 28
<212> TYPE: PRT
<213> ORGANISM: artificial
<220> FEATURE:
<223> OTHER INFORMATION: Synthetic polypeptide

<400> SEQUENCE: 269

Val Lys Lys Leu Leu Phe Ala Ile Pro Leu Leu Leu Gly Leu Ala Ser
1               5                   10                  15

Pro Arg Ser Arg Met Ala His His His His His His
            20                  25

<210> SEQ ID NO 270
<211> LENGTH: 28
<212> TYPE: PRT
<213> ORGANISM: artificial
<220> FEATURE:
<223> OTHER INFORMATION: Synthetic polypeptide

<400> SEQUENCE: 270

Val Lys Lys Leu Leu Phe Ala Ile Pro Leu Leu Thr Leu Ser Asn Arg
1               5                   10                  15

Ser Ala Trp Ser Met Ala His His His His His His
            20                  25

<210> SEQ ID NO 271
<211> LENGTH: 28
<212> TYPE: PRT
<213> ORGANISM: artificial
<220> FEATURE:
<223> OTHER INFORMATION: Synthetic polypeptide

<400> SEQUENCE: 271

Val Lys Lys Leu Leu Phe Ala Ile Pro Leu Leu Ser Leu Tyr Pro Thr
1               5                   10                  15

Arg Ser Thr Ala Met Ala His His His His His His
            20                  25

<210> SEQ ID NO 272
<211> LENGTH: 28
<212> TYPE: PRT
<213> ORGANISM: artificial
<220> FEATURE:
<223> OTHER INFORMATION: Synthetic polypeptide

<400> SEQUENCE: 272

Val Lys Lys Leu Leu Phe Ala Ile Pro Leu Leu Thr Thr Leu Ser Arg
1               5                   10                  15

Pro Ser Phe Ser Met Ala His His His His His His
            20                  25

<210> SEQ ID NO 273
<211> LENGTH: 28
<212> TYPE: PRT
<213> ORGANISM: artificial
<220> FEATURE:
<223> OTHER INFORMATION: Synthetic polypeptide

<400> SEQUENCE: 273

Val Lys Lys Leu Leu Phe Ala Ile Pro Leu Tyr Phe Ser Arg Pro Pro
1               5                   10                  15
```

Gln Pro Ser Ser Met Ala His His His His His
            20                  25

<210> SEQ ID NO 274
<211> LENGTH: 28
<212> TYPE: PRT
<213> ORGANISM: artificial
<220> FEATURE:
<223> OTHER INFORMATION: Synthetic polypeptide

<400> SEQUENCE: 274

Val Lys Lys Leu Leu Phe Ala Ile Pro Leu Thr Met Ser Ser Pro Pro
1               5                   10                  15

Arg Ser Thr Ser Met Ala His His His His His His
            20                  25

<210> SEQ ID NO 275
<211> LENGTH: 28
<212> TYPE: PRT
<213> ORGANISM: artificial
<220> FEATURE:
<223> OTHER INFORMATION: Synthetic polypeptide

<400> SEQUENCE: 275

Val Lys Lys Leu Leu Phe Ala Ile Pro Leu Tyr Phe Leu Arg Ile Ser
1               5                   10                  15

Pro Ser Ala Ser Met Ala His His His His His His
            20                  25

<210> SEQ ID NO 276
<211> LENGTH: 28
<212> TYPE: PRT
<213> ORGANISM: artificial
<220> FEATURE:
<223> OTHER INFORMATION: Synthetic polypeptide

<400> SEQUENCE: 276

Val Lys Lys Leu Leu Phe Ala Ile Pro Leu Leu Phe Leu Arg Pro Ser
1               5                   10                  15

Ala Ala Arg Pro Met Ala His His His His His His
            20                  25

<210> SEQ ID NO 277
<211> LENGTH: 28
<212> TYPE: PRT
<213> ORGANISM: artificial
<220> FEATURE:
<223> OTHER INFORMATION: Synthetic polypeptide

<400> SEQUENCE: 277

Val Lys Lys Leu Leu Phe Ala Ile Pro Leu Leu Trp Ser Ser Ser Arg
1               5                   10                  15

Pro Thr Ser Gln Met Ala His His His His His His
            20                  25

<210> SEQ ID NO 278
<211> LENGTH: 28
<212> TYPE: PRT
<213> ORGANISM: artificial
<220> FEATURE:
<223> OTHER INFORMATION: Synthetic polypeptide

<400> SEQUENCE: 278

Val Lys Lys Leu Leu Phe Ala Ile Pro Leu Tyr Leu Val Cys Ser Arg
1               5                   10                  15

```
Pro Leu His Ala Met Ala His His His His His
            20                  25

<210> SEQ ID NO 279
<211> LENGTH: 28
<212> TYPE: PRT
<213> ORGANISM: artificial
<220> FEATURE:
<223> OTHER INFORMATION: Synthetic polypeptide

<400> SEQUENCE: 279

Val Lys Lys Leu Leu Phe Ala Ile Pro Leu Val Leu Gln Arg Pro Pro
1               5                   10                  15

Ser Pro Asn Thr Met Ala His His His His His
            20                  25

<210> SEQ ID NO 280
<211> LENGTH: 28
<212> TYPE: PRT
<213> ORGANISM: artificial
<220> FEATURE:
<223> OTHER INFORMATION: Synthetic polypeptide

<400> SEQUENCE: 280

Val Lys Lys Leu Leu Phe Ala Ile Pro Leu Ala Met Ala Ser Phe Arg
1               5                   10                  15

Pro Arg Asp Gln Met Ala His His His His His
            20                  25

<210> SEQ ID NO 281
<211> LENGTH: 28
<212> TYPE: PRT
<213> ORGANISM: artificial
<220> FEATURE:
<223> OTHER INFORMATION: Synthetic polypeptide

<400> SEQUENCE: 281

Val Lys Lys Leu Leu Phe Ala Ile Pro Leu Ser Arg Ser Leu Ala Met
1               5                   10                  15

Gln Pro Leu Pro Met Ala His His His His His
            20                  25

<210> SEQ ID NO 282
<211> LENGTH: 28
<212> TYPE: PRT
<213> ORGANISM: artificial
<220> FEATURE:
<223> OTHER INFORMATION: Synthetic polypeptide

<400> SEQUENCE: 282

Val Lys Lys Leu Leu Phe Ala Ile Pro Leu Leu Ser Ser Leu Arg Ser
1               5                   10                  15

Ser Asn Pro Glu Met Ala His His His His His
            20                  25

<210> SEQ ID NO 283
<211> LENGTH: 28
<212> TYPE: PRT
<213> ORGANISM: artificial
<220> FEATURE:
<223> OTHER INFORMATION: Synthetic polypeptide

<400> SEQUENCE: 283

Val Lys Lys Leu Leu Phe Ala Ile Pro Leu Ser Ile Leu Ile Asn Phe
```

-continued

```
1               5                   10                  15
Arg Ala Ser Ser Met Ala His His His His His His
            20                  25

<210> SEQ ID NO 284
<211> LENGTH: 28
<212> TYPE: PRT
<213> ORGANISM: artificial
<220> FEATURE:
<223> OTHER INFORMATION: Synthetic polypeptide

<400> SEQUENCE: 284

Val Lys Lys Leu Leu Phe Ala Ile Pro Leu Tyr Trp Arg Ser Phe Trp
1               5                   10                  15

Glu Pro Pro Ala Met Ala His His His His His His
            20                  25

<210> SEQ ID NO 285
<211> LENGTH: 28
<212> TYPE: PRT
<213> ORGANISM: artificial
<220> FEATURE:
<223> OTHER INFORMATION: Synthetic polypeptide

<400> SEQUENCE: 285

Val Lys Lys Leu Leu Phe Ala Ile Pro Leu Tyr Leu Ala Ala Pro Arg
1               5                   10                  15

Ser Thr Val Ala Met Ala His His His His His His
            20                  25

<210> SEQ ID NO 286
<211> LENGTH: 28
<212> TYPE: PRT
<213> ORGANISM: artificial
<220> FEATURE:
<223> OTHER INFORMATION: Synthetic polypeptide

<400> SEQUENCE: 286

Val Lys Lys Leu Leu Phe Ala Ile Pro Leu Gln Tyr Ser Ala Phe Ser
1               5                   10                  15

Met Ser Pro Arg Met Ala His His His His His His
            20                  25

<210> SEQ ID NO 287
<211> LENGTH: 28
<212> TYPE: PRT
<213> ORGANISM: artificial
<220> FEATURE:
<223> OTHER INFORMATION: Synthetic polypeptide

<400> SEQUENCE: 287

Val Lys Lys Leu Leu Phe Ala Ile Pro Leu Tyr Leu Val Ser Ser Lys
1               5                   10                  15

Asn Ser Tyr Pro Met Ala His His His His His His
            20                  25

<210> SEQ ID NO 288
<211> LENGTH: 28
<212> TYPE: PRT
<213> ORGANISM: artificial
<220> FEATURE:
<223> OTHER INFORMATION: Synthetic polypeptide

<400> SEQUENCE: 288
```

```
Val Lys Lys Leu Leu Phe Ala Ile Pro Leu Gly Leu Ser Val Ser Phe
1               5                   10                  15

Arg Thr Ser Ala Met Ala His His His His His His
            20                  25
```

<210> SEQ ID NO 289
<211> LENGTH: 28
<212> TYPE: PRT
<213> ORGANISM: artificial
<220> FEATURE:
<223> OTHER INFORMATION: Synthetic polypeptide

<400> SEQUENCE: 289

```
Val Lys Lys Leu Leu Phe Ala Ile Pro Leu Ala Met Leu Glu Pro Thr
1               5                   10                  15

Arg Ser Ser Ala Met Ala His His His His His His
            20                  25
```

<210> SEQ ID NO 290
<211> LENGTH: 28
<212> TYPE: PRT
<213> ORGANISM: artificial
<220> FEATURE:
<223> OTHER INFORMATION: Synthetic polypeptide

<400> SEQUENCE: 290

```
Val Lys Lys Leu Leu Phe Ala Ile Pro Leu Ser Leu Ser Leu His Arg
1               5                   10                  15

Pro Ala Leu Ala Met Ala His His His His His His
            20                  25
```

<210> SEQ ID NO 291
<211> LENGTH: 28
<212> TYPE: PRT
<213> ORGANISM: artificial
<220> FEATURE:
<223> OTHER INFORMATION: Synthetic polypeptide

<400> SEQUENCE: 291

```
Val Lys Lys Leu Leu Phe Ala Ile Pro Leu Leu Ser Ala Ser Ala Arg
1               5                   10                  15

Gly Ser Tyr Ala Met Ala His His His His His His
            20                  25
```

<210> SEQ ID NO 292
<211> LENGTH: 28
<212> TYPE: PRT
<213> ORGANISM: artificial
<220> FEATURE:
<223> OTHER INFORMATION: Synthetic polypeptide

<400> SEQUENCE: 292

```
Val Lys Lys Leu Leu Phe Ala Ile Pro Leu Tyr Leu Ala Val Thr His
1               5                   10                  15

Arg Ala Tyr Ser Met Ala His His His His His His
            20                  25
```

<210> SEQ ID NO 293
<211> LENGTH: 28
<212> TYPE: PRT
<213> ORGANISM: artificial
<220> FEATURE:
<223> OTHER INFORMATION: Synthetic polypeptide

<400> SEQUENCE: 293

Val Lys Lys Leu Leu Phe Ala Ile Pro Leu Phe Phe Ser Leu Ser Arg
1               5                   10                  15

Tyr Ser Leu Ala Met Ala His His His His His His
                20                  25

<210> SEQ ID NO 294
<211> LENGTH: 28
<212> TYPE: PRT
<213> ORGANISM: artificial
<220> FEATURE:
<223> OTHER INFORMATION: Synthetic polypeptide

<400> SEQUENCE: 294

Val Lys Lys Leu Leu Phe Ala Ile Pro Leu Tyr Leu Ser Ala Pro Arg
1               5                   10                  15

His Ala Ser Pro Met Ala His His His His His His
                20                  25

<210> SEQ ID NO 295
<211> LENGTH: 28
<212> TYPE: PRT
<213> ORGANISM: artificial
<220> FEATURE:
<223> OTHER INFORMATION: Synthetic polypeptide

<400> SEQUENCE: 295

Val Lys Lys Leu Leu Phe Ala Ile Pro Leu Trp Ser Phe Ser Arg Leu
1               5                   10                  15

Pro Ser Ser Asp Met Ala His His His His His His
                20                  25

<210> SEQ ID NO 296
<211> LENGTH: 28
<212> TYPE: PRT
<213> ORGANISM: artificial
<220> FEATURE:
<223> OTHER INFORMATION: Synthetic polypeptide

<400> SEQUENCE: 296

Val Lys Lys Leu Leu Phe Ala Ile Pro Leu Tyr Leu Ser Leu Thr Lys
1               5                   10                  15

Pro Ser Leu Ser Met Ala His His His His His His
                20                  25

<210> SEQ ID NO 297
<211> LENGTH: 28
<212> TYPE: PRT
<213> ORGANISM: artificial
<220> FEATURE:
<223> OTHER INFORMATION: Synthetic polypeptide

<400> SEQUENCE: 297

Val Lys Lys Leu Leu Phe Ala Ile Pro Leu Ser Ser Pro Ala Thr Glu
1               5                   10                  15

Val Leu Ser Pro Met Ala His His His His His His
                20                  25

<210> SEQ ID NO 298
<211> LENGTH: 28
<212> TYPE: PRT
<213> ORGANISM: artificial
<220> FEATURE:
<223> OTHER INFORMATION: Synthetic polypeptide

```
<400> SEQUENCE: 298

Val Lys Lys Leu Leu Phe Ala Ile Pro Leu Thr Leu Phe Leu Gln Arg
1               5                   10                  15

Ser Ser Leu Ala Met Ala His His His His His His
            20                  25

<210> SEQ ID NO 299
<211> LENGTH: 28
<212> TYPE: PRT
<213> ORGANISM: artificial
<220> FEATURE:
<223> OTHER INFORMATION: Synthetic polypeptide

<400> SEQUENCE: 299

Val Lys Lys Leu Leu Phe Ala Ile Pro Leu Val Phe Thr Arg Val Pro
1               5                   10                  15

His Lys Pro Ser Met Ala His His His His His His
            20                  25

<210> SEQ ID NO 300
<211> LENGTH: 28
<212> TYPE: PRT
<213> ORGANISM: artificial
<220> FEATURE:
<223> OTHER INFORMATION: Synthetic polypeptide

<400> SEQUENCE: 300

Val Lys Lys Leu Leu Phe Ala Ile Pro Leu Ala Ile Thr Arg Ser Ser
1               5                   10                  15

Gln Phe Pro Ser Met Ala His His His His His His
            20                  25

<210> SEQ ID NO 301
<211> LENGTH: 28
<212> TYPE: PRT
<213> ORGANISM: artificial
<220> FEATURE:
<223> OTHER INFORMATION: Synthetic polypeptide

<400> SEQUENCE: 301

Val Lys Lys Leu Leu Phe Ala Ile Pro Leu Leu Gly Asp Leu Arg Ser
1               5                   10                  15

Ser Pro Asp Ala Met Ala His His His His His His
            20                  25

<210> SEQ ID NO 302
<211> LENGTH: 28
<212> TYPE: PRT
<213> ORGANISM: artificial
<220> FEATURE:
<223> OTHER INFORMATION: Synthetic polypeptide

<400> SEQUENCE: 302

Val Lys Lys Leu Leu Phe Ala Ile Pro Leu Val Thr Thr Leu Ser Thr
1               5                   10                  15

Arg Cys Tyr Ala Met Ala His His His His His His
            20                  25

<210> SEQ ID NO 303
<211> LENGTH: 28
<212> TYPE: PRT
<213> ORGANISM: artificial
<220> FEATURE:
<223> OTHER INFORMATION: Synthetic polypeptide
```

```
<400> SEQUENCE: 303

Val Lys Lys Leu Leu Phe Ala Ile Pro Leu Phe Asp Ala Ser Leu Glu
1               5                   10                  15

Gly Pro Ala Met Met Ala His His His His His His
            20                  25

<210> SEQ ID NO 304
<211> LENGTH: 28
<212> TYPE: PRT
<213> ORGANISM: artificial
<220> FEATURE:
<223> OTHER INFORMATION: Synthetic polypeptide

<400> SEQUENCE: 304

Val Lys Lys Leu Leu Phe Ala Ile Pro Leu Tyr Phe Ser Ser Pro Ser
1               5                   10                  15

Ser Arg Ala Pro Met Ala His His His His His His
            20                  25

<210> SEQ ID NO 305
<211> LENGTH: 28
<212> TYPE: PRT
<213> ORGANISM: artificial
<220> FEATURE:
<223> OTHER INFORMATION: Synthetic polypeptide

<400> SEQUENCE: 305

Val Lys Lys Leu Leu Phe Ala Ile Pro Leu Trp Phe Ser Phe Pro Phe
1               5                   10                  15

Arg Ser Ala Ala Met Ala His His His His His His
            20                  25

<210> SEQ ID NO 306
<211> LENGTH: 28
<212> TYPE: PRT
<213> ORGANISM: artificial
<220> FEATURE:
<223> OTHER INFORMATION: Synthetic polypeptide

<400> SEQUENCE: 306

Val Lys Lys Leu Leu Phe Ala Ile Pro Leu Tyr Leu Ser Met Ser Ser
1               5                   10                  15

Pro Ala Arg Ser Met Ala His His His His His His
            20                  25

<210> SEQ ID NO 307
<211> LENGTH: 28
<212> TYPE: PRT
<213> ORGANISM: artificial
<220> FEATURE:
<223> OTHER INFORMATION: Synthetic polypeptide

<400> SEQUENCE: 307

Val Lys Lys Leu Leu Phe Ala Ile Pro Leu Ser Trp Ser Leu Cys Arg
1               5                   10                  15

Pro Val Cys Ala Met Ala His His His His His His
            20                  25

<210> SEQ ID NO 308
<211> LENGTH: 28
<212> TYPE: PRT
<213> ORGANISM: artificial
<220> FEATURE:
```

```
<223> OTHER INFORMATION: Synthetic polypeptide

<400> SEQUENCE: 308

Val Lys Lys Leu Leu Phe Ala Ile Pro Leu Leu Tyr Cys Trp Pro Arg
1               5                   10                  15

His Ser Trp Ser Met Ala His His His His His His
            20                  25

<210> SEQ ID NO 309
<211> LENGTH: 28
<212> TYPE: PRT
<213> ORGANISM: artificial
<220> FEATURE:
<223> OTHER INFORMATION: Synthetic polypeptide

<400> SEQUENCE: 309

Val Lys Lys Leu Leu Phe Ala Ile Pro Leu Ile Phe Tyr Thr Thr Arg
1               5                   10                  15

Ser Ser Leu Ser Met Ala His His His His His His
            20                  25

<210> SEQ ID NO 310
<211> LENGTH: 28
<212> TYPE: PRT
<213> ORGANISM: artificial
<220> FEATURE:
<223> OTHER INFORMATION: Synthetic polypeptide

<400> SEQUENCE: 310

Val Lys Lys Leu Leu Phe Ala Ile Pro Leu Ile Tyr Thr Leu Arg Ser
1               5                   10                  15

His Ser Met Thr Met Ala His His His His His His
            20                  25

<210> SEQ ID NO 311
<211> LENGTH: 28
<212> TYPE: PRT
<213> ORGANISM: artificial
<220> FEATURE:
<223> OTHER INFORMATION: Synthetic polypeptide

<400> SEQUENCE: 311

Val Lys Lys Leu Leu Phe Ala Ile Pro Leu Pro Val Pro Ser Leu Leu
1               5                   10                  15

Gly Ser Ala Asp Met Ala His His His His His His
            20                  25

<210> SEQ ID NO 312
<211> LENGTH: 28
<212> TYPE: PRT
<213> ORGANISM: artificial
<220> FEATURE:
<223> OTHER INFORMATION: Synthetic polypeptide

<400> SEQUENCE: 312

Val Lys Lys Leu Leu Phe Ala Ile Pro Leu Ser Leu Ser Leu Asn Ser
1               5                   10                  15

Arg Ser Tyr Pro Met Ala His His His His His His
            20                  25

<210> SEQ ID NO 313
<211> LENGTH: 28
<212> TYPE: PRT
<213> ORGANISM: artificial
```

<220> FEATURE:
<223> OTHER INFORMATION: Synthetic polypeptide

<400> SEQUENCE: 313

Val Lys Lys Leu Leu Phe Ala Ile Pro Leu Phe Ser Pro Thr Ser Gln
1               5                   10                  15

Glu Ile Arg His Met Ala His His His His His His
            20                  25

<210> SEQ ID NO 314
<211> LENGTH: 28
<212> TYPE: PRT
<213> ORGANISM: artificial
<220> FEATURE:
<223> OTHER INFORMATION: Synthetic polypeptide

<400> SEQUENCE: 314

Val Lys Lys Leu Leu Phe Ala Ile Pro Leu Tyr Phe Ser Cys Pro Leu
1               5                   10                  15

Arg Val Ala Ser Met Ala His His His His His His
            20                  25

<210> SEQ ID NO 315
<211> LENGTH: 28
<212> TYPE: PRT
<213> ORGANISM: artificial
<220> FEATURE:
<223> OTHER INFORMATION: Synthetic polypeptide

<400> SEQUENCE: 315

Val Lys Lys Leu Leu Phe Ala Ile Pro Leu Val Leu Ser Leu Asn Arg
1               5                   10                  15

Gly Val Phe Ala Met Ala His His His His His His
            20                  25

<210> SEQ ID NO 316
<211> LENGTH: 28
<212> TYPE: PRT
<213> ORGANISM: artificial
<220> FEATURE:
<223> OTHER INFORMATION: Synthetic polypeptide

<400> SEQUENCE: 316

Val Lys Lys Leu Leu Phe Ala Ile Pro Leu Ser Pro Gln Val Leu Ser
1               5                   10                  15

Ser Ser Pro Gly Met Ala His His His His His His
            20                  25

<210> SEQ ID NO 317
<211> LENGTH: 28
<212> TYPE: PRT
<213> ORGANISM: artificial
<220> FEATURE:
<223> OTHER INFORMATION: Synthetic polypeptide

<400> SEQUENCE: 317

Val Lys Lys Leu Leu Phe Ala Ile Pro Leu Tyr Val Asn Ala Met Ser
1               5                   10                  15

Ser Pro Arg Pro Met Ala His His His His His His
            20                  25

<210> SEQ ID NO 318
<211> LENGTH: 28
<212> TYPE: PRT

<213> ORGANISM: artificial
<220> FEATURE:
<223> OTHER INFORMATION: Synthetic polypeptide

<400> SEQUENCE: 318

Val Lys Lys Leu Leu Phe Ala Ile Pro Leu Tyr Phe Thr Phe Val Arg
1               5                   10                  15

Ser Ser Trp Cys Met Ala His His His His His His
            20                  25

<210> SEQ ID NO 319
<211> LENGTH: 28
<212> TYPE: PRT
<213> ORGANISM: artificial
<220> FEATURE:
<223> OTHER INFORMATION: Synthetic polypeptide

<400> SEQUENCE: 319

Val Lys Lys Leu Leu Phe Ala Ile Pro Leu Phe Asp Leu Ser Ser Asp
1               5                   10                  15

Ser Val Ser Pro Met Ala His His His His His His
            20                  25

<210> SEQ ID NO 320
<211> LENGTH: 28
<212> TYPE: PRT
<213> ORGANISM: artificial
<220> FEATURE:
<223> OTHER INFORMATION: Synthetic polypeptide

<400> SEQUENCE: 320

Val Lys Lys Leu Leu Phe Ala Ile Pro Leu Tyr Ile Leu Phe Trp Arg
1               5                   10                  15

Asn Thr His Ala Met Ala His His His His His His
            20                  25

<210> SEQ ID NO 321
<211> LENGTH: 28
<212> TYPE: PRT
<213> ORGANISM: artificial
<220> FEATURE:
<223> OTHER INFORMATION: Synthetic polypeptide

<400> SEQUENCE: 321

Val Lys Lys Leu Leu Phe Ala Ile Pro Leu Ser Cys Phe Leu Ser Arg
1               5                   10                  15

Ser Ala Phe Ser Met Ala His His His His His His
            20                  25

<210> SEQ ID NO 322
<211> LENGTH: 28
<212> TYPE: PRT
<213> ORGANISM: artificial
<220> FEATURE:
<223> OTHER INFORMATION: Synthetic polypeptide

<400> SEQUENCE: 322

Val Lys Lys Leu Leu Phe Ala Ile Pro Leu Phe Phe Met Ile Thr Ser
1               5                   10                  15

Lys Ser Arg Ser Met Ala His His His His His His
            20                  25

<210> SEQ ID NO 323
<211> LENGTH: 28

```
<212> TYPE: PRT
<213> ORGANISM: artificial
<220> FEATURE:
<223> OTHER INFORMATION: Synthetic polypeptide

<400> SEQUENCE: 323

Val Lys Lys Leu Leu Phe Ala Ile Pro Leu Ile Val Ser Ser Ser Arg
1               5                   10                  15

Gly Ser Phe Ala Met Ala His His His His His His
            20                  25

<210> SEQ ID NO 324
<211> LENGTH: 28
<212> TYPE: PRT
<213> ORGANISM: artificial
<220> FEATURE:
<223> OTHER INFORMATION: Synthetic polypeptide

<400> SEQUENCE: 324

Val Lys Lys Leu Leu Phe Ala Ile Pro Leu Ala Ala Ser Arg Pro Leu
1               5                   10                  15

Ser Pro Ala Ala Met Ala His His His His His His
            20                  25

<210> SEQ ID NO 325
<211> LENGTH: 28
<212> TYPE: PRT
<213> ORGANISM: artificial
<220> FEATURE:
<223> OTHER INFORMATION: Synthetic polypeptide

<400> SEQUENCE: 325

Val Lys Lys Leu Leu Phe Ala Ile Pro Leu Trp Leu Phe Ser Pro Leu
1               5                   10                  15

Arg Ser Tyr Ser Met Ala His His His His His His
            20                  25

<210> SEQ ID NO 326
<211> LENGTH: 28
<212> TYPE: PRT
<213> ORGANISM: artificial
<220> FEATURE:
<223> OTHER INFORMATION: Synthetic polypeptide

<400> SEQUENCE: 326

Val Lys Lys Leu Leu Phe Ala Ile Pro Leu Phe Leu Ser Tyr Val Arg
1               5                   10                  15

Pro Leu Ser Ala Met Ala His His His His His His
            20                  25

<210> SEQ ID NO 327
<211> LENGTH: 28
<212> TYPE: PRT
<213> ORGANISM: artificial
<220> FEATURE:
<223> OTHER INFORMATION: Synthetic polypeptide

<400> SEQUENCE: 327

Val Lys Lys Leu Leu Phe Ala Ile Pro Leu Phe Ile Phe Thr Pro Arg
1               5                   10                  15

Ser Val His Ser Met Ala His His His His His His
            20                  25

<210> SEQ ID NO 328
```

```
<211> LENGTH: 28
<212> TYPE: PRT
<213> ORGANISM: artificial
<220> FEATURE:
<223> OTHER INFORMATION: Synthetic polypeptide

<400> SEQUENCE: 328

Val Lys Lys Leu Leu Phe Ala Ile Pro Leu Val Ser Ser Ile Tyr Lys
1               5                   10                  15
Asn Ser Pro Pro Met Ala His His His His His His
            20                  25

<210> SEQ ID NO 329
<211> LENGTH: 28
<212> TYPE: PRT
<213> ORGANISM: artificial
<220> FEATURE:
<223> OTHER INFORMATION: Synthetic polypeptide

<400> SEQUENCE: 329

Val Lys Lys Leu Leu Phe Ala Ile Pro Leu Met Ser Asp Ser Thr Ala
1               5                   10                  15
Pro Ser Phe Ala Met Ala His His His His His His
            20                  25

<210> SEQ ID NO 330
<211> LENGTH: 28
<212> TYPE: PRT
<213> ORGANISM: artificial
<220> FEATURE:
<223> OTHER INFORMATION: Synthetic polypeptide

<400> SEQUENCE: 330

Val Lys Lys Leu Leu Phe Ala Ile Pro Leu Thr Leu Pro Gln Pro Arg
1               5                   10                  15
Phe Pro Ser Pro Met Ala His His His His His His
            20                  25

<210> SEQ ID NO 331
<211> LENGTH: 28
<212> TYPE: PRT
<213> ORGANISM: artificial
<220> FEATURE:
<223> OTHER INFORMATION: Synthetic polypeptide

<400> SEQUENCE: 331

Val Lys Lys Leu Leu Phe Ala Ile Pro Leu Ser Leu Leu Ala Asp Ser
1               5                   10                  15
Pro Arg Arg Pro Met Ala His His His His His His
            20                  25

<210> SEQ ID NO 332
<211> LENGTH: 28
<212> TYPE: PRT
<213> ORGANISM: artificial
<220> FEATURE:
<223> OTHER INFORMATION: Synthetic polypeptide

<400> SEQUENCE: 332

Val Lys Lys Leu Leu Phe Ala Ile Pro Leu Phe Thr Asp Asn Ser Gly
1               5                   10                  15
Glu Pro Ser Leu Met Ala His His His His His His
            20                  25
```

<210> SEQ ID NO 333
<211> LENGTH: 28
<212> TYPE: PRT
<213> ORGANISM: artificial
<220> FEATURE:
<223> OTHER INFORMATION: Synthetic polypeptide

<400> SEQUENCE: 333

Val Lys Lys Leu Leu Phe Ala Ile Pro Leu Tyr Cys Met Pro Met Ser
1               5                   10                  15

Arg Thr Cys Ala Met Ala His His His His His His
            20                  25

<210> SEQ ID NO 334
<211> LENGTH: 28
<212> TYPE: PRT
<213> ORGANISM: artificial
<220> FEATURE:
<223> OTHER INFORMATION: Synthetic polypeptide

<400> SEQUENCE: 334

Val Lys Lys Leu Leu Phe Ala Ile Pro Leu Met Ser Arg Leu Ser Tyr
1               5                   10                  15

His Thr Pro Ser Met Ala His His His His His His
            20                  25

<210> SEQ ID NO 335
<211> LENGTH: 28
<212> TYPE: PRT
<213> ORGANISM: artificial
<220> FEATURE:
<223> OTHER INFORMATION: Synthetic polypeptide

<400> SEQUENCE: 335

Val Lys Lys Leu Leu Phe Ala Ile Pro Leu Leu Ser Asn Ser Arg Val
1               5                   10                  15

Pro Pro Ser Ser Met Ala His His His His His His
            20                  25

<210> SEQ ID NO 336
<211> LENGTH: 28
<212> TYPE: PRT
<213> ORGANISM: artificial
<220> FEATURE:
<223> OTHER INFORMATION: Synthetic polypeptide

<400> SEQUENCE: 336

Val Lys Lys Leu Leu Phe Ala Ile Pro Leu Phe Phe Ala Ser Met Arg
1               5                   10                  15

His Thr Gln Ala Met Ala His His His His His His
            20                  25

<210> SEQ ID NO 337
<211> LENGTH: 28
<212> TYPE: PRT
<213> ORGANISM: artificial
<220> FEATURE:
<223> OTHER INFORMATION: Synthetic polypeptide

<400> SEQUENCE: 337

Val Lys Lys Leu Leu Phe Ala Ile Pro Leu Leu Leu Ser Thr Ile Lys
1               5                   10                  15

Thr Ser Phe Ser Met Ala His His His His His His
            20                  25

<210> SEQ ID NO 338
<211> LENGTH: 28
<212> TYPE: PRT
<213> ORGANISM: artificial
<220> FEATURE:
<223> OTHER INFORMATION: Synthetic polypeptide

<400> SEQUENCE: 338

Val Lys Lys Leu Leu Phe Ala Ile Pro Leu Phe Gln Gln Ser Ser Leu
1               5                   10                  15

Ser Ser Val Pro Met Ala His His His His His His
            20                  25

<210> SEQ ID NO 339
<211> LENGTH: 28
<212> TYPE: PRT
<213> ORGANISM: artificial
<220> FEATURE:
<223> OTHER INFORMATION: Synthetic polypeptide

<400> SEQUENCE: 339

Val Lys Lys Leu Leu Phe Ala Ile Pro Leu Thr Leu Ile Leu Ser His
1               5                   10                  15

Arg Ser Ser Ala Met Ala His His His His His His
            20                  25

<210> SEQ ID NO 340
<211> LENGTH: 28
<212> TYPE: PRT
<213> ORGANISM: artificial
<220> FEATURE:
<223> OTHER INFORMATION: Synthetic polypeptide

<400> SEQUENCE: 340

Val Lys Lys Leu Leu Phe Ala Ile Pro Leu Ser Phe Ser Arg Asp Pro
1               5                   10                  15

Ser Phe Thr Ser Met Ala His His His His His His
            20                  25

<210> SEQ ID NO 341
<211> LENGTH: 28
<212> TYPE: PRT
<213> ORGANISM: artificial
<220> FEATURE:
<223> OTHER INFORMATION: Synthetic polypeptide

<400> SEQUENCE: 341

Val Lys Lys Leu Leu Phe Ala Ile Pro Leu Ala Leu Ser Pro Thr Arg
1               5                   10                  15

His Thr Leu Ala Met Ala His His His His His His
            20                  25

<210> SEQ ID NO 342
<211> LENGTH: 28
<212> TYPE: PRT
<213> ORGANISM: artificial
<220> FEATURE:
<223> OTHER INFORMATION: Synthetic polypeptide

<400> SEQUENCE: 342

Val Lys Lys Leu Leu Phe Ala Ile Pro Leu Asn Ile Leu Phe Thr Val
1               5                   10                  15

Arg Val Tyr Ala Met Ala His His His His His His
            20                  25

```
<210> SEQ ID NO 343
<211> LENGTH: 28
<212> TYPE: PRT
<213> ORGANISM: artificial
<220> FEATURE:
<223> OTHER INFORMATION: Synthetic polypeptide

<400> SEQUENCE: 343

Val Lys Lys Leu Leu Phe Ala Ile Pro Leu Leu Ala Ser Leu Ser Ala
1               5                   10                  15

Arg Cys His Gly Met Ala His His His His His His
            20                  25

<210> SEQ ID NO 344
<211> LENGTH: 28
<212> TYPE: PRT
<213> ORGANISM: artificial
<220> FEATURE:
<223> OTHER INFORMATION: Synthetic polypeptide

<400> SEQUENCE: 344

Val Lys Lys Leu Leu Phe Ala Ile Pro Leu Ser Val Thr Leu Ser Leu
1               5                   10                  15

Arg Ala Ser Ala Met Ala His His His His His His
            20                  25

<210> SEQ ID NO 345
<211> LENGTH: 28
<212> TYPE: PRT
<213> ORGANISM: artificial
<220> FEATURE:
<223> OTHER INFORMATION: Synthetic polypeptide

<400> SEQUENCE: 345

Val Lys Lys Leu Leu Phe Ala Ile Pro Leu Ser His Asp Pro Leu Leu
1               5                   10                  15

Leu Ser Ser Pro Met Ala His His His His His His
            20                  25

<210> SEQ ID NO 346
<211> LENGTH: 28
<212> TYPE: PRT
<213> ORGANISM: artificial
<220> FEATURE:
<223> OTHER INFORMATION: Synthetic polypeptide

<400> SEQUENCE: 346

Val Lys Lys Leu Leu Phe Ala Ile Pro Leu Leu Trp Ser Leu Ser Ser
1               5                   10                  15

Arg Gly Met Thr Met Ala His His His His His His
            20                  25

<210> SEQ ID NO 347
<211> LENGTH: 28
<212> TYPE: PRT
<213> ORGANISM: artificial
<220> FEATURE:
<223> OTHER INFORMATION: Synthetic polypeptide

<400> SEQUENCE: 347

Val Lys Lys Leu Leu Phe Ala Ile Pro Leu Leu Ile Ser Tyr Cys Arg
1               5                   10                  15

Pro Val Ser Ser Met Ala His His His His His His
```

```
                20                  25

<210> SEQ ID NO 348
<211> LENGTH: 28
<212> TYPE: PRT
<213> ORGANISM: artificial
<220> FEATURE:
<223> OTHER INFORMATION: Synthetic polypeptide

<400> SEQUENCE: 348

Val Lys Lys Leu Leu Phe Ala Ile Pro Leu His Ser Val Glu Leu Pro
1               5                   10                  15

Ala Ser Pro Ala Met Ala His His His His His His
            20                  25

<210> SEQ ID NO 349
<211> LENGTH: 28
<212> TYPE: PRT
<213> ORGANISM: artificial
<220> FEATURE:
<223> OTHER INFORMATION: Synthetic polypeptide

<400> SEQUENCE: 349

Val Lys Lys Leu Leu Phe Ala Ile Pro Leu Leu Leu Ser Thr Ser Arg
1               5                   10                  15

Ser Ser Ser Gly Met Ala His His His His His His
            20                  25

<210> SEQ ID NO 350
<211> LENGTH: 28
<212> TYPE: PRT
<213> ORGANISM: artificial
<220> FEATURE:
<223> OTHER INFORMATION: Synthetic polypeptide

<400> SEQUENCE: 350

Val Lys Lys Leu Leu Phe Ala Ile Pro Leu Trp Phe Ser Cys Ser Arg
1               5                   10                  15

Phe Ala Leu Ser Met Ala His His His His His His
            20                  25

<210> SEQ ID NO 351
<211> LENGTH: 28
<212> TYPE: PRT
<213> ORGANISM: artificial
<220> FEATURE:
<223> OTHER INFORMATION: Synthetic polypeptide

<400> SEQUENCE: 351

Val Lys Lys Leu Leu Phe Ala Ile Pro Leu Val Cys Thr Leu Ser Ser
1               5                   10                  15

Arg Ala Phe Ser Met Ala His His His His His His
            20                  25

<210> SEQ ID NO 352
<211> LENGTH: 28
<212> TYPE: PRT
<213> ORGANISM: artificial
<220> FEATURE:
<223> OTHER INFORMATION: Synthetic polypeptide

<400> SEQUENCE: 352

Val Lys Lys Leu Leu Phe Ala Ile Pro Leu Tyr Ser Pro Leu Ala Arg
1               5                   10                  15
```

```
Asn Pro Phe Ser Met Ala His His His His His
            20                  25

<210> SEQ ID NO 353
<211> LENGTH: 28
<212> TYPE: PRT
<213> ORGANISM: artificial
<220> FEATURE:
<223> OTHER INFORMATION: Synthetic polypeptide

<400> SEQUENCE: 353

Val Lys Lys Leu Leu Phe Ala Ile Pro Leu Phe Phe Ala Phe Ser Arg
1               5                   10                  15

Gln Ser Ser Gly Met Ala His His His His His
            20                  25

<210> SEQ ID NO 354
<211> LENGTH: 28
<212> TYPE: PRT
<213> ORGANISM: artificial
<220> FEATURE:
<223> OTHER INFORMATION: Synthetic polypeptide

<400> SEQUENCE: 354

Val Lys Lys Leu Leu Phe Ala Ile Pro Leu Thr Phe Ser Ile Phe Ser
1               5                   10                  15

Arg Ala Leu Ala Met Ala His His His His His
            20                  25

<210> SEQ ID NO 355
<211> LENGTH: 28
<212> TYPE: PRT
<213> ORGANISM: artificial
<220> FEATURE:
<223> OTHER INFORMATION: Synthetic polypeptide

<400> SEQUENCE: 355

Val Lys Lys Leu Leu Phe Ala Ile Pro Leu Ser Leu Phe Phe Ser Ala
1               5                   10                  15

Arg Ala Ile Ala Met Ala His His His His His
            20                  25

<210> SEQ ID NO 356
<211> LENGTH: 28
<212> TYPE: PRT
<213> ORGANISM: artificial
<220> FEATURE:
<223> OTHER INFORMATION: Synthetic polypeptide

<400> SEQUENCE: 356

Val Lys Lys Leu Leu Phe Ala Ile Pro Leu Ser Gln Pro Ser Leu Cys
1               5                   10                  15

Asp Pro Val Pro Met Ala His His His His His
            20                  25

<210> SEQ ID NO 357
<211> LENGTH: 28
<212> TYPE: PRT
<213> ORGANISM: artificial
<220> FEATURE:
<223> OTHER INFORMATION: Synthetic polypeptide

<400> SEQUENCE: 357

Val Lys Lys Leu Leu Phe Ala Ile Pro Leu Leu Ala Ser Tyr His Arg
1               5                   10                  15
```

```
Val Ala Phe Ala Met Ala His His His His His
            20                  25

<210> SEQ ID NO 358
<211> LENGTH: 28
<212> TYPE: PRT
<213> ORGANISM: artificial
<220> FEATURE:
<223> OTHER INFORMATION: Synthetic polypeptide

<400> SEQUENCE: 358

Val Lys Lys Leu Leu Phe Ala Ile Pro Leu Trp Gln Leu Trp Gln Leu
1               5                   10                  15

Pro Ser Arg Pro Met Ala His His His His His
            20                  25

<210> SEQ ID NO 359
<211> LENGTH: 28
<212> TYPE: PRT
<213> ORGANISM: artificial
<220> FEATURE:
<223> OTHER INFORMATION: Synthetic polypeptide

<400> SEQUENCE: 359

Val Lys Lys Leu Leu Phe Ala Ile Pro Leu Phe Thr Pro Met Tyr Arg
1               5                   10                  15

Pro Thr Ser Pro Met Ala His His His His His
            20                  25

<210> SEQ ID NO 360
<211> LENGTH: 28
<212> TYPE: PRT
<213> ORGANISM: artificial
<220> FEATURE:
<223> OTHER INFORMATION: Synthetic polypeptide

<400> SEQUENCE: 360

Val Lys Lys Leu Leu Phe Ala Ile Pro Leu Leu Leu Ser Leu His Arg
1               5                   10                  15

Phe Ser Phe Ala Met Ala His His His His His
            20                  25

<210> SEQ ID NO 361
<211> LENGTH: 28
<212> TYPE: PRT
<213> ORGANISM: artificial
<220> FEATURE:
<223> OTHER INFORMATION: Synthetic polypeptide

<400> SEQUENCE: 361

Val Lys Lys Leu Leu Phe Ala Ile Pro Leu Ser Tyr Ser His Pro Gln
1               5                   10                  15

Asn Ala Leu Ala Met Ala His His His His His
            20                  25

<210> SEQ ID NO 362
<211> LENGTH: 28
<212> TYPE: PRT
<213> ORGANISM: artificial
<220> FEATURE:
<223> OTHER INFORMATION: Synthetic polypeptide

<400> SEQUENCE: 362

Val Lys Lys Leu Leu Phe Ala Ile Pro Leu Tyr Val Leu Arg Ser Asp
```

```
                1               5                  10                  15
Ala Ser Trp Gly Met Ala His His His His His His
            20                  25

<210> SEQ ID NO 363
<211> LENGTH: 28
<212> TYPE: PRT
<213> ORGANISM: artificial
<220> FEATURE:
<223> OTHER INFORMATION: Synthetic polypeptide

<400> SEQUENCE: 363

Val Lys Lys Leu Leu Phe Ala Ile Pro Leu Phe Ser Gly Pro Pro Phe
1               5                  10                  15

Asp Arg Thr Ser Met Ala His His His His His His
            20                  25

<210> SEQ ID NO 364
<211> LENGTH: 28
<212> TYPE: PRT
<213> ORGANISM: artificial
<220> FEATURE:
<223> OTHER INFORMATION: Synthetic polypeptide

<400> SEQUENCE: 364

Val Lys Lys Leu Leu Phe Ala Ile Pro Leu Phe Cys Ala Leu Ser Arg
1               5                  10                  15

Phe Thr His Ala Met Ala His His His His His His
            20                  25

<210> SEQ ID NO 365
<211> LENGTH: 28
<212> TYPE: PRT
<213> ORGANISM: artificial
<220> FEATURE:
<223> OTHER INFORMATION: Synthetic polypeptide

<400> SEQUENCE: 365

Val Lys Lys Leu Leu Phe Ala Ile Pro Leu Phe Ser Leu Ser Arg Pro
1               5                  10                  15

Val Pro Pro Leu Met Ala His His His His His His
            20                  25

<210> SEQ ID NO 366
<211> LENGTH: 28
<212> TYPE: PRT
<213> ORGANISM: artificial
<220> FEATURE:
<223> OTHER INFORMATION: Synthetic polypeptide

<400> SEQUENCE: 366

Val Lys Lys Leu Leu Phe Ala Ile Pro Leu Ser Met Asp Ser Phe Ser
1               5                  10                  15

Arg Pro Phe Phe Met Ala His His His His His His
            20                  25

<210> SEQ ID NO 367
<211> LENGTH: 28
<212> TYPE: PRT
<213> ORGANISM: artificial
<220> FEATURE:
<223> OTHER INFORMATION: Synthetic polypeptide

<400> SEQUENCE: 367
```

Val Lys Lys Leu Leu Phe Ala Ile Pro Leu Tyr Thr Ile Ile Pro Ser
1               5                   10                  15

Arg Ala Ser Ser Met Ala His His His His His His
            20                  25

<210> SEQ ID NO 368
<211> LENGTH: 28
<212> TYPE: PRT
<213> ORGANISM: artificial
<220> FEATURE:
<223> OTHER INFORMATION: Synthetic polypeptide

<400> SEQUENCE: 368

Val Lys Lys Leu Leu Phe Ala Ile Pro Leu Val Pro Ser Ala Asn Pro
1               5                   10                  15

Pro Pro Leu Ser Met Ala His His His His His His
            20                  25

<210> SEQ ID NO 369
<211> LENGTH: 28
<212> TYPE: PRT
<213> ORGANISM: artificial
<220> FEATURE:
<223> OTHER INFORMATION: Synthetic polypeptide

<400> SEQUENCE: 369

Val Lys Lys Leu Leu Phe Ala Ile Pro Leu Tyr Leu Ile Lys Pro Pro
1               5                   10                  15

Glu Gly Phe Ser Met Ala His His His His His His
            20                  25

<210> SEQ ID NO 370
<211> LENGTH: 28
<212> TYPE: PRT
<213> ORGANISM: artificial
<220> FEATURE:
<223> OTHER INFORMATION: Synthetic polypeptide

<400> SEQUENCE: 370

Val Lys Lys Leu Leu Phe Ala Ile Pro Leu Ile Ser Thr Leu His Phe
1               5                   10                  15

Arg Ala Phe Gly Met Ala His His His His His His
            20                  25

<210> SEQ ID NO 371
<211> LENGTH: 28
<212> TYPE: PRT
<213> ORGANISM: artificial
<220> FEATURE:
<223> OTHER INFORMATION: Synthetic polypeptide

<400> SEQUENCE: 371

Val Lys Lys Leu Leu Phe Ala Ile Pro Leu Val Arg Val Met Cys Gly
1               5                   10                  15

His Ser Tyr Ala Met Ala His His His His His His
            20                  25

<210> SEQ ID NO 372
<211> LENGTH: 28
<212> TYPE: PRT
<213> ORGANISM: artificial
<220> FEATURE:
<223> OTHER INFORMATION: Synthetic polypeptide

<400> SEQUENCE: 372

Val Lys Lys Leu Leu Phe Ala Ile Pro Leu Val Leu Ser Leu Ser Arg
1               5                   10                  15

Thr Phe Ser Gly Met Ala His His His His His His
                20                  25

<210> SEQ ID NO 373
<211> LENGTH: 28
<212> TYPE: PRT
<213> ORGANISM: artificial
<220> FEATURE:
<223> OTHER INFORMATION: Synthetic polypeptide

<400> SEQUENCE: 373

Val Lys Lys Leu Leu Phe Ala Ile Pro Leu Trp Cys Ala Leu Ser Arg
1               5                   10                  15

Gln Ser Met Pro Met Ala His His His His His His
                20                  25

<210> SEQ ID NO 374
<211> LENGTH: 28
<212> TYPE: PRT
<213> ORGANISM: artificial
<220> FEATURE:
<223> OTHER INFORMATION: Synthetic polypeptide

<400> SEQUENCE: 374

Val Lys Lys Leu Leu Phe Ala Ile Pro Leu Tyr Phe Trp Ser Leu Arg
1               5                   10                  15

Val Ser Trp Pro Met Ala His His His His His His
                20                  25

<210> SEQ ID NO 375
<211> LENGTH: 28
<212> TYPE: PRT
<213> ORGANISM: artificial
<220> FEATURE:
<223> OTHER INFORMATION: Synthetic polypeptide

<400> SEQUENCE: 375

Val Lys Lys Leu Leu Phe Ala Ile Pro Leu Tyr Ile Leu Ser Pro Arg
1               5                   10                  15

Leu Pro Pro Pro Met Ala His His His His His His
                20                  25

<210> SEQ ID NO 376
<211> LENGTH: 28
<212> TYPE: PRT
<213> ORGANISM: artificial
<220> FEATURE:
<223> OTHER INFORMATION: Synthetic polypeptide

<400> SEQUENCE: 376

Val Lys Lys Leu Leu Phe Ala Ile Pro Leu Val Val Ala Ala His Arg
1               5                   10                  15

Phe Ser Tyr Ala Met Ala His His His His His His
                20                  25

<210> SEQ ID NO 377
<211> LENGTH: 28
<212> TYPE: PRT
<213> ORGANISM: artificial
<220> FEATURE:
<223> OTHER INFORMATION: Synthetic polypeptide

```
<400> SEQUENCE: 377

Val Lys Lys Leu Leu Phe Ala Ile Pro Leu Tyr Val His Leu Thr Ser
1               5                   10                  15

Lys Ala Ile Pro Met Ala His His His His His His
                20                  25

<210> SEQ ID NO 378
<211> LENGTH: 28
<212> TYPE: PRT
<213> ORGANISM: artificial
<220> FEATURE:
<223> OTHER INFORMATION: Synthetic polypeptide

<400> SEQUENCE: 378

Val Lys Lys Leu Leu Phe Ala Ile Pro Leu Ser Leu Thr Leu Tyr Arg
1               5                   10                  15

Ser Gly Trp Ser Met Ala His His His His His His
                20                  25

<210> SEQ ID NO 379
<211> LENGTH: 28
<212> TYPE: PRT
<213> ORGANISM: artificial
<220> FEATURE:
<223> OTHER INFORMATION: Synthetic polypeptide

<400> SEQUENCE: 379

Val Lys Lys Leu Leu Phe Ala Ile Pro Leu Tyr Tyr Ala Leu Ser Gly
1               5                   10                  15

Arg Pro Val Thr Met Ala His His His His His His
                20                  25

<210> SEQ ID NO 380
<211> LENGTH: 28
<212> TYPE: PRT
<213> ORGANISM: artificial
<220> FEATURE:
<223> OTHER INFORMATION: Synthetic polypeptide

<400> SEQUENCE: 380

Val Lys Lys Leu Leu Phe Ala Ile Pro Leu Met Leu Ser Leu Met Arg
1               5                   10                  15

Gln Ser Ala Pro Met Ala His His His His His His
                20                  25

<210> SEQ ID NO 381
<211> LENGTH: 28
<212> TYPE: PRT
<213> ORGANISM: artificial
<220> FEATURE:
<223> OTHER INFORMATION: Synthetic polypeptide

<400> SEQUENCE: 381

Val Lys Lys Leu Leu Phe Ala Ile Pro Leu Val Val Pro Phe Tyr Ala
1               5                   10                  15

Arg Pro Leu Thr Arg Ile Gln Thr Pro His His His
                20                  25

<210> SEQ ID NO 382
<211> LENGTH: 28
<212> TYPE: PRT
<213> ORGANISM: artificial
<220> FEATURE:
<223> OTHER INFORMATION: Synthetic polypeptide
```

<400> SEQUENCE: 382

Val Lys Lys Leu Leu Phe Ala Ile Pro Leu Val Val Pro Phe Tyr Leu
1               5                   10                  15

Thr Gln Leu Ser Arg Arg Glu Pro Ser His His His
            20                  25

<210> SEQ ID NO 383
<211> LENGTH: 28
<212> TYPE: PRT
<213> ORGANISM: artificial
<220> FEATURE:
<223> OTHER INFORMATION: Synthetic polypeptide

<400> SEQUENCE: 383

Val Lys Lys Leu Leu Phe Ala Ile Pro Leu Val Val Pro Phe Tyr Ala
1               5                   10                  15

Arg Ser Leu Ala Thr Ser Pro Ser Arg His His His
            20                  25

<210> SEQ ID NO 384
<211> LENGTH: 28
<212> TYPE: PRT
<213> ORGANISM: artificial
<220> FEATURE:
<223> OTHER INFORMATION: Synthetic polypeptide

<400> SEQUENCE: 384

Val Lys Lys Leu Leu Phe Ala Ile Pro Leu Val Val Pro Phe Tyr Pro
1               5                   10                  15

Ala Arg Ser Tyr Met Leu Val Arg Pro His His His
            20                  25

<210> SEQ ID NO 385
<211> LENGTH: 28
<212> TYPE: PRT
<213> ORGANISM: artificial
<220> FEATURE:
<223> OTHER INFORMATION: Synthetic polypeptide

<400> SEQUENCE: 385

Val Lys Lys Leu Leu Phe Ala Ile Pro Leu Val Val Pro Phe Tyr Ser
1               5                   10                  15

Arg Ser Tyr Met Leu Leu Ser Arg Pro His His His
            20                  25

<210> SEQ ID NO 386
<211> LENGTH: 28
<212> TYPE: PRT
<213> ORGANISM: artificial
<220> FEATURE:
<223> OTHER INFORMATION: Synthetic polypeptide

<400> SEQUENCE: 386

Val Lys Lys Leu Leu Phe Ala Ile Pro Leu Val Val Pro Phe Tyr Thr
1               5                   10                  15

Arg Ser Ala Leu Ala Phe Phe Leu Pro His His His
            20                  25

<210> SEQ ID NO 387
<211> LENGTH: 28
<212> TYPE: PRT
<213> ORGANISM: artificial
<220> FEATURE:

<223> OTHER INFORMATION: Synthetic polypeptide

<400> SEQUENCE: 387

Val Lys Lys Leu Leu Phe Ala Ile Pro Leu Val Val Pro Phe Tyr Ser
1               5                   10                  15

Arg Gly Phe Thr Leu Pro Arg Leu Ile His His His
            20                  25

<210> SEQ ID NO 388
<211> LENGTH: 28
<212> TYPE: PRT
<213> ORGANISM: artificial
<220> FEATURE:
<223> OTHER INFORMATION: Synthetic polypeptide

<400> SEQUENCE: 388

Val Lys Lys Leu Leu Phe Ala Ile Pro Leu Val Val Pro Phe Tyr Ser
1               5                   10                  15

Ser Ala Phe Thr Arg Pro Ile Arg Pro His His His
            20                  25

<210> SEQ ID NO 389
<211> LENGTH: 28
<212> TYPE: PRT
<213> ORGANISM: artificial
<220> FEATURE:
<223> OTHER INFORMATION: Synthetic polypeptide

<400> SEQUENCE: 389

Val Lys Lys Leu Leu Phe Ala Ile Pro Leu Val Val Pro Phe Tyr Thr
1               5                   10                  15

Arg Tyr Ser His Ala Phe Met Leu Ile His His His
            20                  25

<210> SEQ ID NO 390
<211> LENGTH: 28
<212> TYPE: PRT
<213> ORGANISM: artificial
<220> FEATURE:
<223> OTHER INFORMATION: Synthetic polypeptide

<400> SEQUENCE: 390

Val Lys Lys Leu Leu Phe Ala Ile Pro Leu Val Val Pro Phe Tyr Ala
1               5                   10                  15

Arg Pro Met Ser Met Phe Arg Ser Asp His His His
            20                  25

<210> SEQ ID NO 391
<211> LENGTH: 28
<212> TYPE: PRT
<213> ORGANISM: artificial
<220> FEATURE:
<223> OTHER INFORMATION: Synthetic polypeptide

<400> SEQUENCE: 391

Val Lys Lys Leu Leu Phe Ala Ile Pro Leu Val Val Pro Phe Tyr Ala
1               5                   10                  15

Ser Ser Met Ser Gln Tyr Arg Gln Asn His His His
            20                  25

<210> SEQ ID NO 392
<211> LENGTH: 28
<212> TYPE: PRT
<213> ORGANISM: artificial

<220> FEATURE:
<223> OTHER INFORMATION: Synthetic polypeptide

<400> SEQUENCE: 392

Val Lys Lys Leu Leu Phe Ala Ile Pro Leu Val Val Pro Phe Tyr Ala
1               5                   10                  15

Arg Ser Tyr Ser Arg Pro Pro Ser Ile His His His
            20                  25

<210> SEQ ID NO 393
<211> LENGTH: 28
<212> TYPE: PRT
<213> ORGANISM: artificial
<220> FEATURE:
<223> OTHER INFORMATION: Synthetic polypeptide

<400> SEQUENCE: 393

Val Lys Lys Leu Leu Phe Ala Ile Pro Leu Val Val Pro Phe Tyr Ala
1               5                   10                  15

Ser Ser Met Ser Arg Leu Arg Pro His His His His
            20                  25

<210> SEQ ID NO 394
<211> LENGTH: 28
<212> TYPE: PRT
<213> ORGANISM: artificial
<220> FEATURE:
<223> OTHER INFORMATION: Synthetic polypeptide

<400> SEQUENCE: 394

Val Lys Lys Leu Leu Phe Ala Ile Pro Leu Val Val Pro Phe Tyr Cys
1               5                   10                  15

Arg Ser Leu Ser Arg Pro Met Leu Val His His His
            20                  25

<210> SEQ ID NO 395
<211> LENGTH: 28
<212> TYPE: PRT
<213> ORGANISM: artificial
<220> FEATURE:
<223> OTHER INFORMATION: Synthetic polypeptide

<400> SEQUENCE: 395

Val Lys Lys Leu Leu Phe Ala Ile Pro Leu Val Val Pro Phe Tyr Ser
1               5                   10                  15

Arg Ser Met Ser Leu His Pro Thr Ala His His His
            20                  25

<210> SEQ ID NO 396
<211> LENGTH: 28
<212> TYPE: PRT
<213> ORGANISM: artificial
<220> FEATURE:
<223> OTHER INFORMATION: Synthetic polypeptide

<400> SEQUENCE: 396

Val Lys Lys Leu Leu Phe Ala Ile Pro Leu Val Val Pro Phe Tyr Thr
1               5                   10                  15

Arg Ser Met Thr Arg Leu Ala Pro Pro His His His
            20                  25

<210> SEQ ID NO 397
<211> LENGTH: 28
<212> TYPE: PRT

```
<213> ORGANISM: artificial
<220> FEATURE:
<223> OTHER INFORMATION: Synthetic polypeptide

<400> SEQUENCE: 397

Val Lys Lys Leu Leu Phe Ala Ile Pro Leu Val Val Pro Phe Tyr Thr
1               5                   10                  15

Arg Ala Met Ser Val Ser His Lys Thr His His His
            20                  25

<210> SEQ ID NO 398
<211> LENGTH: 28
<212> TYPE: PRT
<213> ORGANISM: artificial
<220> FEATURE:
<223> OTHER INFORMATION: Synthetic polypeptide

<400> SEQUENCE: 398

Val Lys Lys Leu Leu Phe Ala Ile Pro Leu Val Val Pro Phe Tyr Leu
1               5                   10                  15

Leu Ala Pro Lys Pro Ser Val Lys Arg His His His
            20                  25

<210> SEQ ID NO 399
<211> LENGTH: 28
<212> TYPE: PRT
<213> ORGANISM: artificial
<220> FEATURE:
<223> OTHER INFORMATION: Synthetic polypeptide

<400> SEQUENCE: 399

Val Lys Lys Leu Leu Phe Ala Ile Pro Leu Val Val Pro Phe Tyr Ser
1               5                   10                  15

Arg Pro Ala Pro Ala Leu Ser Arg Leu His His His
            20                  25

<210> SEQ ID NO 400
<211> LENGTH: 28
<212> TYPE: PRT
<213> ORGANISM: artificial
<220> FEATURE:
<223> OTHER INFORMATION: Synthetic polypeptide

<400> SEQUENCE: 400

Val Lys Lys Leu Leu Phe Ala Ile Pro Leu Val Val Pro Phe Tyr Ala
1               5                   10                  15

Lys Ala Met Ser Ala Arg Tyr Gln Ser His His His
            20                  25

<210> SEQ ID NO 401
<211> LENGTH: 28
<212> TYPE: PRT
<213> ORGANISM: artificial
<220> FEATURE:
<223> OTHER INFORMATION: Synthetic polypeptide

<400> SEQUENCE: 401

Val Lys Lys Leu Leu Phe Ala Ile Pro Leu Val Val Pro Phe Tyr Phe
1               5                   10                  15

Ala Ser Gln Arg Ser Ser Pro Ile Arg His His His
            20                  25

<210> SEQ ID NO 402
<211> LENGTH: 28
```

-continued

```
<212> TYPE: PRT
<213> ORGANISM: artificial
<220> FEATURE:
<223> OTHER INFORMATION: Synthetic polypeptide

<400> SEQUENCE: 402

Val Lys Lys Leu Leu Phe Ala Ile Pro Leu Val Val Pro Phe Tyr Cys
1               5                   10                  15

Leu Ser Phe Thr Ser Ala Arg Phe Gln His His His
            20                  25

<210> SEQ ID NO 403
<211> LENGTH: 28
<212> TYPE: PRT
<213> ORGANISM: artificial
<220> FEATURE:
<223> OTHER INFORMATION: Synthetic polypeptide

<400> SEQUENCE: 403

Val Lys Lys Leu Leu Phe Ala Ile Pro Leu Val Val Pro Phe Tyr Pro
1               5                   10                  15

Ser Ala Ser Ser Arg Leu Ser Pro Lys His His His
            20                  25

<210> SEQ ID NO 404
<211> LENGTH: 28
<212> TYPE: PRT
<213> ORGANISM: artificial
<220> FEATURE:
<223> OTHER INFORMATION: Synthetic polypeptide

<400> SEQUENCE: 404

Val Lys Lys Leu Leu Phe Ala Ile Pro Leu Val Val Pro Phe Tyr Ala
1               5                   10                  15

Arg Ser Tyr Thr Arg Val Pro Leu Ala His His His
            20                  25

<210> SEQ ID NO 405
<211> LENGTH: 28
<212> TYPE: PRT
<213> ORGANISM: artificial
<220> FEATURE:
<223> OTHER INFORMATION: Synthetic polypeptide

<400> SEQUENCE: 405

Val Lys Lys Leu Leu Phe Ala Ile Pro Leu Val Val Pro Phe Tyr Ala
1               5                   10                  15

Arg Ser Leu Thr Phe Leu Pro Pro Arg His His His
            20                  25

<210> SEQ ID NO 406
<211> LENGTH: 28
<212> TYPE: PRT
<213> ORGANISM: artificial
<220> FEATURE:
<223> OTHER INFORMATION: Synthetic polypeptide

<400> SEQUENCE: 406

Val Lys Lys Leu Leu Phe Ala Ile Pro Leu Val Val Pro Phe Tyr Thr
1               5                   10                  15

Thr Arg Val Asn Ala Phe Met Leu Val His His His
            20                  25

<210> SEQ ID NO 407
```

```
<211> LENGTH: 28
<212> TYPE: PRT
<213> ORGANISM: artificial
<220> FEATURE:
<223> OTHER INFORMATION: Synthetic polypeptide

<400> SEQUENCE: 407

Val Lys Lys Leu Leu Phe Ala Ile Pro Leu Val Val Pro Phe Tyr Gln
1               5                   10                  15
Ala Phe Arg Pro Val Pro Val Arg Asn His His His
            20                  25

<210> SEQ ID NO 408
<211> LENGTH: 28
<212> TYPE: PRT
<213> ORGANISM: artificial
<220> FEATURE:
<223> OTHER INFORMATION: Synthetic polypeptide

<400> SEQUENCE: 408

Val Lys Lys Leu Leu Phe Ala Ile Pro Leu Val Val Pro Phe Tyr Thr
1               5                   10                  15
Ser Gly Met Ser Arg Leu Arg Ser Trp His His His
            20                  25

<210> SEQ ID NO 409
<211> LENGTH: 28
<212> TYPE: PRT
<213> ORGANISM: artificial
<220> FEATURE:
<223> OTHER INFORMATION: Synthetic polypeptide

<400> SEQUENCE: 409

Val Lys Lys Leu Leu Phe Ala Ile Pro Leu Val Val Pro Phe Tyr Ser
1               5                   10                  15
Arg Ser Pro Ser Gln Leu Ser Ser Arg His His His
            20                  25

<210> SEQ ID NO 410
<211> LENGTH: 28
<212> TYPE: PRT
<213> ORGANISM: artificial
<220> FEATURE:
<223> OTHER INFORMATION: Synthetic polypeptide

<400> SEQUENCE: 410

Val Lys Lys Leu Leu Phe Ala Ile Pro Leu Val Val Pro Phe Tyr Ala
1               5                   10                  15
Phe Ser Leu Ser Arg Thr Ser Ser Lys His His His
            20                  25

<210> SEQ ID NO 411
<211> LENGTH: 28
<212> TYPE: PRT
<213> ORGANISM: artificial
<220> FEATURE:
<223> OTHER INFORMATION: Synthetic polypeptide

<400> SEQUENCE: 411

Val Lys Lys Leu Leu Phe Ala Ile Pro Leu Val Val Pro Phe Tyr Phe
1               5                   10                  15
His Arg Val Gln Gln Phe Ser Pro Ala His His His
            20                  25
```

```
<210> SEQ ID NO 412
<211> LENGTH: 28
<212> TYPE: PRT
<213> ORGANISM: artificial
<220> FEATURE:
<223> OTHER INFORMATION: Synthetic polypeptide

<400> SEQUENCE: 412

Val Lys Lys Leu Leu Phe Ala Ile Pro Leu Val Val Pro Phe Tyr Leu
1               5                   10                  15

Asp Ser Met Leu Thr Phe Arg Arg Ser His His His
            20                  25

<210> SEQ ID NO 413
<211> LENGTH: 28
<212> TYPE: PRT
<213> ORGANISM: artificial
<220> FEATURE:
<223> OTHER INFORMATION: Synthetic polypeptide

<400> SEQUENCE: 413

Val Lys Lys Leu Leu Phe Ala Ile Pro Leu Val Val Pro Phe Tyr Cys
1               5                   10                  15

Arg Ser Leu Thr Ser Pro Leu Arg Met His His His
            20                  25

<210> SEQ ID NO 414
<211> LENGTH: 28
<212> TYPE: PRT
<213> ORGANISM: artificial
<220> FEATURE:
<223> OTHER INFORMATION: Synthetic polypeptide

<400> SEQUENCE: 414

Val Lys Lys Leu Leu Phe Ala Ile Pro Leu Val Val Pro Phe Tyr Ser
1               5                   10                  15

Arg Ser Ala Ser Phe Leu Arg Pro Ile His His His
            20                  25

<210> SEQ ID NO 415
<211> LENGTH: 28
<212> TYPE: PRT
<213> ORGANISM: artificial
<220> FEATURE:
<223> OTHER INFORMATION: Synthetic polypeptide

<400> SEQUENCE: 415

Val Lys Lys Leu Leu Phe Ala Ile Pro Leu Val Val Pro Phe Tyr Met
1               5                   10                  15

Thr Phe Gln Ser Asn Ser Pro Arg Gly His His His
            20                  25

<210> SEQ ID NO 416
<211> LENGTH: 28
<212> TYPE: PRT
<213> ORGANISM: artificial
<220> FEATURE:
<223> OTHER INFORMATION: Synthetic polypeptide

<400> SEQUENCE: 416

Val Lys Lys Leu Leu Phe Ala Ile Pro Leu Val Val Pro Phe Tyr Cys
1               5                   10                  15

Arg Pro Met Thr Leu Arg Gln Pro Val His His His
            20                  25
```

```
<210> SEQ ID NO 417
<211> LENGTH: 28
<212> TYPE: PRT
<213> ORGANISM: artificial
<220> FEATURE:
<223> OTHER INFORMATION: Synthetic polypeptide

<400> SEQUENCE: 417

Val Lys Lys Leu Leu Phe Ala Ile Pro Leu Val Val Pro Phe Tyr Val
1               5                   10                  15

Arg Pro Met Ser Arg Val Ile Met Ser His His His
            20                  25

<210> SEQ ID NO 418
<211> LENGTH: 28
<212> TYPE: PRT
<213> ORGANISM: artificial
<220> FEATURE:
<223> OTHER INFORMATION: Synthetic polypeptide

<400> SEQUENCE: 418

Val Lys Lys Leu Leu Phe Ala Ile Pro Leu Val Val Pro Phe Tyr Ser
1               5                   10                  15

Tyr Gly Phe Ser Arg Pro Phe Ser Lys His His His
            20                  25

<210> SEQ ID NO 419
<211> LENGTH: 28
<212> TYPE: PRT
<213> ORGANISM: artificial
<220> FEATURE:
<223> OTHER INFORMATION: Synthetic polypeptide

<400> SEQUENCE: 419

Val Lys Lys Leu Leu Phe Ala Ile Pro Leu Val Val Pro Phe Tyr Thr
1               5                   10                  15

Arg Ser Cys Phe Ala Phe Met Leu Pro His His His
            20                  25

<210> SEQ ID NO 420
<211> LENGTH: 28
<212> TYPE: PRT
<213> ORGANISM: artificial
<220> FEATURE:
<223> OTHER INFORMATION: Synthetic polypeptide

<400> SEQUENCE: 420

Val Lys Lys Leu Leu Phe Ala Ile Pro Leu Val Val Pro Phe Tyr Ala
1               5                   10                  15

Phe Ser Gly Ala Phe Arg Gln Ser Gln His His His
            20                  25

<210> SEQ ID NO 421
<211> LENGTH: 28
<212> TYPE: PRT
<213> ORGANISM: artificial
<220> FEATURE:
<223> OTHER INFORMATION: Synthetic polypeptide

<400> SEQUENCE: 421

Val Lys Lys Leu Leu Phe Ala Ile Pro Leu Val Val Pro Phe Tyr Leu
1               5                   10                  15

Arg Ala Gly Ser Phe Ser Ala Ala Pro His His His
            20                  25
```

<210> SEQ ID NO 422
<211> LENGTH: 28
<212> TYPE: PRT
<213> ORGANISM: artificial
<220> FEATURE:
<223> OTHER INFORMATION: Synthetic polypeptide

<400> SEQUENCE: 422

Val Lys Lys Leu Leu Phe Ala Ile Pro Leu Val Val Pro Phe Tyr Ser
1               5                   10                  15

His Ser Met Ala Pro Pro Ser Arg Arg His His His
            20                  25

<210> SEQ ID NO 423
<211> LENGTH: 28
<212> TYPE: PRT
<213> ORGANISM: artificial
<220> FEATURE:
<223> OTHER INFORMATION: Synthetic polypeptide

<400> SEQUENCE: 423

Val Lys Lys Leu Leu Phe Ala Ile Pro Leu Val Val Pro Phe Tyr Cys
1               5                   10                  15

Arg Ser Gly Thr Phe Gly Asn Ile Gly His His His
            20                  25

<210> SEQ ID NO 424
<211> LENGTH: 28
<212> TYPE: PRT
<213> ORGANISM: artificial
<220> FEATURE:
<223> OTHER INFORMATION: Synthetic polypeptide

<400> SEQUENCE: 424

Val Lys Lys Leu Leu Phe Ala Ile Pro Leu Val Val Pro Phe Tyr Ala
1               5                   10                  15

Arg Ser Met Ala Ser Thr Pro Leu Ala His His His
            20                  25

<210> SEQ ID NO 425
<211> LENGTH: 28
<212> TYPE: PRT
<213> ORGANISM: artificial
<220> FEATURE:
<223> OTHER INFORMATION: Synthetic polypeptide

<400> SEQUENCE: 425

Val Lys Lys Leu Leu Phe Ala Ile Pro Leu Val Val Pro Phe Tyr Val
1               5                   10                  15

Tyr Pro Leu Ala Pro Arg Leu Arg Asp His His His
            20                  25

<210> SEQ ID NO 426
<211> LENGTH: 28
<212> TYPE: PRT
<213> ORGANISM: artificial
<220> FEATURE:
<223> OTHER INFORMATION: Synthetic polypeptide

<400> SEQUENCE: 426

Val Lys Lys Leu Leu Phe Ala Ile Pro Leu Val Val Pro Phe Tyr Ser
1               5                   10                  15

Leu Pro Trp Arg Arg Thr Pro Phe Gln His His His 20                  25

<210> SEQ ID NO 427
<211> LENGTH: 28
<212> TYPE: PRT
<213> ORGANISM: artificial
<220> FEATURE:
<223> OTHER INFORMATION: Synthetic polypeptide

<400> SEQUENCE: 427

Val Lys Lys Leu Leu Phe Ala Ile Pro Leu Val Val Pro Phe Tyr Met
1               5                   10                  15

Arg Thr Pro Pro Leu Ser Gln Arg Ile His His His
                20                  25

<210> SEQ ID NO 428
<211> LENGTH: 28
<212> TYPE: PRT
<213> ORGANISM: artificial
<220> FEATURE:
<223> OTHER INFORMATION: Synthetic polypeptide

<400> SEQUENCE: 428

Val Lys Lys Leu Leu Phe Ala Ile Pro Leu Val Val Pro Phe Tyr Ala
1               5                   10                  15

Arg Ser Leu Ser Ser Tyr Asn Ala Val His His His
                20                  25

<210> SEQ ID NO 429
<211> LENGTH: 28
<212> TYPE: PRT
<213> ORGANISM: artificial
<220> FEATURE:
<223> OTHER INFORMATION: Synthetic polypeptide

<400> SEQUENCE: 429

Val Lys Lys Leu Leu Phe Ala Ile Pro Leu Val Val Pro Phe Tyr Val
1               5                   10                  15

His Ala Leu Ala Arg Lys Ser Gln Phe His His His
                20                  25

<210> SEQ ID NO 430
<211> LENGTH: 28
<212> TYPE: PRT
<213> ORGANISM: artificial
<220> FEATURE:
<223> OTHER INFORMATION: Synthetic polypeptide

<400> SEQUENCE: 430

Val Lys Lys Leu Leu Phe Ala Ile Pro Leu Val Val Pro Phe Tyr Ser
1               5                   10                  15

Arg Ser Phe Ser Ser Pro Ser Ile Thr His His His
                20                  25

<210> SEQ ID NO 431
<211> LENGTH: 28
<212> TYPE: PRT
<213> ORGANISM: artificial
<220> FEATURE:
<223> OTHER INFORMATION: Synthetic polypeptide

<400> SEQUENCE: 431

Val Lys Lys Leu Leu Phe Ala Ile Pro Leu Val Val Pro Phe Tyr Cys
1               5                   10                  15

Arg Ala Leu Ser Lys Pro Leu Pro Pro His His His
            20                  25

<210> SEQ ID NO 432
<211> LENGTH: 28
<212> TYPE: PRT
<213> ORGANISM: artificial
<220> FEATURE:
<223> OTHER INFORMATION: Synthetic polypeptide

<400> SEQUENCE: 432

Val Lys Lys Leu Leu Phe Ala Ile Pro Leu Val Val Pro Phe Tyr Cys
1               5                   10                  15
Arg Pro Ser Ala Pro Lys Met Leu Leu His His His
            20                  25

<210> SEQ ID NO 433
<211> LENGTH: 28
<212> TYPE: PRT
<213> ORGANISM: artificial
<220> FEATURE:
<223> OTHER INFORMATION: Synthetic polypeptide

<400> SEQUENCE: 433

Val Lys Lys Leu Leu Phe Ala Ile Pro Leu Val Val Pro Phe Tyr Ser
1               5                   10                  15
Arg Ser Met Ser Tyr Phe Gln Pro Leu His His His
            20                  25

<210> SEQ ID NO 434
<211> LENGTH: 28
<212> TYPE: PRT
<213> ORGANISM: artificial
<220> FEATURE:
<223> OTHER INFORMATION: Synthetic polypeptide

<400> SEQUENCE: 434

Val Lys Lys Leu Leu Phe Ala Ile Pro Leu Val Val Pro Phe Tyr Thr
1               5                   10                  15
Arg Ser Leu Ser Arg Ser Ile Pro His His His His
            20                  25

<210> SEQ ID NO 435
<211> LENGTH: 28
<212> TYPE: PRT
<213> ORGANISM: artificial
<220> FEATURE:
<223> OTHER INFORMATION: Synthetic polypeptide

<400> SEQUENCE: 435

Val Lys Lys Leu Leu Phe Ala Ile Pro Leu Val Val Pro Phe Tyr Ser
1               5                   10                  15
Gln Leu His Gln Ser Pro Gly Asn Pro His His His
            20                  25

<210> SEQ ID NO 436
<211> LENGTH: 28
<212> TYPE: PRT
<213> ORGANISM: artificial
<220> FEATURE:
<223> OTHER INFORMATION: Synthetic polypeptide

<400> SEQUENCE: 436

Val Lys Lys Leu Leu Phe Ala Ile Pro Leu Val Val Pro Phe Tyr Thr
1               5                   10                  15

Arg Ala Ile Ala Arg Pro Pro Tyr Thr His His His
            20                  25

<210> SEQ ID NO 437
<211> LENGTH: 28
<212> TYPE: PRT
<213> ORGANISM: artificial
<220> FEATURE:
<223> OTHER INFORMATION: Synthetic polypeptide

<400> SEQUENCE: 437

Val Lys Lys Leu Leu Phe Ala Ile Pro Leu Val Val Pro Phe Tyr Ala
1               5                   10                  15

Arg Ser Leu Ser Thr Val Arg Phe Pro His His His
            20                  25

<210> SEQ ID NO 438
<211> LENGTH: 28
<212> TYPE: PRT
<213> ORGANISM: artificial
<220> FEATURE:
<223> OTHER INFORMATION: Synthetic polypeptide

<400> SEQUENCE: 438

Val Lys Lys Leu Leu Phe Ala Ile Pro Leu Val Val Pro Phe Tyr Thr
1               5                   10                  15

Arg Ala Phe Ser Ser Pro Leu Ser Asn His His His
            20                  25

<210> SEQ ID NO 439
<211> LENGTH: 28
<212> TYPE: PRT
<213> ORGANISM: artificial
<220> FEATURE:
<223> OTHER INFORMATION: Synthetic polypeptide

<400> SEQUENCE: 439

Val Lys Lys Leu Leu Phe Ala Ile Pro Leu Val Val Pro Phe Tyr Asn
1               5                   10                  15

Arg Thr Pro Thr Ile Gln Arg Asp Ser His His His
            20                  25

<210> SEQ ID NO 440
<211> LENGTH: 28
<212> TYPE: PRT
<213> ORGANISM: artificial
<220> FEATURE:
<223> OTHER INFORMATION: Synthetic polypeptide

<400> SEQUENCE: 440

Val Lys Lys Leu Leu Phe Ala Ile Pro Leu Val Val Pro Phe Tyr Ala
1               5                   10                  15

Arg Ala Val Ser Arg Thr Val Pro Thr His His His
            20                  25

<210> SEQ ID NO 441
<211> LENGTH: 28
<212> TYPE: PRT
<213> ORGANISM: artificial
<220> FEATURE:
<223> OTHER INFORMATION: Synthetic polypeptide

<400> SEQUENCE: 441

Val Lys Lys Leu Leu Phe Ala Ile Pro Leu Val Val Pro Phe Tyr Ala

```
                1               5                  10                  15
Gln Ser Met Ala Val Pro Ile Ser Thr His His His
            20                  25
```

<210> SEQ ID NO 442
<211> LENGTH: 28
<212> TYPE: PRT
<213> ORGANISM: artificial
<220> FEATURE:
<223> OTHER INFORMATION: Synthetic polypeptide

<400> SEQUENCE: 442

```
Val Lys Lys Leu Leu Phe Ala Ile Pro Leu Val Val Pro Phe Tyr Pro
1               5                  10                  15
Gln Pro Ser Arg Gly Phe Met Leu Ile His His His
            20                  25
```

<210> SEQ ID NO 443
<211> LENGTH: 28
<212> TYPE: PRT
<213> ORGANISM: artificial
<220> FEATURE:
<223> OTHER INFORMATION: Synthetic polypeptide

<400> SEQUENCE: 443

```
Val Lys Lys Leu Leu Phe Ala Ile Pro Leu Val Val Pro Phe Tyr Thr
1               5                  10                  15
Arg Ser Met Val Phe Pro Ala Lys Val His His His
            20                  25
```

<210> SEQ ID NO 444
<211> LENGTH: 28
<212> TYPE: PRT
<213> ORGANISM: artificial
<220> FEATURE:
<223> OTHER INFORMATION: Synthetic polypeptide

<400> SEQUENCE: 444

```
Val Lys Lys Leu Leu Phe Ala Ile Pro Leu Val Val Pro Phe Tyr Ser
1               5                  10                  15
Arg Ser Met Thr Leu Lys Gly Pro Glu His His His
            20                  25
```

<210> SEQ ID NO 445
<211> LENGTH: 28
<212> TYPE: PRT
<213> ORGANISM: artificial
<220> FEATURE:
<223> OTHER INFORMATION: Synthetic polypeptide

<400> SEQUENCE: 445

```
Val Lys Lys Leu Leu Phe Ala Ile Pro Leu Val Val Pro Phe Tyr Ala
1               5                  10                  15
Phe Pro Phe Ser Arg Gln Pro Asn Ala His His His
            20                  25
```

<210> SEQ ID NO 446
<211> LENGTH: 28
<212> TYPE: PRT
<213> ORGANISM: artificial
<220> FEATURE:
<223> OTHER INFORMATION: Synthetic polypeptide

<400> SEQUENCE: 446

Val Lys Lys Leu Leu Phe Ala Ile Pro Leu Val Val Pro Phe Tyr Ser
1               5                   10                  15

Arg Ala Leu Thr Ser Ile Ser Gly Met His His His
                20                  25

<210> SEQ ID NO 447
<211> LENGTH: 28
<212> TYPE: PRT
<213> ORGANISM: artificial
<220> FEATURE:
<223> OTHER INFORMATION: Synthetic polypeptide

<400> SEQUENCE: 447

Val Lys Lys Leu Leu Phe Ala Ile Pro Leu Val Val Pro Phe Tyr Cys
1               5                   10                  15

Arg Gly Met Ser Leu Asn Val Thr Arg His His His
                20                  25

<210> SEQ ID NO 448
<211> LENGTH: 28
<212> TYPE: PRT
<213> ORGANISM: artificial
<220> FEATURE:
<223> OTHER INFORMATION: Synthetic polypeptide

<400> SEQUENCE: 448

Val Lys Lys Leu Leu Phe Ala Ile Pro Leu Val Val Pro Phe Tyr Ser
1               5                   10                  15

His Trp Arg Thr Gln Arg Pro Pro Glu His His His
                20                  25

<210> SEQ ID NO 449
<211> LENGTH: 28
<212> TYPE: PRT
<213> ORGANISM: artificial
<220> FEATURE:
<223> OTHER INFORMATION: Synthetic polypeptide

<400> SEQUENCE: 449

Val Lys Lys Leu Leu Phe Ala Ile Pro Leu Val Val Pro Phe Tyr Ala
1               5                   10                  15

Arg Ser Phe Ser Ser Pro Pro Gly Pro His His His
                20                  25

<210> SEQ ID NO 450
<211> LENGTH: 28
<212> TYPE: PRT
<213> ORGANISM: artificial
<220> FEATURE:
<223> OTHER INFORMATION: Synthetic polypeptide

<400> SEQUENCE: 450

Val Lys Lys Leu Leu Phe Ala Ile Pro Leu Val Val Pro Phe Tyr Ile
1               5                   10                  15

Phe Pro Ile Glu Ala Ser Ala Arg Arg His His His
                20                  25

<210> SEQ ID NO 451
<211> LENGTH: 28
<212> TYPE: PRT
<213> ORGANISM: artificial
<220> FEATURE:
<223> OTHER INFORMATION: Synthetic polypeptide

<400> SEQUENCE: 451

Val Lys Lys Leu Leu Phe Ala Ile Pro Leu Val Val Pro Phe Tyr Ala
1               5                   10                  15

Ser Ser Met Ala Leu Arg Pro Arg Val His His His
            20                  25

<210> SEQ ID NO 452
<211> LENGTH: 28
<212> TYPE: PRT
<213> ORGANISM: artificial
<220> FEATURE:
<223> OTHER INFORMATION: Synthetic polypeptide

<400> SEQUENCE: 452

Val Lys Lys Leu Leu Phe Ala Ile Pro Leu Val Val Pro Phe Tyr Ser
1               5                   10                  15

Arg Ala Phe Ser Ser Thr Pro Ala Met His His His
            20                  25

<210> SEQ ID NO 453
<211> LENGTH: 28
<212> TYPE: PRT
<213> ORGANISM: artificial
<220> FEATURE:
<223> OTHER INFORMATION: Synthetic polypeptide

<400> SEQUENCE: 453

Val Lys Lys Leu Leu Phe Ala Ile Pro Leu Val Val Pro Phe Tyr Ser
1               5                   10                  15

Arg Ser Met Val Leu Gln Gly Pro Thr His His His
            20                  25

<210> SEQ ID NO 454
<211> LENGTH: 28
<212> TYPE: PRT
<213> ORGANISM: artificial
<220> FEATURE:
<223> OTHER INFORMATION: Synthetic polypeptide

<400> SEQUENCE: 454

Val Lys Lys Leu Leu Phe Ala Ile Pro Leu Val Val Pro Phe Tyr Ser
1               5                   10                  15

Arg Ser Met Thr Ser Pro Pro Tyr Ile His His His
            20                  25

<210> SEQ ID NO 455
<211> LENGTH: 28
<212> TYPE: PRT
<213> ORGANISM: artificial
<220> FEATURE:
<223> OTHER INFORMATION: Synthetic polypeptide

<400> SEQUENCE: 455

Val Lys Lys Leu Leu Phe Ala Ile Pro Leu Val Val Pro Phe Tyr Ala
1               5                   10                  15

Asn Arg Pro Gln Ser Thr Lys Asn Ile His His His
            20                  25

<210> SEQ ID NO 456
<211> LENGTH: 28
<212> TYPE: PRT
<213> ORGANISM: artificial
<220> FEATURE:
<223> OTHER INFORMATION: Synthetic polypeptide

<400> SEQUENCE: 456

Val Lys Lys Leu Leu Phe Ala Ile Pro Leu Val Val Pro Phe Tyr Ser
1               5                   10                  15

Arg Ala Leu Thr Met Thr Pro Ser Phe His His His
            20                  25

<210> SEQ ID NO 457
<211> LENGTH: 28
<212> TYPE: PRT
<213> ORGANISM: artificial
<220> FEATURE:
<223> OTHER INFORMATION: Synthetic polypeptide

<400> SEQUENCE: 457

Val Lys Lys Leu Leu Phe Ala Ile Pro Leu Val Val Pro Phe Tyr Pro
1               5                   10                  15

Thr Arg Leu Phe Ala Phe Met Leu Thr His His His
            20                  25

<210> SEQ ID NO 458
<211> LENGTH: 28
<212> TYPE: PRT
<213> ORGANISM: artificial
<220> FEATURE:
<223> OTHER INFORMATION: Synthetic polypeptide

<400> SEQUENCE: 458

Val Lys Lys Leu Leu Phe Ala Ile Pro Leu Val Val Pro Phe Tyr Ser
1               5                   10                  15

Arg Ala Met Ser Pro Ile Pro Arg Gln His His His
            20                  25

<210> SEQ ID NO 459
<211> LENGTH: 28
<212> TYPE: PRT
<213> ORGANISM: artificial
<220> FEATURE:
<223> OTHER INFORMATION: Synthetic polypeptide

<400> SEQUENCE: 459

Val Lys Lys Leu Leu Phe Ala Ile Pro Leu Val Val Pro Phe Tyr Ala
1               5                   10                  15

Arg Ser Met Gly Ser Met Trp Gln Leu His His His
            20                  25

<210> SEQ ID NO 460
<211> LENGTH: 28
<212> TYPE: PRT
<213> ORGANISM: artificial
<220> FEATURE:
<223> OTHER INFORMATION: Synthetic polypeptide

<400> SEQUENCE: 460

Val Lys Lys Leu Leu Phe Ala Ile Pro Leu Val Val Pro Phe Tyr Ser
1               5                   10                  15

Phe Ser Met Thr Arg Ser Ser Pro Leu His His His
            20                  25

<210> SEQ ID NO 461
<211> LENGTH: 28
<212> TYPE: PRT
<213> ORGANISM: artificial
<220> FEATURE:
<223> OTHER INFORMATION: Synthetic polypeptide

```
<400> SEQUENCE: 461

Val Lys Lys Leu Leu Phe Ala Ile Pro Leu Val Val Pro Phe Tyr Ser
1               5                   10                  15

Phe Ser Phe Thr Arg Gln Pro Leu Pro His His His
            20                  25

<210> SEQ ID NO 462
<211> LENGTH: 28
<212> TYPE: PRT
<213> ORGANISM: artificial
<220> FEATURE:
<223> OTHER INFORMATION: Synthetic polypeptide

<400> SEQUENCE: 462

Val Lys Lys Leu Leu Phe Ala Ile Pro Leu Val Val Pro Phe Tyr Asn
1               5                   10                  15

Arg Val Pro Ser Pro Ala Ser Gln Thr His His His
            20                  25

<210> SEQ ID NO 463
<211> LENGTH: 28
<212> TYPE: PRT
<213> ORGANISM: artificial
<220> FEATURE:
<223> OTHER INFORMATION: Synthetic polypeptide

<400> SEQUENCE: 463

Val Lys Lys Leu Leu Phe Ala Ile Pro Leu Val Val Pro Phe Tyr Ser
1               5                   10                  15

Phe Ser Phe Ser Lys Pro Arg Phe Ser His His His
            20                  25

<210> SEQ ID NO 464
<211> LENGTH: 28
<212> TYPE: PRT
<213> ORGANISM: artificial
<220> FEATURE:
<223> OTHER INFORMATION: Synthetic polypeptide

<400> SEQUENCE: 464

Val Lys Lys Leu Leu Phe Ala Ile Pro Leu Val Val Pro Phe Tyr Ala
1               5                   10                  15

Arg Ser Leu Thr Gln Phe Ser Ser Val His His His
            20                  25

<210> SEQ ID NO 465
<211> LENGTH: 28
<212> TYPE: PRT
<213> ORGANISM: artificial
<220> FEATURE:
<223> OTHER INFORMATION: Synthetic polypeptide

<400> SEQUENCE: 465

Val Lys Lys Leu Leu Phe Ala Ile Pro Leu Val Val Pro Phe Tyr Ala
1               5                   10                  15

Arg Cys Phe Ser Ser Pro Val Ala Leu His His His
            20                  25

<210> SEQ ID NO 466
<211> LENGTH: 28
<212> TYPE: PRT
<213> ORGANISM: artificial
<220> FEATURE:
```

<223> OTHER INFORMATION: Synthetic polypeptide

<400> SEQUENCE: 466

Val Lys Lys Leu Leu Phe Ala Ile Pro Leu Val Val Pro Phe Tyr Gly
1               5                   10                  15
Ala Ser Ser Trp Trp Leu Phe Pro Ser His His His
            20                  25

<210> SEQ ID NO 467
<211> LENGTH: 28
<212> TYPE: PRT
<213> ORGANISM: artificial
<220> FEATURE:
<223> OTHER INFORMATION: Synthetic polypeptide

<400> SEQUENCE: 467

Val Lys Lys Leu Leu Phe Ala Ile Pro Leu Val Val Pro Phe Tyr Thr
1               5                   10                  15
Pro Pro Gln Gln Gln Ala Leu Leu Ser His His His
            20                  25

<210> SEQ ID NO 468
<211> LENGTH: 28
<212> TYPE: PRT
<213> ORGANISM: artificial
<220> FEATURE:
<223> OTHER INFORMATION: Synthetic polypeptide

<400> SEQUENCE: 468

Val Lys Lys Leu Leu Phe Ala Ile Pro Leu Val Val Pro Phe Tyr Ser
1               5                   10                  15
Arg Gly Phe Ser Met Ala Phe Phe Pro His His His
            20                  25

<210> SEQ ID NO 469
<211> LENGTH: 28
<212> TYPE: PRT
<213> ORGANISM: artificial
<220> FEATURE:
<223> OTHER INFORMATION: Synthetic polypeptide

<400> SEQUENCE: 469

Val Lys Lys Leu Leu Phe Ala Ile Pro Leu Val Val Pro Phe Tyr Ser
1               5                   10                  15
Leu Ala Met Ser Arg Pro Gln Ala Ser His His His
            20                  25

<210> SEQ ID NO 470
<211> LENGTH: 28
<212> TYPE: PRT
<213> ORGANISM: artificial
<220> FEATURE:
<223> OTHER INFORMATION: Synthetic polypeptide

<400> SEQUENCE: 470

Val Lys Lys Leu Leu Phe Ala Ile Pro Leu Val Val Pro Phe Tyr Thr
1               5                   10                  15
Tyr Ala Leu Thr Thr Phe Gln Ser Val His His His
            20                  25

<210> SEQ ID NO 471
<211> LENGTH: 28
<212> TYPE: PRT
<213> ORGANISM: artificial

<220> FEATURE:
<223> OTHER INFORMATION: Synthetic polypeptide

<400> SEQUENCE: 471

Val Lys Lys Leu Leu Phe Ala Ile Pro Leu Val Val Pro Phe Tyr Gln
1               5                   10                  15

His Ala Phe Thr Arg Pro Phe Arg Val His His His
            20                  25

<210> SEQ ID NO 472
<211> LENGTH: 28
<212> TYPE: PRT
<213> ORGANISM: artificial
<220> FEATURE:
<223> OTHER INFORMATION: Synthetic polypeptide

<400> SEQUENCE: 472

Val Lys Lys Leu Leu Phe Ala Ile Pro Leu Val Val Pro Phe Tyr Ser
1               5                   10                  15

Arg Ala Phe Ser Ser Pro Ser Gly Ser His His His
            20                  25

<210> SEQ ID NO 473
<211> LENGTH: 28
<212> TYPE: PRT
<213> ORGANISM: artificial
<220> FEATURE:
<223> OTHER INFORMATION: Synthetic polypeptide

<400> SEQUENCE: 473

Val Lys Lys Leu Leu Phe Ala Ile Pro Leu Val Val Pro Phe Tyr Thr
1               5                   10                  15

Ser Ala Leu Ala Arg Ser Pro Arg Val His His His
            20                  25

<210> SEQ ID NO 474
<211> LENGTH: 28
<212> TYPE: PRT
<213> ORGANISM: artificial
<220> FEATURE:
<223> OTHER INFORMATION: Synthetic polypeptide

<400> SEQUENCE: 474

Val Lys Lys Leu Leu Phe Ala Ile Pro Leu Val Val Pro Phe Tyr Cys
1               5                   10                  15

Arg Ala Met Ser Ser Pro Phe Arg Pro His His His
            20                  25

<210> SEQ ID NO 475
<211> LENGTH: 28
<212> TYPE: PRT
<213> ORGANISM: artificial
<220> FEATURE:
<223> OTHER INFORMATION: Synthetic polypeptide

<400> SEQUENCE: 475

Val Lys Lys Leu Leu Phe Ala Ile Pro Leu Val Val Pro Phe Tyr Ser
1               5                   10                  15

Thr Phe Ala Arg Ser Phe Met Leu Thr His His His
            20                  25

<210> SEQ ID NO 476
<211> LENGTH: 28
<212> TYPE: PRT

```
<213> ORGANISM: artificial
<220> FEATURE:
<223> OTHER INFORMATION: Synthetic polypeptide

<400> SEQUENCE: 476

Val Lys Lys Leu Leu Phe Ala Ile Pro Leu Val Val Pro Phe Tyr Phe
1               5                   10                  15

Pro Leu Ser Ser Arg Ala Phe Met Leu His His His
            20                  25

<210> SEQ ID NO 477
<211> LENGTH: 28
<212> TYPE: PRT
<213> ORGANISM: artificial
<220> FEATURE:
<223> OTHER INFORMATION: Synthetic polypeptide

<400> SEQUENCE: 477

Val Lys Lys Leu Leu Phe Ala Ile Pro Leu Val Val Pro Phe Tyr Ser
1               5                   10                  15

Arg Ser Met Ser Thr Ser Pro Ile Leu His His His
            20                  25

<210> SEQ ID NO 478
<211> LENGTH: 28
<212> TYPE: PRT
<213> ORGANISM: artificial
<220> FEATURE:
<223> OTHER INFORMATION: Synthetic polypeptide

<400> SEQUENCE: 478

Val Lys Lys Leu Leu Phe Ala Ile Pro Leu Val Val Pro Phe Tyr Ser
1               5                   10                  15

Phe Gly Leu Gln Leu Pro Gln Pro Phe His His His
            20                  25

<210> SEQ ID NO 479
<211> LENGTH: 28
<212> TYPE: PRT
<213> ORGANISM: artificial
<220> FEATURE:
<223> OTHER INFORMATION: Synthetic polypeptide

<400> SEQUENCE: 479

Val Lys Lys Leu Leu Phe Ala Ile Pro Leu Val Val Pro Phe Tyr Ser
1               5                   10                  15

Arg Ser Met Ser Leu Ser Ser Asp Leu His His His
            20                  25

<210> SEQ ID NO 480
<211> LENGTH: 28
<212> TYPE: PRT
<213> ORGANISM: artificial
<220> FEATURE:
<223> OTHER INFORMATION: Synthetic polypeptide

<400> SEQUENCE: 480

Val Lys Lys Leu Leu Phe Ala Ile Pro Leu Val Val Pro Phe Tyr Ala
1               5                   10                  15

Phe Pro Leu Ala Arg Arg Pro Ile Asn His His His
            20                  25

<210> SEQ ID NO 481
<211> LENGTH: 28
```

-continued

<212> TYPE: PRT
<213> ORGANISM: artificial
<220> FEATURE:
<223> OTHER INFORMATION: Synthetic polypeptide

<400> SEQUENCE: 481

Val Lys Lys Leu Leu Phe Ala Ile Pro Leu Val Val Pro Phe Tyr Thr
1               5                   10                  15

Ser Cys Arg Ala Met Thr Leu Pro Arg His His His
            20                  25

<210> SEQ ID NO 482
<211> LENGTH: 28
<212> TYPE: PRT
<213> ORGANISM: artificial
<220> FEATURE:
<223> OTHER INFORMATION: Synthetic polypeptide

<400> SEQUENCE: 482

Val Lys Lys Leu Leu Phe Ala Ile Pro Leu Val Val Pro Phe Tyr Thr
1               5                   10                  15

Tyr Pro Phe Ser Arg Ala Gly Pro Pro His His His
            20                  25

<210> SEQ ID NO 483
<211> LENGTH: 28
<212> TYPE: PRT
<213> ORGANISM: artificial
<220> FEATURE:
<223> OTHER INFORMATION: Synthetic polypeptide

<400> SEQUENCE: 483

Val Lys Lys Leu Leu Phe Ala Ile Pro Leu Val Val Pro Phe Tyr Ala
1               5                   10                  15

Asn Gln Gln Ala Leu Pro Phe Gln Leu His His His
            20                  25

<210> SEQ ID NO 484
<211> LENGTH: 28
<212> TYPE: PRT
<213> ORGANISM: artificial
<220> FEATURE:
<223> OTHER INFORMATION: Synthetic polypeptide

<400> SEQUENCE: 484

Val Lys Lys Leu Leu Phe Ala Ile Pro Leu Val Val Pro Phe Tyr Gly
1               5                   10                  15

Trp Ser Met Ser Leu Arg Ser Ser His His His
            20                  25

<210> SEQ ID NO 485
<211> LENGTH: 28
<212> TYPE: PRT
<213> ORGANISM: artificial
<220> FEATURE:
<223> OTHER INFORMATION: Synthetic polypeptide

<400> SEQUENCE: 485

Val Lys Lys Leu Leu Phe Ala Ile Pro Leu Val Val Pro Phe Tyr Ser
1               5                   10                  15

Pro Gln Val Val Thr Arg Lys Asp Leu His His His
            20                  25

<210> SEQ ID NO 486

<211> LENGTH: 28
<212> TYPE: PRT
<213> ORGANISM: artificial
<220> FEATURE:
<223> OTHER INFORMATION: Synthetic polypeptide

<400> SEQUENCE: 486

Val Lys Lys Leu Leu Phe Ala Ile Pro Leu Val Val Pro Phe Tyr Leu
1               5                   10                  15
Arg Asn Ala His Ala Met Ala Ser Ala His His His
            20                  25

<210> SEQ ID NO 487
<211> LENGTH: 28
<212> TYPE: PRT
<213> ORGANISM: artificial
<220> FEATURE:
<223> OTHER INFORMATION: Synthetic polypeptide

<400> SEQUENCE: 487

Val Lys Lys Leu Leu Phe Ala Ile Pro Leu Val Val Pro Phe Tyr Ser
1               5                   10                  15
Arg Ser Gly Ser Phe Asn Val Thr Pro His His His
            20                  25

<210> SEQ ID NO 488
<211> LENGTH: 28
<212> TYPE: PRT
<213> ORGANISM: artificial
<220> FEATURE:
<223> OTHER INFORMATION: Synthetic polypeptide

<400> SEQUENCE: 488

Val Lys Lys Leu Leu Phe Ala Ile Pro Leu Val Val Pro Phe Tyr Ser
1               5                   10                  15
Arg Pro Leu Ser Arg Val Pro Val Phe His His His
            20                  25

<210> SEQ ID NO 489
<211> LENGTH: 28
<212> TYPE: PRT
<213> ORGANISM: artificial
<220> FEATURE:
<223> OTHER INFORMATION: Synthetic polypeptide

<400> SEQUENCE: 489

Val Lys Lys Leu Leu Phe Ala Ile Pro Leu Val Val Pro Phe Tyr Ser
1               5                   10                  15
Lys Arg Met Pro Pro Pro Ile Ser Gln His His His
            20                  25

<210> SEQ ID NO 490
<211> LENGTH: 28
<212> TYPE: PRT
<213> ORGANISM: artificial
<220> FEATURE:
<223> OTHER INFORMATION: Synthetic polypeptide

<400> SEQUENCE: 490

Val Lys Lys Leu Leu Phe Ala Ile Pro Leu Val Val Pro Phe Tyr Thr
1               5                   10                  15
Arg Ser Met Ser Ser Leu Pro Ser Pro His His His
            20                  25

```
<210> SEQ ID NO 491
<211> LENGTH: 28
<212> TYPE: PRT
<213> ORGANISM: artificial
<220> FEATURE:
<223> OTHER INFORMATION: Synthetic polypeptide

<400> SEQUENCE: 491

Val Lys Lys Leu Leu Phe Ala Ile Pro Leu Val Val Pro Phe Tyr Cys
1               5                   10                  15

Arg Ser Ser Ser Ser Ile Phe Pro Leu His His His
            20                  25

<210> SEQ ID NO 492
<211> LENGTH: 28
<212> TYPE: PRT
<213> ORGANISM: artificial
<220> FEATURE:
<223> OTHER INFORMATION: Synthetic polypeptide

<400> SEQUENCE: 492

Val Lys Lys Leu Leu Phe Ala Ile Pro Leu Val Val Pro Phe Tyr Arg
1               5                   10                  15

Ser Ala His Ala Met Ser Ile Gln Thr His His His
            20                  25

<210> SEQ ID NO 493
<211> LENGTH: 28
<212> TYPE: PRT
<213> ORGANISM: artificial
<220> FEATURE:
<223> OTHER INFORMATION: Synthetic polypeptide

<400> SEQUENCE: 493

Val Lys Lys Leu Leu Phe Ala Ile Pro Leu Val Val Pro Phe Tyr Gly
1               5                   10                  15

Tyr Cys Phe Ser Ala Arg Ile Ile Arg His His His
            20                  25

<210> SEQ ID NO 494
<211> LENGTH: 28
<212> TYPE: PRT
<213> ORGANISM: artificial
<220> FEATURE:
<223> OTHER INFORMATION: Synthetic polypeptide

<400> SEQUENCE: 494

Val Lys Lys Leu Leu Phe Ala Ile Pro Leu Val Val Pro Phe Tyr Pro
1               5                   10                  15

His Leu Ser Pro Leu Gln Pro Gln Gln His His His
            20                  25

<210> SEQ ID NO 495
<211> LENGTH: 28
<212> TYPE: PRT
<213> ORGANISM: artificial
<220> FEATURE:
<223> OTHER INFORMATION: Synthetic polypeptide

<400> SEQUENCE: 495

Val Lys Lys Leu Leu Phe Ala Ile Pro Leu Val Val Pro Phe Tyr Ser
1               5                   10                  15

Phe Ser Phe Ser Arg Phe Pro Gly Leu His His His
            20                  25
```

<210> SEQ ID NO 496
<211> LENGTH: 28
<212> TYPE: PRT
<213> ORGANISM: artificial
<220> FEATURE:
<223> OTHER INFORMATION: Synthetic polypeptide

<400> SEQUENCE: 496

Val Lys Lys Leu Leu Phe Ala Ile Pro Leu Val Val Pro Phe Tyr Ser
1               5                   10                  15

Ser Ser Met Ser Leu Arg Pro Gln Phe His His His
            20                  25

<210> SEQ ID NO 497
<211> LENGTH: 28
<212> TYPE: PRT
<213> ORGANISM: artificial
<220> FEATURE:
<223> OTHER INFORMATION: Synthetic polypeptide

<400> SEQUENCE: 497

Val Lys Lys Leu Leu Phe Ala Ile Pro Leu Val Val Pro Phe Tyr Ser
1               5                   10                  15

Ser Pro Arg Ala Arg Pro Val Pro Pro His His His
            20                  25

<210> SEQ ID NO 498
<211> LENGTH: 28
<212> TYPE: PRT
<213> ORGANISM: artificial
<220> FEATURE:
<223> OTHER INFORMATION: Synthetic polypeptide

<400> SEQUENCE: 498

Val Lys Lys Leu Leu Phe Ala Ile Pro Leu Val Val Pro Phe Tyr Ala
1               5                   10                  15

Arg Ser Leu Ser Ala Leu Ser Pro Tyr His His His
            20                  25

<210> SEQ ID NO 499
<211> LENGTH: 28
<212> TYPE: PRT
<213> ORGANISM: artificial
<220> FEATURE:
<223> OTHER INFORMATION: Synthetic polypeptide

<400> SEQUENCE: 499

Val Lys Lys Leu Leu Phe Ala Ile Pro Leu Val Val Pro Phe Tyr Pro
1               5                   10                  15

Val Arg Gln Leu His Thr Asn Leu Arg His His His
            20                  25

<210> SEQ ID NO 500
<211> LENGTH: 28
<212> TYPE: PRT
<213> ORGANISM: artificial
<220> FEATURE:
<223> OTHER INFORMATION: Synthetic polypeptide

<400> SEQUENCE: 500

Val Lys Lys Leu Leu Phe Ala Ile Pro Leu Val Val Pro Phe Tyr Pro
1               5                   10                  15

Thr Thr Ser Thr Pro Tyr Gln Ser Pro His His His
            20                  25

```
<210> SEQ ID NO 501
<211> LENGTH: 28
<212> TYPE: PRT
<213> ORGANISM: artificial
<220> FEATURE:
<223> OTHER INFORMATION: Synthetic polypeptide

<400> SEQUENCE: 501

Val Lys Lys Leu Leu Phe Ala Ile Pro Leu Val Val Pro Phe Tyr Val
1               5                   10                  15

Asn Ala Leu Thr Phe Leu Pro Ser Gln His His His
            20                  25

<210> SEQ ID NO 502
<211> LENGTH: 28
<212> TYPE: PRT
<213> ORGANISM: artificial
<220> FEATURE:
<223> OTHER INFORMATION: Synthetic polypeptide

<400> SEQUENCE: 502

Val Lys Lys Leu Leu Phe Ala Ile Pro Leu Val Val Pro Phe Tyr Ala
1               5                   10                  15

Arg Ser Leu Ser Ser Pro Leu Thr Leu His His His
            20                  25

<210> SEQ ID NO 503
<211> LENGTH: 28
<212> TYPE: PRT
<213> ORGANISM: artificial
<220> FEATURE:
<223> OTHER INFORMATION: Synthetic polypeptide

<400> SEQUENCE: 503

Val Lys Lys Leu Leu Phe Ala Ile Pro Leu Val Val Pro Phe Tyr Thr
1               5                   10                  15

Arg Pro Pro Thr Val Gly Leu Arg Gln His His His
            20                  25

<210> SEQ ID NO 504
<211> LENGTH: 28
<212> TYPE: PRT
<213> ORGANISM: artificial
<220> FEATURE:
<223> OTHER INFORMATION: Synthetic polypeptide

<400> SEQUENCE: 504

Val Lys Lys Leu Leu Phe Ala Ile Pro Leu Val Val Pro Phe Tyr Thr
1               5                   10                  15

Arg Ala Leu Ser Pro Met Ser Trp Gln His His His
            20                  25

<210> SEQ ID NO 505
<211> LENGTH: 28
<212> TYPE: PRT
<213> ORGANISM: artificial
<220> FEATURE:
<223> OTHER INFORMATION: Synthetic polypeptide

<400> SEQUENCE: 505

Val Lys Lys Leu Leu Phe Ala Ile Pro Leu Val Val Pro Phe Tyr Val
1               5                   10                  15

Phe Pro Phe Ser Arg Pro Leu Leu Arg His His His
```

```
                20                  25

<210> SEQ ID NO 506
<211> LENGTH: 28
<212> TYPE: PRT
<213> ORGANISM: artificial
<220> FEATURE:
<223> OTHER INFORMATION: Synthetic polypeptide

<400> SEQUENCE: 506

Val Lys Lys Leu Leu Phe Ala Ile Pro Leu Val Val Pro Phe Tyr Val
1               5                   10                  15

Pro Arg Cys Leu Ser Met Ser Leu Gly His His His
                20                  25

<210> SEQ ID NO 507
<211> LENGTH: 28
<212> TYPE: PRT
<213> ORGANISM: artificial
<220> FEATURE:
<223> OTHER INFORMATION: Synthetic polypeptide

<400> SEQUENCE: 507

Val Lys Lys Leu Leu Phe Ala Ile Pro Leu Val Val Pro Phe Tyr Gln
1               5                   10                  15

Gln Pro Ser Phe His Pro Ile Ser Arg His His His
                20                  25

<210> SEQ ID NO 508
<211> LENGTH: 28
<212> TYPE: PRT
<213> ORGANISM: artificial
<220> FEATURE:
<223> OTHER INFORMATION: Synthetic polypeptide

<400> SEQUENCE: 508

Val Lys Lys Leu Leu Phe Ala Ile Pro Leu Val Val Pro Phe Tyr Ser
1               5                   10                  15

Lys Ala Phe Ser Ser Phe Gln Ala Ser His His His
                20                  25

<210> SEQ ID NO 509
<211> LENGTH: 28
<212> TYPE: PRT
<213> ORGANISM: artificial
<220> FEATURE:
<223> OTHER INFORMATION: Synthetic polypeptide

<400> SEQUENCE: 509

Val Lys Lys Leu Leu Phe Ala Ile Pro Leu Val Val Pro Phe Tyr Gly
1               5                   10                  15

Tyr Ser Met Ser Gln Ser Gly Leu Thr His His His
                20                  25

<210> SEQ ID NO 510
<211> LENGTH: 28
<212> TYPE: PRT
<213> ORGANISM: artificial
<220> FEATURE:
<223> OTHER INFORMATION: Synthetic polypeptide

<400> SEQUENCE: 510

Val Lys Lys Leu Leu Phe Ala Ile Pro Leu Val Val Pro Phe Tyr Ala
1               5                   10                  15
```

Gln Ala Leu Thr Thr Arg Gly Leu Ala His His His
            20                  25

<210> SEQ ID NO 511
<211> LENGTH: 28
<212> TYPE: PRT
<213> ORGANISM: artificial
<220> FEATURE:
<223> OTHER INFORMATION: Synthetic polypeptide

<400> SEQUENCE: 511

Val Lys Lys Leu Leu Phe Ala Ile Pro Leu Val Val Pro Phe Tyr Val
1               5                   10                  15
Lys Ser Leu Thr Arg Pro Ala Phe Leu His His His
            20                  25

<210> SEQ ID NO 512
<211> LENGTH: 28
<212> TYPE: PRT
<213> ORGANISM: artificial
<220> FEATURE:
<223> OTHER INFORMATION: Synthetic polypeptide

<400> SEQUENCE: 512

Val Lys Lys Leu Leu Phe Ala Ile Pro Leu Val Val Pro Phe Tyr Ala
1               5                   10                  15
Gln Ser Arg Leu Arg Val Tyr Pro Pro His His His
            20                  25

<210> SEQ ID NO 513
<211> LENGTH: 28
<212> TYPE: PRT
<213> ORGANISM: artificial
<220> FEATURE:
<223> OTHER INFORMATION: Synthetic polypeptide

<400> SEQUENCE: 513

Val Lys Lys Leu Leu Phe Ala Ile Pro Leu Val Val Pro Phe Tyr Pro
1               5                   10                  15
Ala Ile Gly Phe Met Leu Leu Arg Tyr His His His
            20                  25

<210> SEQ ID NO 514
<211> LENGTH: 28
<212> TYPE: PRT
<213> ORGANISM: artificial
<220> FEATURE:
<223> OTHER INFORMATION: Synthetic polypeptide

<400> SEQUENCE: 514

Val Lys Lys Leu Leu Phe Ala Ile Pro Leu Val Val Pro Phe Tyr Ser
1               5                   10                  15
Phe Gly Thr Leu Val Arg Pro Arg Pro His His His
            20                  25

<210> SEQ ID NO 515
<211> LENGTH: 28
<212> TYPE: PRT
<213> ORGANISM: artificial
<220> FEATURE:
<223> OTHER INFORMATION: Synthetic polypeptide

<400> SEQUENCE: 515

Val Lys Lys Leu Leu Phe Ala Ile Pro Leu Val Val Pro Phe Tyr Ile
1               5                   10                  15

Arg Arg Pro Val Asp Pro Val Met Pro His His His
            20                  25

<210> SEQ ID NO 516
<211> LENGTH: 28
<212> TYPE: PRT
<213> ORGANISM: artificial
<220> FEATURE:
<223> OTHER INFORMATION: Synthetic polypeptide

<400> SEQUENCE: 516

Val Lys Lys Leu Leu Phe Ala Ile Pro Leu Val Val Pro Phe Tyr Phe
1               5                   10                  15

Pro Leu Arg Gln Thr His Arg Tyr Pro His His His
            20                  25

<210> SEQ ID NO 517
<211> LENGTH: 28
<212> TYPE: PRT
<213> ORGANISM: artificial
<220> FEATURE:
<223> OTHER INFORMATION: Synthetic polypeptide

<400> SEQUENCE: 517

Val Lys Lys Leu Leu Phe Ala Ile Pro Leu Val Val Pro Phe Tyr Thr
1               5                   10                  15

His Ser Met Gln Arg Pro Thr Gly Arg His His His
            20                  25

<210> SEQ ID NO 518
<211> LENGTH: 28
<212> TYPE: PRT
<213> ORGANISM: artificial
<220> FEATURE:
<223> OTHER INFORMATION: Synthetic polypeptide

<400> SEQUENCE: 518

Val Lys Lys Leu Leu Phe Ala Ile Pro Leu Val Val Pro Phe Tyr Arg
1               5                   10                  15

His Thr Gln Leu Ser Ser Ser Thr Ser His His His
            20                  25

<210> SEQ ID NO 519
<211> LENGTH: 28
<212> TYPE: PRT
<213> ORGANISM: artificial
<220> FEATURE:
<223> OTHER INFORMATION: Synthetic polypeptide

<400> SEQUENCE: 519

Val Lys Lys Leu Leu Phe Ala Ile Pro Leu Val Val Pro Phe Tyr Ser
1               5                   10                  15

Cys Gly Phe Ser Arg Leu Ser Lys Ala His His His
            20                  25

<210> SEQ ID NO 520
<211> LENGTH: 28
<212> TYPE: PRT
<213> ORGANISM: artificial
<220> FEATURE:
<223> OTHER INFORMATION: Synthetic polypeptide

<400> SEQUENCE: 520

Val Lys Lys Leu Leu Phe Ala Ile Pro Leu Val Val Pro Phe Tyr Ser

```
                1               5                   10                  15
Arg Ser Phe Ser Gln Leu Pro His Ile His His His
                20                  25
```

<210> SEQ ID NO 521
<211> LENGTH: 28
<212> TYPE: PRT
<213> ORGANISM: artificial
<220> FEATURE:
<223> OTHER INFORMATION: Synthetic polypeptide

<400> SEQUENCE: 521

```
Val Lys Lys Leu Leu Phe Ala Ile Pro Leu Val Val Pro Phe Tyr Ser
1               5                   10                  15
Ser Ser Met Ser Gln Leu Arg Pro Phe His His His
                20                  25
```

<210> SEQ ID NO 522
<211> LENGTH: 28
<212> TYPE: PRT
<213> ORGANISM: artificial
<220> FEATURE:
<223> OTHER INFORMATION: Synthetic polypeptide

<400> SEQUENCE: 522

```
Val Lys Lys Leu Leu Phe Ala Ile Pro Leu Val Val Pro Phe Tyr Cys
1               5                   10                  15
Arg Thr Thr Phe Ala Leu Gln Ser Ser His His His
                20                  25
```

<210> SEQ ID NO 523
<211> LENGTH: 28
<212> TYPE: PRT
<213> ORGANISM: artificial
<220> FEATURE:
<223> OTHER INFORMATION: Synthetic polypeptide

<400> SEQUENCE: 523

```
Val Lys Lys Leu Leu Phe Ala Ile Pro Leu Val Val Pro Phe Tyr Ala
1               5                   10                  15
Gln Ser Met Ser Ile Arg His Asn Asn His His His
                20                  25
```

<210> SEQ ID NO 524
<211> LENGTH: 28
<212> TYPE: PRT
<213> ORGANISM: artificial
<220> FEATURE:
<223> OTHER INFORMATION: Synthetic polypeptide

<400> SEQUENCE: 524

```
Val Lys Lys Leu Leu Phe Ala Ile Pro Leu Val Val Pro Phe Tyr Asn
1               5                   10                  15
Ser Arg Phe Arg Thr Thr Pro Pro Ser His His His
                20                  25
```

<210> SEQ ID NO 525
<211> LENGTH: 28
<212> TYPE: PRT
<213> ORGANISM: artificial
<220> FEATURE:
<223> OTHER INFORMATION: Synthetic polypeptide

<400> SEQUENCE: 525

Val Lys Lys Leu Leu Phe Ala Ile Pro Leu Val Val Pro Phe Tyr Ser
1               5                   10                  15

Val Ser Met Ser Arg Tyr Gln Leu Ser His His His
            20                  25

<210> SEQ ID NO 526
<211> LENGTH: 28
<212> TYPE: PRT
<213> ORGANISM: artificial
<220> FEATURE:
<223> OTHER INFORMATION: Synthetic polypeptide

<400> SEQUENCE: 526

Val Lys Lys Leu Leu Phe Ala Ile Pro Leu Val Val Pro Phe Tyr Ser
1               5                   10                  15

Ser Gly Ala Ser Arg Leu Arg Ile Leu His His His
            20                  25

<210> SEQ ID NO 527
<211> LENGTH: 28
<212> TYPE: PRT
<213> ORGANISM: artificial
<220> FEATURE:
<223> OTHER INFORMATION: Synthetic polypeptide

<400> SEQUENCE: 527

Val Lys Lys Leu Leu Phe Ala Ile Pro Leu Val Val Pro Phe Tyr Cys
1               5                   10                  15

Trp Ser Leu Ser Arg Pro Arg Leu Leu His His His
            20                  25

<210> SEQ ID NO 528
<211> LENGTH: 28
<212> TYPE: PRT
<213> ORGANISM: artificial
<220> FEATURE:
<223> OTHER INFORMATION: Synthetic polypeptide

<400> SEQUENCE: 528

Val Lys Lys Leu Leu Phe Ala Ile Pro Leu Val Val Pro Phe Tyr Thr
1               5                   10                  15

Ser Arg Ser Thr Lys Leu Thr Pro Ser His His His
            20                  25

<210> SEQ ID NO 529
<211> LENGTH: 28
<212> TYPE: PRT
<213> ORGANISM: artificial
<220> FEATURE:
<223> OTHER INFORMATION: Synthetic polypeptide

<400> SEQUENCE: 529

Val Lys Lys Leu Leu Phe Ala Ile Pro Leu Val Val Pro Phe Tyr Ser
1               5                   10                  15

Arg Val Ser Val Ala Phe Met Leu Met His His His
            20                  25

<210> SEQ ID NO 530
<211> LENGTH: 28
<212> TYPE: PRT
<213> ORGANISM: artificial
<220> FEATURE:
<223> OTHER INFORMATION: Synthetic polypeptide

<400> SEQUENCE: 530

Val Lys Lys Leu Leu Phe Ala Ile Pro Leu Val Val Pro Phe Tyr Cys
1               5                   10                  15

Leu Gly Arg Ser Met Ala Pro Gly Pro His His His
                20                  25

<210> SEQ ID NO 531
<211> LENGTH: 28
<212> TYPE: PRT
<213> ORGANISM: artificial
<220> FEATURE:
<223> OTHER INFORMATION: Synthetic polypeptide

<400> SEQUENCE: 531

Val Lys Lys Leu Leu Phe Ala Ile Pro Leu Val Val Pro Phe Tyr Phe
1               5                   10                  15

Val His Arg Arg Asp Ser Ser Ser Leu His His His
                20                  25

<210> SEQ ID NO 532
<211> LENGTH: 28
<212> TYPE: PRT
<213> ORGANISM: artificial
<220> FEATURE:
<223> OTHER INFORMATION: Synthetic polypeptide

<400> SEQUENCE: 532

Val Lys Lys Leu Leu Phe Ala Ile Pro Leu Val Val Pro Phe Tyr Ser
1               5                   10                  15

Leu Gly Phe Ser Arg Leu Thr Ser Leu His His His
                20                  25

<210> SEQ ID NO 533
<211> LENGTH: 28
<212> TYPE: PRT
<213> ORGANISM: artificial
<220> FEATURE:
<223> OTHER INFORMATION: Synthetic polypeptide

<400> SEQUENCE: 533

Val Lys Lys Leu Leu Phe Ala Ile Pro Leu Val Val Pro Phe Tyr Ala
1               5                   10                  15

Ser Ala Leu Ser Arg Arg Val Pro Gln His His His
                20                  25

<210> SEQ ID NO 534
<211> LENGTH: 28
<212> TYPE: PRT
<213> ORGANISM: artificial
<220> FEATURE:
<223> OTHER INFORMATION: Synthetic polypeptide

<400> SEQUENCE: 534

Val Lys Lys Leu Leu Phe Ala Ile Pro Leu Val Val Pro Phe Tyr Thr
1               5                   10                  15

Tyr Pro Ala Ser Trp Pro Arg Leu Arg His His His
                20                  25

<210> SEQ ID NO 535
<211> LENGTH: 28
<212> TYPE: PRT
<213> ORGANISM: artificial
<220> FEATURE:
<223> OTHER INFORMATION: Synthetic polypeptide

<400> SEQUENCE: 535

Val Lys Lys Leu Leu Phe Ala Ile Pro Leu Val Val Pro Phe Tyr Ser
1               5                   10                  15
Arg Val Ser Leu Ala Val Thr Pro Ser His His His
            20                  25

<210> SEQ ID NO 536
<211> LENGTH: 28
<212> TYPE: PRT
<213> ORGANISM: artificial
<220> FEATURE:
<223> OTHER INFORMATION: Synthetic polypeptide

<400> SEQUENCE: 536

Val Lys Lys Leu Leu Phe Ala Ile Pro Leu Val Val Pro Phe Tyr Asn
1               5                   10                  15
Asn Pro Phe Ser Ser Leu Ser Gln Gln His His His
            20                  25

<210> SEQ ID NO 537
<211> LENGTH: 28
<212> TYPE: PRT
<213> ORGANISM: artificial
<220> FEATURE:
<223> OTHER INFORMATION: Synthetic polypeptide

<400> SEQUENCE: 537

Val Lys Lys Leu Leu Phe Ala Ile Pro Leu Val Val Pro Phe Tyr Arg
1               5                   10                  15
Pro Leu Pro Arg Pro Phe Ala Gly Asn His His His
            20                  25

<210> SEQ ID NO 538
<211> LENGTH: 28
<212> TYPE: PRT
<213> ORGANISM: artificial
<220> FEATURE:
<223> OTHER INFORMATION: Synthetic polypeptide

<400> SEQUENCE: 538

Val Lys Lys Leu Leu Phe Ala Ile Pro Leu Val Val Pro Phe Tyr Gly
1               5                   10                  15
Phe Ser Met Thr Gln Tyr Leu Pro Gln His His His
            20                  25

<210> SEQ ID NO 539
<211> LENGTH: 28
<212> TYPE: PRT
<213> ORGANISM: artificial
<220> FEATURE:
<223> OTHER INFORMATION: Synthetic polypeptide

<400> SEQUENCE: 539

Val Lys Lys Leu Leu Phe Ala Ile Pro Leu Val Val Pro Phe Tyr Ser
1               5                   10                  15
Ser Ala Leu Ser Arg Ser Phe Tyr Pro His His His
            20                  25

<210> SEQ ID NO 540
<211> LENGTH: 28
<212> TYPE: PRT
<213> ORGANISM: artificial
<220> FEATURE:
<223> OTHER INFORMATION: Synthetic polypeptide

```
<400> SEQUENCE: 540

Val Lys Lys Leu Leu Phe Ala Ile Pro Leu Val Val Pro Phe Tyr Thr
1               5                   10                  15

Gln Gln Arg Cys Phe Ala Met His Ile His His His
            20                  25

<210> SEQ ID NO 541
<211> LENGTH: 28
<212> TYPE: PRT
<213> ORGANISM: artificial
<220> FEATURE:
<223> OTHER INFORMATION: Synthetic polypeptide

<400> SEQUENCE: 541

Val Lys Lys Leu Leu Phe Ala Ile Pro Leu Val Val Pro Phe Tyr Ile
1               5                   10                  15

Lys His Phe Tyr Asn Ser Arg Pro Ser His His His
            20                  25

<210> SEQ ID NO 542
<211> LENGTH: 28
<212> TYPE: PRT
<213> ORGANISM: artificial
<220> FEATURE:
<223> OTHER INFORMATION: Synthetic polypeptide

<400> SEQUENCE: 542

Val Lys Lys Leu Leu Phe Ala Ile Pro Leu Val Val Pro Phe Tyr Phe
1               5                   10                  15

Thr Arg Leu Pro Lys Glu Ser Ser Pro His His His
            20                  25

<210> SEQ ID NO 543
<211> LENGTH: 28
<212> TYPE: PRT
<213> ORGANISM: artificial
<220> FEATURE:
<223> OTHER INFORMATION: Synthetic polypeptide

<400> SEQUENCE: 543

Val Lys Lys Leu Leu Phe Ala Ile Pro Leu Val Val Pro Phe Tyr Leu
1               5                   10                  15

Pro Ala Gln Pro Arg Val Thr Arg Thr His His His
            20                  25

<210> SEQ ID NO 544
<211> LENGTH: 28
<212> TYPE: PRT
<213> ORGANISM: artificial
<220> FEATURE:
<223> OTHER INFORMATION: Synthetic polypeptide

<400> SEQUENCE: 544

Val Lys Lys Leu Leu Phe Ala Ile Pro Leu Val Val Pro Phe Tyr Leu
1               5                   10                  15

Arg Ser Met Thr Leu Asn Thr Ser Thr His His His
            20                  25

<210> SEQ ID NO 545
<211> LENGTH: 28
<212> TYPE: PRT
<213> ORGANISM: artificial
<220> FEATURE:
```

<223> OTHER INFORMATION: Synthetic polypeptide

<400> SEQUENCE: 545

Val Lys Lys Leu Leu Phe Ala Ile Pro Leu Val Val Pro Phe Tyr Pro
1               5                   10                  15

Asp Thr Phe Ser Tyr Ser Ser Gln Asp His His His
            20                  25

<210> SEQ ID NO 546
<211> LENGTH: 28
<212> TYPE: PRT
<213> ORGANISM: artificial
<220> FEATURE:
<223> OTHER INFORMATION: Synthetic polypeptide

<400> SEQUENCE: 546

Val Lys Lys Leu Leu Phe Ala Ile Pro Leu Val Val Pro Phe Tyr Phe
1               5                   10                  15

Arg Asn Pro Gln Leu Pro Ser Ser Ala His His His
            20                  25

<210> SEQ ID NO 547
<211> LENGTH: 28
<212> TYPE: PRT
<213> ORGANISM: artificial
<220> FEATURE:
<223> OTHER INFORMATION: Synthetic polypeptide

<400> SEQUENCE: 547

Val Lys Lys Leu Leu Phe Ala Ile Pro Leu Val Val Pro Phe Tyr Phe
1               5                   10                  15

Arg Pro Asp Arg Thr Pro Pro Ser Ser His His His
            20                  25

<210> SEQ ID NO 548
<211> LENGTH: 28
<212> TYPE: PRT
<213> ORGANISM: artificial
<220> FEATURE:
<223> OTHER INFORMATION: Synthetic polypeptide

<400> SEQUENCE: 548

Val Lys Lys Leu Leu Phe Ala Ile Pro Leu Val Val Pro Phe Tyr Gln
1               5                   10                  15

Ser His Thr Ile Leu Pro Leu Pro Ala His His His
            20                  25

<210> SEQ ID NO 549
<211> LENGTH: 28
<212> TYPE: PRT
<213> ORGANISM: artificial
<220> FEATURE:
<223> OTHER INFORMATION: Synthetic polypeptide

<400> SEQUENCE: 549

Val Lys Lys Leu Leu Phe Ala Ile Pro Leu Val Val Pro Phe Tyr Ser
1               5                   10                  15

Ser Ala Phe Gln Pro Met Val Ser Ser His His His
            20                  25

<210> SEQ ID NO 550
<211> LENGTH: 28
<212> TYPE: PRT
<213> ORGANISM: artificial

<220> FEATURE:
<223> OTHER INFORMATION: Synthetic polypeptide

<400> SEQUENCE: 550

Val Lys Lys Leu Leu Phe Ala Ile Pro Leu Val Val Pro Phe Tyr Gln
1               5                   10                  15

Ser Arg Arg Leu Pro Ile Leu Pro Leu His His His
            20                  25

<210> SEQ ID NO 551
<211> LENGTH: 28
<212> TYPE: PRT
<213> ORGANISM: artificial
<220> FEATURE:
<223> OTHER INFORMATION: Synthetic polypeptide

<400> SEQUENCE: 551

Val Lys Lys Leu Leu Phe Ala Ile Pro Leu Val Val Pro Phe Tyr Gly
1               5                   10                  15

Gln Ala Tyr Leu Pro Ala Pro Gln Leu His His His
            20                  25

<210> SEQ ID NO 552
<211> LENGTH: 28
<212> TYPE: PRT
<213> ORGANISM: artificial
<220> FEATURE:
<223> OTHER INFORMATION: Synthetic polypeptide

<400> SEQUENCE: 552

Val Lys Lys Leu Leu Phe Ala Ile Pro Leu Val Val Pro Phe Tyr Thr
1               5                   10                  15

Ser Arg Pro Arg Glu Thr Leu Phe Leu His His His
            20                  25

<210> SEQ ID NO 553
<211> LENGTH: 28
<212> TYPE: PRT
<213> ORGANISM: artificial
<220> FEATURE:
<223> OTHER INFORMATION: Synthetic polypeptide

<400> SEQUENCE: 553

Val Lys Lys Leu Leu Phe Ala Ile Pro Leu Val Val Pro Phe Tyr Thr
1               5                   10                  15

Ala Ala Ser Val Val Arg Ser Arg Asp His His His
            20                  25

<210> SEQ ID NO 554
<211> LENGTH: 28
<212> TYPE: PRT
<213> ORGANISM: artificial
<220> FEATURE:
<223> OTHER INFORMATION: Synthetic polypeptide

<400> SEQUENCE: 554

Val Lys Lys Leu Leu Phe Ala Ile Pro Leu Val Val Pro Phe Tyr Val
1               5                   10                  15

Arg Gly Ala Ala Pro Lys Phe Ser Val His His His
            20                  25

<210> SEQ ID NO 555
<211> LENGTH: 28
<212> TYPE: PRT

-continued

```
<213> ORGANISM: artificial
<220> FEATURE:
<223> OTHER INFORMATION: Synthetic polypeptide

<400> SEQUENCE: 555

Val Lys Lys Leu Leu Phe Ala Ile Pro Leu Val Val Pro Phe Tyr Phe
1               5                   10                  15

Arg His Gln Pro Ala Ser Val Ser Thr His His His
            20                  25

<210> SEQ ID NO 556
<211> LENGTH: 28
<212> TYPE: PRT
<213> ORGANISM: artificial
<220> FEATURE:
<223> OTHER INFORMATION: Synthetic polypeptide

<400> SEQUENCE: 556

Val Lys Lys Leu Leu Phe Ala Ile Pro Leu Val Val Pro Phe Tyr Pro
1               5                   10                  15

Thr Asn Ala Ile Ala Phe Phe Leu Gln His His His
            20                  25

<210> SEQ ID NO 557
<211> LENGTH: 28
<212> TYPE: PRT
<213> ORGANISM: artificial
<220> FEATURE:
<223> OTHER INFORMATION: Synthetic polypeptide

<400> SEQUENCE: 557

Val Lys Lys Leu Leu Phe Ala Ile Pro Leu Val Val Pro Phe Tyr Leu
1               5                   10                  15

Lys Ser Leu Arg Ser Asp Thr Pro Asn His His His
            20                  25

<210> SEQ ID NO 558
<211> LENGTH: 28
<212> TYPE: PRT
<213> ORGANISM: artificial
<220> FEATURE:
<223> OTHER INFORMATION: Synthetic polypeptide

<400> SEQUENCE: 558

Val Lys Lys Leu Leu Phe Ala Ile Pro Leu Val Val Pro Phe Tyr Ile
1               5                   10                  15

Lys Arg Pro Leu Pro Leu Ala Pro Thr His His His
            20                  25

<210> SEQ ID NO 559
<211> LENGTH: 28
<212> TYPE: PRT
<213> ORGANISM: artificial
<220> FEATURE:
<223> OTHER INFORMATION: Synthetic polypeptide

<400> SEQUENCE: 559

Val Lys Lys Leu Leu Phe Ala Ile Pro Leu Val Val Pro Phe Tyr Ala
1               5                   10                  15

Ser Ser Ser Lys Ser Arg Phe Met Leu His His His
            20                  25

<210> SEQ ID NO 560
<211> LENGTH: 28
```

```
<212> TYPE: PRT
<213> ORGANISM: artificial
<220> FEATURE:
<223> OTHER INFORMATION: Synthetic polypeptide

<400> SEQUENCE: 560

Val Lys Lys Leu Leu Phe Ala Ile Pro Leu Val Val Pro Phe Tyr Pro
1               5                   10                  15

Trp Lys Pro Arg Leu Leu Pro Pro Gln His His His
            20                  25

<210> SEQ ID NO 561
<211> LENGTH: 28
<212> TYPE: PRT
<213> ORGANISM: artificial
<220> FEATURE:
<223> OTHER INFORMATION: Synthetic polypeptide

<400> SEQUENCE: 561

Val Lys Lys Leu Leu Phe Ala Ile Pro Leu Val Val Pro Phe Tyr Ser
1               5                   10                  15

Arg Gly Phe Met Leu Thr Leu Arg Tyr His His His
            20                  25

<210> SEQ ID NO 562
<211> LENGTH: 28
<212> TYPE: PRT
<213> ORGANISM: artificial
<220> FEATURE:
<223> OTHER INFORMATION: Synthetic polypeptide

<400> SEQUENCE: 562

Val Lys Lys Leu Leu Phe Ala Ile Pro Leu Val Val Pro Phe Tyr Cys
1               5                   10                  15

Lys Ala Arg Gly Ile Met Pro Val Phe His His His
            20                  25

<210> SEQ ID NO 563
<211> LENGTH: 28
<212> TYPE: PRT
<213> ORGANISM: artificial
<220> FEATURE:
<223> OTHER INFORMATION: Synthetic polypeptide

<400> SEQUENCE: 563

Val Lys Lys Leu Leu Phe Ala Ile Pro Leu Val Val Pro Phe Tyr Ala
1               5                   10                  15

Ser Leu Pro Arg Leu Thr Ser Gln Ser His His His
            20                  25

<210> SEQ ID NO 564
<211> LENGTH: 28
<212> TYPE: PRT
<213> ORGANISM: artificial
<220> FEATURE:
<223> OTHER INFORMATION: Synthetic polypeptide

<400> SEQUENCE: 564

Val Lys Lys Leu Leu Phe Ala Ile Pro Leu Val Val Pro Phe Tyr Gln
1               5                   10                  15

Ser Ser Ala Phe Ser Tyr Met Leu Ser His His His
            20                  25

<210> SEQ ID NO 565
```

```
<211> LENGTH: 28
<212> TYPE: PRT
<213> ORGANISM: artificial
<220> FEATURE:
<223> OTHER INFORMATION: Synthetic polypeptide

<400> SEQUENCE: 565

Val Lys Lys Leu Leu Phe Ala Ile Pro Leu Val Val Pro Phe Tyr Ser
1               5                   10                  15
Phe Ser Ser Gln Arg Phe Leu Arg Pro His His His
            20                  25

<210> SEQ ID NO 566
<211> LENGTH: 28
<212> TYPE: PRT
<213> ORGANISM: artificial
<220> FEATURE:
<223> OTHER INFORMATION: Synthetic polypeptide

<400> SEQUENCE: 566

Val Lys Lys Leu Leu Phe Ala Ile Pro Leu Val Val Pro Phe Tyr Thr
1               5                   10                  15
Ser Ser Asn Thr Ser Arg Arg Phe Pro His His His
            20                  25

<210> SEQ ID NO 567
<211> LENGTH: 28
<212> TYPE: PRT
<213> ORGANISM: artificial
<220> FEATURE:
<223> OTHER INFORMATION: Synthetic polypeptide

<400> SEQUENCE: 567

Val Lys Lys Leu Leu Phe Ala Ile Pro Leu Val Val Pro Phe Tyr Asn
1               5                   10                  15
Gln Thr Ala Ala Thr Ala Pro Pro Arg His His His
            20                  25

<210> SEQ ID NO 568
<211> LENGTH: 28
<212> TYPE: PRT
<213> ORGANISM: artificial
<220> FEATURE:
<223> OTHER INFORMATION: Synthetic polypeptide

<400> SEQUENCE: 568

Val Lys Lys Leu Leu Phe Ala Ile Pro Leu Val Val Pro Phe Tyr Gly
1               5                   10                  15
Ala Pro Leu Ser Trp Arg Arg Ser Tyr His His His
            20                  25

<210> SEQ ID NO 569
<211> LENGTH: 28
<212> TYPE: PRT
<213> ORGANISM: artificial
<220> FEATURE:
<223> OTHER INFORMATION: Synthetic polypeptide

<400> SEQUENCE: 569

Val Lys Lys Leu Leu Phe Ala Ile Pro Leu Val Val Pro Phe Tyr Cys
1               5                   10                  15
Arg Ser Val Trp Cys Ile Pro Arg Pro His His His
            20                  25
```

```
<210> SEQ ID NO 570
<211> LENGTH: 28
<212> TYPE: PRT
<213> ORGANISM: artificial
<220> FEATURE:
<223> OTHER INFORMATION: Synthetic polypeptide

<400> SEQUENCE: 570

Val Lys Lys Leu Leu Phe Ala Ile Pro Leu Val Val Pro Phe Tyr Ala
1               5                   10                  15

Lys Ala Cys Leu Arg Pro Leu Gln Thr His His His
            20                  25

<210> SEQ ID NO 571
<211> LENGTH: 28
<212> TYPE: PRT
<213> ORGANISM: artificial
<220> FEATURE:
<223> OTHER INFORMATION: Synthetic polypeptide

<400> SEQUENCE: 571

Val Lys Lys Leu Leu Phe Ala Ile Pro Leu Val Val Pro Phe Tyr Cys
1               5                   10                  15

Leu Ala Ser Ser His Arg His Arg Pro His His His
            20                  25

<210> SEQ ID NO 572
<211> LENGTH: 28
<212> TYPE: PRT
<213> ORGANISM: artificial
<220> FEATURE:
<223> OTHER INFORMATION: Synthetic polypeptide

<400> SEQUENCE: 572

Val Lys Lys Leu Leu Phe Ala Ile Pro Leu Val Val Pro Phe Tyr Leu
1               5                   10                  15

Arg Ala Asp Ser Leu Ala Pro Lys Ser His His His
            20                  25

<210> SEQ ID NO 573
<211> LENGTH: 28
<212> TYPE: PRT
<213> ORGANISM: artificial
<220> FEATURE:
<223> OTHER INFORMATION: Synthetic polypeptide

<400> SEQUENCE: 573

Val Lys Lys Leu Leu Phe Ala Ile Pro Leu Val Val Pro Phe Tyr Ser
1               5                   10                  15

Val Pro Gln Phe Ser Gly Arg Ser Arg His His His
            20                  25

<210> SEQ ID NO 574
<211> LENGTH: 28
<212> TYPE: PRT
<213> ORGANISM: artificial
<220> FEATURE:
<223> OTHER INFORMATION: Synthetic polypeptide

<400> SEQUENCE: 574

Val Lys Lys Leu Leu Phe Ala Ile Pro Leu Val Val Pro Phe Tyr Val
1               5                   10                  15

Tyr Pro Ala Arg Phe Pro Ala Lys Thr His His His
            20                  25
```

```
<210> SEQ ID NO 575
<211> LENGTH: 28
<212> TYPE: PRT
<213> ORGANISM: artificial
<220> FEATURE:
<223> OTHER INFORMATION: Synthetic polypeptide

<400> SEQUENCE: 575

Val Lys Lys Leu Leu Phe Ala Ile Pro Leu Val Val Pro Phe Tyr Asn
1               5                   10                  15

Phe Met Leu Arg His Pro Gln Thr Phe His His His
            20                  25

<210> SEQ ID NO 576
<211> LENGTH: 28
<212> TYPE: PRT
<213> ORGANISM: artificial
<220> FEATURE:
<223> OTHER INFORMATION: Synthetic polypeptide

<400> SEQUENCE: 576

Val Lys Lys Leu Leu Phe Ala Ile Pro Leu Val Val Pro Phe Tyr Tyr
1               5                   10                  15

Val Pro Arg Phe Pro Pro Lys Ser Ala His His His
            20                  25

<210> SEQ ID NO 577
<211> LENGTH: 28
<212> TYPE: PRT
<213> ORGANISM: artificial
<220> FEATURE:
<223> OTHER INFORMATION: Synthetic polypeptide

<400> SEQUENCE: 577

Val Lys Lys Leu Leu Phe Ala Ile Pro Leu Val Val Pro Phe Tyr Leu
1               5                   10                  15

Ser Pro Met Ser Arg Thr Arg Tyr Val His His His
            20                  25

<210> SEQ ID NO 578
<211> LENGTH: 28
<212> TYPE: PRT
<213> ORGANISM: artificial
<220> FEATURE:
<223> OTHER INFORMATION: Synthetic polypeptide

<400> SEQUENCE: 578

Val Lys Lys Leu Leu Phe Ala Ile Pro Leu Val Val Pro Phe Tyr Thr
1               5                   10                  15

Tyr Pro Leu Thr Lys Pro Tyr Arg Pro His His His
            20                  25

<210> SEQ ID NO 579
<211> LENGTH: 28
<212> TYPE: PRT
<213> ORGANISM: artificial
<220> FEATURE:
<223> OTHER INFORMATION: Synthetic polypeptide

<400> SEQUENCE: 579

Val Lys Lys Leu Leu Phe Ala Ile Pro Leu Val Val Pro Phe Tyr Ser
1               5                   10                  15

Ser Tyr Trp Ser His Arg Lys Pro Pro His His His
            20                  25
```

<210> SEQ ID NO 580
<211> LENGTH: 28
<212> TYPE: PRT
<213> ORGANISM: artificial
<220> FEATURE:
<223> OTHER INFORMATION: Synthetic polypeptide

<400> SEQUENCE: 580

Val Lys Lys Leu Leu Phe Ala Ile Pro Leu Val Val Pro Phe Tyr Ser
1               5                   10                  15

Pro Arg Thr Phe Ala Phe Phe Leu Met His His His
            20                  25

<210> SEQ ID NO 581
<211> LENGTH: 28
<212> TYPE: PRT
<213> ORGANISM: artificial
<220> FEATURE:
<223> OTHER INFORMATION: Synthetic polypeptide

<400> SEQUENCE: 581

Val Lys Lys Leu Leu Phe Ala Ile Pro Leu Val Val Pro Phe Tyr Leu
1               5                   10                  15

Gly Pro Gly Ile Arg Lys Lys Pro Ala His His His
            20                  25

<210> SEQ ID NO 582
<211> LENGTH: 28
<212> TYPE: PRT
<213> ORGANISM: artificial
<220> FEATURE:
<223> OTHER INFORMATION: Synthetic polypeptide

<400> SEQUENCE: 582

Val Lys Lys Leu Leu Phe Ala Ile Pro Leu Val Val Pro Phe Tyr Thr
1               5                   10                  15

Arg Leu Cys Val Ala Lys Val Ala Gly His His His
            20                  25

<210> SEQ ID NO 583
<211> LENGTH: 28
<212> TYPE: PRT
<213> ORGANISM: artificial
<220> FEATURE:
<223> OTHER INFORMATION: Synthetic polypeptide

<400> SEQUENCE: 583

Val Lys Lys Leu Leu Phe Ala Ile Pro Leu Val Val Pro Phe Tyr Arg
1               5                   10                  15

Ser Leu Pro Ala Ser Gly Ala Ser Arg His His His
            20                  25

<210> SEQ ID NO 584
<211> LENGTH: 28
<212> TYPE: PRT
<213> ORGANISM: artificial
<220> FEATURE:
<223> OTHER INFORMATION: Synthetic polypeptide

<400> SEQUENCE: 584

Val Lys Lys Leu Leu Phe Ala Ile Pro Leu Val Val Pro Phe Tyr Ala
1               5                   10                  15

Ser Pro Arg Val Lys Ser Tyr Ser Pro His His His

```
            20                  25

<210> SEQ ID NO 585
<211> LENGTH: 28
<212> TYPE: PRT
<213> ORGANISM: artificial
<220> FEATURE:
<223> OTHER INFORMATION: Synthetic polypeptide

<400> SEQUENCE: 585

Val Lys Lys Leu Leu Phe Ala Ile Pro Leu Val Val Pro Phe Tyr Pro
1               5                   10                  15

Ser Arg Thr Phe Ala Phe Tyr Leu Val His His His
            20                  25

<210> SEQ ID NO 586
<211> LENGTH: 28
<212> TYPE: PRT
<213> ORGANISM: artificial
<220> FEATURE:
<223> OTHER INFORMATION: Synthetic polypeptide

<400> SEQUENCE: 586

Val Lys Lys Leu Leu Phe Ala Ile Pro Leu Val Val Pro Phe Tyr Gln
1               5                   10                  15

Gln Glu Phe Ala Met Ala His His His His His
            20                  25

<210> SEQ ID NO 587
<211> LENGTH: 28
<212> TYPE: PRT
<213> ORGANISM: artificial
<220> FEATURE:
<223> OTHER INFORMATION: Synthetic polypeptide

<400> SEQUENCE: 587

Val Lys Lys Leu Leu Phe Ala Ile Pro Leu Val Val Pro Phe Tyr Pro
1               5                   10                  15

Gln Ser Ser Lys Ala Phe Phe Leu Asn His His His
            20                  25

<210> SEQ ID NO 588
<211> LENGTH: 28
<212> TYPE: PRT
<213> ORGANISM: artificial
<220> FEATURE:
<223> OTHER INFORMATION: Synthetic polypeptide

<400> SEQUENCE: 588

Val Lys Lys Leu Leu Phe Ala Ile Pro Leu Val Val Pro Phe Tyr Val
1               5                   10                  15

Lys Ala Leu Arg Gly Ser Tyr Pro Thr His His His
            20                  25

<210> SEQ ID NO 589
<211> LENGTH: 28
<212> TYPE: PRT
<213> ORGANISM: artificial
<220> FEATURE:
<223> OTHER INFORMATION: Synthetic polypeptide

<400> SEQUENCE: 589

Val Lys Lys Leu Leu Phe Ala Ile Pro Leu Val Val Pro Phe Tyr Thr
1               5                   10                  15
```

Gln Pro Ser Gln Val Arg Tyr Met Leu His His His
            20                  25

<210> SEQ ID NO 590
<211> LENGTH: 28
<212> TYPE: PRT
<213> ORGANISM: artificial
<220> FEATURE:
<223> OTHER INFORMATION: Synthetic polypeptide

<400> SEQUENCE: 590

Val Lys Lys Leu Leu Phe Ala Ile Pro Leu Val Val Pro Phe Tyr Ser
1               5                   10                  15

Ala Arg Gly Gln His Val Arg Pro Pro His His His
            20                  25

<210> SEQ ID NO 591
<211> LENGTH: 28
<212> TYPE: PRT
<213> ORGANISM: artificial
<220> FEATURE:
<223> OTHER INFORMATION: Synthetic polypeptide

<400> SEQUENCE: 591

Val Lys Lys Leu Leu Phe Ala Ile Pro Leu Val Val Pro Phe Tyr Ser
1               5                   10                  15

Thr Arg Cys Pro Gly Phe Phe Leu Gln His His His
            20                  25

<210> SEQ ID NO 592
<211> LENGTH: 28
<212> TYPE: PRT
<213> ORGANISM: artificial
<220> FEATURE:
<223> OTHER INFORMATION: Synthetic polypeptide

<400> SEQUENCE: 592

Val Lys Lys Leu Leu Phe Ala Ile Pro Leu Val Val Pro Phe Tyr Cys
1               5                   10                  15

Pro Ser Val Phe Ser Arg Thr Pro Pro His His His
            20                  25

<210> SEQ ID NO 593
<211> LENGTH: 28
<212> TYPE: PRT
<213> ORGANISM: artificial
<220> FEATURE:
<223> OTHER INFORMATION: Synthetic polypeptide

<400> SEQUENCE: 593

Val Lys Lys Leu Leu Phe Ala Ile Pro Leu Val Val Pro Phe Tyr Asp
1               5                   10                  15

Ala Ser Ser Trp Arg His Phe Leu Ser His His His
            20                  25

<210> SEQ ID NO 594
<211> LENGTH: 18
<212> TYPE: PRT
<213> ORGANISM: artificial sequence
<220> FEATURE:
<223> OTHER INFORMATION: the wild-type M13 signal peptide N-terminal
      to gene III

<400> SEQUENCE: 594

Met Lys Lys Leu Leu Phe Ala Ile Pro Leu Val Val Pro Phe Tyr Ser

His Ser

<210> SEQ ID NO 595
<211> LENGTH: 22
<212> TYPE: PRT
<213> ORGANISM: artificial sequence
<220> FEATURE:
<223> OTHER INFORMATION: the pelB signal sequence of Pectobacterium
     wasabiae

<400> SEQUENCE: 595

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 596
<211> LENGTH: 30
<212> TYPE: PRT
<213> ORGANISM: artificial sequence
<220> FEATURE:
<223> OTHER INFORMATION: Signal peptide
<220> FEATURE:
<221> NAME/KEY: VARIANT
<222> LOCATION: (6)..(6)
<223> OTHER INFORMATION: A, C, F, G, I, L, M, P, Q, S, V, W, or Y
<220> FEATURE:
<221> NAME/KEY: VARIANT
<222> LOCATION: (7)..(7)
<223> OTHER INFORMATION: A, D, F, G, H, I, L, M, N, P, S, T, V, or W
<220> FEATURE:
<221> NAME/KEY: VARIANT
<222> LOCATION: (8)..(8)
<223> OTHER INFORMATION: A, F, G, L, M, P, Q, R, S, T, V, or W
<220> FEATURE:
<221> NAME/KEY: VARIANT
<222> LOCATION: (9)..(9)
<223> OTHER INFORMATION: A, F, G, H, I, L, M, P, Q, R, S, T, V, W, or Y
<220> FEATURE:
<221> NAME/KEY: VARIANT
<222> LOCATION: (10)..(10)
<223> OTHER INFORMATION: A, C, D, F, G, H, I, L, M, P, Q, R, S, T, V, W,
     or Y
<220> FEATURE:
<221> NAME/KEY: VARIANT
<222> LOCATION: (11)..(11)
<223> OTHER INFORMATION: A, C, D, F, G, H, I, K, L, M, N, P, Q, R, S, T,
     V, W, or Y
<220> FEATURE:
<221> NAME/KEY: VARIANT
<222> LOCATION: (12)..(12)
<223> OTHER INFORMATION: A, C, D, F, G, H, I, K, L, M, N, P, Q, R, S, T,
     V, W, or Y
<220> FEATURE:
<221> NAME/KEY: VARIANT
<222> LOCATION: (13)..(13)
<223> OTHER INFORMATION: A, C, D, E, F, G, H, I, K, L, M, N, P, Q, R, S,
     T, V, W, or Y
<220> FEATURE:
<221> NAME/KEY: VARIANT
<222> LOCATION: (14)..(14)
<223> OTHER INFORMATION: A, C, D, E, F, G, H, I, L, M, N, P, Q, R, S, T,
     V,W, or Y
<220> FEATURE:
<221> NAME/KEY: VARIANT
<222> LOCATION: (15)..(15)
<223> OTHER INFORMATION: A, C, D, E, F, G, H, I, K, L, M, N, P, Q, R, S,
     T, V,W, or Y

<400> SEQUENCE: 596

Val Lys Lys Leu Leu Xaa Xaa Xaa Xaa Xaa Xaa Xaa Xaa Xaa Xaa Ala
1               5                   10                  15

Ala Gln Pro Ala Met Ala His His His His His Gly His
            20                  25                  30

<210> SEQ ID NO 597
<211> LENGTH: 30
<212> TYPE: PRT
<213> ORGANISM: artificial sequence
<220> FEATURE:
<223> OTHER INFORMATION: Signal peptide
<220> FEATURE:
<221> NAME/KEY: VARIANT
<222> LOCATION: (11)..(11)
<223> OTHER INFORMATION: A, C, F, G, H, I, L, M, N, P, Q, S, T, V, W, or
      Y
<220> FEATURE:
<221> NAME/KEY: VARIANT
<222> LOCATION: (12)..(12)
<223> OTHER INFORMATION: A, C, D, F, G, H, I, L, M, P, Q, R, S, T, V, W,
      or Y
<220> FEATURE:
<221> NAME/KEY: VARIANT
<222> LOCATION: (13)..(13)
<223> OTHER INFORMATION: A, C, D, F, G, H, I, L, M, N, P, Q, R, S, T, V,
      W, or Y
<220> FEATURE:
<221> NAME/KEY: VARIANT
<222> LOCATION: (14)..(14)
<223> OTHER INFORMATION: A, C, E, F, H, I, K, L, M, N, P, Q, R, S, T, V,
      W, or Y
<220> FEATURE:
<221> NAME/KEY: VARIANT
<222> LOCATION: (15)..(15)
<223> OTHER INFORMATION: A, C, D, F, H, I, L, M, N, P, Q, R, S, T, V, W,
      or Y
<220> FEATURE:
<221> NAME/KEY: VARIANT
<222> LOCATION: (16)..(16)
<223> OTHER INFORMATION: A, C, D, E, F, G, H, K, L, M, P, Q, R, S, T, V,
      W, or Y
<220> FEATURE:
<221> NAME/KEY: VARIANT
<222> LOCATION: (17)..(17)
<223> OTHER INFORMATION: A, D, E, F, G, H, K, L, M, N, P, Q, R, S, T, V,
      or Y
<220> FEATURE:
<221> NAME/KEY: VARIANT
<222> LOCATION: (18)..(18)
<223> OTHER INFORMATION: A, C, F, G, I, K, L, M, N, P, Q, R, S, T, or V
<220> FEATURE:
<221> NAME/KEY: VARIANT
<222> LOCATION: (19)..(19)
<223> OTHER INFORMATION: A, C, D, F, H, I, L, M, N, P, Q, R, S, T, V, W,
      or Y
<220> FEATURE:
<221> NAME/KEY: VARIANT
<222> LOCATION: (20)..(20)
<223> OTHER INFORMATION: A, C, D, E, F, G, H, L, M, P, Q, R, S, or T

<400> SEQUENCE: 597

Val Lys Lys Leu Leu Phe Ala Ile Pro Leu Xaa Xaa Xaa Xaa Xaa Xaa
1               5                   10                  15

Xaa Xaa Xaa Xaa Met Ala His His His His His Gly His
            20                  25                  30

<210> SEQ ID NO 598
<211> LENGTH: 30
<212> TYPE: PRT
<213> ORGANISM: artificial sequence
<220> FEATURE:
<223> OTHER INFORMATION: Signal peptide
<220> FEATURE:
<221> NAME/KEY: VARIANT
<222> LOCATION: (16)..(16)
<223> OTHER INFORMATION: A, C, D, F, G, I, L, M, N, P, Q, R, S, T, V, or

```
                              Y
<220> FEATURE:
<221> NAME/KEY: VARIANT
<222> LOCATION: (17)..(17)
<223> OTHER INFORMATION: A, C, D, F, G, H, K, L, N, P, Q, R, S, T, V, W,
      or Y
<220> FEATURE:
<221> NAME/KEY: VARIANT
<222> LOCATION: (18)..(18)
<223> OTHER INFORMATION: A, C, E, F, G, H, I, K, L, M, N, P, Q, R, S, T,
      V, W, or Y
<220> FEATURE:
<221> NAME/KEY: VARIANT
<222> LOCATION: (19)..(19)
<223> OTHER INFORMATION: A, C, D, F, G, H, I, L, M, N, P, Q, R, S, T, V,
      W, or Y
<220> FEATURE:
<221> NAME/KEY: VARIANT
<222> LOCATION: (20)..(20)
<223> OTHER INFORMATION: A, C, E, F, G, H, I, K, L, M, N, P, Q, R, S, T,
      W, or Y
<220> FEATURE:
<221> NAME/KEY: VARIANT
<222> LOCATION: (21)..(21)
<223> OTHER INFORMATION: A, C, D, E, F, G, H, I, K, L, M, N, P, Q, R, S,
      T, V, W, or Y
<220> FEATURE:
<221> NAME/KEY: VARIANT
<222> LOCATION: (22)..(22)
<223> OTHER INFORMATION: A, D, E, F, G, H, I, K, L, M, N, P, Q, R, S, T,
      V, or Y
<220> FEATURE:
<221> NAME/KEY: VARIANT
<222> LOCATION: (23)..(23)
<223> OTHER INFORMATION: A, E, F, G, H, I, K, L, M, N, P, Q, R, S, T, V,
      W, or Y
<220> FEATURE:
<221> NAME/KEY: VARIANT
<222> LOCATION: (24)..(24)
<223> OTHER INFORMATION: A, D, F, G, H, I, K, L, M, N, P, Q, R, S, T, V,
      W, or Y
<220> FEATURE:
<221> NAME/KEY: VARIANT
<222> LOCATION: (25)..(25)
<223> OTHER INFORMATION: A, D, E, F, G, H, I, K, L, M, N, P, Q, R, S, T,
      V, or Y

<400> SEQUENCE: 598

Val Lys Lys Leu Leu Phe Ala Ile Pro Leu Val Val Pro Phe Tyr Xaa
1               5                   10                  15

Xaa Xaa Xaa Xaa Xaa Xaa Xaa Xaa Xaa His His His Gly His
            20                  25                  30

<210> SEQ ID NO 599
<211> LENGTH: 4
<212> TYPE: PRT
<213> ORGANISM: Artificial sequence
<220> FEATURE:
<223> OTHER INFORMATION: Synthetic peptide

<400> SEQUENCE: 599

Ile Glu Gly Arg
1

<210> SEQ ID NO 600
<211> LENGTH: 15
<212> TYPE: PRT
<213> ORGANISM: Artificial sequence
<220> FEATURE:
<223> OTHER INFORMATION: Synthetic peptide

<400> SEQUENCE: 600

Gly Gly Gly Gly Ser Ile Glu Gly Arg Ser Gly Gly Gly Gly Ser
```

<210> SEQ ID NO 601
<211> LENGTH: 15
<212> TYPE: PRT
<213> ORGANISM: Artificial sequence
<220> FEATURE:
<223> OTHER INFORMATION: Synthetic peptide

<400> SEQUENCE: 601

Gly Gly Gly Gly Ser Gly Gly Gly Gly Ser Gly Gly Gly Gly Ser
1               5                   10                  15

<210> SEQ ID NO 602
<211> LENGTH: 162
<212> TYPE: DNA
<213> ORGANISM: Artificial sequence
<220> FEATURE:
<223> OTHER INFORMATION: Synthetic polynucleotide
<220> FEATURE:
<221> NAME/KEY: CDS
<222> LOCATION: (1)..(162)

<400> SEQUENCE: 602 atg acc atg att acg cca agc ttt gga gcc ttt ttt ttg gag att ttc        48
Met Thr Met Ile Thr Pro Ser Phe Gly Ala Phe Phe Leu Glu Ile Phe
1               5                   10                  15 aac gtg aaa aaa tta tta ttc gca att cct tta gtt gtt cct ttc tat       96
Asn Val Lys Lys Leu Leu Phe Ala Ile Pro Leu Val Val Pro Phe Tyr
            20                  25                  30 gcg gcc cag ccg gcc atg gcc cat cat cac cac cat cat ggc cac ggg      144
Ala Ala Gln Pro Ala Met Ala His His His His His His Gly His Gly
        35                  40                  45 tcc ggc gat att caa atg                                              162
Ser Gly Asp Ile Gln Met
    50

<210> SEQ ID NO 603
<211> LENGTH: 54
<212> TYPE: PRT
<213> ORGANISM: Artificial sequence
<220> FEATURE:
<223> OTHER INFORMATION: Synthetic Construct

<400> SEQUENCE: 603

Met Thr Met Ile Thr Pro Ser Phe Gly Ala Phe Phe Leu Glu Ile Phe
1               5                   10                  15

Asn Val Lys Lys Leu Leu Phe Ala Ile Pro Leu Val Val Pro Phe Tyr
            20                  25                  30

Ala Ala Gln Pro Ala Met Ala His His His His His His Gly His Gly
        35                  40                  45

Ser Gly Asp Ile Gln Met
    50

<210> SEQ ID NO 604
<211> LENGTH: 97
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature

```
<222> LOCATION: (40)..(40)
<223> OTHER INFORMATION: k is g or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (43)..(43)
<223> OTHER INFORMATION: k is g or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (46)..(46)
<223> OTHER INFORMATION: k is g or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (49)..(49)
<223> OTHER INFORMATION: k is g or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (52)..(52)
<223> OTHER INFORMATION: k is g or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (55)..(55)
<223> OTHER INFORMATION: k is g or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (58)..(58)
<223> OTHER INFORMATION: k is g or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (61)..(61)
<223> OTHER INFORMATION: k is g or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (64)..(64)
<223> OTHER INFORMATION: k is g or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (67)..(67)
<223> OTHER INFORMATION: k is g or t

<400> SEQUENCE: 604
cttttttttg gagattttca acgtgaaaaa attattannk nnknnknnkn nknnknnknn      60
```
knnknnkgcg gcccagccgg ccatggccca tcatcac     97

<210> SEQ ID NO 605
<211> LENGTH: 94
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (37)..(37)
<223> OTHER INFORMATION: k is g or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (40)..(40)
<223> OTHER INFORMATION: k is g or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (43)..(43)
<223> OTHER INFORMATION: k is g or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (46)..(46)
<223> OTHER INFORMATION: k is g or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (49)..(49)
<223> OTHER INFORMATION: k is g or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (52)..(52)
<223> OTHER INFORMATION: k is g or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (55)..(55)
<223> OTHER INFORMATION: k is g or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (58)..(58)
<223> OTHER INFORMATION: k is g or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature

```
<222> LOCATION: (61)..(61)
<223> OTHER INFORMATION: k is g or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (64)..(64)
<223> OTHER INFORMATION: k is g or t

<400> SEQUENCE: 605
caacgtgaaa aaattattat tcgcaattcc tttannknnk nnknnknnkn nknnknnknn      60
knnkatggcc catcatcacc accatcatgg ccac                                 94

<210> SEQ ID NO 606
<211> LENGTH: 92
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (43)..(43)
<223> OTHER INFORMATION: k is g or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (46)..(46)
<223> OTHER INFORMATION: k is g or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (49)..(49)
<223> OTHER INFORMATION: k is g or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (52)..(52)
<223> OTHER INFORMATION: k is g or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (55)..(55)
<223> OTHER INFORMATION: k is g or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (58)..(58)
<223> OTHER INFORMATION: k is g or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (61)..(61)
```

```
<223> OTHER INFORMATION: k is g or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (64)..(64)
<223> OTHER INFORMATION: k is g or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (67)..(67)
<223> OTHER INFORMATION: k is g or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (70)..(70)
<223> OTHER INFORMATION: k is g or t

<400> SEQUENCE: 606
aaaattatta ttcgcaattc ctttagttgt tcctttctat nnknnknnkn nknnknnknn    60
knnknnknnk caccatcatg gccacgggtc cg                                  92

<210> SEQ ID NO 607
<211> LENGTH: 900
<212> TYPE: DNA
<213> ORGANISM: Artificial sequence
<220> FEATURE:
<223> OTHER INFORMATION: Synthetic polynucleotide
<220> FEATURE:
<221> NAME/KEY: CDS
<222> LOCATION: (1)..(900)
<220> FEATURE:
<221> NAME/KEY: misc_feature
<222> LOCATION: (862)..(864)
<223> OTHER INFORMATION: Amber stop codon

<400> SEQUENCE: 607
```

| | | | | | | | | | | | | | | | | |
|---|---|---|---|---|---|---|---|---|---|---|---|---|---|---|---|---|
| tta | gtt | gtt | cct | ttc | tat | gcg | gcc | cag | ccg | gcc | atg | gcc | cat | cat | cac | 48 |
| Leu | Val | Val | Pro | Phe | Tyr | Ala | Ala | Gln | Pro | Ala | Met | Ala | His | His | His | |
| 1 | | | | 5 | | | | | 10 | | | | | 15 | | |
| cac | cat | cat | ggc | cac | ggg | tcc | ggc | gat | att | caa | atg | acc | cag | agc | ccg | 96 |
| His | His | His | Gly | His | Gly | Ser | Gly | Asp | Ile | Gln | Met | Thr | Gln | Ser | Pro | |
| | | 20 | | | | | 25 | | | | | 30 | | | | |
| agc | agc | ctg | agc | gcg | agc | gtg | gga | gat | cgc | gtg | acc | att | acc | tgc | cgt | 144 |
| Ser | Ser | Leu | Ser | Ala | Ser | Val | Gly | Asp | Arg | Val | Thr | Ile | Thr | Cys | Arg | |
| | | 35 | | | | | 40 | | | | | 45 | | | | |
| gcg | agc | cag | gat | gtt | agc | acg | gcg | gtc | gca | tgg | tat | cag | cag | aaa | cca | 192 |
| Ala | Ser | Gln | Asp | Val | Ser | Thr | Ala | Val | Ala | Trp | Tyr | Gln | Gln | Lys | Pro | |
| 50 | | | | | 55 | | | | | 60 | | | | | | |
| ggc | aaa | gcg | ccg | aaa | ctt | ctg | ata | tac | tct | gcg | tcc | ttc | ctg | tat | agc | 240 |
| Gly | Lys | Ala | Pro | Lys | Leu | Leu | Ile | Tyr | Ser | Ala | Ser | Phe | Leu | Tyr | Ser | |
| 65 | | | | 70 | | | | | 75 | | | | | 80 | | |
| ggc | gtg | ccg | tcg | cgt | ttt | tcg | ggc | agt | ggc | agc | ggc | acg | gac | ttt | acc | 288 |
| Gly | Val | Pro | Ser | Arg | Phe | Ser | Gly | Ser | Gly | Ser | Gly | Thr | Asp | Phe | Thr | |
| | | | | 85 | | | | | 90 | | | | | 95 | | |
| ctg | acg | ata | tct | tcc | tta | caa | ccg | gag | gat | ttt | gcg | acc | tac | tac | tgt | 336 |
| Leu | Thr | Ile | Ser | Ser | Leu | Gln | Pro | Glu | Asp | Phe | Ala | Thr | Tyr | Tyr | Cys | |
| | | | 100 | | | | | 105 | | | | | 110 | | | |
| caa | cag | cat | tat | acc | aca | ccg | ccg | acc | ttc | ggt | tgt | ggc | acc | aaa | gtg | 384 |
| Gln | Gln | His | Tyr | Thr | Thr | Pro | Pro | Thr | Phe | Gly | Cys | Gly | Thr | Lys | Val | |

```
                    115                 120                 125
gaa atc aaa cgc gga ggg gga ggt agc atc gag ggc cgt agc gga ggt        432
Glu Ile Lys Arg Gly Gly Gly Gly Ser Ile Glu Gly Arg Ser Gly Gly
    130                 135                 140 ggc ggg agc gaa gtg cag ctg gtg gaa tcg gga ggc ggt ctg gtg caa        480
Gly Gly Ser Glu Val Gln Leu Val Glu Ser Gly Gly Gly Leu Val Gln
145                 150                 155                 160 cct ggc ggc agc ctt cgt ctg agc tgt gcg gcg agc ggg ttc acc att        528
Pro Gly Gly Ser Leu Arg Leu Ser Cys Ala Ala Ser Gly Phe Thr Ile
                165                 170                 175 agc gat tac tgg att cat tgg gtg cgt caa gct ccc ggc aag tgt ctg        576
Ser Asp Tyr Trp Ile His Trp Val Arg Gln Ala Pro Gly Lys Cys Leu
            180                 185                 190 gag tgg gtc gcg ggc att acg ccc gct ggc ggt tac aca tat tat gcc        624
Glu Trp Val Ala Gly Ile Thr Pro Ala Gly Gly Tyr Thr Tyr Tyr Ala
        195                 200                 205 gac agc gtg aaa ggt cgc ttt acg att agt gcg gac acc agc aaa aat        672
Asp Ser Val Lys Gly Arg Phe Thr Ile Ser Ala Asp Thr Ser Lys Asn
    210                 215                 220 acc gcg tac ctg cag atg aat agc ctg cgt gcg gaa gac aca gcg gtg        720
Thr Ala Tyr Leu Gln Met Asn Ser Leu Arg Ala Glu Asp Thr Ala Val
225                 230                 235                 240 tat tat tgc gcg cgt ttc gtg ttt ttt ctg ccg tat gcg atg gat tat        768
Tyr Tyr Cys Ala Arg Phe Val Phe Phe Leu Pro Tyr Ala Met Asp Tyr
                245                 250                 255 tgg ggg cag ggc acc ctt gtt acc gtg agc tcg gca tca gcg gcc gca        816
Trp Gly Gln Gly Thr Leu Val Thr Val Ser Ser Ala Ser Ala Ala Ala
            260                 265                 270 ggt gcg ccg gtg ccg tat ccg gat ccg ctg gaa ccg cgt gcc gca tag        864
Gly Ala Pro Val Pro Tyr Pro Asp Pro Leu Glu Pro Arg Ala Ala
        275                 280                 285 act gtt gaa agt tgt tta gca aaa cct cat aca gaa                        900
Thr Val Glu Ser Cys Leu Ala Lys Pro His Thr Glu
    290                 295
```

<210> SEQ ID NO 608
<211> LENGTH: 287
<212> TYPE: PRT
<213> ORGANISM: Artificial sequence
<220> FEATURE:
<223> OTHER INFORMATION: Synthetic Construct

<400> SEQUENCE: 608

```
Leu Val Val Pro Phe Tyr Ala Ala Gln Pro Ala Met Ala His His
1               5                   10                  15

His His His Gly His Gly Ser Gly Asp Ile Gln Met Thr Gln Ser Pro
                20                  25                  30

Ser Ser Leu Ser Ala Ser Val Gly Asp Arg Val Thr Ile Thr Cys Arg
            35                  40                  45

Ala Ser Gln Asp Val Ser Thr Ala Val Ala Trp Tyr Gln Gln Lys Pro
        50                  55                  60

Gly Lys Ala Pro Lys Leu Leu Ile Tyr Ser Ala Ser Phe Leu Tyr Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gln His Tyr Thr Thr Pro Pro Thr Phe Gly Cys Gly Thr Lys Val
        115                 120                 125
```

```
Glu Ile Lys Arg Gly Gly Gly Ser Ile Glu Gly Arg Ser Gly Gly
    130                 135                 140

Gly Gly Ser Glu Val Gln Leu Val Glu Ser Gly Gly Leu Val Gln
145                 150                 155                 160

Pro Gly Gly Ser Leu Arg Leu Ser Cys Ala Ala Ser Gly Phe Thr Ile
                165                 170                 175

Ser Asp Tyr Trp Ile His Trp Val Arg Gln Ala Pro Gly Lys Cys Leu
            180                 185                 190

Glu Trp Val Ala Gly Ile Thr Pro Ala Gly Gly Tyr Thr Tyr Tyr Ala
        195                 200                 205

Asp Ser Val Lys Gly Arg Phe Thr Ile Ser Ala Asp Thr Ser Lys Asn
    210                 215                 220

Thr Ala Tyr Leu Gln Met Asn Ser Leu Arg Ala Glu Asp Thr Ala Val
225                 230                 235                 240

Tyr Tyr Cys Ala Arg Phe Val Phe Phe Leu Pro Tyr Ala Met Asp Tyr
                245                 250                 255

Trp Gly Gln Gly Thr Leu Val Thr Val Ser Ser Ala Ser Ala Ala Ala
                260                 265                 270

Gly Ala Pro Val Pro Tyr Pro Asp Pro Leu Glu Pro Arg Ala Ala
                275                 280                 285

<210> SEQ ID NO 609
<211> LENGTH: 12
<212> TYPE: PRT
<213> ORGANISM: Artificial sequence
<220> FEATURE:
<223> OTHER INFORMATION: Synthetic Construct

<400> SEQUENCE: 609

Thr Val Glu Ser Cys Leu Ala Lys Pro His Thr Glu
1               5                   10
```

PHAGE DISPLAYING SYSTEM EXPRESSING SINGLE CHAIN ANTIBODY

RELATED APPLICATIONS

This application is a divisional of U.S. application Ser. No. 12/854,632, filed on Aug. 11, 2010, which claims priority to U.S. Provisional Application No. 61/232,819, filed on Aug. 11, 2009. The contents of both prior applications are incorporated by reference in their entirety.

FIELD OF THE INVENTION

The present invention is related to a phage displaying system expressing disulfide-stabilized single chain antibody variable fragments (sc-dsFv).

BACKGROUND OF THE INVENTION

A single chain variable fragment (scFv) is a single polypeptide chain antibody fragment having a light chain variable domain and a heavy chain variable domain, with a flexible linkage peptide connecting the two domains. An scFv displayed as a fusion protein N-terminal to the pIII minor capsid protein on filamentous phage surface is one of the most prominent methods in antibody engineering. It was reported that the small size of the scFv enabled superior tissue-penetrating capabilities over whole IgG or Fab fragment, making scFv an ideal scaffold for designing tumor-homing molecules carrying therapeutic or imaging agents (Michnick, S. W., and Sidhu, S. S. (2008) *Nat Chem Biol* 4(6), 326-329).

Yet, under practical application conditions, an scFv scaffold tends to form aggregation. The aggregation has much to do with the stability of the two variable domains and the dimeric interface. The instability of the scFv structure also compromises the fidelity in reproducing the antibody gene products on phage surface, causing biases in favor of more stable scFv molecules over the less stable ones, or selecting non-folded structures on phage surfaces but nevertheless binding to an antigen. This structural instability thus impacts negatively on the applications of scFv in biotechnology and medical uses.

One way to stabilize the scFv scaffold is to engineer a disulfide bond between the two Fv domains, so that the variable domains can be covalently linked with a disulfide bond. Single chain disulfide-stabilized Fv fragment (sc-dsFv) format was constructed in a single polypeptide chain, as in scFv, with a disulfide framework region (Young, N. M. et al., (1995) *FEBS Lett* 377(2), 135-139; Worn, A., and Pluckthun, A. (1999) *Biochemistry* 38(27), 8739-8750). The sc-dsFv molecules could be expressed in *E. coli*, but not be expressed on phage surface or as soluble form secreted by *E. coli* in a culture medium, mostly due to severely decreased yield because of the introduction of interface cysteines (Worn, A., and Pluckthun, A. (2001) *J Mol Biol* 305(5), 989-1010).

Up to now, phage-displayed sc-dsFv libraries and their applications have not been established.

BRIEF SUMMARY OF THE INVENTION

The invention provides a methodology to systematically optimize the signal sequences for phage-displayed protein expression, for which the expression with conventional signal sequences was not viable. The optimized signal sequences and related discovering methodologies led to the establishment of phage display systems with the sc-dsFv format, enabling the demonstration and comparison of the performance of the sc-dsFv phage display platform with that of the conventional scFv platform.

Accordingly, in one aspect, the present invention provides a nucleic acid library for identifying a signal peptide that facilitates production of disulfide-stabilized single chain antibody. The library includes a plurality of expression constructs, each of which includes: a first nucleotide sequence encoding a signal peptide, and a second nucleotide sequence encoding a single chain antibody capable of forming an interface disulfide bond. The second nucleotide sequence is located 3' downstream to the first nucleotide. The signal peptide has the amino acid sequence of:

(a) VKKLLX$_1$X$_2$X$_3$X$_4$X$_5$X$_6$X$_7$X$_8$X$_9$X$_{10}$AAQPAMA HHHHHHGH (SEQ ID NO:1), (b) VKKLLFAIPLX$_1$X$_2$X$_3$X$_4$X$_5$X$_6$X$_7$X$_8$X$_9$X$_{10}$MAHH HHHHGH (SEQ ID NO:2), or (c) VKKLLFAIPLVVPFYX$_1$X$_2$X$_3$X$_4$X$_5$X$_6$X$_7$X$_8$X$_9$X$_{10}$ HHHGH (SEQ ID NO:3).

each of X$_1$-X$_{10}$ in (a), (b), and (c) is one of the 20 naturally occurring amino acid residues.

In another aspect, the invention provides a host cell library for identifying a signal peptide that facilitates production of disulfide-stabilized single chain antibody. The library includes a plurality of host cells each containing an expression construct that includes: a first nucleotide sequence encoding a signal peptide, and a second nucleotide sequence encoding a single chain antibody capable of forming an interface disulfide bond; the second nucleotide sequence is located 3' downstream to the first nucleotide; the signal peptide has the amino acid sequence of (a) VKKLLX$_1$X$_2$X$_3$X$_4$X$_5$X$_6$X$_7$X$_8$X$_9$X$_{10}$AAQPAMAH HHHHHGH (SEQ ID NO:1), (b) VKKLLFAIPLX$_1$X$_2$X$_3$X$_4$X$_5$X$_6$X$_7$X$_8$X$_9$X$_{10}$MAHH HHHHGH (SEQ ID NO:2), or (c) VKKLLFAIPLVVPFYX$_1$X$_2$X$_3$X$_4$X$_5$X$_6$X$_7$X$_8$X$_9$X$_{10}$ HHHGH (SEQ ID NO:3).

each of X$_1$-X$_{10}$ in (a), (b), and (c) is one of the 20 naturally occurring amino acid residues.

In another aspect, the invention provides a phage library for identifying a signal peptide that facilitates production of disulfide-stabilized single chain antibody. The library has a plurality of phage particles each containing a disulfide-stabilized single chain antibody fused with a coat protein on the surface of the phage. The phage library is prepared by the steps of: providing a host cell containing an expression construct, and culturing the host cell in a medium under conditions allowing expression of the plurality of phage particles; the expression construct that includes a first nucleotide sequence encoding a signal peptide, a second nucleotide sequence encoding a single chain antibody capable of faulting an interface disulfide bond, the second nucleotide sequence being located 3' downstream to the first nucleotide, and a third nucleotide sequence encoding a phage envelop protein; the third nucleotide sequence being located 3' downstream to the second nucleotide sequence; the signal peptide has the amino acid sequence of (a) VKKLLX$_1$X$_2$X$_3$X$_4$X$_5$X$_6$X$_7$X$_8$X$_9$X$_{10}$AAQPAMA HHH-HHHGH (SEQ ID NO:1),
(b) VKKLLFAIPLX$_1$X$_2$X$_3$X$_4$X$_5$X$_6$X$_7$X$_8$X$_9$X$_{10}$MAHHH HHHGH (SEQ ID NO:2), or
(c) VKKLLFAIPLVVPFYX$_1$X$_2$X$_3$X$_4$X$_5$X$_6$X$_7$X$_8$X$_9$X$_{10}$H HHGH (SEQ ID NO:3),
each of X$_1$-X$_{10}$ in (a), (b), and (c) being one of the 20 naturally occurring amino acid residues.

In addition, the invention provides a sc-dsFv phage display platform. According to the invention, a large scale screening for optimal signal sequences was carried out. In one example of the invention, the signal sequences that were effective for phage-displayed sc-dsFv and non-fusion soluble sc-dsFv secretion in *E. coli* Amber suppressor strain ER2738 were screened to obtain the sequence preference patterns emerged from the optimum signal sequences.

In still another aspect, the present invention provides an isolated nucleic acid, having a first nucleotide sequence encoding a signal peptide, and a second nucleotide sequence encoding a single chain antibody capable of forming an interface disulfide bond. The signal peptide has the amino acid sequence of
(a)
VKKLLX$_1$X$_2$X$_3$X$_4$X$_5$X$_6$X$_7$X$_8$X$_9$X$_{10}$AAQPAMAHHH HHHGH (SEQ ID NO:596), in which X$_1$ is A, C, F, G, I, L, M, P, Q, S, V, W, or Y; X$_2$ is A, D, F, G, H, I, L, M, N, P, S, T, V, or W; X$_3$ is A, F, G, L, M, P, Q, R, S, T, V, or W; X$_4$ is A, F, G, H, I, L, M, P, Q, R, S, T, V, W, or Y; X$_5$ is A, C, D, F, G, H, I, L, M, P, Q, R, S, T, V, W, or Y; X$_6$ is A, C, D, F, G, H, I, K, L, M, N, P, Q, R, S, T, V, W, or Y; X$_7$ is A, C, D, F, G, H, I, K, L, M, N, P, Q, R, S, T, V, W, or Y; X$_8$ is A, C, D, E, F, G, H, I, K, L, M, N, P, Q, R, S, T, V, W, or Y; X$_9$ is A, C, D, E, F, G, H, I, L, M, N, P, Q, R, S, T, V, W, or Y; and X$_{10}$ is A, C, D, E, F, G, H, I, K, L, M, N, P, Q, R, S, T, V, W, or Y;
(b)
VKKLLFAIPLX$_1$X$_2$X$_3$X$_4$X$_5$X$_6$X$_7$X$_8$X$_9$X$_{10}$MAHHHH HHGH (SEQ ID NO:597), in which X$_1$ A, C, F, G, H, I, L, M, N, P, Q, S, T, V, W, or Y; X$_2$ is A, C, D, F, G, H, I, L, M, P, Q, R, S, T, V, W, or Y; X$_3$ is A, C, D, F, G, H, I, L, M, N, P, Q, R, S, T, V, W, or Y; X$_4$ is A, C, E, F, H, 1, K, L, M, N, P, Q, R, S, T, V, W, or Y; X$_5$ is A, C, D, F, H, I, L, M, N, P, Q, R, S, T, V, W, or Y; X$_6$ is A, C, D, E, F, G, H, K, L, M, P, Q, R, S, T, V, W, or Y; X$_7$ is A, D, E, F, G, H, K, L, M, N, P, Q, R, S, T, V, or Y; X$_8$ is A, C, F, G, I, K, L, M, N, P, Q, R, S, T, or V, X$_9$ is A, C, D, F, H, L, M, N, P, Q, R, S, T, V, W, or Y; and X$_{10}$ is A, C, D, E, F, G, H, L, M, P, Q, R, S, or T; or
(c)
VKKLLFAIPLVVPFYX$_1$X$_2$X$_3$X$_4$X$_5$X$_6$X$_7$X$_8$X$_9$X$_{10}$HH HGH (SEQ ID NO:598), in which X$_1$ is A, C, D, F, G, I, L, M, N, P, Q, R, S, T, V, or Y; X$_2$ is A, C, D, F, G, H, K, L, N, P, Q, R, S, T, V, W, or Y; X$_3$ is A, C, E, F, G, H, I, K, L, M, N, P, Q, R, S, T, V, W, or Y; X$_4$ is A, C, D, F, G, H, I, L, M, N, P, Q, R, S, T, V, W, or Y; X$_5$ is A, C, E, F, G, H, I, K, L, M, N, P, Q, R, S, T, W, or Y; X$_6$ is A, C, D, E, F, G, H, I, K, L, M, N, P, Q, R, S, T, V, W, or Y; X$_7$ is A, D, E, F, G, H, K, L, M, N, P, Q, R, S, T, V, or Y; X$_8$ is A, E, F, G, H, I, K, L, M, N, P, Q, R, S, T, V, W, or Y; X$_9$ is A, D, F, G, H, I, K, L, M, N, P, Q, R, S, T, V, W, or Y; and X$_{10}$ is A, D, E, F, G, H, I, K, L, M, N, P, Q, R, S, T, V, or Y.

In a further aspect, the present invention provides a host cell containing the nucleic acid described above.

In a further more aspect, the present invention provides a phage containing a disulfide-stabilized single chain antibody fused with its coat protein on the surface. The phage is prepared by a method having the steps of: providing the above-described host cell, and culturing the host cell in a medium under conditions allowing expression of the phage.

In further another aspect, the present invention provides a method for producing a disulfide-stabilized single chain antibody. The method includes the steps of providing a host cell containing an expression construct, and culturing the host cell in a medium under conditions allowing expression of the disulfide-stabilized single chain antibody. The expression construct includes a first nucleotide sequence encoding a signal peptide, and a second nucleotide sequence encoding a single chain antibody capable of forming an interface disulfide bond; the signal peptide has the amino acid sequence of:
(a)
VKKLLX$_1$X$_2$X$_3$X$_4$X$_5$X$_6$X$_7$X$_8$X$_9$X$_{10}$AAQPAMAHHH HHHGH (SEQ ID NO:596), in which X$_1$ is A, C, F, G, I, L, M, P, Q, S, V, W, or Y; X$_2$ is A, D, F, G, H, I, L, M, N, P, S, T, V, or W; X$_3$ is A, F, G, L, M, P, Q, R, S, T, V, or W; X$_4$ is A, F, G, H, I, L, M, P, Q, R, S, T, V, W, or Y; X$_5$ is A, C, D, F, G, H, I, L, M, P, Q, R, S, T, V, W, or Y; X$_6$ is A, C, D, F, G, H, I, K, L, M, N, P, Q, R, S, T, V, W, or Y; X$_7$ is A, C, D, F, G, H, I, K, L, M, N, P, Q, R, S, T, V, W, or Y; X$_8$ is A, C, D, E, F, G, H, I, K, L, M, N, P, Q, R, S, T, V, W, or Y; X$_9$ is A, C, D, E, F, G, H, I, L, M, N, P, Q, R, S, T, V, W, or Y; and X$_{10}$ is A, C, D, E, F, G, H, I, K, L, M, N, P, Q, R, S, T, V, W, or Y;
(b)
VKKLLFAIPLX$_1$X$_2$X$_3$X$_4$X$_5$X$_6$X$_7$X$_8$X$_9$X$_{10}$MAHHHH HHGH (SEQ ID NO:597), in which X$_1$ A, C, F, G, H, I, L, M, N, P, Q, S, T, V, W, or Y; X$_2$ is A, C, D, F, G, H, I, L, M, P, Q, R, S, T, V, W, or Y; X$_3$ is A, C, D, F, G, H, I, L, M, N, P, Q, R, S, T, V, W, or Y; X$_4$ is A, C, E, F, H, I, K, L, M, N, P, Q, R, S, T, V, W, or Y; X$_5$ is A, C, D, F, H, I, L, M, N, P, Q, R, S, T, V, W, or Y; X$_6$ is A, C, D, E, F, G, H, K, L, M, P, Q, R, S, T, V, W, or Y; X$_7$ is A, D, E, F, G, H, K, L, M, N, P, Q, R, S, T, V, or Y; X$_8$ is A, C, F, G, I, K, L, M, N, P, Q, R, S, T, or V, X$_9$ is A, C, D, F, H, I, L, M, N, P, Q, R, S, T, V, W, or Y; and X$_{10}$ is A, C, D, E, F, G, H, L, M, P, Q, R, S, or T; or
(c) VKKLLFAIPLVVPFYX$_1$X$_2$X$_3$X$_4$X$_5$X$_6$X$_7$X$_8$X$_9$X$_{10}$H HHGH (SEQ ID NO:598), in which X$_1$ is A, C, D, F, G, I, L, M, N, P, Q, R, S, T, V, or Y; X$_2$ is A, C, D, F, G, H, K, L, N, P, Q, R, S, T, V, W, or Y; X$_3$ is A, C, E, F, G, H, I, K, L, M, N, P, Q, R, S, T, V, W, or Y; X$_4$ is A, C, D, F, G, H, I, L, M, N, P, Q, R, S, T, V, W, or Y; X$_5$ is A, C, E, F, G, H, I, K, L, M, N, P, Q, R, S, T, W, or Y; X$_6$ is A, C, D, E, F, G, H, I, K, L, M, N, P, Q, R, S, T, V, W, or Y; X$_7$ is A, D, E, F, G, H, K, L, M, N, P, Q, R, S, T, V, or Y; X$_8$ is A, E, F, G, H, I, K, L, M, N, P, Q, R, S, T, V, W, or Y; X$_9$ is A, D, F, G, H, I, K, L, M, N, P, Q, R, S, T, V, W, or Y; and X$_{10}$ is A, D, E, F, G, H, I, K, L, M, N, P, Q, R, S, T, V, or Y.

In addition, the present invention provides a new signal peptide that facilitates production of disulfide-stabilized single chain antibody, and the nucleic acid encoding the signal peptide.

The details of one or more embodiments of the invention are set forth in the description below. Other features, objects, and advantages of the invention will be apparent from the description and from the claims.

BRIEF DESCRIPTION OF THE DRAWINGS

The foregoing summary, as well as the following detailed description of the invention, will be better understood when read in conjunction with the appended drawings. It should be understood, however, that the invention is not limited to the precise arrangements and instrumentalities shown.

FIG. 1 is a schema showing the signal sequence in pCANTAB5E and the constructs of DNA libraries to diversify the tentative signal sequence responsible for the expression of the phage-displayed pIII fusion proteins.

FIG. 3 is a schema showing the DNA construct of the S5 anti-VEGF sc-dsFv as a pIII fusion protein in the pCANTAB5E phagemid.

FIG. 6A shows a comparison of the extents (percentages) of the interface disulfide bond formation of the sc-dsFv from the optimum signal sequence variants from L4; both of the axes show the ratio (percent) of the ELISA signal for VEGF-binding after the fXa treatment over the ELISA signal for VEGF-binding before the fXa treatment; the y-axis shows the data from secreted sc-dsFv; the x-axis shows the data from phage-displayed sc-dsFv.

DETAILED DESCRIPTION OF THE INVENTION

Figure 2:
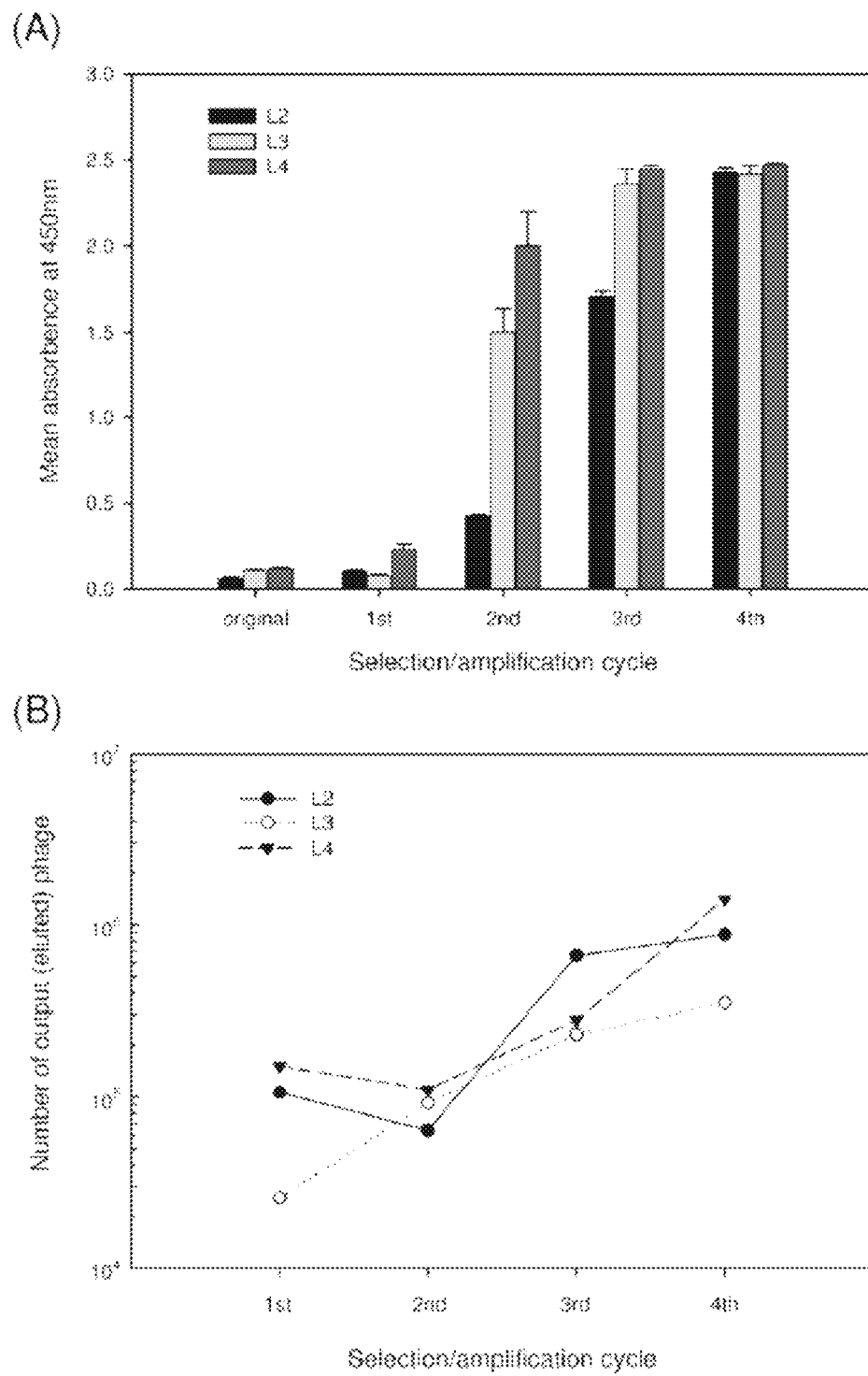
FIG. 2 is a set of diagrams showing the results of the increased binding to VEGF for phage-displayed sc-dsFv signal sequence variants enriched from the three libraries after selection/amplification cycles, including (A) after each round of selection/amplification cycle, the values of the binding of the rescued phage to immobilized VEGF as measured with ELISA. The ELISA signal strengths are shown in the y-axis, as functions of the selection/amplification cycle; and (B) the numbers of output phage particles titered after each round of selection/amplification cycle for each of the three libraries; the output phage titers, as shown in the y-axis, were plotted against the number of the selection/amplification cycles.

Unless defined otherwise, all technical and scientific terms used herein have the meaning commonly understood by a person skilled in the art to which this invention belongs. As used herein, the following terms have the meanings ascribed to them unless specified otherwise.

The articles "a" and "an" are used herein to refer to one or more than one (i.e., at least one) of the grammatical object of the article. By way of example, "an element" means one element or more than one element.

Amino acids can be expressed by three letters or one letters. Table 1 lists standard amino acid abbreviations.

TABLE 1

Standard amino acid abbreviations

| Amino Acid | 3-Letter | 1-Letter |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Very little is known as to why some sc-dsFv constructs could not be expressed on phage surface, and why the disulfide bonds of the newly synthesized preprotein can only be formed in the oxidizing environment of periplasm. The mechanism for the translocation of the nascent unfolded polypeptide chain from the translation site in the cytoplasm across the periplasmic membrane could be a key determinant for the folding. It was unexpectedly found in the invention that for the expression of the displayed protein on the phage surface, alternative sequences in the signal peptide region can modulate the expression level and folding quality of the displayed protein. Accordingly, the invention provides a methodology to systematically optimize the signal sequences for phage-displayed protein expression. Based on the optimized signal sequences and the methodologies of the invention, phage display systems with the sc-dsFv format are established.

According to the present invention, a nucleic acid library for identifying a signal peptide that facilitates production of disulfide-stabilized single chain antibody is provided. The library has a plurality of expression constructs, each of which includes: a first nucleotide sequence encoding a signal peptide, and a second nucleotide sequence encoding a single chain antibody capable of forming an interface disulfide bond. The second nucleotide sequence is located 3' downstream to the first nucleotide. The signal peptide has the amino acid sequence of:

(a)    VKKLLX$_1$X$_2$X$_3$X$_4$X$_5$X$_6$X$_7$X$_8$X$_9$X$_{10}$AAQPAMAHH HHHHGH (SEQ ID NO:1), (b)    VKKLLFAIPLX$_1$X$_2$X$_3$X$_4$X$_5$X$_6$X$_7$X$_8$X$_9$X$_{10}$MAHHH HHHGH (SEQ ID NO:2), or (c)    VKKLLFAIPLVVPFYX$_1$X$_2$X$_3$X$_4$X$_5$X$_6$X$_7$X$_8$X$_9$X$_{10}$H HHGH (SEQ ID NO:3), each of $X_1$-$X_{10}$ in (a), (b), and (c) being one of the 20 naturally occurring amino acid residues.

In one embodiment, each of the expression constructs further includes a third nucleotide encoding a phage coat protein, and the third nucleotide sequence being located 3' downstream to the second nucleotide.

The term "signal peptide" or "signal sequence" used herein refers to a short (i.e. 3-60 amino acids long) peptide chain that directs the transport of a protein. The signal peptide is known to be responsible for the sec system-dependent translocation of the sc-dsFv-pIII fusion from the translation site in cytoplasm across the periplasmic membrane, a critical process for the integration of the displayed protein on the recombinant phage. Considering the vast signal peptide sequence space needed to be explored, the present invention provides biological combinatorial strategies to diversify the signal peptide sequences with synthetic phage display libraries. The variants in the phage libraries were selected and screened for high expression capabilities, so as to identify the key regions of the signal peptide sequences, including the optimal amino acid sequences, positions and types that are effectively responsible for the sc-dsFv expression on phage surface.

The term "single chain variable fragment" or "scFv" used herein refers to a single polypeptide chain antibody fragment construct encoding a first variable region and a second variable region, with a flexible linkage peptide connecting the two domains. The first and the second variable region can be either a light chain or a heavy chain variable region. The recombinant antibody fragment frequently retains antigen-recognizing capability rivaling that of the parent antibody. One shortcoming of the scFv scaffold is the aggregation tendency of the scFv molecules under physiological and storage conditions. The aggregation mechanism has much to do with the stability of the two variable domains and the dimeric interface. This structural instability has thus impacted negatively on the utilities of scFv, leading to uncertainties to the outcomes of the selected and screened scFv molecules in terms of their potential applications in biomedicine.

The term "disulfide-stabilized single chain antibody variable fragment" or "sc-dsFv" used herein refers to a single polypeptide chain containing two variable regions capable of forming an interface disulfide bond, where each of the two variable regions may be a heavy chain variable region or a light chain variable region. According to the invention, the sc-dsFv-pIII fusion protein can be prepared by using the optimal signal sequences capable of directing the sc-dsFv expression on phage surface.

In an embodiment of the invention, the overlapping segments encompassing the complete signal sequence region governing the protein trafficking of the model anti-VEGF sc-dsFv fusion protein were searched with biological combinatorial methodology for sequence preferences leading to effective expression of the sc-dsFv. The engineering platform established for the disulfide-stabilized antibody variable domain fragment as demonstrated could be used to prepare many of scFv molecules in a more stable structure, which could be carried out under harsh conditions, and have longer shelf-life.

According to one embodiment of the invention, to select signal sequences for effective expression of anti-VEGF sc-dsFv on M13 phage surface, phage display libraries L2, L3 and L4 were constructed to diversify the signal sequence as shown in FIG. 1, where M13PIII-pelB indicated the signal sequence being the wild type signal sequence for pIII in M13 phage genome in connection with pelB peptidase cleavage site. The complexities of the L2, L3 and L4 phage display library were $3.1 \times 10^9$, $3.7 \times 10^9$, and $1.5 \times 10^9$, respectively. These libraries were designed to efficiently diversify the signal peptide sequences on identifying the optimum signal peptides for expression sc-dsFv.

In one example of the invention, the expression construct is a phagemid. Among the expression constructs, the nucleotide sequence of the signal peptide, sc-dsFv and the phage coat protein could be operatively linked in a random order. In one preferred example of the invention, the second nucleotide sequence encoding sc-dsFv is located 3' downstream to the first nucleotide encoding the signal peptide, and the third nucleotide sequence encoding the phage coat protein is located 3' downstream to the second nucleotide sequence.

In one embodiment of the invention, a sc-dsFv library, containing more than one billion sc-dsFv variants, is propagated with an *E. coli* vector of bacterial phage origin following the method as described by McCafferty, J. et al. (*Nature* 348(6301), 552-554, 1990). The recombinant phages displaying the sc-dsFv variants can be selected or screened for antigen-binding and re-amplified with the host cells, i.e. *E. coli*.

Furthermore, the present invention provides a host cell library for identifying a signal peptide that facilitates production of disulfide-stabilized single chain antibody. The library includes a plurality of host cells each containing the aforementioned expression constructs.

The present invention also provides a phage library for identifying a signal peptide that facilitates production of disulfide-stabilized single chain antibody. The library includes a plurality of phage particles each containing a disulfide-stabilized single chain antibody fused with a coat protein on the surface of said phage. The phage library is prepared by the steps of: providing a host cell containing an expression construct, and culturing the host cell in a medium under conditions allowing expression of the plurality of phage particles. The expression construct includes (1) a first nucleotide sequence encoding a signal peptide, (2) a second nucleotide sequence encoding a single chain antibody capable of forming an interface disulfide bond, the second nucleotide sequence being located 3' downstream to the first nucleotide, and (3) a third nucleotide sequence encoding a phage envelop protein, the third nucleotide sequence being located 3' downstream to the second nucleotide sequence. The signal peptide has the amino acid sequence of (a)    VKKLLX$_1$X$_2$X$_3$X$_4$X$_5$X$_6$X$_7$X$_8$X$_9$X$_{10}$AAQPAMAH HHHHHGH (SEQ ID NO:1), (b)    VKKLLFAIPLX$_1$X$_2$X$_3$X$_4$X$_5$X$_6$X$_7$X$_8$X$_9$X$_{10}$MAHHH HHHGH (SEQ ID NO:2), or (c) VKKLLFAIPLVVPFYX$_1$X$_2$X$_3$X$_4$X$_5$X$_6$X$_7$X$_8$X$_9$X$_{10}$HHGH (SEQ ID NO:3), each of X$_1$-X$_{10}$ in (a), (b), and (c) is one of the 20 naturally occurring amino acid residues.

On the other hand, a sc-dsFv engineering platform is established for preparation of scFv molecules in a more stable structure in the present invention. Accordingly, the present invention provides an isolated nucleic acid that has a first nucleotide sequence encoding a signal peptide, and a second nucleotide sequence encoding a single chain antibody capable of forming an interface disulfide bond. The second nucleotide sequence is located 3' downstream to the first nucleotide. The signal peptide has the amino acid sequence of (a) VKKLLX$_1$X$_2$X$_3$X$_4$X$_5$X$_6$X$_7$X$_8$X$_9$X$_{10}$AAQPAMAHHHHHHGH (SEQ ID NO:596), in which X$_1$ is A, C, F, G, I, L, M, P, Q, S, V, W, or Y; X$_2$ is A, D, F, G, H, I, L, M, N, P, S, T, V, or W; X$_3$ is A, F, G, L, M, P, Q, R, S, T, V, or W; X$_4$ is A, F, G, H, I, L, M, P, Q, R, S, T, V, W, or Y; X$_5$ is A, C, D, F, G, H, I, L, M, P, Q, R, S, T, V, W, or Y; X$_6$ is A, C, D, F, G, H, I, K, L, M, N, P, Q, R, S, T, V, W, or Y; X$_7$ is A, C, D, F, G, H, I, K, L, M, N, P, Q, R, S, T, V, W, or Y; X$_8$ is A, C, D, E, F, G, H, I, K, L, M, N, P, Q, R, S, T, V, W, or Y; X$_9$ is A, C, D, E, F, G, H, I, L, M, N, P, Q, R, S, T, V, W, or Y; and X$_{10}$ is A, C, D, E, F, G, H, I, K, L, M, N, P, Q, R, S, T, V, W, or Y;

(b) VKKLLFAIPLX$_1$X$_2$X$_3$X$_4$X$_5$X$_6$X$_7$X$_8$X$_9$X$_{10}$MAHHHHHHGH (SEQ ID NO:597), in which X$_1$ is A, C, F, G, H, I, L, M, N, P, Q, S, T, V, W, or Y; X$_2$ is A, C, D, F, G, H, I, L, M, P, Q, R, S, T, V, W, or Y; X$_3$ is A, C, D, F, G, H, I, L, M, N, P, Q, R, S, T, V, W, or Y; X$_4$ is A, C, E, F, H, I, K, L, M, N, P, Q, R, S, T, V, W, or Y; X$_5$ is A, C, D, F, H, I, L, M, N, P, Q, R, S, T, V, W, or Y; X$_6$ is A, C, D, E, F, G, H, K, L, M, P, Q, R, S, T, V, W, or Y; X$_7$ is A, D, E, F, G, H, K, L, M, N, P, Q, R, S, T, V, or Y; X$_8$ is A, C, F, G, I, K, L, M, N, P, Q, R, S, T, or V; X$_9$ is A, C, D, F, H, I, L, M, N, P, Q, R, S, T, V, W, or Y; and X$_{10}$ is A, C, D, E, F, G, H, L, M, P, Q, R, S, or T; or (c) VKKLLFAIPLVVPFYX$_1$X$_2$X$_3$X$_4$X$_5$X$_6$X$_7$X$_8$X$_9$X$_{10}$HHGH (SEQ ID NO:598), in which X$_1$ is A, C, D, F, G, I, L, M, N, P, Q, R, S, T, V, or Y; X$_2$ is A, C, D, F, G, H, K, L, N, P, Q, R, S, T, V, W, or Y; X$_3$ is A, C, E, F, G, H, I, K, L, M, N, P, Q, R, S, T, V, W, or Y; X$_4$ is A, C, D, F, G, H, I, L, M, N, P, Q, R, S, T, V, W, or Y; X$_5$ is A, C, E, F, G, H, I, K, L, M, N, P, Q, R, S, T, W, or Y; X$_6$ is A, C, D, E, F, G, H, I, K, L, M, N, P, Q, R, S, T, V, W, or Y; X$_7$ is A, D, E, F, G, H, I, K, L, M, N, P, Q, R, S, T, V, or Y; X$_8$ is A, E, F, G, H, I, K, L, M, N, P, Q, R, S, T, V, W, or Y; X$_9$ is A, D, F, G, H, I, K, L, M, N, P, Q, R, S, T, V, W, or Y; and X$_{10}$ is A, D, E, F, G, H, I, K, L, M, N, P, Q, R, S, T, V, or Y.

According to the invention, the nucleic acid further includes a third nucleotide encoding a phage coat protein. The third nucleotide sequence is located 3' downstream to the second nucleotide sequence.

In one example of the invention, anti-VEGF sc-dsFv phage display platform was developed. As shown in FIG. 1, expression constructs for identifying a signal peptide that facilitates production of disulfide-stabilized single chain antibody were designed. Each of the three DNA libraries (L2, L3, and L4) contained ten consecutive NNK degenerate codons covering overlapping regions around the signal sequence. N stands for A, G, T, or C, 25% each; K stands for G or T, 50% each. The NNK degenerated codon represents 32 possible triplet combinations, encoding all 20 natural amino acids and an amber stop codon (TAG). Each of the phage display libraries was selected for binding against immobilized VEGF. The trends of enrichment of the VEGF-binding phage variants from each of the three libraries, plotted as functions of the number of selection/amplification cycle, are shown in FIG. 2. The enrichment trends were similar among the variants from the three libraries. This result indicates that the signal sequence regions covered by the three signal sequence libraries (see FIG. 1) can all be optimized to increase the expression of the correctly folded anti-VEGF sc-dsFv on phage surface.

In order to further identify binding variants, more than 3000 colonies were randomly selected from each of the libraries L2, L3, and L4 after selection/amplification cycles for enrichment of the binding variants. These phage colonies were individually rescued and spotted on nitrocellulose membranes coated with VEGF (100 μg/30 ml). According to the invention, each of the signal peptides having the amino acid sequences of SEQ ID NOS: 5-593 as listed in Tables 2, 3 and 4 was obtained and proved to be capable of facilitating the expression of the sc-dsFv on phage surface. After normalization based on the standard phage solution signals in each of the blocks, the phage-displayed scFv expression efficiency for each of the samples was calculated with the following equation:

$$\text{Ratio} = \frac{\text{sample}(CV)}{\text{sample}(C0)} \bigg/ \frac{\text{control}(CV)}{\text{control}(C0)}$$

The value of the sample (CV) is the average normalized signal from VEGF-coated membrane; that of the sample (C0) is the averaged normalized signal from the un-coated and un-blocked membrane. Similarly, those of the control (CV) and control (C0) are the averaged normalized signals for the control phage in the same block where the sample signals are measured on corresponding membrane. The ratio derived from the equation was used to rank the efficiency of the sample phage binding to the immobilized VEGF. All the phage samples with measurable binding strengths with the immobilized VEGF were ranked; the signal sequences of the top fifty ranked phage samples are shown and marked with "*" in Tables 2-4.

Accordingly, new signal peptides that facilitate production of disulfide-stabilized single chain antibody were obtained (see Example 2). In the embodiment of the invention, the signal peptide selected from the group consisting of the peptides having the amino acid sequences set forth in SEQ ID NOS: 5-593 were proved to facilitate production of disulfide-stabilized single chain antibody. On the other hand, a new isolated nucleic acid encoding the above mentioned signal peptide was provided as well.

In a preferred embodiment of the invention, the signal peptide selected from the peptides having the amino acid sequences set forth in SEQ ID NOS: 5-16, 18-19, 21-29, 31-36, 38-42, 45, 48-53, 55, 57-64, 255-304, 381-429 and 476 was obtained and proved to facilitate production of disulfide-stabilized single chain antibody. Accordingly, the preferred isolated nucleic acid encoding each signal peptide as mentioned was also provided.

In one example of the present invention, the anti-VEGF sc-dsFv was developed by using the signal peptides as identified and obtained by the method of the present invention. In another example, anti-H5 sc-dsFv against influenza virus was developed (see FIG. 5).

Figure 4:
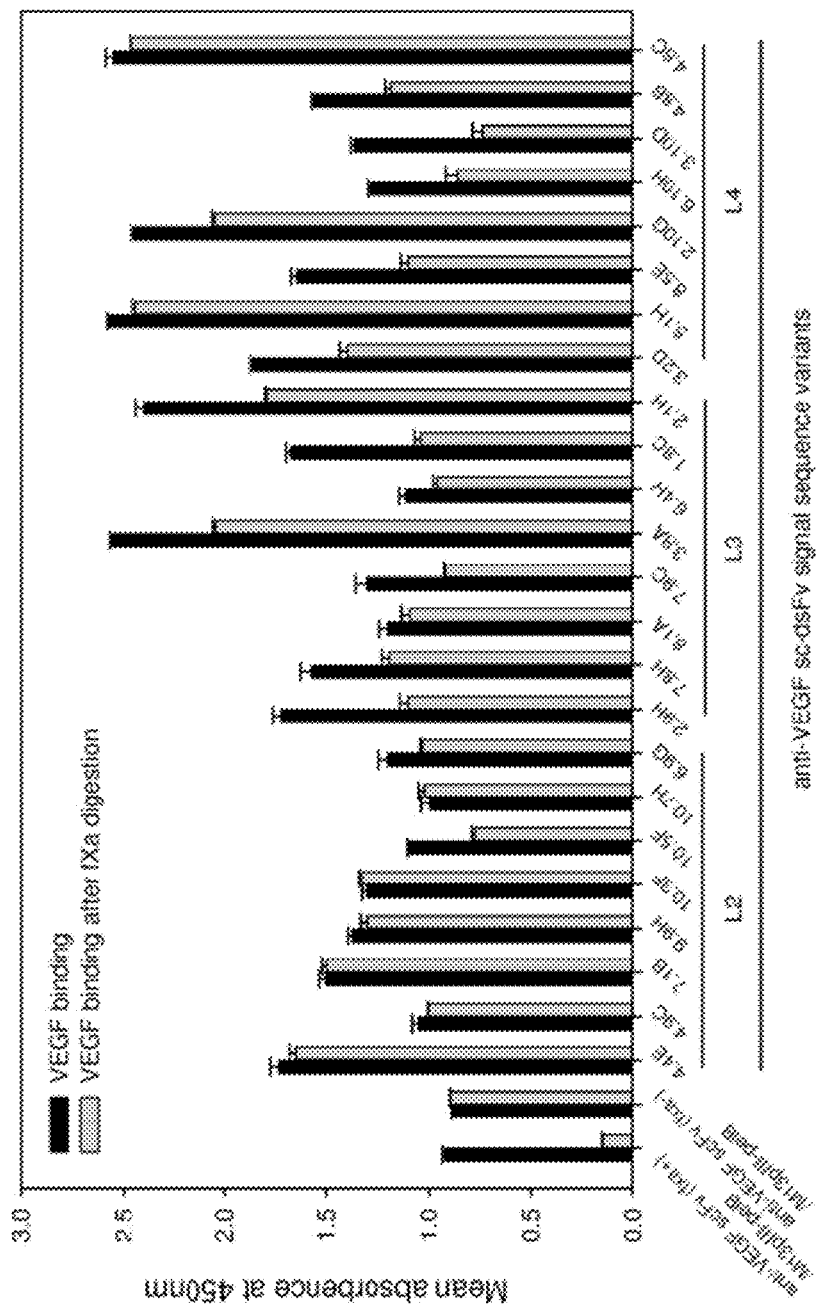
FIG. 4 is a diagram showing VEGF-binding strengths of the phage-displayed anti-VEGF sc-dsFv's from various signal sequence variants with or without fXa digestion. Eight variants with maximal fXa digestion resistance from a 96-well ELISA plate containing 96 randomly picked variants were selected from each of the VEGF-binding enriched libraries after the 4$^{th}$ round of selection/amplification cycle. These variants were cultured and the rescued phages were allowed to bind to immobilized VEGF with (grey histogram) and without (black histogram) the fXa treatment, and the VEGF-binding strengths (y-axis) were measured with ELISA. The error bars were derived from three repeats of the ELISA measurement.

In order to confirm the formation of disulfide bond in the phage-displayed sc-dsFv variants of the present invention, a fXa substrate sequence (-IEGR-) in the linker sequence between the two variable domains was constructed. As shown in FIG. 4, without the fXa treatment, both anti-VEGF scFv (fXa+) and scFv(fXa−) bound to immobilized VEGF. In contrast, with the fXa treatment, only the anti-VEGF scFv(fXa−)

bound to immobilized VEGF. The cleavage of the fXa substrate sequence in the phage-displayed anti-VEGF scFv (fXa+) resulted in separation of the variable domains, which in turn abolished the affinity of the phage-displayed scFv against immobilized VEGF. The anti-VEGF scFv(fXa−) was quite insensitive to the treatment of fXa, indicating that no other fXa substrate sequences exist in the displayed protein.

Unexpectedly, it was found in the present invention that each of the signal peptides having the amino acid sequences of SEQ ID NOS: 5-593 as listed in Tables 2-4 enabled the expression and proper folding of the sc-dsFv structure on the phage-displayed platform. In addition, they resulted in secretion of the soluble non-fusion sc-dsFv in culture media.

Accordingly, the present invention also provides a method for producing a disulfide-stabilized single chain antibody. The method includes providing a host cell containing an expression construct, and culturing the host cell in a medium under conditions allowing expression of the disulfide-stabilized single chain antibody. The expression construct includes a first nucleotide sequence encoding a signal peptide, and a second nucleotide sequence encoding a single chain antibody capable of forming an interface disulfide bond. The second nucleotide sequence is located 3′ downstream to the first nucleotide. The signal peptide has the amino acid sequence of:

(a)
VKKLLX$_1$X$_2$X$_3$X$_4$X$_5$X$_6$X$_7$X$_8$X$_9$X$_{10}$AAQPAMAHHHH HHGH (SEQ ID NO:596), in which X$_1$ is A, C, F, G, I, L, M, P, Q, S, V, W, or Y; X$_2$ is A, D, F, G, H, I, L, M, N, P, S, T, V, or W; X$_3$ is A, F, G, L, M, P, Q, R, S, T, V, or W; X$_4$ is A, F, G, H, I, L, M, P, Q, R, S, T, V, W, or Y; X$_5$ is A, C, D, F, G, H, I, L, M, P, Q, R, S, T, V, W, or Y; X$_6$ is A, C, D, F, G, H, I, K, L, M, N, P, Q, R, S, T, V, W, or Y; X$_7$ is A, C, D, F, G, H, I, K, L, M, N, P, Q, R, S, T, V, W, or Y; X$_8$ is A, C, D, E, F, G, H, I, K, L, M, N, P, Q, R, S, T, V, W, or Y; X$_9$ is A, C, D, E, F, G, H, I, L, M, N, P, Q, R, S, T, V, W, or Y; and X$_{10}$ is A, C, D, E, F, G, H, I, K, L, M, N, P, Q, R, S, T, V, W, or Y;

(b)
VKKLLFAIPLX$_1$X$_2$X$_3$X$_4$X$_5$X$_6$X$_7$X$_8$X$_9$X$_{10}$MAHHHH HHGH (SEQ ID NO:597), in which X$_1$ A, C, F, G, H, I, L, M, N, P, Q, S, T, V, W, or Y; X$_2$ is A, C, D, F, G, H, I, L, M, P, Q, R, S, T, V, W, or Y; X$_3$ is A, C, D, F, G, H, I, L, M, N, P, Q, R, S, T, V, W, or Y; X$_4$ is A, C, E, F, H, I, K, L, M, N, P, Q, R, S, T, V, W, or Y; X$_5$ is A, C, D, F, H, I, L, M, N, P, Q, R, S, T, V, W, or Y; X$_6$ is A, C, D, E, F, G, H, I, K, L, M, N, P, Q, R, S, T, V, W, or Y; X$_7$ is A, D, E, F, G, H, K, L, M, N, P, Q, R, S, T, V, or Y; X$_8$ is A, C, F, G, I, K, L, M, N, P, Q, R, S, T, or V; X$_9$ is A, C, D, F, H, I, L, M, N, P, Q, R, S, T, V, W, or Y; and X$_{10}$ is A, C, D, E, F, G, H, L, M, P, Q, R, S, or T; or (c)
VKKLLFAIPLVVPFYX$_1$X$_2$X$_3$X$_4$X$_5$X$_6$X$_7$X$_8$X$_9$X$_{10}$HH HGH (SEQ ID NO:598), in which X$_1$ is A, C, D, F, G, I, L, M, N, P, Q, R, S, T, V, or Y; X$_2$ is A, C, D, F, G, H, K, L, N, P, Q, R, S, T, V, W, or Y; X$_3$ is A, C, E, F, G, H, I, K, L, M, N, P, Q, R, S, T, V, W, or Y; X$_4$ is A, C, D, F, G, H, I, L, M, N, P, Q, R, S, T, V, W, or Y; X$_5$ is A, C, E, F, G, H, I, K, L, M, N, P, Q, R, S, T, W, or Y; X$_6$ is A, C, D, E, F, G, H, I, K, L, M, N, P, Q, R, S, T, V, W, or Y; X$_7$ is A, D, E, F, G, H, I, K, L, M, N, P, Q, R, S, T, V, or Y; X$_8$ is A, E, F, G, H, I, K, L, M, N, P, Q, R, S, T, V, W, or Y; X$_9$ is A, D, F, G, H, I, K, L, M, N, P, Q, R, S, T, V, W, or Y; and X$_{10}$ is A, D, E, F, G, H, I, K, L, M, N, P, Q, R, S, T, V, or Y.

Figure 6:
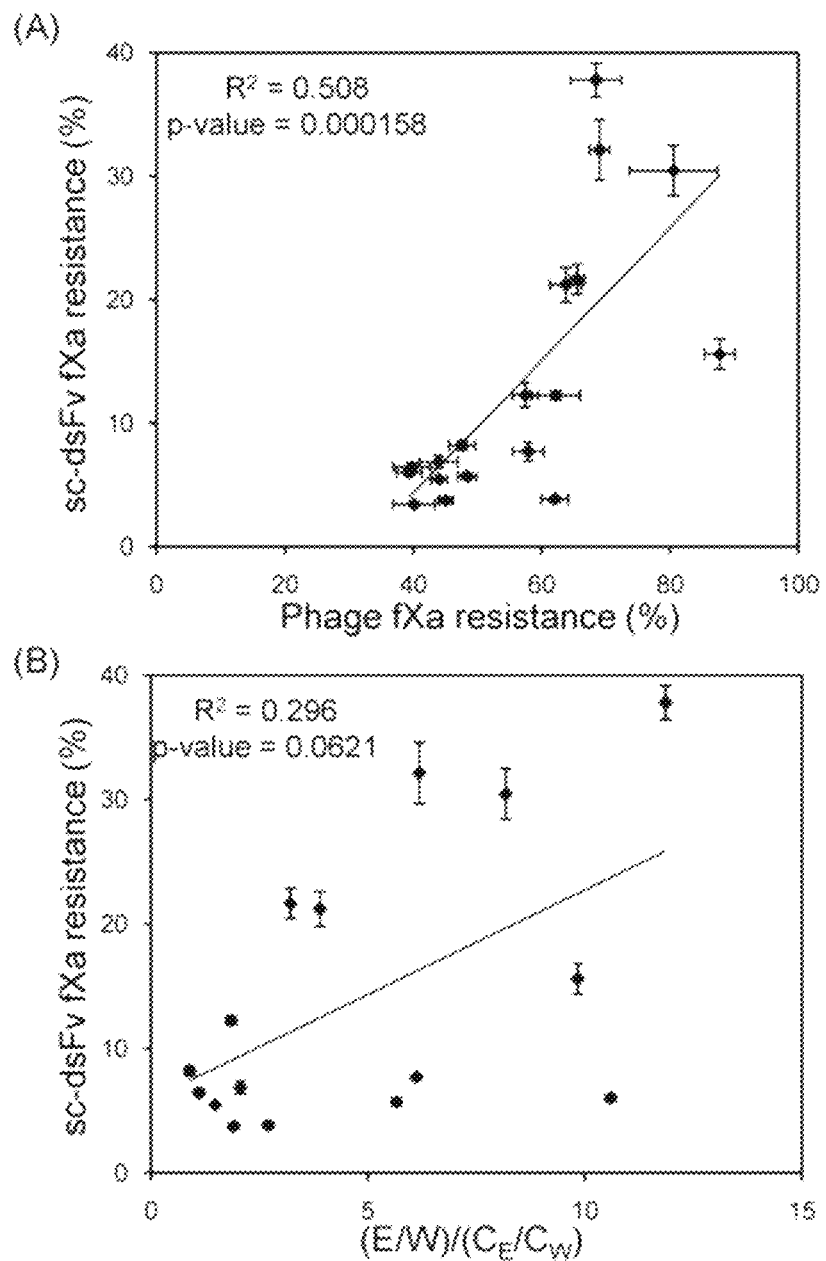
FIGS. 6A and B are diagrams showing correlations between sc-dsFv folding quality and resistance to fXa digestion.
FIG. 6B shows a comparison of the extents (percentages) of the interface disulfide bond formation (y-axis) with the folding quality (x-axis) of the sc-dsFv from the optimum signal sequence variants from L4. The sc-dsFv folding quality (x-axis) is represented as the sc-dsFv-VEGF binding ELISA signal divided by western blot signal probed with anti-E tag antibody (E/W, VEGF binding signal divided by secreted sc-dsFv quantity), and then the ratio is normalized with that of anti VEGF scFv (fXa+) (CE/CW, VEGF binding signal divided by secreted scFv quantity), that is, the folding quality is quantified with the ratio: (E/W)/(CE/CW); the error bars in each data point indicate the standard deviations from three repeats of the experiment; the coefficient of determination $R^2$ and the p-value from Spearman's rank correlation coefficient was shown in each panel.

Similar to the aforementioned experiment, the extent (percentage) of the interface disulfide bond formation of the sc-dsFv from the optimum signal sequence variants from L4 were tested. As shown in FIG. 6A, signal sequence optimization could improve the disulfide bond formation in the sc-dsFv from ~0% up to 40% of the secreted sc-dsFv molecule.

As shown in FIG. 6B, the interface disulfide bond formation enhanced the affinity for the sc-dsFv-VEGF interaction.

In the present invention, a stability test of soluble sc-dsFv was conducted. As shown in FIGS. 7A and 7B, the sc-dsFv antibody fragment scaffold was indeed substantially more stable than the scFv scafold due to the interface disulfide bond in the sc-dsFv constructs.

According to the invention, the concentration of sc-dsFv antibody produced by the method disclosed herein was unexpectedly high, and stable. Thus, the present invention provides the sc-dsFv at a high concentration sufficient for coating on a solid phase to produce an array for detection or diagnosis without aggregation, different from the prior art where sc-Fv tends to precipitate under the same concentration due to aggregation.

Accordingly, the present invention provides an array of disulfide-stabilized single chain antibodies produced by the aforementioned method coated on a solid phase. In one example of the invention, the solid phase may be made from silicon, plastic, nylon, glass, ceramic, photoresist or rubber. In one embodiment of the present invention, a microarray test was established using the disulfide-stabilized single chain antibodies produced by the method of the invention, demonstrating that influenza virus could successfully be detected by an array of a serious dilution of anti-H5 sc-dsFv coated on a glass.

The present invention is further illustrated by the following examples, which are provided for the purpose of demonstration rather than limitation.

EXAMPLES

Preparation 1: VEGF Expression and Purification—Human VEGF-121

Human VEGF-121 (VEGF-A residue 34-135 receptor binding domain) (Fuh, G. et al., (2006) *J. Biol. Chem.*, 281, 6625-6631) was expressed in *E. coli* as inclusion body. The refolding and purification of VEGF-A were carried out as described in Chang, H. J., et al., (2009) *Structure*, 17, 620-631.

Preparation 2: Phage Display Libraries with Diversified Signal Sequences N-terminal to the sc-dsFv-pIII Fusion Protein Phage display libraries with diversified sequences in the signal peptide region N-terminal to the sc-dsFv-pIII fusion protein were constructed with pCANTAB5E phagemid (GE-Amersham Biosciences) as shown in FIG. 1. Primers encoded with the sequence diversification shown in FIG. 1 were synthesized by IDT (Integrated DNA Technologies).

For each of the phage display libraries, phagemid templates were constructed with TAA stop codons inserted in the sequence region for diversification (Huang et al., (2010) *J. Biol. Chem.*, in press). The M13pIII-pelB signal sequence for phage-displayed pIII-fusion protein is a combination of the wild-type M13 signal peptide N-terminal to gene III (MKKLLFAIPLVVPFYSHS) (SEQ ID NO:594) and the pelB signal sequence of *Pectobacterium wasabiae* (MKYLLPTAAAGLLLLAAQPAMA) (SEQ ID NO:595). This merged signal sequence (shown in bold font above) was considered containing the tentative n- h- and c-regions of the signal sequence. DNA libraries were constructed to diversify the amino acid sequence in the key regions. Each of the four of DNA libraries (L2, L3, L7) contained ten consecutive NNK (N stands for 25% of G, C, A, and T, and K stands for 50% of G and T; underlined by dashed lines) degenerate codons covering a portion of the tentative signal sequence.

Also shown in the Figure are the sequences containing TAA stop codons (underlined regions) used as the templates for the library constructions. The oligonucleotide-directed mutagenesis procedure initially proposed by Kunkel (Kunkel et al., (1987) *Methods Enzymol*, 154, 367-382) was used for the phagemid library construction. The TAA stop codons in the phagemid templates ensure that the un-mutated phagemid templates after the mutagenesis procedure are incapable of producing pIII fusion protein for phage surface display (Sidhu and Weiss, (2004) Constructing phage display libraries by oligonucleotide-directed mutagenesis. In: Clackson, T., and Lowman, H. B. (eds). *Phage Display*, 1st Ed., Oxford University Press, New York).

After the oligonucleotide-directed mutagenesis procedure, *E. coli* strand ER2738 was transformed with the phagemid libraries and the recombinant phage particles were rescued with helper phage M13KO7 (GE-Amersham Biosciences). The phage particles were precipitated with PEG/NaCl, and resuspended in PBS. More details of the phage library preparation can be found in a previous publication (Hsu, H. J. et al., (2008) *J Biol Chem* 283(18), 12343-12353).

Seven sc-dsFv variants were constructed on the basis of the phagemid encoding the template anti-VEGF scFv(fXa+): S1(L: Gln38Cys & H:Gln39Cys); S2(L:Gly41Cys & H:Gly42Cys); S3(L:Ala43Cys & H:Gln112Cys); S4(L: Phe98Cys & H:Leu45Cys); S5(L:Gln100Cys & H:Gly44Cys); S6(L:Gln38Cys & H:Leu45Cys); S7(L: Ala43Cys & H:Gln112Cys & L:Gln100Cys & H:Gly44Cys). These cysteine pairs were determined by distance constrain for possible disulfide bonds in the model structure (PDB code: 2FJG).

Preparation 3: Biopanning Against VEGF with Phage-displayed Anti-VEGF sc-dsFv Libraries Maxisorb Immune Tubes (Nunc) were coated with VEGF (25 µg in 1 ml PBS in each tube) at 4° C. overnight. The tubes were blocked with 4 ml of 5% skim milk in PBST (PBS with 0.05% Tween 20) for one hour at room temperature with gentle shaking and then washed with PBST. In each of the tubes, $10^{11}$ colony-forming units (cfu) of phage from each of the phage display libraries were mixed with 1 ml of 5% skim milk. The phage particles were allowed to bind to the immobilized VEGF in the tube at room temperature for two hours under gentle shaking. After the binding, the tubes were washed 10 times with PBST and 2 times with PBS. One milliliter of *E. coli* strand ER2738 in the log phase was added to each of the tubes at room temperature with gentle shaking for 15 minutes. From each tube, the infected *E. coli* was transferred to 10 ml of a 2YT medium containing 20 µg/ml of ampicillin and was titered with 2YT agar plates containing 100 µg/ml of ampicillin. The infected *E. coli* was incubated at 37° C. for one hour with vigorous shaking. Ampicillin was then added to reach final concentration of 100 µg/ml. The culture was incubated for another hour at 37° C. before transferred to final 100 ml 2YT medium (100 µg/ml of ampicillin) containing $10^{11}$ cfu M13KO7 helper phage. After two hours of incubation, kanamycin was added to final concentration of 70 µg/ml. The culture was incubated at 37° C. overnight with vigorous shaking. The phage in the supernatant of the culture was harvested by centrifugation. The phage was titered, precipitated with PEG/NaCl, and resuspended in PBS. The phage solution was ready for the next round of selection.

Preparation 4: Enzyme-linked Immunosorbent Assay (ELISA) for Phage-displayed Anti-VEGF Sc-dsFv Binding Against Immobilized VEGF and Anti-E-tag Antibody Single *E. coli* colonies harboring the selected phagemids were randomly picked using a GENETIX Qpix II colony picker to 96-well deep well culture plates. Each well contained 960 µl 12YT (100 µg/ml of ampicillin and 10 µg/ml of tetracyclin). The culture plates were incubated at 37° C. shaking vigorously for 4 hours before adding 20 µl of M13KO7 helper phage ($10^{11}$ cfu/ml). The plates were then incubated at 37° C. for one hour with vigorous shaking before adding 20 µl of kanamycin to the final concentration of 50 µg/ml. After overnight incubation at 37° C. with vigorous shaking, the cultures were centrifuged at 3000 g for 10 minutes at 4° C. From each well of the culture plates, 100 µl of the supernatant was mixed with 100 µl of 5% skim milk. Half of the phage mixture was added to a corresponding well of a 96-well Maxisorb microtiter plate precoated with VEGF (1 µg/well) and blocked with 5% skim milk; the other half was added to a corresponding well of another microtiter plate precoated with polyclonal goat anti-E-tag antibody (1 µg/well, Novus Biologicals). After one hour incubation at room temperature, the ELISA plates were washed six times with PBST. The phage particles remained on the plates were measured with HRP-labeled mouse anti-M13 antibody (1/3000, GE Healthcare) and TMB substrate (KPL). The reaction was stopped with 50 µl of 1 N HCl and the signal intensity was measured at OD 450 nm.

Preparation 5: Measurement of Interface Disulfide Bond Formation in Phage-displayed Anti-VEGF sc-dsFv Fifty microliters of a freshly prepared phage supernatant (see above) was mixed with 50 µl of a two-fold concentrated reaction buffer containing 1 unit of bovine factor Xa (fXa) (Novagen) in a Maxisorb microtiter plate precoated with VEGF (1 µg/well) and blocked with 5% skim milk. After two hours of enzymatic reaction at 37° C., the phage particles remained bound to the microtiter plate were measured following the same ELISA procedure as described above.

Preparation 6: Western Blot Assay for the Phage-displayed Anti-VEGF Sc-dsFv

Single colony phage was amplified, harvested, precipitated with PEG/NaCl, and resuspended in PBS (see above). Phage particles ($10^{11}$ cfu) were prepared under either a non-reducing or reducing condition before electrophoresis in a 10% SDS-polyacrylamide gel. After the electrophoresis, the proteins in the gel were transferred onto a polyvinylidene fluoride (PVDF) membrane (Millipore). The membrane was blocked with 5% skim milk for 1 hour at room temperature and then incubated with a monoclonal mouse anti-pIII antibody (1/3000 mg/ml, New England Biolabs) for one hour at room temperature. After three washes (5 minutes each) with PBST, the membrane was incubated with HRP-labeled anti-mouse antibody (1/3000, GE Healthcare) for 1 hour at room temperature. After three washes with 10 ml PBST, the membrane was developed with 4-chloro-1-naphthol (4CN) substrate (KPL) until the desired color intensity was achieved.

Preparation 7: Preparation of Non-fusion Soluble scFv/Sc-dsFv

Seven hundred and fifty microliters of mid-log phase ($OD_{600\ nm}$=0.6) *E. coli* host (non-suppressor strain HB2151 or suppressor strain ER2738) grown in a 2YT medium (16 g/L tryptone, 10 g/L yeast extract, 5 g/L NaCl, pH 7.0) was infected with 50 µl of a phage solution ($10^{11}$ cfu/ml). After one hour incubation at 37° C. with shaking, 100 µl ampicillin in a 2YT medium was added to the final concentration of 100 µg/ml. After another hour of incubation, 100 µl isopropyl-beta-D-thiogalactopyranoside (IPTG) in a 2YT medium was added to the final concentration of 1 mM. The culture was kept at 37° C. with vigorous shaking overnight. The secreted soluble scFv or sc-dsFv in the supernatant was separated from the bacterial host by centrifugation at 3000 g for 10 minutes.

Preparation 8: ELISA for Immobilized VEGF Binding

For phage ELISA, each well in a Maxisorb 96-well microtiter plate (Nunc) was coated with 2 µg VEGF at 4° C. overnight. The wells were blocked with 5% skim milk in PBST (137 mM NaCl, 2.7 mM KCl, 10 mM $Na_2HPO_4$, 2 mM $KH_2PO_4$, 0.1% tween20, pH 7.4) for one hour. After 3×300 µl PBST and 2×300 µl PBS washes, 100 µl of a phage solution and 100 µl of 5% skim milk in PBST were added to each well and incubated at room temperature with shaking for one hour. After washing each of the wells three times with 300 µl of PBST each and twice with 300 µl of PBS each, the bound phages were labeled with anti-M13 antibody conjugated with HRP (GE-Amersham) 1/3000 dilution in 5% skim milk in PBST for one hour. The ELISA signal was developed by incubating each well with 100 µl of a TMB solution (KPL Inc.) for 5 minutes. The reaction was stopped with 100 µl N HCl, and the optical density was recorded with VICTOR3 Multilabel Plate Readers (Perkin Elmer) at 450 nm.

For scFv or sc-dsFv ELISA, 100 µl of a soluble scFv solution was used instead of phage solution, and HRP-conjugated protein L (0.5 µg/ml in 5% skim milk in PBS, from Pierce) was used instead of HRP-conjugated anti-M13 antibody. When needed, the ELISA signals were normalized with the signals of the control anti-VEGF scFv in serial dilution.

Preparation 9: fXa Protease Digestion

For phage solutions, 20 µl (1 unit) of bovine factor Xa (fXa) protease (Novagen) in a six-fold concentrated reaction buffer was added to 100 µl of a phage solution at 37° C. After 2 hours of enzymatic reaction, 100 µl of 5% skim milk in PBST was added to the reaction mixture before the VEGF-binding ELISA measurement was carried out in the manner described in the previous section. The fXa resistance percentage was calculated with the ratio of the ELISA reading in the presence of fXa over the ELISA reading in the absence of fXa. The ELISA readings for the ratio were adjusted by shift the baseline determined with the null control ELISA readings. For soluble scFv/sc-dsFv fXa digestion, all procedures were the same except that the enzymatic reaction was carried out for one hour at room temperature.

Preparation 10: Construction of Anti-H5 sc-dsFv Against Influenza Virus

The construction of scFv library derived from mouse spleen after immunization of hemagglutinin from influenza virus was based on the protocols described in "Phage Display, A Laboratory Manual, edited by Carlos F. Barbas III, Dennis R. Burton, Jamie K. Scott, and Gregg J. Silverman, 2001, Cold Spring Harbor Laboratory Press, Cold Spring Harbor, N.Y., USA". In brief, after hemagglutinin immunization, the total RNA derived from mouse spleen was purified by Trizol reagent (Invitrogen) according to the manufacturer's protocols. After cDNA synthesis by reverse transcriptase, the gene fragments encoded heavy and light chains of antibody variable region were amplified by the specific primer sets described in the book mentioned above, respectively. The scFv fragments were synthesized by two-steps PCR reactions, and then cloned into a pCANTAB 5E phagemid vector with the signal sequence derived from the library 2 for sc-dsFv phage production. The library complexity was $4.5 \times 10^7$. After panning against H5, two clones were selected for monospectral binding to H5 (clone 8a) and broad spectral binding to H1, H3 and H5 (clone 12a). These two clones were subjected to disulfide bond formation mutants between L100 and H44 (based on Kabat numbering) and then for sc-dsFv phage production and ELISA detection (8aS5 and 12aS5, respectively).

Preparation 11: Microarray Test for sc-dsFv Binding of H5 Influenza Virus

The just-described sc-dsFv ds-8a or and ds-12a was subcloned into a pET32a vector with thioredoxin as a fusion protein partner at the N-terminus. The thioredoxin-sc-dsFv fusion proteins could be expressed in Rosetta-gami B strain of *E. coli* in a soluble form. After purification and TEV protease digestion to remove thioredoxin, the purified ds-8a protein was found to have a binding affinity and specificity similar to those of H5 based on an ELISA assay and array studies. The protein ds-AV1, ds-12a and ds-8a were spot on glass slides coated with streptavidin as the purified ds-AV1, ds-12a and ds-8a proteins contained a biotinylated Avitag sequence at their C-termini. The highest protein concentration used for this protein array was 8 mg/ml, 8 mg/ml, and 0.8 mg/ml, respectively. These proteins were 2 fold dilution with a 100 mM sodium phosphate buffer, pH 8.5 from the highest protein concentration for 15 times for spotting (10n1/spot), and then the protein of each concentration was spotted for 5 replicates. After spotting, each glass slide was sealed to form 16 distinct squares for reaction. After blocking with 5% BSA for 30 minutes, the H5 influenza virus (about ~$10^7$ PFU/ml) was added to react with spotted sc-dsFvs for 30 minutes. After 3 times wash with a phosphate buffer for 5 minutes each, 40 nm fluorescence beads coated with ds-8a (~$10^7$) were added to each square and incubated for 30 minutes. After 3 times wash again with a phosphate buffer for 5 minutes each, the glass array was air-dried for detection.

Example 1

Selection of Signal Sequences for Effective Expression of Anti-VEGF sc-dsFv on M13 Phage Surface Phage display libraries L2, L3, and L4 were constructed to diversify the signal sequence of the S5 anti-VEGF sc-dsFv-pIII fusion protein as shown in FIG. 1. The complete DNA construct and the amino acid sequence of the S5 anti-VEGF sc-dsFv are shown in FIG. 1. The S5 sequence remained unchanged in all the variants from the libraries. The complexities of the L2, L3, and L4 phage display libraries were $3.1\times10^9$, $3.7\times10^9$, and $1.5\times10^9$, respectively. These libraries were designed to diversify the signal peptide sequences in the h-region, c-region, and a few N-terminal residues of the mature phage-displayed anti-VEGF sc-dsFv.

Each of the phage display libraries was selected for binding against immobilized VEGF. The trends of enrichment of the VEGF-binding phage variants from each of the three libraries, plotted as functions of the number of selection/amplification cycle, are shown in FIG. 2. After four rounds of selection/amplification cycle, the VEGF-binding phage variants were enriched for more than one order of magnitude. The enrichment trends were similar among the variants from the three libraries. This result indicates that the signal sequence regions covered by the three signal sequence libraries (FIG. 1) could all be optimized to increase the expression of the correctly folded anti-VEGF sc-dsFv on phage surface.

Example 2

Interface Disulfide Bond Formation in Anti-VEGF sc-dsFv on M13 Phage Surface In order to test the formation of the disulfide bond in the phage-displayed sc-dsFv variants, we constructed two control phage-displayed anti-VEGF scFv variants: one with a factor Xa cutting site, -IEGR- (SEQ ID NO:599), encoded in the linker peptide connecting the two variable domains (anti-VEGF scFv(fXa+)); the other without this fXa cutting site (anti-VEGF scFv(fXa−)). As shown in FIG. 3, the S5 anti-VEGF sc-dsFv was constructed with a fXa substrate sequence (-IEGR-) in the linker sequence between the two variable domains. The cleavage of the fXa substrate sequence in the phage-displayed anti-VEGF scFv(fXa+) resulted in separation of the variable domains, which in turn abolished the affinity of the phage-displayed scFv against immobilized VEGF. Both phage-displayed scFv's did not have the engineered interface disulfide bond as in S5; the scFv(fXa+) construct had the -IEGR- (SEQ ID NO:599) site in the linker peptide (-(G)$_4$SIEGRS(G)$_4$S-) (SEQ ID NO:600), while the scFv(fXa−) construct had the conventional -(G)$_4$S(G)$_4$S(G)$_4$S- (SEQ ID NO:601) linker peptide.

As shown in FIG. 4, without the fXa treatment, both anti-VEGF scFv(fXa+) and scFv(fXa−) bound to immobilized VEGF. But with the fXa treatment, only the anti-VEGF scFv (fXa−) bound to immobilized VEGF. In contrast, all the S5 signal sequence variants for the phage-displayed sc-dsFv showed substantial increase in resistance to fXa protease activity, indicating that the interface disulfide bonds in the anti-VEGF sc-dsFv's were formed to stabilize the functional dimeric structure after the cleavage of the peptide linker between the two variable domains. The results unambiguously demonstrated that the engineered interface disulfide bond was correctly formed in the phage-displayed S5 anti-VEGF sc-dsFv from some of the signal sequence variants from all three VEGF-binding enriched signal sequence libraries (L2, L3 and L4).

Example 3

Preference Sequence Patterns of the Optimum Signal Peptides in Effective Expression of Functional Anti-VEGF sc-dsFv The functionality of the anti-VEGF sc-dsFv on phage surface was quantified with two quantitative measurements: the affinity of the sc-dsFv against VEGF and the extent of the interface disulfide bond formation. After the tests, 250, 126, and 213 optimum signal sequences were found in L2, L3, and L4 library, respectively, which are summarized as following Tables 2-4. Among them, fifty signal sequence variants with the highest sc-dsFv-VEGF binding affinities selected from more than 3000 random single colonies of the enriched libraries L2, L3, and L4 were marked with the symbol "*." The symbol "q" indicated that the nucleotide sequence TAG (amber stop codon) that could be translated to Gln (Q) with 0.8~20% in *E. coli* amber suppressor strains which were normally used in phage production.

TABLE 2

Preference sequence patterns selected from L2 S5 sc-dsFv library

| No. | Code | Sequence | | | SEQ ID NO: |
|---|---|---|---|---|---|
|  | M13-pelB | VKKLL | FAIPLVVPFY | AAQPAMAHHHHHH | 4 |
| 1 | 1.12B | VKKLL | VLSHLPFMTD | AAQPAMAHHHHHH * | 5 |
| 2 | 9.26.10B | VKKLL | SHWLLSSqLQ | AAQPAMAHHHHHH * | 6 |
| 3 | 2.12A | VKKLL | AMSLAPSVFP | AAQPAMAHHHHHH * | 7 |
| 4 | 9.12A | VKKLL | WSLFFqqLNP | AAQPAMAHHHHHH * | 8 |
| 5 | 2.12F | VKKLL | LLSLLQRPLP | AAQPAMAHHHHHH * | 9 |
| 6 | 1.2H | VKKLL | LSSWLMTRFP | AAQPAMAHHHHHH * | 10 |
| 7 | 6.9G | VKKLL | VLSHFPAFVP | AAQPAMAHHHHHH * | 11 |
| 8 | 1.8F | VKKLL | PLLSLPLPPN | AAQPAMAHHHHHH * | 12 |
| 9 | 7.1B | VKKLL | VLTPMHFSSP | AAQPAMAHHHHHH * | 13 |
| 10 | 9.26.10A | VKKLL | ILALPQSYPL | AAQPAMAHHHHHH * | 14 |
| 11 | 5.4A | VKKLL | qALYFSLPSS | AAQPAMAHHHHHH * | 15 |
| 12 | YJ2.2 | VKKLL | VSAMTSASFP | AAQPAMAHHHHHH * | 16 |
| 13 | 5.2F | VKKLL | LPASWLFGQP | AAQPAMAHHHHHH | 17 |
| 14 | 10.2D | VKKLL | WSLFFqqLNP | AAQPAMAHHHHHH * | 18 |
| 15 | YJ2.34 | VKKLL | FVMALRSSAP | AAQPAMAHHHHHH * | 19 |
| 16 | 3.3F | VKKLL | FLWPFYNGHI | AAQPAMAHHHHHH | 20 |
| 17 | 4.1A | VKKLL | QSFYLSLqLD | AAQPAMAHHHHHH * | 21 |
| 18 | 10.7H | VKKLL | SLTFPFTIHS | AAQPAMAHHHHHH * | 22 |
| 19 | 1.9D | VKKLL | WPVLSPSLFP | AAQPAMAHHHHHH * | 23 |
| 20 | 5.12D | VKKLL | PWLFSTFPSS | AAQPAMAHHHHHH * | 24 |
| 21 | 1.8D | VKKLL | IMSSLPTLSP | AAQPAMAHHHHHH * | 25 |

TABLE 2 -continued

Preference sequence patterns selected from L2 S5 sc-dsFv library

| No. | Code | Sequence | | | SEQ ID NO: |
|---|---|---|---|---|---|
| 22 | 4.11F | VKKLL | IMSRVLAPDF | AAQPAMAHHHHHH * | 26 |
| 23 | 1.7C | VKKLL | FDFWFSSFLq | AAQPAMAHHHHHH * | 27 |
| 24 | 4.8G | VKKLL | YGqLMLLSSD | AAQPAMAHHHHHH * | 28 |
| 25 | 4.4E | VKKLL | PWLFPFHAYP | AAQPAMAHHHHHH * | 29 |
| 26 | 1.12G | VKKLL | LVMTLSRQPF | AAQPAMAHHHHHH | 30 |
| 27 | 4.8A | VKKLL | ASAYLYHGLS | AAQPAMAHHHHHH * | 31 |
| 28 | 4.4C | VKKLL | PFFAGVLqHP | AAQPAMAHHHHHH * | 32 |
| 29 | 3.11A | VKKLL | ALSSPFFHIP | AAQPAMAHHHHHH * | 33 |
| 30 | 10.3F | VKKLL | PTRqPMMYPP | AAQPAMAHHHHHH * | 34 |
| 31 | YJ2.15 | VKKLL | QLLMPFLNSP | AAQPAMAHHHHHH * | 35 |
| 32 | 9.9H | VKKLL | CSLGYACIPP | AAQPAMAHHHHHH * | 36 |
| 33 | 4.9C | VKKLL | LMPWLFNSPP | AAQPAMAHHHHHH | 37 |
| 34 | 3.12B | VKKLL | LDqLAYAALS | AAQPAMAHHHHHH * | 38 |
| 35 | 4.10G | VKKLL | qSTVFFSWLS | AAQPAMAHHHHHH * | 39 |
| 36 | YJ2.18 | VKKLL | LPWALSHQVL | AAQPAMAHHHHHH * | 40 |
| 37 | 7.2E-q | VKKLL | ALTYPAFLYD | AAQPAMAHHHHHH * | 41 |
| 38 | 1.11A | VKKLL | AMAPPMMSMN | AAQPAMAHHHHHH * | 42 |
| 39 | 5.3D | VKKLL | WWSSLFAPSP | AAQPAMAHHHHHH | 43 |
| 40 | 4.6H | VKKLL | GSFILARSMD | AAQPAMAHHHHHH | 44 |
| 41 | 5.11C | VKKLL | MVLTSWHPYP | AAQPAMAHHHHHH * | 45 |
| 42 | 2.8C | VKKLL | FSLRFFFPSS | AAQPAMAHHHHHH | 46 |
| 43 | 2.5F | VKKLL | WLWSTPLFPH | AAQPAMAHHHHHH | 47 |
| 44 | 2.2A | VKKLL | PLLFSLDGDP | AAQPAMAHHHHHH * | 48 |
| 45 | 3.2C-d | VKKLL | SVSLSSYSFY | AAQPAMAHHHHHH * | 49 |
| 46 | 3.1H | VKKLL | LNGTESAqLF | AAQPAMAHHHHHH * | 50 |
| 47 | 6.4A | VKKLL | WHVLPYLPNS | AAQPAMAHHHHHH * | 51 |
| 48 | 4.10E | VKKLL | SIVPLFSPqS | AAQPAMAHHHHHH * | 52 |
| 49 | 7.4H | VKKLL | VMTSPMLAPG | AAQPAMAHHHHHH * | 53 |
| 50 | 2.5H | VKKLL | VLSLPSIAPH | AAQPAMAHHHHHH | 54 |
| 51 | 6.4E | VKKLL | qSLLLLRALL | AAQPAMAHHHHHH * | 55 |
| 52 | 2.1A | VKKLL | FSLPVFFDLP | AAQPAMAHHHHHH | 56 |
| 53 | 4.11D | VKKLL | LLFSMARPLP | AAQPAMAHHHHHH * | 57 |
| 54 | 7.10A | VKKLL | TqAVFPFTFN | AAQPAMAHHHHHH * | 58 |
| 55 | 3.2E | VKKLL | LASWLFRADM | AAQPAMAHHHHHH * | 59 |
| 56 | 5.2E | VKKLL | PFLFPFPSPS | AAQPAMAHHHHHH * | 60 |
| 57 | YJ2.128 | VKKLL | ALSAWSLSQT | AAQPAMAHHHHHH * | 61 |
| 58 | 4.7H | VKKLL | ALLPLFPTqH | AAQPAMAHHHHHH * | 62 |
| 59 | 2.10F | VKKLL | AALASFPPAP | AAQPAMAHHHHHH * | 63 |

TABLE 2 -continued

Preference sequence patterns selected from L2 S5 sc-dsFv library

| No. | Code | Sequence | | | SEQ ID NO: |
|---|---|---|---|---|---|
| 60 | YJ2.22 | VKKLL | LLMPFLNQSP | AAQPAMAHHHHHH * | 64 |
| 61 | 7.5A | VKKLL | FTSGLKLVPP | AAQPAMAHHHHHH | 65 |
| 62 | 6.10F | VKKLL | LqPLLSIYLN | AAQPAMAHHHHHH | 66 |
| 63 | 4.11B | VKKLL | LSSLWSAYMD | AAQPAMAHHHHHH | 67 |
| 64 | 2.5C | VKKLL | LLGqSLMHFQ | AAQPAMAHHHHHH | 68 |
| 65 | YJ2.25 | VKKLL | PQLAMSLPSI | AAQPAMAHHHHHH | 69 |
| 66 | 10.3H | VKKLL | YETMLSSYLY | AAQPAMAHHHHHH | 70 |
| 67 | 3.10D | VKKLL | SLYYFPLVPY | AAQPAMAHHHHHH | 71 |
| 68 | 4.7C | VKKLL | qRTVAAAYFW | AAQPAMAHHHHHH | 72 |
| 69 | 4.12D | VKKLL | FLTWLRYGFP | AAQPAMAHHHHHH | 73 |
| 70 | 6.1A | VKKLL | LLLTLMqPTS | AAQPAMAHHHHHH | 74 |
| 71 | 8.10C | VKKLL | FDFFTHVHLF | AAQPAMAHHHHHH | 75 |
| 72 | 5.6E | VKKLL | ALYPHFVSFT | AAQPAMAHHHHHH | 76 |
| 73 | 4.11E | VKKLL | LPYAIqLFSP | AAQPAMAHHHHHH | 77 |
| 74 | YJ2.5 | VKKLL | WFPLHSSLLP | AAQPAMAHHHHHH | 78 |
| 75 | 4.7A | VKKLL | PALLLATAAF | AAQPAMAHHHHHH | 79 |
| 76 | 3.11C | VKKLL | LASVAWNLDS | AAQPAMAHHHHHH | 80 |
| 77 | YJ2.121 | VKKLL | VGSLLFWPQQ | AAQPAMAHHHHHH | 81 |
| 78 | 4.5F | VKKLL | SPLLFLqNYT | AAQPAMAHHHHHH | 82 |
| 79 | 3.2F | VKKLL | SYWLDFIqVL | AAQPAMAHHHHHH | 83 |
| 80 | 10.3C | VKKLL | VPSFLLSPSP | AAQPAMAHHHHHH | 84 |
| 81 | 9.23.7H | VKKLL | SLYWLTSqPL | AAQPAMAHHHHHH | 85 |
| 82 | 3.9A | VKKLL | FALSSVHSPP | AAQPAMAHHHHHH | 86 |
| 83 | 4.11H | VKKLL | SYYSLLYSYP | AAQPAMAHHHHHH | 87 |
| 84 | 3.1C | VKKLL | LVSGLqPWYF | AAQPAMAHHHHHH | 88 |
| 85 | 2.5A | VKKLL | VLATPLHLSP | AAQPAMAHHHHHH | 89 |
| 86 | 10.6H-q | VKKLL | SLAFPLFTPP | AAQPAMAHHHHHH | 90 |
| 87 | 3.6A | VKKLL | SLVPIFPFST | AAQPAMAHHHHHH | 91 |
| 88 | 8.10D | VKKLL | qPVLFSFFIR | AAQPAMAHHHHHH | 92 |
| 89 | 4.3B | VKKLL | MSqFLNLLSP | AAQPAMAHHHHHH | 93 |
| 90 | 2.3G | VKKLL | WAVqPLFPLN | AAQPAMAHHHHHH | 94 |
| 91 | 5.3H | VKKLL | MFSLVPSPPI | AAQPAMAHHHHHH | 95 |
| 92 | 10.7B | VKKLL | PFFLQPFqFP | AAQPAMAHHHHHH | 96 |
| 93 | 7.2D-q | VKKLL | PDLLASVLPV | AAQPAMAHHHHHH | 97 |
| 94 | 2.9H | VKKLL | FWqFLWPSLP | AAQPAMAHHHHHH | 98 |
| 95 | 6.4A | VKKLL | LLGqFFPNPM | AAQPAMAHHHHHH | 99 |
| 96 | 6.4D | VKKLL | TLSALSQWHP | AAQPAMAHHHHHH | 100 |
| 97 | 9.4D | VKKLL | SLVYFFPFYP | AAQPAMAHHHHHH | 101 |

TABLE 2 -continued

Preference sequence patterns selected from L2 S5 sc-dsFv library

| No. | Code | Sequence | | SEQ ID NO: |
|---|---|---|---|---|
| 98 | 10.2H | VKKLL FAFAPAPFYH | AAQPAMAHHHHHH | 102 |
| 99 | 4.12B | VKKLL FLPFALVPRQ | AAQPAMAHHHHHH | 103 |
| 100 | 4.1F | VKKLL ALWMqLYPQD | AAQPAMAHHHHHH | 104 |
| 101 | YJ2.27 | VKKLL ASILFSHAAP | AAQPAMAHHHHHH | 105 |
| 102 | 2.2C | VKKLL LPLPWSLHLY | AAQPAMAHHHHHH | 106 |
| 103 | 4.9C | VKKLL LPHFMSFWFE | AAQPAMAHHHHHH | 107 |
| 104 | 7.3E | VKKLL LFQPFWPIPY | AAQPAMAHHHHHH | 108 |
| 105 | 4.7F | VKKLL LLFSLGRLPP | AAQPAMAHHHHHH | 109 |
| 106 | 7.12G | VKKLL PLWVLLKDPL | AAQPAMAHHHHHH | 110 |
| 107 | 9.3B | VKKLL MSFATLFPHN | AAQPAMAHHHHHH | 111 |
| 108 | 4.5B | VKKLL qHSLVTSWLC | AAQPAMAHHHHHH | 112 |
| 109 | 5.2H | VKKLL LLFqGAFVGq | AAQPAMAHHHHHH | 113 |
| 110 | 4.4C | VKKLL WMFHSLPFSP | AAQPAMAHHHHHH | 114 |
| 111 | 6.8G | VKKLL LTqLLLTRLH | AAQPAMAHHHHHH | 115 |
| 112 | 4.10A | VKKLL ALTLVPSSYP | AAQPAMAHHHHHH | 116 |
| 113 | 4.5D | VKKLL LPWYMLLSDS | AAQPAMAHHHHHH | 117 |
| 114 | 9.3E | VKKLL VVTqFWPSLP | AAQPAMAHHHHHH | 118 |
| 115 | 4.3G | VKKLL LSTLFLWHVR | AAQPAMAHHHHHH | 119 |
| 116 | 9.7E | VKKLL RSLFFqqLYP | AAQPAMAHHHHHH | 120 |
| 117 | YJ2.30 | VKKLL TLTTLHQTFP | AAQPAMAHHHHHH | 121 |
| 118 | 1.3B | VKKLL SALLAPWYWD | AAQPAMAHHHHHH | 122 |
| 119 | 8.9B | VKKLL AIqqRMQIYT | AAQPAMAHHHHHH | 123 |
| 120 | 3.4E | VKKLL LLFPWFQPPY | AAQPAMAHHHHHH | 124 |
| 121 | 9.23.7E | VKKLL YFTSLLGqFP | AAQPAMAHHHHHH | 125 |
| 122 | 6.3D | VKKLL PVLIFLSEIR | AAQPAMAHHHHHH | 126 |
| 123 | 9.5G | VKKLL VATSLRWAVT | AAQPAMAHHHHHH | 127 |
| 124 | YJ2.54 | VKKLL AQLFHLFATH | AAQPAMAHHHHHH | 128 |
| 125 | 8.6G | VKKLL LqFSALFNSF | AAQPAMAHHHHHH | 129 |
| 126 | 7.12C-q | VKKLL FHLMSMLPPP | AAQPAMAHHHHHH | 130 |
| 127 | 5.4C | VKKLL PVCSqSMFPI | AAQPAMAHHHHHH | 131 |
| 128 | YJ2.48 | VKKLL LLLSSSYQSP | AAQPAMAHHHHHH | 132 |
| 129 | 4.3D | VKKLL LDSLFFHAPL | AAQPAMAHHHHHH | 133 |
| 130 | 7.7A | VKKLL qAWVFSAHQL | AAQPAMAHHHHHH | 134 |
| 131 | YJ2.99 | VKKLL FQALGALTSP | AAQPAMAHHHHHH | 135 |
| 132 | 9.9D | VKKLL CFFFFLqFHP | AAQPAMAHHHHHH | 136 |
| 133 | 4.12F-f | VKKLL CFSHLALPSP | AAQPAMAHHHHHH | 137 |
| 134 | 6.2B | VKKLL FGSWIPFTQM | AAQPAMAHHHHHH | 138 |
| 135 | 4.6F | VKKLL GLGYFNWTLL | AAQPAMAHHHHHH | 139 |

TABLE 2 -continued

Preference sequence patterns selected from L2 S5 sc-dsFv library

| No. | Code | Sequence | SEQ ID NO: |
|---|---|---|---|
| 136 | 10.4A | VKKLL HLFPLFQFHH AAQPAMAHHHHHH | 140 |
| 137 | 5.6B | VKKLL SEHVSSICVL AAQPAMAHHHHHH | 141 |
| 138 | 3.11E | VKKLL FSCLLDPTCP AAQPAMAHHHHHH | 142 |
| 139 | 8.3F | VKKLL LYLLHPSFLP AAQPAMAHHHHHH | 143 |
| 140 | 2.2F | VKKLL WCAPLLYSLR AAQPAMAHHHHHH | 144 |
| 141 | 2.3F | VKKLL FAMFPYTFqT AAQPAMAHHHHHH | 145 |
| 142 | 10.5D | VKKLL LPSLFYVESL AAQPAMAHHHHHH | 146 |
| 143 | 8.8B | VKKLL SLWLSSLSVL AAQPAMAHHHHHH | 147 |
| 144 | YJ2.17 | VKKLL PHLWFLWSLK AAQPAMAHHHHHH | 148 |
| 145 | 7.5B | VKKLL ASDPVWYFLW AAQPAMAHHHHHH | 149 |
| 146 | 10.12D | VKKLL GLPLMGLqSL AAQPAMAHHHHHH | 150 |
| 147 | 2.4H | VKKLL PQLLLLRALS AAQPAMAHHHHHH | 151 |
| 148 | 5.5D | VKKLL APSAFSLHLF AAQPAMAHHHHHH | 152 |
| 149 | 9.4C | VKKLL FqLSSLFVPY AAQPAMAHHHHHH | 153 |
| 150 | 4.5H | VKKLL VPSFLSTMIE AAQPAMAHHHHHH | 154 |
| 151 | 2.7B | VKKLL ASPFFASYLW AAQPAMAHHHHHH | 155 |
| 152 | YJ2.23 | VKKLL LQYLLSPIGY AAQPAMAHHHHHH | 156 |
| 153 | 6.2D | VKKLL VLSVPISAHH AAQPAMAHHHHHH | 157 |
| 154 | 7.4A | VKKLL MMqALSSLPE AAQPAMAHHHHHH | 158 |
| 155 | 4.12B | VKKLL MPAVLATRLT AAQPAMAHHHHHH | 159 |
| 156 | 6.12E | VKKLL PFTAWIIDGW AAQPAMAHHHHHH | 160 |
| 157 | YJ2.125 | VKKLL TQLLPLWQPL AAQPAMAHHHHHH | 161 |
| 158 | YJ2.21 | VKKLL LVPSLLPLTQ AAQPAMAHHHHHH | 162 |
| 159 | 10.12B | VKKLL PIqSCMVIPS AAQPAMAHHHHHH | 163 |
| 160 | YJ2.35 | VKKLL WSLHLATRLL AAQPAMAHHHHHH | 164 |
| 161 | 6.11H | VKKLL qQVLLCSTLR AAQPAMAHHHHHH | 165 |
| 162 | 7.3B | VKKLL LLRYFLDPMY AAQPAMAHHHHHH | 166 |
| 163 | 10.12A | VKKLL IPQFLRSHHR AAQPAMAHHHHHH | 167 |
| 164 | YJ2.6 | VKKLL GVLHLALSLR AAQPAMAHHHHHH | 168 |
| 165 | 4.12C | VKKLL LVTSqFSLVP AAQPAMAHHHHHH | 169 |
| 166 | YJ2.19 | VKKLL PLALSWFQLR AAQPAMAHHHHHH | 170 |
| 167 | YJ2.88 | VKKLL QHQWYPTVLM AAQPAMAHHHHHH | 171 |
| 168 | YJ2.29 | VKKLL LMYWLSKPLS AAQPAMAHHHHHH | 172 |
| 169 | YJ2.8 | VKKLL TQLTLSSSPI AAQPAMAHHHHHH | 173 |
| 170 | YJ2.94 | VKKLL QLTALLSRLI AAQPAMAHHHHHH | 174 |
| 171 | YJ2.107 | VKKLL LMTFGTTPQS AAQPAMAHHHHHH | 175 |
| 172 | YJ2.133 | VKKLL SAFSFSLSST AAQPAMAHHHHHH | 176 |
| 173 | 6.1A | VKKLL APWLVLPHFP AAQPAMAHHHHHH | 177 |

TABLE 2 -continued

Preference sequence patterns selected from L2_S5 sc-dsFv library

| No. | Code | Sequence | | SEQ ID NO: |
|---|---|---|---|---|
| 174 | YJ2.81 | VKKLL HVLSFAPPMP | AAQPAMAHHHHHH | 178 |
| 175 | YJ2.38 | VKKLL NWLFFAHPFS | AAQPAMAHHHHHH | 179 |
| 176 | YJ2.20 | VKKLL QLAVLLGSLR | AAQPAMAHHHHHH | 180 |
| 177 | 7.1D | VKKLL LFGLFYFRAC | AAQPAMAHHHHHH | 181 |
| 178 | YJ2.98 | VKKLL FQFFVVWRLL | AAQPAMAHHHHHH | 182 |
| 179 | YJ2.39 | VKKLL PWAWPPPPFW | AAQPAMAHHHHHH | 183 |
| 180 | YJ2.130 | VKKLL LQLVIVYYLR | AAQPAMAHHHHHH | 184 |
| 181 | YJ2.16 | VKKLL RQSVLLSALH | AAQPAMAHHHHHH | 185 |
| 182 | 3.12E | VKKLL VYGYFLTTFR | AAQPAMAHHHHHH | 186 |
| 183 | YJ2.53 | VKKLL CFSPLFGFHT | AAQPAMAHHHHHH | 187 |
| 184 | YJ2.100 | VKKLL PGYALWQTIP | AAQPAMAHHHHHH | 188 |
| 185 | YJ2.58 | VKKLL QRIFICFFLR | AAQPAMAHHHHHH | 189 |
| 186 | 8.2A | VKKLL PHVFSCqLSA | AAQPAMAHHHHHH | 190 |
| 187 | 5.10A | VKKLL SPLSLSVKLL | AAQPAMAHHHHHH | 191 |
| 188 | 9.2D | VKKLL ARSLFSGSML | AAQPAMAHHHHHH | 192 |
| 189 | YJ2.92 | VKKLL LQFLIVFPLR | AAQPAMAHHHHHH | 193 |
| 190 | YJ2.32 | VKKLL LAVLLGQSLR | AAQPAMAHHHHHH | 194 |
| 191 | YJ2.14 | VKKLL LLSHLFLRLH | AAQPAMAHHHHHH | 195 |
| 192 | 8.4E | VKKLL LAMVFFVTLR | AAQPAMAHHHHHH | 196 |
| 193 | YJ2.117 | VKKLL WLFALPQENV | AAQPAMAHHHHHH | 197 |
| 194 | YJ2.66 | VKKLL HPLVLLSSSP | AAQPAMAHHHHHH | 198 |
| 195 | YJ2.131 | VKKLL LQYLFMLSMR | AAQPAMAHHHHHH | 199 |
| 196 | 4.11H | VKKLL PALLIRYASV | AAQPAMAHHHHHH | 200 |
| 197 | YJ2.78 | VKKLL QQFTSPFLLL | AAQPAMAHHHHHH | 201 |
| 198 | YJ2.44 | VKKLL SPCFFLLYLR | AAQPAMAHHHHHH | 202 |
| 199 | YJ2.90 | VKKLL PGMPLFFTNS | AAQPAMAHHHHHH | 203 |
| 200 | YJ2.47 | VKKLL PQVFFLFRPF | AAQPAMAHHHHHH | 204 |
| 201 | YJ2.110 | VKKLL PFPILLQSPF | AAQPAMAHHHHHH | 205 |
| 202 | YJ2.74 | VKKLL FQACCLFPLQ | AAQPAMAHHHHHH | 206 |
| 203 | YJ2.55 | VKKLL AVVHTMPLFS | AAQPAMAHHHHHH | 207 |
| 204 | YJ2.108 | VKKLL QFSWAFVSIL | AAQPAMAHHHHHH | 208 |
| 205 | YJ2.96 | VKKLL PVCLFWSFFR | AAQPAMAHHHHHH | 209 |
| 206 | YJ2.70 | VKKLL QLLWQQQVPV | AAQPAMAHHHHHH | 210 |
| 207 | YJ2.60 | VKKLL PLQALSWFLR | AAQPAMAHHHHHH | 211 |
| 208 | YJ2.119 | VKKLL FYLLCRLSLQ | AAQPAMAHHHHHH | 212 |
| 209 | YJ2.82 | VKKLL YLQILVICLR | AAQPAMAHHHHHH | 213 |
| 210 | YJ2.63 | VKKLL QLFLIVFPLR | AAQPAMAHHHHHH | 214 |
| 211 | 10.5A | VKKLL PLHFALFFRL | AAQPAMAHHHHHH | 215 |

TABLE 2 -continued

Preference sequence patterns selected from L2 S5 sc-dsFv library

| No. | Code | Sequence | | SEQ ID NO: |
|---|---|---|---|---|
| 212 | YJ2.85 | VKKLL PFPMHLVLPF | AAQPAMAHHHHHH | 216 |
| 213 | YJ2.86 | VKKLL PLLFSPPSLH | AAQPAMAHHHHHH | 217 |
| 214 | YJ2.126 | VKKLL CQSITFSSIW | AAQPAMAHHHHHH | 218 |
| 215 | YJ2.112 | VKKLL WQRLFPFLLI | AAQPAMAHHHHHH | 219 |
| 216 | YJ2.77 | VKKLL MVPFWPFSFT | AAQPAMAHHHHHH | 220 |
| 217 | YJ2.103 | VKKLL QAFPLPPLLV | AAQPAMAHHHHHH | 221 |
| 218 | YJ2.134 | VKKLL PLYLLFRSFV | AAQPAMAHHHHHH | 222 |
| 219 | YJ2.91 | VKKLL HRSMYLSWLY | AAQPAMAHHHHHH | 223 |
| 220 | YJ2.64 | VKKLL LLSTLVRAPY | AAQPAMAHHHHHH | 224 |
| 221 | YJ2.87 | VKKLL PLALSQWFLR | AAQPAMAHHHHHH | 225 |
| 222 | YJ2.116 | VKKLL AQGMIFFLRL | AAQPAMAHHHHHH | 226 |
| 223 | YJ2.62 | VKKLL FCCRLALQFF | AAQPAMAHHHHHH | 227 |
| 224 | YJ2.102 | VKKLL YLQFLSLMLS | AAQPAMAHHHHHH | 228 |
| 225 | YJ2.106 | VKKLL CQATFPTLLC | AAQPAMAHHHHHH | 229 |
| 226 | YJ2.124 | VKKLL ARSYLYFSLS | AAQPAMAHHHHHH | 230 |
| 227 | YJ2.111 | VKKLL YQSSFLPLFW | AAQPAMAHHHHHH | 231 |
| 228 | YJ2.104 | VKKLL SASFLAFRIT | AAQPAMAHHHHHH | 232 |
| 229 | YJ2.67 | VKKLL SVLFLSHYHS | AAQPAMAHHHHHH | 233 |
| 230 | YJ2.105 | VKKLL PLALLYVRLS | AAQPAMAHHHHHH | 234 |
| 231 | YJ2.127 | VKKLL PEFLLLFRFF | AAQPAMAHHHHHH | 235 |
| 232 | YJ2.80 | VKKLL FPSLYAWGGL | AAQPAMAHHHHHH | 236 |
| 233 | YJ2.122 | VKKLL LQAAAFFCWL | AAQPAMAHHHHHH | 237 |
| 234 | YJ2.79 | VKKLL PFFLFCSSLR | AAQPAMAHHHHHH | 238 |
| 235 | YJ2.115 | VKKLL ELTQLWLFHL | AAQPAMAHHHHHH | 239 |
| 236 | YJ2.113 | VKKLL PGVPLLLCFR | AAQPAMAHHHHHH | 240 |
| 237 | YJ2.114 | VKKLL SQAYLSYFLY | AAQPAMAHHHHHH | 241 |
| 238 | YJ2.61 | VKKLL ISYAFLVRVT | AAQPAMAHHHHHH | 242 |
| 239 | YJ2.123 | VKKLL APALLRSILA | AAQPAMAHHHHHH | 243 |
| 240 | YJ2.109 | VKKLL HSHTLLMSLH | AAQPAMAHHHHHH | 244 |
| 241 | YJ2.83 | VKKLL AVSAFVSLVR | AAQPAMAHHHHHH | 245 |
| 242 | YJ2.31 | VKKLL TLITFKFLPH | AAQPAMAHHHHHH | 246 |
| 243 | YJ2.49 | VKKLL QQFAIPLVEF | AAQPAMAHHHHHH | 247 |
| 244 | YJ2.75 | VKKLL MPCLLVYYLE | AAQPAMAHHHHHH | 248 |
| 245 | YJ2.71 | VKKLL RYCLLLQIVR | AAQPAMAHHHHHH | 249 |
| 246 | YJ2.45 | VKKLL SLALLRVSLG | AAQPAMAHHHHHH | 250 |
| 247 | YJ2.68 | VKKLL IIGRIALILR | AAQPAMAHHHHHH | 251 |
| 248 | YJ2.24 | VKKLL PQLICAFILR | AAQPAMAHHHHHH | 252 |

TABLE 2 -continued

Preference sequence patterns selected from L2 S5 sc-dsFv library

| No. | Code | Sequence | SEQ ID NO: |
|---|---|---|---|
| 249 | 8.3E | VKKLL MVPLFPLPLP AAQPAMAHHHHHH | 253 |
| 250 | 8.1B | VKKLL HgAILYYYLN AAQPAMAHHHHHH | 254 |

TABLE 3

Preference sequence patterns selected from L3 S5 sc-dsFv library

| No. | Code | Sequence | SEQ ID NO |
|---|---|---|---|
|  | M13-pelB | VKKLLFAIPL VVPFYAAQPA MAHHHHHH | 4 |
| 1 | 2.1A | VKKLLFAIPL LPAQAMPMSR MAHHHHHH * | 255 |
| 2 | 7.5C | VKKLLFAIPL YFVLVRESSS MAHHHHHH * | 256 |
| 3 | 1.3B | VKKLLFAIPL VLVVSSRTRA MAHHHHHH * | 257 |
| 4 | YJ3.25 | VKKLLFAIPL LLSRPRAVPD MAHHHHHH * | 258 |
| 5 | 3.8A | VKKLLFAIPL CVSVRSPAFA MAHHHHHH * | 259 |
| 6 | 1.6A | VKKLLFAIPL MTTLASRTHA MAHHHHHH * | 260 |
| 7 | 1.4H | VKKLLFAIPL YLSMTRSGAA MAHHHHHH * | 261 |
| 8 | 7.8F | VKKLLFAIPL WLRSSVPVDS MAHHHHHH * | 262 |
| 9 | 7.8H | VKKLLFAIPL LSSLTRDSSS MAHHHHHH * | 263 |
| 10 | 7.5E | VKKLLFAIPL GLFTIRDSFA MAHHHHHH * | 264 |
| 11 | 7.6O | VKKLLFAIPL WLGITKPVWS MAHHHHHH * | 265 |
| 12 | 1.3F | VKKLLFAIPL YTLTPRPVFS MAHHHHHH * | 266 |
| 13 | 1.5F | VKKLLFAIPL qLALSRPSFP MAHHHHHH * | 267 |
| 14 | 14.9A | VKKLLFAIPL SSFLVADQSS MAHHHHHH * | 268 |
| 15 | YJ3.7 | VKKLLFAIPL LLGLASPRSR MAHHHHHH * | 269 |
| 16 | 13.1E | VKKLLFAIPL LTLSNRSAWS MAHHHHHH * | 270 |
| 17 | 2.2C | VKKLLFAIPL LSLYPTRSTA MAHHHHHH * | 271 |
| 18 | YJ3.10 | VKKLLFAIPL LTTLSRPSFS MAHHHHHH * | 272 |
| 19 | 8.1A | VKKLLFAIPL YESRPPqPSS MAHHHHHH * | 273 |
| 20 | 6.2H | VKKLLFAIPL TMSSPPRSTS MAHHHHHH * | 274 |
| 21 | 8.1C | VKKLLFAIPL YFLRISPSAS MAHHHHHH * | 275 |
| 22 | 1.8B | VKKLLFAIPL LFLRPSAARP MAHHHHHH * | 276 |
| 23 | 1.8C | VKKLLFAIPL LWSSSRPTSQ MAHHHHHH * | 277 |
| 24 | YJ3.41 | VKKLLFAIPL YLVCSRPLHA MAHHHHHH * | 278 |
| 25 | 10.8G | VKKLLFAIPL VLQRPPSPNT MAHHHHHH * | 279 |
| 26 | 2.7C | VKKLLFAIPL AMASFRPRDQ MAHHHHHH * | 280 |
| 27 | 7.10C | VKKLLFAIPL SRSLAMQPLP MAHHHHHH * | 281 |
| 28 | 1.2A | VKKLLFAIPL LSSLRSSNPE MAHHHHHH * | 282 |
| 29 | YJ3.4 | VKKLLFAIPL SILINFRASS MAHHHHHH * | 283 |
| 30 | 1.6B | VKKLLFAIPL YWRSFWEPPA MAHHHHHH * | 284 |

TABLE 3 -continued

Preference sequence patterns selected from L3 S5 sc-dsFv library

| No. | Code | Sequence | | | SEQ ID NO |
|---|---|---|---|---|---|
| 31 | 4.8E | VKKLLFAIPL | YLAAPRSTVA | MAHHHHHH * | 285 |
| 32 | 6.7H | VKKLLFAIPL | QYSAFSMSPR | MAHHHHHH * | 286 |
| 33 | 7.9C | VKKLLFAIPL | YLVSSKNSYP | MAHHHHHH * | 287 |
| 34 | YJ3.72 | VKKLLFAIPL | GLSVSFRTSA | MAHHHHHH * | 288 |
| 35 | 4.4C | VKKLLFAIPL | AMLEPTRSSA | MAHHHHHH * | 289 |
| 36 | 11.1B | VKKLLFAIPL | SLSLHRPALA | MAHHHHHH * | 290 |
| 37 | 6.6B | VKKLLFAIPL | LSASARGSYA | MAHHHHHH * | 291 |
| 38 | YJ3.26 | VKKLLFAIPL | YLAVTHRAYS | MAHHHHHH * | 292 |
| 39 | YJ3.44 | VKKLLFAIPL | FFSLSRYSLA | MAHHHHHH * | 293 |
| 40 | 5.4B | VKKLLFAIPL | YLSAPRHASP | MAHHHHHH * | 294 |
| 41 | 5.2D | VKKLLFAIPL | WSFSRLPSSD | MAHHHHHH * | 295 |
| 42 | 12.4E | VKKLLFAIPL | YLSLTKPSLS | MAHHHHHH * | 296 |
| 43 | 14.1C | VKKLLFAIPL | SSPATEVLSP | MAHHHHHH * | 297 |
| 44 | 6.2C | VKKLLFAIPL | TLFLQRSSLA | MAHHHHHH * | 298 |
| 45 | YJ3.6 | VKKLLFAIPL | VFTRVPHKPS | MAHHHHHH * | 299 |
| 46 | 4.1E | VKKLLFAIPL | AITRSSQFPS | MAHHHHHH * | 300 |
| 47 | 6.4H | VKKLLFAIPL | LGDLRSSPDA | MAHHHHHH * | 301 |
| 48 | YJ3.53 | VKKLLFAIPL | VTTLSTRCYA | MAHHHHHH * | 302 |
| 49 | 7.7B | VKKLLFAIPL | FDASLEGPAM | MAHHHHHH * | 303 |
| 50 | 11.3C | VKKLLFAIPL | YFSSPSSRAP | MAHHHHHH * | 304 |
| 51 | 1.12A | VKKLLFAIPL | WFSFPFRSAA | MAHHHHHH | 305 |
| 52 | 12.1A | VKKLLFAIPL | YLSMSSPARS | MAHHHHHH | 306 |
| 53 | 1.12D | VKKLLFAIPL | SWSLCRPVCA | MAHHHHHH | 307 |
| 54 | 4.3G | VKKLLFAIPL | LYCWPRHSWS | MAHHHHHH | 308 |
| 55 | YJ3.38 | VKKLLFAIPL | IFYTTRSSLS | MAHHHHHH | 309 |
| 56 | YJ3.45 | VKKLLFAIPL | IYTLRSHSMT | MAHHHHHH | 310 |
| 57 | 2.9H | VKKLLFAIPL | PVPSLLGSAD | MAHHHHHH | 311 |
| 58 | 9.5A | VKKLLFAIPL | SLSLNSRSYP | MAHHHHHH | 312 |
| 59 | 2.7H | VKKLLFAIPL | FSPTSQEIRH | MAHHHHHH | 313 |
| 60 | 2.2G | VKKLLFAIPL | YFSCPLRVAS | MAHHHHHH | 314 |
| 61 | YJ3.81 | VKKLLFAIPL | VLSLNRGVFA | MAHHHHHH | 315 |
| 62 | 7.4H | VKKLLFAIPL | SPqVLSSSPG | MAHHHHHH | 316 |
| 63 | 4.2C | VKKLLFAIPL | YVNAMSSPRP | MAHHHHHH | 317 |
| 64 | 13.6D | VKKLLFAIPL | YFTFVRSSWC | MAHHHHHH | 318 |
| 65 | 5.8D | VKKLLFAIPL | FDLSSDSVSP | MAHHHHHH | 319 |
| 66 | YJ3.47 | VKKLLFAIPL | YILFWRNTHA | MAHHHHHH | 320 |
| 67 | 13.7A | VKKLLFAIPL | SCFLSRSAFS | MAHHHHHH | 321 |
| 68 | YJ3.83 | VKKLLFAIPL | FFMITSKSRS | MAHHHHHH | 322 |

TABLE 3-continued

Preference sequence patterns selected from L3 S5 sc-dsFv library

| No. | Code | Sequence | | | SEQ ID NO |
|---|---|---|---|---|---|
| 69 | 12.6C | VKKLLFAIPL | IVSSSRGSFA | MAHHHHHH | 323 |
| 70 | 4.10B | VKKLLFAIPL | AASRPLSPAA | MAHHHHHH | 324 |
| 71 | YJ3.46 | VKKLLFAIPL | WLFSPLRSYS | MAHHHHHH | 325 |
| 72 | YJ3.56 | VKKLLFAIPL | FLSYVRPLSA | MAHHHHHH | 326 |
| 73 | 13.5G | VKKLLFAIPL | FIFTPRSVHS | MAHHHHHH | 327 |
| 74 | 2.2E | VKKLLFAIPL | VSSIYKNSPP | MAHHHHHH | 328 |
| 75 | 5.5H | VKKLLFAIPL | MSDSTAPSFA | MAHHHHHH | 329 |
| 76 | 6.4B | VKKLLFAIPL | TLPqPRFPSP | MAHHHHHH | 330 |
| 77 | 7.10G | VKKLLFAIPL | SLLADSPRRP | MAHHHHHH | 331 |
| 78 | 5.3A | VKKLLFAIPL | FTDNSGEPSL | MAHHHHHH | 332 |
| 79 | 11.1E | VKKLLFAIPL | YCMPMSRTCA | MAHHHHHH | 333 |
| 80 | 11.1D | VKKLLFAIPL | MSRLSYHTPS | MAHHHHHH | 334 |
| 81 | 2.2F | VKKLLFAIPL | LSNSRVPPSS | MAHHHHHH | 335 |
| 82 | 15.7A | VKKLLFAIPL | FFASMRHTqA | MAHHHHHH | 336 |
| 83 | YJ3.5 | VKKLLFAIPL | LLSTIKTSFS | MAHHHHHH | 337 |
| 84 | 3.3A | VKKLLFAIPL | FQQSSLSSVP | MAHHHHHH | 338 |
| 85 | 16.11A | VKKLLFAIPL | TLILSHRSSA | MAHHHHHH | 339 |
| 86 | 11.12A | VKKLLFAIPL | SFSRDPSFTS | MAHHHHHH | 340 |
| 87 | 9.1B | VKKLLFAIPL | ALSPTRHTLA | MAHHHHHH | 341 |
| 88 | 13.9A | VKKLLFAIPL | NILFTVRVYA | MAHHHHHH | 342 |
| 89 | YJ3.15 | VKKLLFAIPL | LASLSARCHG | MAHHHHHH | 343 |
| 90 | 12.6B | VKKLLFAIPL | SVTLSLRASA | MAHHHHHH | 344 |
| 91 | 15.8H | VKKLLFAIPL | SHDPLLLSSP | MAHHHHHH | 345 |
| 92 | YJ3.71 | VKKLLFAIPL | LWSLSSRGMT | MAHHHHHH | 346 |
| 93 | YJ3.82 | VKKLLFAIPL | LISYCRPVSS | MAHHHHHH | 347 |
| 94 | 9.1D | VKKLLFAIPL | HSVELPASPA | MAHHHHHH | 348 |
| 95 | 9.6A | VKKLLFAIPL | LLSTSRSSSG | MAHHHHHH | 349 |
| 96 | YJ3.34 | VKKLLFAIPL | WFSCSRFALS | MAHHHHHH | 350 |
| 97 | YJ3.28 | VKKLLFAIPL | VCTLSSRAFS | MAHHHHHH | 351 |
| 98 | 11.1H | VKKLLFAIPL | YSPLARNPFS | MAHHHHHH | 352 |
| 99 | 16.9D | VKKLLFAIPL | FFAFSRQSSG | MAHHHHHH | 353 |
| 100 | YJ3.70 | VKKLLFAIPL | TFSIFSRALA | MAHHHHHH | 354 |
| 101 | YJ3.55 | VKKLLFAIPL | SLFFSARAIA | MAHHHHHH | 355 |
| 102 | 9.7A | VKKLLFAIPL | SQPSLCDPVP | MAHHHHHH | 356 |
| 103 | 10.11A | VKKLLFAIPL | LASYHRVAFA | MAHHHHHH | 357 |
| 104 | 10.1F | VKKLLFAIPL | WQLWQLPSRP | MAHHHHHH | 358 |
| 105 | 16.8A | VKKLLFAIPL | FTPMYRPTSP | MAHHHHHH | 359 |
| 106 | YJ3.27 | VKKLLFAIPL | LLSLHRFSFA | MAHHHHHH | 360 |

TABLE 3 -continued

Preference sequence patterns selected from L3 S5 sc-dsFv library

| No. | Code | Sequence | | | SEQ ID NO |
|---|---|---|---|---|---|
| 107 | 9.5H | VKKLLFAIPL | SYSHPQNALA | MAHHHHHH | 361 |
| 108 | 10.12D | VKKLLFAIPL | YVLRSDASWG | MAHHHHHH | 362 |
| 109 | 4.2D | VKKLLFAIPL | FSGPPFDRTS | MAHHHHHH | 363 |
| 110 | YJ3.66 | VKKLLFAIPL | FCALSRFTHA | MAHHHHHH | 364 |
| 111 | YJ3.24 | VKKLLFAIPL | FSLSRPVPPL | MAHHHHHH | 365 |
| 112 | 10.7D | VKKLLFAIPL | SMDSFSRPFF | MAHHHHHH | 366 |
| 113 | 15.7C | VKKLLFAIPL | YTIIPSRASS | MAHHHHHH | 367 |
| 114 | 15.12C | VKKLLFAIPL | VPSANPPPLS | MAHHHHHH | 368 |
| 115 | 15.7E | VKKLLFAIPL | YLIKPPEGFS | MAHHHHHH | 369 |
| 116 | YJ3.42 | VKKLLFAIPL | ISTLHFRAFG | MAHHHHHH | 370 |
| 117 | YJ3.37 | VKKLLFAIPL | VRVMCGHSYA | MAHHHHHH | 371 |
| 118 | YJ3.67 | VKKLLFAIPL | VLSLSRTFSG | MAHHHHHH | 372 |
| 119 | YJ3.75 | VKKLLFAIPL | WCALSRQSMP | MAHHHHHH | 373 |
| 120 | YJ3.86 | VKKLLFAIPL | YFWSLRVSWP | MAHHHHHH | 374 |
| 121 | YJ3.33 | VKKLLFAIPL | YILSPRLPPP | MAHHHHHH | 375 |
| 122 | YJ3.22 | VKKLLFAIPL | VVAAHRFSYA | MAHHHHHH | 376 |
| 123 | YJ3.62 | VKKLLFAIPL | YVHLTSKAIP | MAHHHHHH | 377 |
| 124 | YJ3.59 | VKKLLFAIPL | SLTLYRSGWS | MAHHHHHH | 378 |
| 125 | YJ3.18 | VKKLLFAIPL | YYALSGRPVT | MAHHHHHH | 379 |
| 126 | YJ3.79 | VKKLLFAIPL | MLSLMRQSAP | MAHHHHHH | 380 |

TABLE 4

Preference sequence patterns selected from L4 S5 sc-dsFv library

| No. | Code | Sequence | | | | SEQ ID NO |
|---|---|---|---|---|---|---|
| | M13-pelB | VKKLLFAIPLVVPFY | AAQPAMAHHH | HHH | | 4 |
| 1 | 1.11A | VKKLLFAIPLVVPFY | ARPLTRIQTP | HHH | * | 381 |
| 2 | 9.3D | VKKLLFAIPLVVPFY | LTQLSRREPS | HHH | * | 382 |
| 3 | 1.6B | VKKLLFAIPLVVPFY | ARSLATSPSR | HHH | * | 383 |
| 4 | 14.5H | VKKLLFAIPLVVPFY | PARSYMLVRP | HHH | * | 384 |
| 5 | 12.2A | VKKLLFAIPLVVPFY | SRSYMLLSRP | HHH | * | 385 |
| 6 | 12.6H | VKKLLFAIPLVVPFY | TRSALAFFLP | HHH | * | 386 |
| 7 | YJ4.13 | VKKLLFAIPLVVPFY | SRGFTLPRLI | HHH | * | 387 |
| 8 | YJ4.1 | VKKLLFAIPLVVPFY | SSAFTRPIRP | HHH | * | 388 |
| 9 | 12.2E | VKKLLFAIPLVVPFY | TRYSHAFMLI | HHH | * | 389 |
| 10 | 6.10B | VKKLLFAIPLVVPFY | ARPMSMFRSD | HHH | * | 390 |
| 11 | 8.4D | VKKLLFAIPLVVPFY | ASSMSqYRQN | HHH | * | 391 |
| 12 | 5.9H | VKKLLFAIPLVVPFY | ARSYSRPPSI | HHH | * | 392 |
| 13 | 10.8A | VKKLLFAIPLVVPFY | ASSMSRLRPH | HHH | * | 393 |

TABLE 4 -continued

Preference sequence patterns selected from L4 S5 sc-dsFv library

| No. | Code | Sequence | | | SEQ ID NO |
|---|---|---|---|---|---|
| 14 | YJ4.3 | VKKLLFAIPLVVPFY | CRSLSRPMLV | HHH * | 394 |
| 15 | 4.6C | VKKLLFAIPLVVPFY | SRSMSLHPTA | HHH * | 395 |
| 16 | CM11 | VKKLLFAIPLVVPFY | TRSMTRLAPP | HHH * | 396 |
| 17 | 9.8H | VKKLLFAIPLVVPFY | TRAMSVSHKT | HHH * | 397 |
| 18 | 13.1F | VKKLLFAIPLVVPFY | LLAPKPSVKR | HHH * | 398 |
| 19 | 9.7A | VKKLLFAIPLVVPFY | SRPAPALSRL | HHH * | 399 |
| 20 | 15.9C | VKKLLFAIPLVVPFY | AKAMSARYQS | HHH * | 400 |
| 21 | CM18 | VKKLLFAIPLVVPFY | FASQRSSPIR | HHH * | 401 |
| 22 | CM24 | VKKLLFAIPLVVPFY | CLSFTSARFq | HHH * | 402 |
| 23 | 12.1A | VKKLLFAIPLVVPFY | PSASSRLSPK | HHH * | 403 |
| 24 | 2.10G | VKKLLFAIPLVVPFY | ARSYTRVPLA | HHH * | 404 |
| 25 | CM2 | VKKLLFAIPLVVPFY | ARSLTFLPPR | HHH * | 405 |
| 26 | 9.4C | VKKLLFAIPLVVPFY | TTRVNAFMLV | HHH * | 406 |
| 27 | 11.11H | VKKLLFAIPLVVPFY | QAFRPVPVRN | HHH * | 407 |
| 28 | 11.8H | VKKLLFAIPLVVPFY | TSGMSRLRSW | HHH * | 408 |
| 29 | 1.12C | VKKLLFAIPLVVPFY | SRSPSQLSSR | HHH * | 409 |
| 30 | 16.12H | VKKLLFAIPLVVPFY | AFSLSRTSSK | HHH * | 410 |
| 31 | 3.11F | VKKLLFAIPLVVPFY | FHRVQQFSPA | HHH * | 411 |
| 32 | 9.2B | VKKLLFAIPLVVPFY | LDSMLTFRRS | HHH * | 412 |
| 33 | CM40 | VKKLLFAIPLVVPFY | CRSLTSPLRM | HHH * | 413 |
| 34 | 15.5B | VKKLLFAIPLVVPFY | SRSASFLRPI | HHH * | 414 |
| 35 | 9.2F | VKKLLFAIPLVVPFY | MTFqSNSPRG | HHH * | 415 |
| 36 | CM38 | VKKLLFAIPLVVPFY | CRPMTLRqPV | HHH * | 416 |
| 37 | CM5 | VKKLLFAIPLVVPFY | VRPMSRVIMS | HHH * | 417 |
| 38 | CM36 | VKKLLFAIPLVVPFY | SYGFSRPFSK | HHH * | 418 |
| 39 | 11.9G | VKKLLFAIPLVVPFY | TRSCFAFMLP | HHH * | 419 |
| 40 | 6.8B | VKKLLFAIPLVVPFY | AFSGAFRQSQ | HHH * | 420 |
| 41 | 16.6B | VKKLLFAIPLVVPFY | LRAGSFSAAP | HHH * | 421 |
| 42 | CM22 | VKKLLFAIPLVVPFY | SHSMAPPSRR | HHH * | 422 |
| 43 | CM31 | VKKLLFAIPLVVPFY | CRSGTFGNIG | HHH * | 423 |
| 44 | 11.5F | VKKLLFAIPLVVPFY | ARSMASTPLA | HHH * | 424 |
| 45 | YJ4.2 | VKKLLFAIPLVVPFY | VYPLAPRLRD | HHH * | 425 |
| 46 | 6.10H | VKKLLFAIPLVVPFY | SLPWRRTPFQ | HHH * | 426 |
| 47 | 10.3D | VKKLLFAIPLVVPFY | MRTPPLSqRI | HHH * | 427 |
| 48 | CM28 | VKKLLFAIPLVVPFY | ARSLSSYNAV | HHH * | 428 |
| 49 | 12.4D | VKKLLFAIPLVVPFY | VHALARKSQF | HHH * | 429 |
| 50 | CM25 | VKKLLFAIPLVVPFY | SRSFSSPSIT | HHH | 430 |
| 51 | 13.5A | VKKLLFAIPLVVPFY | CRALSKPLPP | HMH | 431 |

TABLE 4 -continued

Preference sequence patterns selected from L4 S5 sc-dsFv library

| No. | Code | Sequence | | | SEQ ID NO |
|---|---|---|---|---|---|
| 52 | 12.6C | VKKLLFAIPLVVPFY | CRPSAPKMLL | HHH | 432 |
| 53 | CM16 | VKKLLFAIPLVVPFY | SRSMSYFqPL | HHH | 433 |
| 54 | 4.2C | VKKLLFAIPLVVPFY | TRSLSRSIPH | HHH | 434 |
| 55 | 16.6C | VKKLLFAIPLVVPFY | SQLHqSPGNP | HHH | 435 |
| 56 | 10.10A | VKKLLFAIPLVVPFY | TRAIARPPYT | HHH | 436 |
| 57 | 10.11G | VKKLLFAIPLVVPFY | ARSLSTVRFP | HHH | 437 |
| 58 | CM8 | VKKLLFAIPLVVPFY | TRAFSSPLSN | HHH | 438 |
| 59 | 9.6D | VKKLLFAIPLVVPFY | NRTPTIqRDS | HHH | 439 |
| 60 | 8.4B | VKKLLFAIPLVVPFY | ARAVSRTVPT | HHH | 440 |
| 61 | 8.5E | VKKLLFAIPLVVPFY | AqSMAVPIST | HHH | 441 |
| 62 | 13.2C | VKKLLFAIPLVVPFY | PqPSRGFMLI | HHH | 442 |
| 63 | CM10 | VKKLLFAIPLVVPFY | TRSMVFPAKV | HHH | 443 |
| 64 | CM26 | VKKLLFAIPLVVPFY | SRSMTLKGPE | HHH | 444 |
| 65 | CM17 | VKKLLFAIPLVVPFY | AFPFSRQPNA | HHH | 445 |
| 66 | CM7 | VKKLLFAIPLVVPFY | SRALTSISGM | HHH | 446 |
| 67 | CM6 | VKKLLFAIPLVVPFY | CRGMSLNVTR | HHH | 447 |
| 68 | 6.10C | VKKLLFAIPLVVPFY | SHWRTQRPPE | HHH | 448 |
| 69 | CM45 | VKKLLFAIPLVVPFY | ARSFSSPPGP | HHH | 449 |
| 70 | 13.1G | VKKLLFAIPLVVPFY | IFPIEASARR | HHH | 450 |
| 71 | CM39 | VKKLLFAIPLVVPFY | ASSMALRPRV | HHH | 451 |
| 72 | YJ4.74 | VKKLLFAIPLVVPFY | SRAFSSTPAM | HHH | 452 |
| 73 | 1.7F | VKKLLFAIPLVVPFY | SRSMVLQGPT | HHH | 453 |
| 74 | YJ4.28 | VKKLLFAIPLVVPFY | SRSMTSPPYI | HHH | 454 |
| 75 | 10.3B | VKKLLFAIPLVVPFY | ANRPQSTKNI | HHH | 455 |
| 76 | YJ4.56 | VKKLLFAIPLVVPFY | SRALTMTPSF | HHH | 456 |
| 77 | 4.6H | VKKLLFAIPLVVPFY | PTRLFAFMLT | HHH | 457 |
| 78 | 14.12A | VKKLLFAIPLVVPFY | SRAMSPIPRQ | HHH | 458 |
| 79 | CM29 | VKKLLFAIPLVVPFY | ARSMGSMWQL | HHH | 459 |
| 80 | YJ4.42 | VKKLLFAIPLVVPFY | SFSMTRSSPL | HHH | 460 |
| 81 | CM42 | VKKLLFAIPLVVPFY | SFSFTRqPLP | HHH | 461 |
| 82 | YJ4.33 | VKKLLFAIPLVVPFY | NRVPSPASQT | HHH | 462 |
| 83 | YJ4.23 | VKKLLFAIPLVVPFY | SFSFSKPRFS | HHH | 463 |
| 84 | CM27 | VKKLLFAIPLVVPFY | ARSLTQFSSV | HHH | 464 |
| 85 | YJ4.39 | VKKLLFAIPLVVPFY | ARCFSSPVAL | HHH | 465 |
| 86 | 11.3B | VKKLLFAIPLVVPFY | GASSWWLFPS | HHH | 466 |
| 87 | YJ4.84 | VKKLLFAIPLVVPFY | TPPQQQALLS | HHH | 467 |
| 88 | 14.1F | VKKLLFAIPLVVPFY | SRGFSMAFFP | HHH | 468 |
| 89 | CM33 | VKKLLFAIPLVVPFY | SLAMSRPqAS | HHH | 469 |

TABLE 4 -continued

Preference sequence patterns selected from L4 S5 sc-dsFv library

| No. | Code | Sequence | | | SEQ ID NO |
|---|---|---|---|---|---|
| 90 | 13.12C | VKKLLFAIPLVVPFY | TYALTTFqSV | HHH | 470 |
| 91 | YJ4.44 | VKKLLFAIPLVVPFY | QHAFTRPFRV | HHH | 471 |
| 92 | CM30 | VKKLLFAIPLVVPFY | SRAFSSPSGS | HHH | 472 |
| 93 | 13.11G | VKKLLFAIPLVVPFY | TSALARSPRV | HHH | 473 |
| 94 | 4.8E | VKKLLFAIPLVVPFY | CRAMSSPFRP | HHH | 474 |
| 95 | 4.2B | VKKLLFAIPLVVPFY | STFARSFMLT | HHH | 475 |
| 96 | 9.2D | VKKLLFAIPLVVPFY | FPLSSRAFML | HHH * | 476 |
| 97 | YJ4.71 | VKKLLFAIPLVVPFY | SRSMSTSPIL | HHH | 477 |
| 98 | 9.6H | VKKLLFAIPLVVPFY | SFGLqLPqPF | HHH | 478 |
| 99 | CM37 | VKKLLFAIPLVVPFY | SRSMSLSSDL | HHH | 479 |
| 100 | 16.3E | VKKLLFAIPLVVPFY | AFPLARRPIN | HHH | 480 |
| 101 | 12.1B | VKKLLFAIPLVVPFY | TSCRAMTLPR | HHH | 481 |
| 102 | CM23 | VKKLLFAIPLVVPFY | TYPFSRAGPP | HHH | 482 |
| 103 | YJ4.47 | VKKLLFAIPLVVPFY | ANQQALPFQL | HHH | 483 |
| 104 | YJ4.38 | VKKLLFAIPLVVPFY | GWSMSLRSHS | HHH | 484 |
| 105 | 4.11H | VKKLLFAIPLVVPFY | SPQVVTRKDL | HHH | 485 |
| 106 | 12.9G | VKKLLFAIPLVVPFY | LRNAHAMASA | HHH | 486 |
| 107 | CM44 | VKKLLFAIPLVVPFY | SRSGSFNVTP | HHH | 487 |
| 108 | 11.3E | VKKLLFAIPLVVPFY | SRPLSRVPVF | HHH | 488 |
| 109 | 11.9F | VKKLLFAIPLVVPFY | SKRMPPPISq | HHH | 489 |
| 110 | CM34 | VKKLLFAIPLVVPFY | TRSMSSLPSP | HHH | 490 |
| 111 | 14.11DV | KKLLFAIPLVVPFY | CRSSSSIFPL | HHH | 491 |
| 112 | CM15 | VKKLLFAIPLVVPFY | RSAHAMSIQT | HHH | 492 |
| 113 | 10.1H | VKKLLFAIPLVVPFY | GYCFSARIIR | HHH | 493 |
| 114 | 9.10A | VKKLLFAIPLVVPFY | PHLSPLqPQq | HHH | 494 |
| 115 | CM43 | VKKLLFAIPLVVPFY | SFSFSRFPGL | HHH | 495 |
| 116 | YJ4.48 | VKKLLFAIPLVVPFY | SSSMSLRPQF | HHH | 496 |
| 117 | 11.11DV | KKLLFAIPLVVPFY | SSPRARPVPP | HHH | 497 |
| 118 | CM46 | VKKLLFAIPLVVPFY | ARSLSALSPY | HHH | 498 |
| 119 | 12.5C | VKKLLFAIPLVVPFY | PVRqLHTNLR | HHH | 499 |
| 120 | 10.2F | VKKLLFAIPLVVPFY | PITSTPYqSP | HHH | 500 |
| 121 | CM21 | VKKLLFAIPLVVPFY | VNALTFLPSq | HHH | 501 |
| 122 | CM41 | VKKLLFAIPLVVPFY | ARSLSSPLTL | HHH | 502 |
| 123 | YJ4.25 | VKKLLFAIPLVVPFY | TRPPTVGLRQ | HHH | 503 |
| 124 | CM14 | VKKLLFAIPLVVPFY | TRALSPMSWq | HHH | 504 |
| 125 | YJ4.6 | VKKLLFAIPLVVPFY | VFPFSRPLLR | HHH | 505 |
| 126 | CM1 | VKKLLFAIPLVVPFY | VPRCLSMSLG | HHH | 506 |
| 127 | YJ4.87 | VKKLLFAIPLVVPFY | QQPSFHPISR | HHH | 507 |

TABLE 4 -continued

Preference sequence patterns selected from L4 S5 sc-dsFv library

| No. | Code | Sequence | | | SEQ ID NO |
|---|---|---|---|---|---|
| 128 | CM32 | VKKLLFAIPLVVPFY | SKAFSSFqAS | HHH | 508 |
| 129 | 10.6H | VKKLLFAIPLVVPFY | GYSMSqSGLT | HHH | 509 |
| 130 | YJ4.40 | VKKLLFAIPLVVPFY | AQALTTRGLA | HHH | 510 |
| 131 | YJ4.26 | VKKLLFAIPLVVPFY | VKSLTRPAFL | HHH | 511 |
| 132 | 12.4F | VKKLLFAIPLVVPFY | AqSRLRVYPP | HHH | 512 |
| 133 | 4.5B | VKKLLFAIPLVVPFY | PAIGFMLLRY | HHH | 513 |
| 134 | 12.3D | VKKLLFAIPLVVPFY | SFGTLVRPRP | HHH | 514 |
| 135 | CM3 | VKKLLFAIPLVVPFY | IRRPVDPVMP | HHH | 515 |
| 136 | YJ4.19 | VKKLLFAIPLVVPFY | FPLRQTHRYP | HHH | 516 |
| 137 | 13.2H | VKKLLFAIPLVVPFY | THSMQRPTGR | HHH | 517 |
| 138 | 10.5D | VKKLLFAIPLVVPFY | RHTqLSSSTS | HHH | 518 |
| 139 | 15.10D | VKKLLFAIPLVVPFY | SCGFSRLSKA | HHH | 519 |
| 140 | CM35 | VKKLLFAIPLVVPFY | SRSFSQLPHI | HHH | 520 |
| 141 | YJ4.43 | VKKLLFAIPLVVPFY | SSSMSQLRPF | HHH | 521 |
| 142 | 10.2B | VKKLLFAIPLVVPFY | CRTTFALQSS | HHH | 522 |
| 143 | CM19 | VKKLLFAIPLVVPFY | AQSMSIRHNN | HHH | 523 |
| 144 | 11.4E | VKKLLFAIPLVVPFY | NSRFRTTPPS | HHH | 524 |
| 145 | CM20 | VKKLLFAIPLVVPFY | SVSMSRYQLS | HHH | 525 |
| 146 | CM12 | VKKLLFAIPLVVPFY | SSGASRLRIL | HHH | 526 |
| 147 | YJ4.81 | VKKLLFAIPLVVPFY | CWSLSRPRLL | HHH | 527 |
| 148 | 10.1C | VKKLLFAIPLVVPFY | TSRSTKLTPS | HHH | 528 |
| 149 | 11.6D | VKKLLFAIPLVVPFY | SRVSVAFMLM | HHH | 529 |
| 150 | YJ4.72 | VKKLLFAIPLVVPFY | CLGRSMAPGP | HHH | 530 |
| 151 | 14.1A | VKKLLFAIPLVVPFY | FVHRRDSSSL | HHH | 531 |
| 152 | YJ4.24 | VKKLLFAIPLVVPFY | SLGFSRLTSL | HHH | 532 |
| 153 | 13.2B | VKKLLFAIPLVVPFY | ASALSRRVPq | HHH | 533 |
| 154 | 11.6B | VKKLLFAIPLVVPFY | TYPASWPRLR | HHH | 534 |
| 155 | 9.2G | VKKLLFAIPLVVPFY | SRVSLAVTPS | HHH | 535 |
| 156 | 10.11B | VKKLLFAIPLVVPFY | NNPFSSISqq | HHH | 536 |
| 157 | 11.8D | VKKLLFAIPLVVPFY | RPLPRPFAGN | HHH | 537 |
| 158 | CM4 | VKKLLFAIPLVVPFY | GFSMTQYLPq | HHH | 538 |
| 159 | YJ4.75 | VKKLLFAIPLVVPFY | SSALSRSFYP | HHH | 539 |
| 160 | YJ4.61 | VKKLLFAIPLVVPFY | TQQRCFAMHI | HHH | 540 |
| 161 | YJ4.85 | VKKLLFAIPLVVPFY | IKHFYNSRPS | HHH | 541 |
| 162 | YJ4.51 | VKKLLFAIPLVVPFY | FTRLPKESSP | HHH | 542 |
| 163 | 9.6G | VKKLLFAIPLVVPFY | LPAQPRVTRT | HHH | 543 |
| 164 | CM13 | VKKLLFAIPLVVPFY | LRSMTLNTST | HHH | 544 |
| 165 | YJ4.35 | VKKLLFAIPLVVPFY | PDTFSYSSQD | HHH | 545 |

TABLE 4 -continued

Preference sequence patterns selected from L4 S5 sc-dsFv library

| No. | Code | Sequence | | | SEQ ID NO |
|---|---|---|---|---|---|
| 166 | YJ4.41 | VKKLLFAIPLVVPFY | FRNPQLPSSA | HHH | 546 |
| 167 | YJ4.50 | VKKLLFAIPLVVPFY | FRPDRTPPSS | HHH | 547 |
| 168 | 9.8C | VKKLLFAIPLVVPFY | qSHTILPLPA | HHH | 548 |
| 169 | CM9 | VKKLLFAIPLVVPFY | SSAFqPMVSS | HHH | 549 |
| 170 | 9.7H | VKKLLFAIPLVVPFY | QSRRLPILPL | HHH | 550 |
| 171 | YJ4.31 | VKKLLFAIPLVVPFY | GQAYLPAPQL | HHH | 551 |
| 172 | 9.11B | VKKLLFAIPLVVPFY | TSRPRETLFL | HHH | 552 |
| 173 | 9.3G | VKKLLFAIPLVVPFY | TAASVVRSRD | HHH | 553 |
| 174 | 10.5F | VKKLLFAIPLVVPFY | VRGAAPKFSV | HHH | 554 |
| 175 | YJ4.14 | VKKLLFAIPLVVPFY | FRHQPASVST | HHH | 555 |
| 176 | 9.8B | VKKLLFAIPLVVPFY | PTNAIAFFLq | HHH | 556 |
| 177 | YJ4.59 | VKKLLFAIPLVVPFY | LKSLRSDTPN | HHH | 557 |
| 178 | YJ4.22 | VKKLLFAIPLVVPFY | IKRPLPLAPT | HHH | 558 |
| 179 | 11.11F | VKKLLFAIPLVVPFY | ASSSKSRFML | HHH | 559 |
| 180 | YJ4.82 | VKKLLFAIPLVVPFY | PWKPRLLPPQ | HHH | 560 |
| 181 | 9.1H | VKKLLFAIPLVVPFY | SRGFMLTLRY | HHH | 561 |
| 182 | 9.8E | VKKLLFAIPLVVPFY | CKARGIMPVF | HHH | 562 |
| 183 | YJ4.17 | VKKLLFAIPLVVPFY | ASLPRLTSQS | HHH | 563 |
| 184 | 11.2B | VKKLLFAIPLVVPFY | qSSAFSYMLS | HHH | 564 |
| 185 | 10.7A | VKKLLFAIPLVVPFY | SFSSQRFLRP | HHH | 565 |
| 186 | 9.7G | VKKLLFAIPLVVPFY | TSSNTSRRFP | HHH | 566 |
| 187 | 11.10B | VKKLLFAIPLVVPFY | NqTAATAPPR | HHH | 567 |
| 188 | 10.8G | VKKLLFAIPLVVPFY | GAPLSWRRSY | HHH | 568 |
| 189 | 9.10D | VKKLLFAIPLVVPFY | CRSVWCIPRP | HHH | 569 |
| 190 | 9.1C | VKKLLFAIPLVVPFY | AKACLRPLQT | HHH | 570 |
| 191 | 9.6F | VKKLLFAIPLVVPFY | CLASSHRHRP | HHH | 571 |
| 192 | 11.3H | VKKLLFAIPLVVPFY | LRADSLAPKS | HHH | 572 |
| 193 | 9.9F | VKKLLFAIPLVVPFY | SVPQFSGRSR | HHH | 573 |
| 194 | YJ4.78 | VKKLLFAIPLVVPFY | VYPARFPAKT | HHH | 574 |
| 195 | YJ4.21 | VKKLLFAIPLVVPFY | NFMLRHPQTF | HHH | 575 |
| 196 | YJ4.32 | VKKLLFAIPLVVPFY | YVPRFPPKSA | HHH | 576 |
| 197 | YJ4.86 | VKKLLFAIPLVVPFY | LSPMSRTRYV | HHH | 577 |
| 198 | YJ4.66 | VKKLLFAIPLVVPFY | TYPLTKPYRP | HHH | 578 |
| 199 | YJ4.83 | VKKLLFAIPLVVPFY | SSYWSHRKPP | HHH | 579 |
| 200 | 10.8C | VKKLLFAIPLVVPFY | SPRTFAFFLM | HHH | 580 |
| 201 | 11.1A | VKKLLFAIPLVVPFY | LGPGIRKKPA | HHH | 581 |
| 202 | 9.4E | VKKLLFAIPLVVPFY | TRLCVAKVAG | HHH | 582 |
| 203 | 11.2E | VKKLLFAIPLVVPFY | RSLPASGASR | HHH | 583 |

TABLE 4 -continued

Preference sequence patterns selected from L4 S5 sc-dsFv library

| No. | Code | Sequence | | | SEQ ID NO |
|---|---|---|---|---|---|
| 204 | 10.5E | VKKLLFAIPLVVPFY | ASPRVKSYSP | HHH | 584 |
| 205 | 9.10F | VKKLLFAIPLVVPFY | PSRTFAFYLV | HHH | 585 |
| 206 | 9.4H | VKKLLFAIPLVVPFY | qqEFAMAHHH | HHH | 586 |
| 207 | 11.8B | VKKLLFAIPLVVPFY | PqSSKAFFLN | HHH | 587 |
| 208 | 11.2F | VKKLLFAIPLVVPFY | VKALRGSYPT | HHH | 588 |
| 209 | 11.7F | VKKLLFAIPLVVPFY | TqPSqVRYML | HHH | 589 |
| 210 | 11.9C | VKKLLFAIPLVVPFY | SARGqHVRPP | HHH | 590 |
| 211 | 10.11C | VKKLLFAIPLVVPFY | STRCPGFFLq | HHH | 591 |
| 212 | 11.6E | VKKLLFAIPLVVPFY | CPSVFSRTPP | HHH | 592 |
| 213 | 11.3A | VKKLLFAIPLVVPFY | DASSWRHFLS | HHH | 593 |

Example 4

Production of sc-dsFv against H5 of Influenza Virus and Microarray Test

Figure 5:
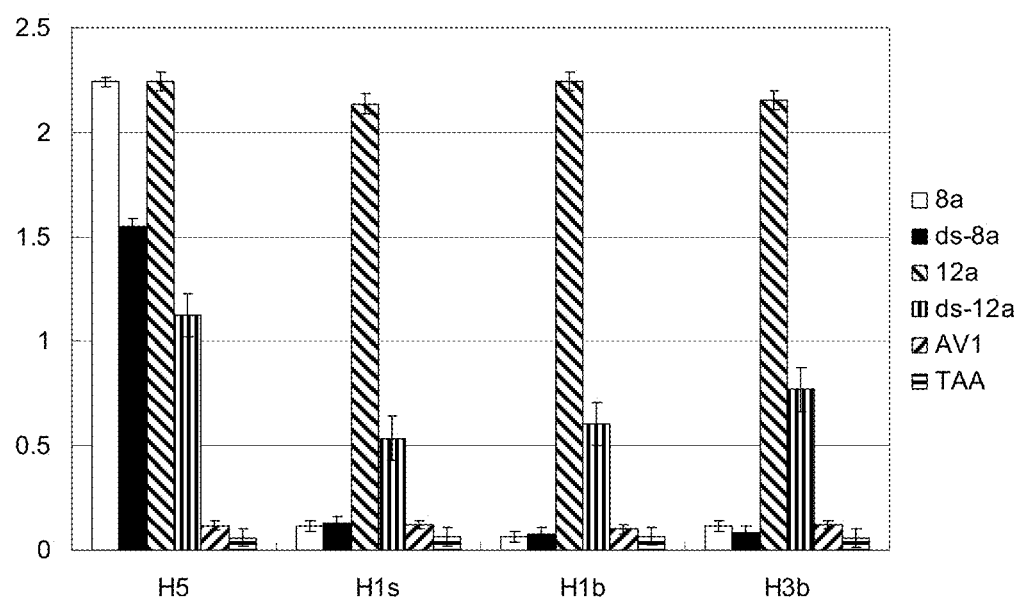
FIG. 5 is a diagram showing the binding strengths of phage-displayed anti-HAs scFv/sc-dsFv. One of the scFv phages with specific binding ability to H5, 8a, and the other one with broad-spectrum ability to HAs, 12a, were engineered to disulfide-stabilized scFv (ds-scFv) formats; the sc-dsFv construct was different from the scFv construct in the mutations (L:Gly100Cys & H:Gly44Cys). Av1 was negative control of an scFv displayed on the phage; and TAA means the phage does not contain any displayed protein; and various HA subtypes were precoated to ELISA wells to determined binding activity, and the error bars were derived from three repeats of the ELISA measurements.

As described above, scFvs (8a and 12a) and their disulfide forms (ds-8a and ds-12a, respectively) to various hemagglutins (HAs) from different serotypes of influenza virus were developed. As shown in FIG. 5, the results indicated that selected scFv phage clones against H5 of influenza virus could be introduced to sc-dsFv directly but had lower binding affinity as compared with original scFvs. These results also suggested that the binding affinity could be enhanced by sc-dsFv phage panning procedures with the signal sequences described above.

The 8aS5 protein could be concentrated to 6 mg/ml without precipitation. The array studies suggested that 4 ng/spot of ds-8a protein could detect ~$10^7$ viruses in solution by using 40 nm fluorescence beads. In conclusion, the signal sequence derived from sc-dsFv phage production against VEGF from monoclonal antibody could be applied for sc-dsFv phage production against hemagglutinin from natural antibody repertoire. The binding affinity could be enhanced by sc-dsFv phage panning procedures to produce sc-dsFv with high binding capacity and better stability than scFv for further applications.

Example 5

Soluble Non-fusion sc-dsFv Expressed with Suppressor E. coli Strain

The signal sequences resulting in the successful expression of the displayed sc-dsFv on phage rescued from suppressor E. coli strain ER2738 were more likely to result in secretion of the soluble non-fusion anti-VEGF sc-dsFv in a culture medium. Signal sequence phage library L4 was selected for binding to immobilized VEGF and the VEGF-binding enriched phage variants were amplified for the next round of selection/amplification cycle. The selection/amplification cycle was repeated for four rounds. After each round of selection/amplification cycle, a random collection of 96 phage variants were picked from the amplified phage population. These phage variants were used to infect E. coli ER2738 and the soluble sc-dsFv was expressed in the overnight cultures, which were tested for binding to immobilized VEGF with ELISA.

These random collections of phage variants were also used to infect E. coli HB2151 for the same assay to determine the sc-dsFv secretion. The result showed that, with ER2738 as the host, 0%, 0%, 2%, and 14% of the phage variants from $1^{st}$, $2^{nd}$, $3^{rd}$, and $4^{th}$ round of selection/amplification cycle respectively secreted functional sc-dsFv binding to VEGF with ELISA signal greater than $OD_{450\ nm}$>0.6. But this trend was not found in the experiment with E. coli strain HB2151. This result indicated that signal sequence alteration could restore the secretion of the soluble non-fusion sc-dsFv and that the search for the optimum signal sequences could be facilitated with phage-based selection/amplification cycles on signal sequence libraries. This conclusion is applicable only to the E. coli suppressor strain ER2738 as the bacteria host for the M13 phage.

Example 6

Interface Disulfide Bond Formation in the sc-dsFv

One measurement for the folding quality of the sc-dsFv is the extent of the interface disulfide bond formation in the sc-dsFv. This measurement was determined by the ratio of the sc-dsFv-VEGF binding ELISA signal after the fXa (bovine factor Xa) treatment over that before the fXa treatment. FXa cleaves substrate sequence -IEGR- in the linker peptide connecting the two variable domains in the sc-dsFv construct. If the interface disulfide bond was not formed in the sc-dsFv, the cleavage of the linker peptide would result in dissociation of the variable domains and abolishment of the affinity against VEGF. Hence the ratio reflects the percentage of interface disulfide bond formation in the sc-dsFv. This measurement was validated with the positive control (anti-VEGF scFv (fXa+)/M13pIII-pelB with -IEGR- (SEQ ID NO:599) in the linker peptide but without the interface disulfide bond) and the negative control (anti-VEGF scFv(fXa−)/M13pIII-pelB without both the fXa cutting site and the interface disulfide bond).

FIG. 6A compared the extent of the interface disulfide bond formation in the secreted soluble sc-dsFv with the disulfide bond formation in the sc-dsFv displayed on phage surface for the signal sequence variants from the L4 library. Strong correlation between the two measurement is evident ($R^2$=0.508, p-value=0.000158). As shown in FIG. 6A, signal sequence optimization could improve the disulfide bond formation in the sc-dsFv from ~0% up to 40% of the secreted sc-dsFv molecule.

Another folding quality of the sc-dsFv was determined by the ratio of the normalized sc-dsFv-VEGF binding ELISA signal over the normalized quantity of the secreted sc-dsFv determined by electrophoresis and Western blot analysis. FIG. 6B compared the extent of the interface disulfide bond formation in the secreted soluble sc-dsFv with the folding qualities derived from electrophoresis and ELISA measurements for the signal sequence variants from the L4 library. The positive correlation ($R^2$=0.296, p-value=0.062) shown in FIG. 6B indicated that the interface disulfide bond formation enhanced the affinity for the sc-dsFv-VEGF interaction. The plot also indicated that the selected variants resulted in secreted sc-dsFv with up to more than 10-fold VEGF-binding signals per unit quantity of secreted sc-dsFv compared with the positive control scFv(fXa+)/M13pIII-pelB, indicating that the secreted sc-dsFv from these signal sequence variants folded into antibody-like structure substantially more effectively that the scFv construct. This is most likely due to the stabilizing interface disulfide bond that is formed in the sc-dsFv but is absent in the scFv construct.

Example 7

Figure 7:
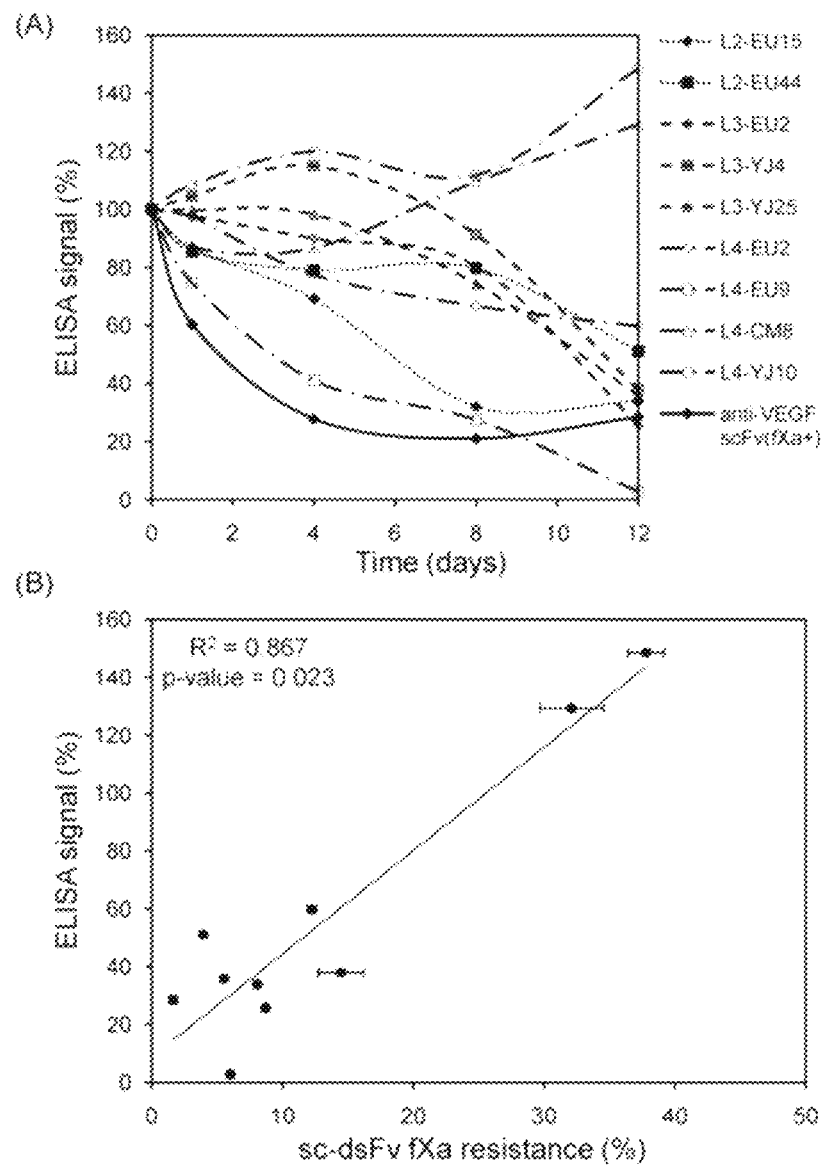
FIGS. 7A and B are diagrams showing stability test of soluble sc-dsFv; including FIG. 7A showing the results of the soluble sc-dsFv incubated at 37° C. as the indicated time shown in the x-axis, and the binding capacities estimated with ELISA against VEGF, shown in y-axis; the ELISA signal was normalized against that of the secreted protein kept at 4° C.
FIG. 7B showing the fXa resistance percentages of the soluble sc-dsFv plotted against the end binding capacities after 12 days of incubation in 37° C.; the error bars in each data point indicate the standard deviations from three repeats of the experiment, and the coefficient of determination $R^2$ and the p-value from Spearman's rank correlation coefficient are shown in the panel.

Correlation between the Stability of sc-dsFv and the Extent of the Interface Disulfide Bond Formation in the sc-dsFv The effect of interface disulfide bond in stabilizing the sc-dsFv structure was demonstrated in FIG. 7. Secreted sc-dsFv from representative variants selected from each of the three libraries were expressed and incubated at 37° C. for 12 days and the affinities of the sc-dsFv's against VEGF were measured along the course of incubation. FIG. 7A shows the VEGF-binding affinity plotted against the time course of incubation for each of the selected variants. The VEGF affinity for the control anti-VEGF scFv dropped rapidly in the first few days of incubation, while a few variants from L4 library resulted in stable secreted sc-dsFv that were even gaining affinities against VEGF compared with freshly prepared secreted protein, presumably due to the increasingly stabilized sc-dsFv with the formation of the interface disulfide bond. The correlation between the two measurements shown in FIG. 7B is strong ($R^2$=0.867 p-value=0.023), indicating that the interface disulfide bond could be one of the most important factors in stabilizing the secreted sc-dsFv in the culture medium.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

We claim:

1. An isolated nucleic acid, comprising
   a first nucleotide sequence encoding a signal peptide, and
   a second nucleotide sequence encoding a single chain antibody capable of forming an interface disulfide bond, the second nucleotide sequence being located 3' downstream to the first nucleotide, wherein the signal peptide has the amino acid sequence of
   VKKLLX$_1$X$_2$X$_3$X$_4$X$_5$X$_6$X$_7$X$_8$X$_9$X$_{10}$AAQPAMA HHH-HHHGH (SEQ ID NO:596), in which X$_1$ is A, C, F, G, I, L, M, P, Q, S, V, W, or Y; X$_2$ is A, D, F, G, H, I, L, M, N, P, S, T, V, or W; X$_3$ is A, F, G, L, M, P, Q, R, S, T, V, or W; X$_4$ is A, F, G, H, I, L, M, P, Q, R, S, T, V, W, or Y; X$_5$ is A, C, D, F, G, H, I, L, M, P, Q, R, S, T, V, W, or Y; X$_6$ is A, C, D, F, G, H, I, K, L, M, N, P, Q, R, S, T, V, W, or Y; X$_7$ is A, C, D, F, G, H, I, K, L, M, N, P, Q, R, S, T, V, W, or Y; X$_8$ is A, C, D, E, F, G, H, I, K, L, M, N, P, Q, R, S, T, V, W, or Y; X$_9$ is A, C, D, E, F, G, H, I, L, M, N, P, Q, R, S, T, V, W, or Y; and X$_{10}$ is A, C, D, E, F, G, H, I, K, L, M, N, P, Q, R, S, T, V, W, or Y.

2. The nucleic acid of claim 1, further comprising a third nucleotide encoding a phage coat protein, the third nucleotide sequence being located 3' downstream to the second nucleotide sequence.

3. The nucleic acid of claim 1, wherein the nucleic acid is an expression vector for expression a fusion protein containing the signal peptide and the single chain antibody.

4. The nucleic acid of claim 1, wherein the single chain antibody contains a first variable region, a second variable region, and a protein linker connecting the first and the second variable region, wherein the first and the second variable region are stabilized by an interface disulfide bond.

5. The nucleic acid library of claim 4, wherein the first variable region is a heavy chain variable region (V$_H$) or a light chain variable region (V$_L$).

6. The nucleic acid library of claim 4, wherein the second variable region is a heavy chain variable region (V$_H$) or a light chain variable region (V$_L$).

7. The nucleic acid of claim 3, wherein the expression vector is a phagemid.

8. A host cell containing the nucleic acid of claim 4.

9. A phage containing a disulfide-stabilized single chain antibody fused with its coat protein on the surface, wherein the phage is prepared by the method comprising the steps of:
   providing a host cell of claim 8, and
   culturing the host cell in a medium under conditions allowing expression of the phage.

10. A method for producing a disulfide-stabilized single chain antibody, comprising
   providing a host cell containing an expression construct, and
   culturing the host cell in a medium under conditions allowing expression of the disulfide-stabilized single chain antibody, wherein the expression construct includes a first nucleotide sequence encoding a signal peptide, and a second nucleotide sequence encoding a single chain antibody capable of forming an interface disulfide bond, the second nucleotide sequence being located 3' downstream to the first nucleotide, and wherein the signal peptide has the amino acid sequence of VKKLLX$_1$X$_2$X$_3$X$_4$X$_5$X$_6$X$_7$X$_8$X$_9$X$_{10}$AAQPAMAHHHHHHGH (SEQ ID NO:596), in which X$_1$ is A, C, F, G, I, L, M, P, Q, S, V, W, or Y; X$_2$ is A, D, F, G, H, I, L, M, N, P, S, T, V, or W; X$_3$ is A, F, G, L, M, P, Q, R, S, T, V, or W; X$_4$ is A, F, G, H, I, L, M, P, Q, R, S, T, V, W, or Y; X$_5$ is A, C, D, F, G, H, I, L, M, P, Q, R, S, T, V, W, or Y; X$_6$ is A, C, D, F, G, H, I, K, L, M, N, P, Q, R, S, T, V, W, or Y; X$_7$ is A, C, D, F, G, H, I, K, L, M, N, P, Q, R, S, T, V, W, or Y; X$_8$ is A, C, D, E, F, G, H, I, K, L, M, N, P, Q, R, S, T, V, W, or Y; X$_9$ is A, C, D, E, F, G, H, I, L, M, N, P, Q, R, S, T, V, W, or Y; and X$_{10}$ is A, C, D, E, F, G, H, I, K, L, M, N, P, Q, R, S, T, V, W, or Y.

11. The method of claim 10, wherein the single chain antibody contains a first variable region, a second variable region, and a protein linker connecting the first and the second variable region, wherein the first and the second variable region are stabilized by an interface disulfide bond.

12. The method of claim 11, wherein the first variable region is a heavy chain variable region (V$_H$) or a light chain variable region (V$_L$).

13. The method of claim 11, wherein the second variable region is a heavy chain variable region (V$_H$) or a light chain variable region (V$_L$).

14. The method of claim 10, further comprising, after the culturing step, collecting the medium for isolating the disulfide-stabilized single chain antibody.

15. The method of claim 10, wherein the expression construct is a phagemid that further includes a third nucleotide encoding a phage envelope protein, the third nucleotide sequence being located 3' downstream to the second nucleotide sequence.

16. The method of claim 15, further comprising, after the culturing step, collecting the medium for isolating phage particles that display the disulfide-stabilized single chain antibody.

* * * * *